United States Patent
Robinson et al.

(10) Patent No.: US 11,022,611 B2
(45) Date of Patent: Jun. 1, 2021

(54) METHODS AND SYSTEMS FOR DIAGNOSIS AND TREATMENT OF VIRAL INFECTIONS

(71) Applicant: Nirmidas Biotech, Inc., Palo Alto, CA (US)

(72) Inventors: Joshua T. Robinson, Belmont, CA (US); Meijie Tang, Cupertino, CA (US); Su Zhao, Santa Clara, CA (US); Anna Hsu Pao, Burlingame, CA (US); Hongjie Dai, Cupertino, CA (US); Bo Zhang, Sunnyvale, CA (US); Jeyarama Subramanian Ananta Narayanan, Sunnyvale, CA (US)

(73) Assignee: Nirmidas Biotech, Inc., Palo Alto, CA (US)

(*) Notice: Subject to any disclaimer, the term of this patent is extended or adjusted under 35 U.S.C. 154(b) by 50 days.

(21) Appl. No.: 16/096,929

(22) PCT Filed: May 3, 2017

(86) PCT No.: PCT/US2017/030896
§ 371 (c)(1),
(2) Date: Oct. 26, 2018

(87) PCT Pub. No.: WO2017/192756
PCT Pub. Date: Nov. 9, 2017

(65) Prior Publication Data
US 2020/0158728 A1     May 21, 2020

Related U.S. Application Data

(60) Provisional application No. 62/459,550, filed on Feb. 15, 2017, provisional application No. 62/368,983, filed on Jul. 29, 2016, provisional application No. 62/331,233, filed on May 3, 2016.

(51) Int. Cl.
| | |
|---|---|
| *A61K 39/00* | (2006.01) |
| *A61K 39/12* | (2006.01) |
| *A61K 38/00* | (2006.01) |
| *A61K 39/295* | (2006.01) |
| *A61K 39/395* | (2006.01) |
| *G01N 33/569* | (2006.01) |
| *G01N 33/68* | (2006.01) |

(52) U.S. Cl.
CPC ... *G01N 33/56983* (2013.01); *G01N 33/6854* (2013.01); *G01N 2333/181* (2013.01); *G01N 2333/185* (2013.01); *G01N 2469/20* (2013.01)

(58) Field of Classification Search
CPC ........ A61K 2039/5258; A61K 2039/53; A61K 2039/54; A61K 2039/545; A61K 2039/57
See application file for complete search history.

(56) References Cited

FOREIGN PATENT DOCUMENTS

| EP | 1985709 A1 | * | 4/2007 |
|---|---|---|---|
| EP | 1985709 | | 10/2008 |
| WO | WO-2015/038797 | | 3/2015 |
| WO | WO-2015/134560 | | 9/2015 |
| WO | WO2015134560 | * | 9/2015 |
| WO | WO2016/022071 | * | 2/2016 |
| WO | WO-2016/022071 | | 2/2016 |

OTHER PUBLICATIONS

De Souza et al., "Use of an immunoglobulin G avidity test to discriminate between primary and secondary dengue virus infection", J Clin Microbiol, 2004, 42:1782-1784.*
De Souza et al., "Use of an Immunoglobulin G Avidity Test to Discriminate between Primary and Secondary Dengue Virus Infections", Journal of Clinical Microbiology, 2004, vol. 42, No. 4, p. 1782-1784.
Haddow et al., "Genetic Characterization of Zika Virus Strains: Geographic Expansion of the Asian Lineage", PLoS Negl Trop Dis, 2012, 6(2), e1477, p. 1-7.
International Search Report and Written Opinion for International Application No. PCT/US2017/030896 dated Jul. 13, 2017. (20 pages).
Zhang et al., "Diagnosis of Zika virus infection on a nanotechnology platform." Nature Medicine, 2017, 23(5), p. 548-550.

* cited by examiner

*Primary Examiner* — Barry A Chestnut

(57) ABSTRACT

Disclosed herein are systems and methods for detecting and diagnosing flaviviral or alphaviral infections in subjects in need thereof. The systems and methods of the disclosure enable rapid testing of small volumes of biological sample with the ability to reliably distinguish between flavival and alphaviral infections and determine whether the viral infection is acute or chronic.

23 Claims, 39 Drawing Sheets

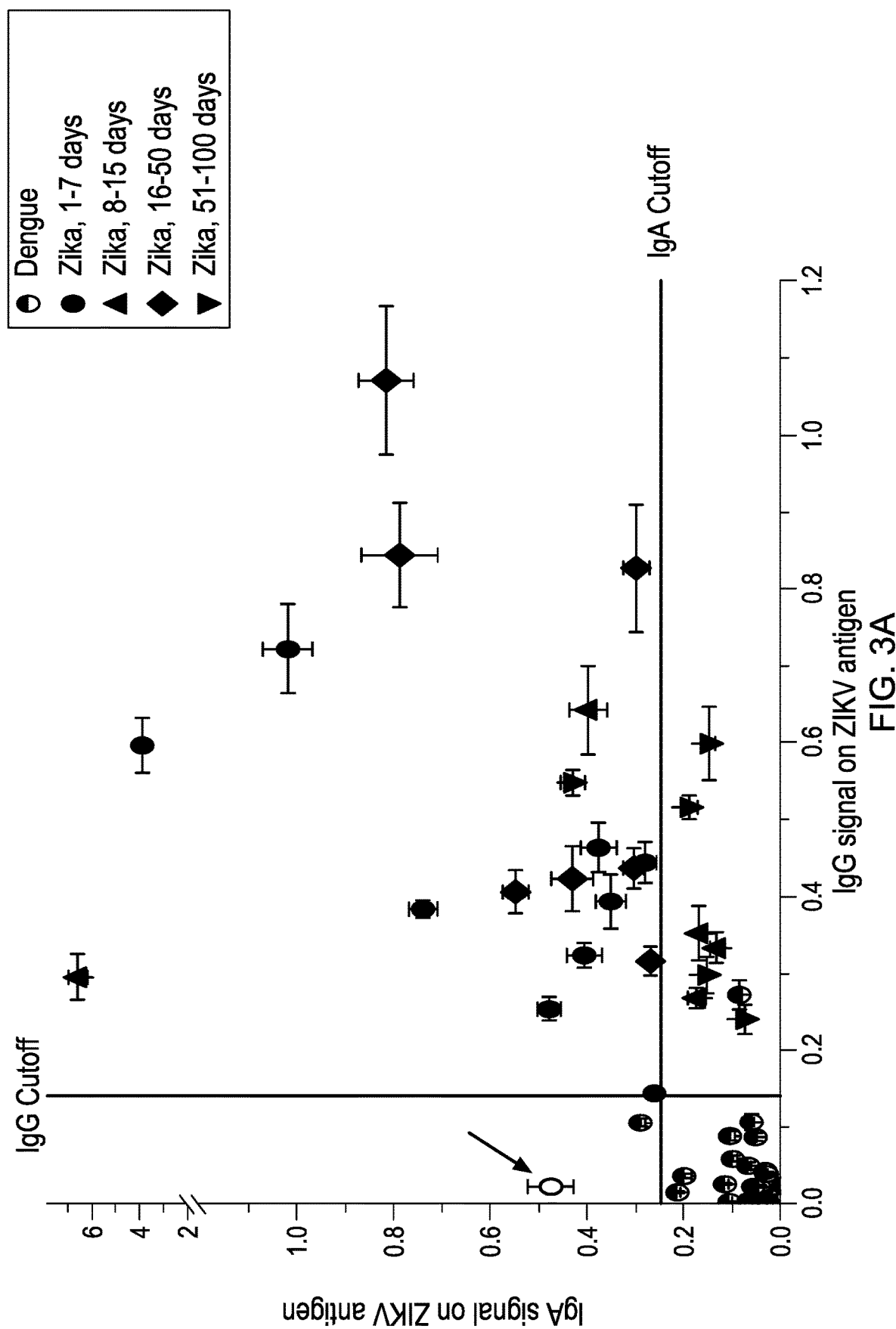

METHODS AND SYSTEMS FOR DIAGNOSIS AND TREATMENT OF VIRAL INFECTIONS

CROSS-REFERENCE TO RELATED APPLICATIONS

This application is a U.S. National Stage Application under 35 U.S.C. § 371 of International Application No. PCT/US2017/030896, filed May 3, 2017, which application claims the benefit of U.S. Provisional Application No. 62/331,233, filed May 3, 2016, U.S. Provisional Application No. 62/368,983, filed Jul. 29, 2016 and U.S. Provisional Application No. 62/459,550, filed Feb. 15, 2017, the entire contents of each of which are incorporated herein by reference.

BACKGROUND

The recent spread of Zika virus (ZIKV) in South America and severe birth defects resulting from infection during pregnancy have drawn attention to ZIKV worldwide. Currently, the Centers for Disease Control and Prevention (CDC) diagnostic algorithm for acute ZIKV infection currently recommends initial testing be performed using ZIKV reverse transcriptase-polymerase chain reaction (RT-PCR) on specimens collected within the first 7 days of the onset of symptoms. This recommendation takes into account the relatively short duration of viremia and the extensive cross-reactivity observed in ZIKV IgM serological assays. While ZIKV RT-PCR tests may provide ZIKV diagnosis and the opportunity for multiplex diagnosis of CHIKV and DENV infection, given the high incidence of mild or asymptomatic ZIKV infections, patients may not present to medical attention at a time when viremia is detectable by RT-PCR. The CDC therefore recommends that ZIKV IgM antibody testing also be performed on serum specimens collected 4 or more days after the onset of illness. However, the Zika MAC-ELISA assay, the only IgM assay authorized by CDC under Emergency Use Authorization (EUA), takes three days to complete and requires a confirmatory test by plaque reduction neutralization testing (PRNT) to resolve the false-positive issue due to cross reactivity. Plaque reduction neutralization testing (PRNT), the current gold standard test for ZIKV infection, is a highly complex method that has a long turnaround time and limited availability, and is unable to distinguish between antibody isotypes. Furthermore, research have shown the historical use of a 4-fold higher titer by PRNT may not be capable of discriminating ZIKV infection from other flavivirus infections in people who have been previously infected with or vaccinated against a related flavivirus (i.e., secondary flavivirus infection). In the recent ZIKV outbreak in Colombia, <10% ZIKV diagnoses were confirmed by RT-PCR, while >90% relied on symptoms and patient history that the individual lived or traveled in an area with laboratory antibodies selected from confirmed ZIKV circulation prior to onset of symptoms. Therefore, the availability of a serological test with a wide diagnostic window and the ability to differentiate ZIKV infection from DENV infection is needed.

SUMMARY

In certain aspects, the disclosure provides a method for detecting antibodies selected from IgA and IgG in a biological sample of a subject, the method comprising: (a) obtaining a biological sample from the subject; (b) contacting a first portion of said biological sample with one or multiple flaviviral or alphaviral antigens wherein said flaviviral or alphaviral antigen binds to one or both of IgA and IgG thereby forming immune complexes; (c) detecting antibodies selected from IgA and IgG in the biological sample by detecting antibodies selected from IgA and IgG bound to each of said flaviviral or alphaviral antigen. In certain embodiments, the detecting comprises detecting a level of antibodies selected from IgA and IgG bound to said flaviviral or alphaviral antigen in said biological sample. In certain embodiments, the flaviviral or alphaviral antigens are selected from a Zika virus antigen, Dengue virus antigen, yellow fever virus antigen, tick-borne encephalitis virus antigen, Japanese Encephalitis virus (JEV), West Nile virus antigen, mayaro virus antigen, and Chikungunya virus antigen. The flaviviral antigens may be selected from a Zika virus antigen, Dengue virus antigen. The flaviviral antigen may be Zika virus antigen.

The method for detecting antibodies selected from IgA and IgG in a biological sample of a subject may further comprise a step (b1) of contacting the immune complexes of step (b) with a protein denaturing agent, wherein said a mild protein denaturing agent is present in a concentration sufficient to destabilize immune complexes containing antibodies of low avidity, but not sufficient to destabilize immune complexes containing antibodies of high avidity, wherein said step (b1) follows step (b) and precedes step (c). The method may further comprise a step (c1), wherein step (c1) comprises evaluating avidity of IgG by taking a ratio of the level of said IgG in step (c) to a control value of IgG in a second portion of said biological sample not exposed to said protein denaturing agent, wherein when the ratio is about 0.5 or less the avidity is low and when the ratio is about 0.6 or greater than said avidity is high, wherein said step (c1) follows step (c). The contacting of step (b1) may comprise incubating said immune complexes with a protein denaturing agent for a period of about 1 minute to about 25 minutes, such as about 10 minutes to about 20 minutes. The incubating may be followed by a rinse step to remove said protein denaturing agent, and unbound and low avidity antibodies, wherein said rinse step precedes step (c).

In certain embodiments, the protein denaturing agent is selected from urea, formamide, guanidine, sodium salicylate, dimethyl sulfoxide, and propylene glycol and combinations thereof. The protein denaturing agent may comprise urea.

In certain aspects, the disclosure provides a method of diagnosing Zika virus infection in a subject, the method comprising: (a) obtaining a biological sample from a subject; (b) contacting a first portion of said biological sample with a Zika virus antigen wherein said Zika virus antigen binds to antibodies selected from IgA and IgG thereby forming immune complexes; (c) detecting antibodies selected from IgA and IgG in the biological sample by detecting antibodies selected from IgA and IgG bound to said Zika virus antigen; and (d) diagnosing the subject with Zika virus infection when the presence of antibodies selected from IgA and IgG in the biological sample is detected.

In certain aspects, the disclosure provides a method of diagnosing and treating Zika virus infection in a subject in need thereof, the method comprising: (a) obtaining a biological sample from a subject; (b) contacting a first portion of said biological sample with a Zika virus antigen wherein said Zika virus antigen binds to antibodies selected from IgA and IgG thereby forming immune complexes; (c) detecting antibodies selected from IgA and IgG in said biological sample by detecting antibodies selected from IgA and IgG bound to said Zika virus antigen; (d) diagnosing the subject with Zika virus infection when the presence of antibodies selected from IgA and IgG in the biological sample is detected; and optionally (e) administering an effective amount of an anti-viral agent to the diagnosed subject.

In certain aspects, the disclosure provides a method of diagnosing Zika virus infection in a female subject and preventing diseases due to fetal transmission of said infection, the method comprising: (a) obtaining a biological sample from a female subject; (b) contacting a first portion of said biological sample with a Zika virus antigen wherein said Zika virus antigen binds to antibodies selected from IgA and IgG thereby forming immune complexes; (c) detecting antibodies selected from IgA and IgG in said biological sample by detecting antibodies selected from IgA and IgG bound to said Zika virus antigen; (d) diagnosing the subject with Zika virus infection when the presence of antibodies selected from IgA and IgG in the biological sample is detected; and optionally (e) administering a contraceptive to the diagnosed subject.

In certain embodiments, the method of diagnosing Zika virus infection in a subject, the method of diagnosing and treating Zika virus infection in a subject, and/or the method of diagnosing Zika virus infection in a female subject and preventing diseases due to fetal transmission of said infection further comprises a step (b1) of contacting the immune complexes of step (b) with a protein denaturing agent, wherein said protein denaturing agent is present in a concentration sufficient to destabilize immune complexes containing antibodies of low avidity, but not sufficient to destabilize immune complexes containing antibodies of high avidity, wherein said step (b1) follows step (b) and precedes step (c).

In certain embodiments, the method of diagnosing Zika virus infection in a subject, the method of diagnosing and treating Zika virus infection in a subject, and/or the method of diagnosing Zika virus infection in a female subject and preventing diseases due to fetal transmission of said infection further comprises a step (c1), wherein step (c1) comprises evaluating avidity of IgG by taking a ratio of the level of said IgG in step (c) to a control value of IgG in a second portion of said biological sample not exposed to said protein denaturing agent, wherein when the ratio is less than 0.5 said avidity is low and when the ratio is greater than 0.6 said avidity is high, wherein step (c1) follows step (c) and precedes step (d). Step (d) may further comprise diagnosing said subject with an acute infection when said avidity is low and diagnosing said subject with a chronic infection when said avidity is high. In certain embodiments, the contacting of step (b1) comprises incubating said immune complexes with a protein denaturing agent for a period of about 1 minute to about 25 minutes, such as about 10 minutes to about 20 minutes. In certain embodiments, the incubating is followed by a rinse step to remove said protein denaturing agent, and unbound and low avidity antibodies.

In certain embodiments, the protein denaturing agent is selected from urea, formamide, guanidine, sodium salicylate, dimethyl sulfoxide, and propylene glycol and combinations thereof. The protein denaturing agent may comprise urea.

In certain embodiments, the detecting comprises detecting a level of antibodies selected from IgA and IgG bound to said Zika virus antigen in said biological sample. The detecting may comprise detecting a first detectable label, wherein said first detectable label is associated with a first antibody that binds to said IgA bound to said Zika antigen. The first antibody may be an antihuman IgA antibody. The first detectable label may emit a signal of a primary wavelength. In certain embodiments, the detecting comprises detecting a second detectable label, wherein said second detectable label is associated with a second antibody that binds to said IgG bound to said Zika antigen. The second antibody may be an antihuman IgG antibody. The second detectable label may emit a signal of a secondary wavelength. The primary wavelength may be different from the secondary wavelength.

In certain embodiments, the diagnosing comprises comparing said level of IgG bound to said Zika virus antigen to a Dengue-based cutoff value of a reference chronically Dengue infected patient population, wherein when said level of IgG bound to said Zika virus antigen is greater than said Dengue-based cutoff value, said subject is diagnosed with Zika virus infection. The Dengue-based cutoff value may be about two to five standard deviations above a mean value of the levels of IgG bound to said Zika virus antigen measured in the biological samples of said reference chronically Dengue infected patient population. The Dengue-based cutoff value may be about two or about three standard deviations above a mean value of the levels of IgG bound to said Zika virus antigen measured in the biological samples of said reference chronically Dengue infected patient population. The reference Dengue infected patient population may not have any prior or current Zika virus infection.

In certain embodiments, the diagnosing comprises comparing said level of IgA bound to said Zika virus antigen to a healthy control cutoff value of a reference healthy patient population, wherein when said level of IgA bound to said Zika virus antigen is greater than said healthy control cutoff value, said subject is diagnosed with acute Zika virus infection. The healthy control cutoff value may be about two to about five standard deviations above a mean value of the levels of IgA bound to said Zika virus antigen measured from biological samples of said reference healthy patient population. The healthy patient population may not have any prior or current Zika virus infection or Dengue virus infection.

In certain embodiments, the biological sample is collected from said subject within ninety days of initial exposure of said subject to Zika virus or within ninety days following the onset of symptoms of Zika virus of said subject. The biological sample may be collected from said subject within fifty days of initial exposure of said subject to Zika virus or within fifty days following the onset of symptoms of Zika virus of said subject. The biological sample may be collected from said subject within ten days of initial exposure of said subject to Zika virus or within ten days following the onset of symptoms of Zika virus of said subject. The biological sample may be collected from said subject within five days of initial exposure of said subject to Zika virus or within ten days following the onset of symptoms of Zika virus of said subject.

In certain embodiments, the method is performed on two or more biological samples collected from said patient at different times following initial exposure of said subject to Zika virus or following onset of symptoms of Zika virus of said subject. In certain embodiments, the detecting comprises detecting both of IgA and IgG bound to said Zika virus antigen in said biological sample. The detecting antibodies selected from IgG and IgA bound to said Zika virus antigen may be performed by using any of: microarray platforms based on plasmonic and non-plasmonic substrates including metals, glass, quartz and nitrocellulose, ELISA, digital ELISA, lateral flow assays, Luminex, chemiluminescence assays, bead-based fluorescence assays, and electrochemical luminescence assays or a combination thereof. The biological sample may be selected from whole blood, plasma, serum, and saliva. The biological sample may have a volume of from about 0.5 to about 500 microliters.

In certain embodiments, the subject is diagnosed with Zika virus infection within four weeks of the onset of symptoms of a viral infection. The subject may be diagnosed with Zika virus infection within one week of the onset of symptoms of a viral infection. The Zika virus antigen may comprise a recombinant Zika viral antigen. The recombinant Zika viral antigen may be a Zika virus NS1 or NS5 protein. The recombinant Zika viral antigen may be Uganda MR 766 and Suriname Z1106033.

In certain embodiments, the diagnosing accurately distinguishes between Zika virus infection and other flaviviral or alphaviral infections in 90% or more of subjects tested. The diagnosing may accurately distinguish between Zika virus infection and Dengue virus infection in 90% or more of subjects tested.

In certain aspects, the disclosure provides a method of diagnosing a first and second viral infection in a subject, the method comprising: (a) obtaining a biological sample from a subject; (b) contacting a first portion of said biological sample with a first viral antigen and a second viral antigen independently selected from flaviviral antigens and alphaviral antigens thereby forming immune complexes; (c) detecting antibodies selected from IgA, IgM, and IgG in said biological sample by detecting antibodies selected from IgA, IgM, and IgG bound to said first viral antigen and antibodies selected from IgA, IgM, and IgG bound to said second viral antigen; and (d) diagnosing said subject with said first viral infection upon detecting antibodies selected from IgA, IgM, and IgG bound to said first viral antigen and diagnosing the subject with said second viral infection upon detecting antibodies selected from IgA and IgG bound to said second viral antigen.

In certain embodiments, the method of diagnosing a first and second viral infection in a subject further comprises a step (b1) of contacting the immune complexes of step (b) with a protein denaturing agent, wherein said protein denaturing agent is present in a concentration sufficient to destabilize immune complexes containing antibodies of low avidity, but not sufficient to destabilize immune complexes containing antibodies of high avidity, wherein said step (b1) follows step (b) and precedes step (c). In certain embodiments, the method of diagnosing a first and second viral infection in a subject further comprises a step (c1), wherein step (c1) comprises evaluating avidity of IgG by taking a ratio of the level of said IgG in step (c) to a control value of IgG in a second portion of said biological sample not exposed to said protein denaturing agent, wherein when the ratio is less than 0.5 said avidity is low and when the ratio is greater than 0.6 said avidity is high, wherein step (c1) follows step (c) and precedes step (d). The step (d) may further comprise diagnosing said subject with an acute infection when said avidity is low and diagnosing said subject with a chronic infection when said avidity is high. The said contacting of step (b1) may comprise incubating said immune complexes with a protein denaturing agent for a period of about 1 minute to about 25 minutes, such as about 10 minutes to about 20 minutes. The incubating may be followed by a rinse step to remove said protein denaturing agent, and unbound and low avidity antibodies. The protein denaturing agent may be selected from urea, formamide, guanidine, sodium salicylate, dimethyl sulfoxide, and propylene glycol and combinations thereof. The protein denaturing agent may comprise urea.

In certain embodiments, the first viral infection and second viral infection are independently selected from flaviviral infections and alphaviral infections. The flaviviral infections and alphaviral infections may be selected from Zika virus, Dengue virus, yellow fever virus, tick-borne encephalitis virus, West Nile virus, mayaro virus, and Chikungunya virus.

In certain embodiments, the diagnosing accurately distinguishes between said first and second viral infections in 90% or more of subjects tested. The diagnosing may accurately distinguish between Zika virus infection and other flaviviral or alphaviral infections in 90% or more of subjects tested. The diagnosing may accurately distinguish between Zika virus infection and Dengue virus infection in 90% or more of subjects tested.

In certain embodiments, the first viral antigen is selected from Zika virus antigen, Dengue virus antigen, yellow fever virus antigen, tick-borne encephalitis virus antigen, West Nile virus antigen, mayaro virus antigen, and Chikungunya virus antigen. In certain embodiments, the second viral antigen is selected from Zika virus antigen, Dengue virus antigen, yellow fever virus antigen, tick-borne encephalitis virus antigen, West Nile virus antigen, mayaro virus antigen, and Chikungunya virus antigen. The first viral antigen may be a Zika virus antigen and said second viral antigen may be a Dengue virus antigen.

In certain embodiments, the detecting comprises detecting a level of antibodies selected from IgA, IgM, and IgG bound to said first viral antigen in said biological sample. The detecting may comprise detecting a level of antibodies selected from IgA, IgM, and IgG bound to said second viral antigen in said biological sample. The first viral antigen may be isolated from said second viral antigen. The first viral antigen may be isolated from said second viral antigen in separate vessels. The detecting IgG bound to said first or second viral antigens may comprise detecting a first wavelength of light and detecting IgA or IgM bound to said first or second viral antigens comprises detecting a second wavelength of light. The first wavelength of light may be different from said second wavelength of light.

In certain embodiments, the detecting antibodies selected from IgA and IgG bound to said first and second viral antigen is performed by using any one of: microarray platforms on plasmonic and non-plasmonic substrates including metals, glass, quartz and nitrocellulose, ELISA, digital-ELISA, lateral flow assays, Luminex, chemiluminescence assays, bead-based fluorescence assays, and electrochemical luminescence assays. In certain embodiments, the first and second viral antigens are associated with a substrate comprising a first and second region wherein said first viral antigen is associated with said first region and said second viral antigen is associated with said second region.

In certain embodiments, the substrate is plasmonically active. The substrate may comprise a metallic film arranged on said substrate in a manner that enhances near infrared fluorescence by 5-fold to 100-fold or more relative to the substrate without said metallic film. The substrate may comprises a metallic film arranged discontinuously on said substrate wherein said metallic film has isolated island areas of between about 100 $nm^2$ and 40,000 $nm^2$ in surface-exposed area, said isolated islands being separated by gaps of about 10 to about 60 nm. The metallic film may comprise a metal selected from gold and silver.

In certain embodiments, the method of diagnosing a first and second viral infection in a subject further comprises diagnosing a third, fourth, fifth, sixth, or seventh viral infection, the method further comprising: in step (b), contacting said biological sample with a third, fourth, fifth or sixth viral antigen independently selected from flaviviral antigens and alphaviral antigens; in step (c), detecting antibodies selected from IgA, IgM, and IgG in said biological sample by detecting antibodies selected from IgA, IgM, and IgG bound to said third, fourth, fifth or sixth viral antigen; and in step (d), diagnosing said subject with said third viral infection upon detecting antibodies selected from IgA and IgG bound to said third viral antigen, diagnosing said subject with said fourth viral infection upon detecting antibodies selected from IgA and IgG bound to said fourth viral antigen, diagnosing said subject with said fifth viral infection upon detecting antibodies selected from IgA and IgG bound to said fifth viral antigen, and diagnosing the subject with said sixth viral infection upon detecting antibodies selected from IgA and IgG bound to said sixth viral antigen.

In certain embodiments, steps (b) to (c) together and in order are performed in 2 hours or less. In certain embodiments, steps (b), (c) and (d) performed together and in order are performed in 2 hours or less. In certain embodiments, the biological sample has a volume of from about 0.5 to about 500 microliters, such as about 0.5 to about 20 microliters.

In certain aspects, the disclosure provides a method for determining the extent of binding of one or more antibodies in a biological sample to flaviviral or alphaviral antigens, comprising the steps of: (a) contacting a first portion of said biological sample with said flaviviral or alphaviral antigens, under conditions which permit immune complexes to form; (b) contacting said immune complexes with a protein denaturing agent, wherein said protein denaturing agent is present in a concentration sufficient to destabilize immune complexes containing antibodies of low avidity, but not sufficient to destabilize immune complexes containing antibodies of high avidity; and (c) determining the extent of binding of one or more antibodies selected from IgG in said biological sample to said antigens. In certain embodiments, the antigens are immobilized on a substrate.

In certain embodiments, the method for determining the extent of binding of one or more antibodies in a biological sample to flaviviral or alphaviral antigens further comprises evaluating avidity of said antibodies by taking a ratio of the levels of said IgG in step (c) to control values of IgG in a second portion of said biological sample not exposed to said protein denaturing agent, wherein when the ratio is about 0.5 or less said avidity is low and when the ratio is about 0.6 or greater said avidity is high.

In certain embodiments, the control values of IgG are obtained by evaluating a second portion of biological sample following steps (a) and (c) of the method and excluding step (b). The control values of IgG may be obtained by evaluating a second portion of said biological sample following steps (a), (b) and (c) of the method and excluding step (b1). When the avidity is low, the infection in said biological sample may be classified as acute and when the avidity is high, infection in said biological sample may be classified as chronic.

In certain aspects, the disclosure provides a method for determining the extent of binding of IgG antibodies in a biological sample of a subject to flaviviral or alphaviral antigens, comprising the steps of: (a) providing a substrate with a surface comprising antigens bound to said surface, wherein said antigens are selected from flaviviral and alphaviral antigens; (b) contacting said surface with a first portion of a biological sample under conditions which permit immune complexes to form between said antibodies and said antigens; (c) performing a wash step on said substrate, wherein said wash step comprises contacting said surface of said substrate with a protein denaturing agent in a concentration sufficient to destabilize immune complexes containing antibodies of low avidity, but not sufficient to destabilize immune complexes containing antibodies of high avidity; and (d) detecting the level IgG bound to said flaviviral or alphaviral antigens in said biological sample.

In certain embodiments, the contacting of step (c) comprises incubating said surface of said substrate with a protein denaturing agent for a period of about 1 minute to about 25 minutes, such as of about 10 minutes to about 20 minutes. In certain embodiments, the incubating is followed by a rinse step to remove said protein denaturing agent, and unbound and low avidity antibodies.

In certain embodiments, the detecting comprises contacting said substrate with one or more detectable labels associated with anti-IgG. In certain embodiments, the method for determining the extent of binding of IgG antibodies in a biological sample of a subject to flaviviral or alphaviral antigens further comprises evaluating avidity of said antibodies by taking a ratio of the level of IgG in step (d) to a control value of IgG of a second portion of biological sample not exposed to said wash step, wherein when said ratio is about 0.5 or less said avidity is low and when said ratio is about 0.6 or greater said avidity is high. The control value of IgG may be obtained by evaluating a second portion of biological sample following steps (a), (b), and (d), and excluding wash step (c). When the avidity is low, infection in said biological sample may be classified as acute and when said avidity is high, infection in said biological sample may be classified as chronic.

The biological sample of the systems and methods described herein may be selected from whole blood, plasma, serum, urine, and saliva. The biological sample may have a volume of about 0.5 μL to about 500 μL, such as about 0.5 μL to about 20 μL. The protein denaturing agent may be selected from urea, formamide, guanidine, sodium salicylate, dimethyl sulfoxide, and propylene glycol and combinations thereof. The protein denaturing agent may comprise urea. The substrate may comprise plasmonic nanostructures. The substrate may comprise a bead or a 96 well plate. The substrate may comprise metal, glass, polystyrene, quartz, silica, nylon, nitrocellulose, polyvinyl chloride, polydimethyl siloxane, polyvinylidene fluoride, polydopamine, silicon, silicon dioxide, a polymer, iron oxide, plastic and combinations thereof. The substrate may comprise a metallic film on said surface of said substrate. The flaviviral or alphaviral antigens may be selected from a Zika virus antigen, Dengue virus antigen, yellow fever virus antigen, tick-borne encephalitis virus antigen, Japanese Encephalitis virus (JEV), West Nile virus antigen, mayaro virus antigen, and Chikungunya virus antigen. The flaviviral antigens may be selected from a Zika virus antigen and a Dengue virus antigen. The flaviviral antigen may be Zika virus antigen. In some embodiments, the method comprises repeating the steps of the method a second time on a sample from the subject. Repeating the method a second time may occur when the method is performed the first time less than 14 days after initial exposure of the subject to the first virus or second virus or less than 14 days after initial onset of viral infection symptoms. Repeating the method a second time may occur 14 days or more after initial exposure of the subject to the first virus or second virus or 14 days or more after initial onset of viral infection symptoms.

In certain aspects, the disclosure provides a kit for diagnosing a viral infection in a subject, the kit comprising: a substrate with a plasmonic film; one or more viral antigens wherein said one or more viral antigens is immobilized on said substrate; and instructions for using said substrate to assay for the presence of a infection in a sample. The one or more viral antigens of the kit may be selected from a Zika virus antigen, Dengue virus antigen, yellow fever virus antigen, tick-borne encephalitis virus antigen, Japanese Encephalitis virus (JEV), West Nile virus antigen, mayaro virus antigen, and Chikungunya virus antigen. The one or more viral antigens of the kit may be selected from a Zika virus antigen and a Dengue virus antigen. The Zika virus antigen may be a recombinant Zika viral antigen, e.g., Zika virus NS1 protein, Zika virus NS5 protein, Uganda MR 766 and Suriname Z1106033.

The kit may further comprise a protein denaturing agent. The protein denaturing agent may be selected from urea, formamide, guanidine, sodium salicylate, dimethyl sulfoxide, and propylene glycol and combinations thereof. The protein denaturing agent may comprise urea.

In certain embodiments, the kit may further comprise one or more detectable labels associated with an antihuman IgA or an antihuman IgG antibody, one or more diluent buffers, one or more washing buffers.

In certain embodiments, the kit comprises a substrate with a plasmonic film, wherein the plasmonic film enhances near infrared fluorescence by 5-fold to 100-fold or more relative to the substrate without said metallic film. The plasmonic film may be discontinuous Au or Au/Ag film having isolated islands, e.g., with areas of from about 2000 $nm^2$ to about 40,000 $nm^2$, said isolated islands being separated by gaps from 10 nm to 60 nm. In certain embodiments, the plasmonic film has plasmonic resonance peaks from about 500 nm to 1400 nm.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows an example 2D plot for IgG/IgA antibody levels against Zika antigen, for samples having a Dengue infection (half-filled circle), or Zika infection at the specified range of days after the onset of symptoms (filled circle-1-7 days; point-up triangle-8-15 days; diamond-16-50 days; point-down triangle-51-100 days). Compared to Zika samples, Dengue samples showed lower Zika IgG and IgA levels. The illustrated IgG cutoff represents 3 standard deviations above the mean Zika IgG levels detected for Dengue samples. The illustrated IgA cutoff represents 3 standard deviations above the mean Zika IgA levels detected for control samples.

DETAILED DESCRIPTION

Figure 1A:
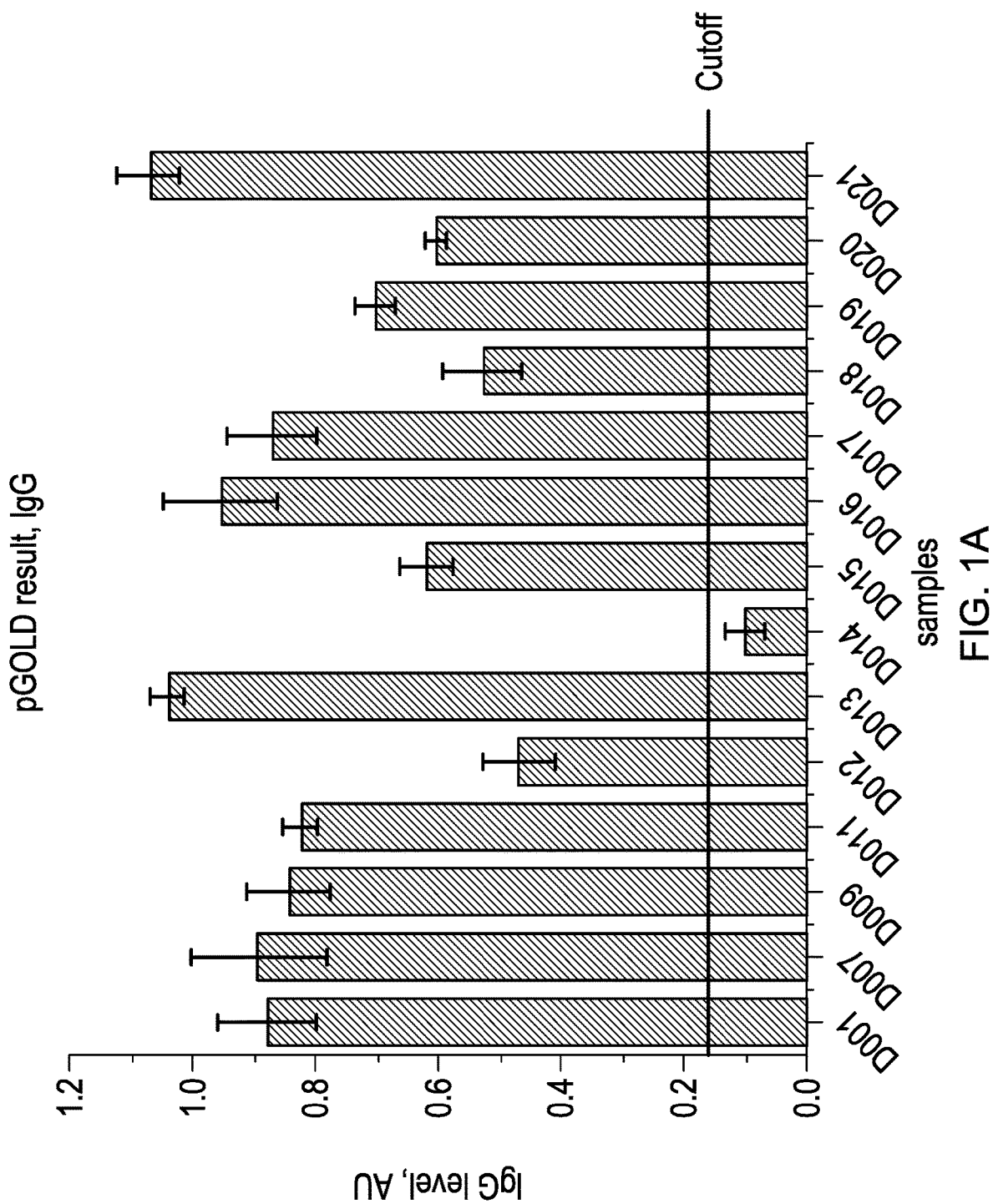
FIGS. 1A-B show example Dengue IgG and IgM antibody levels detected on a plasmonic gold substrate (pGOLD).
Figure 1B:
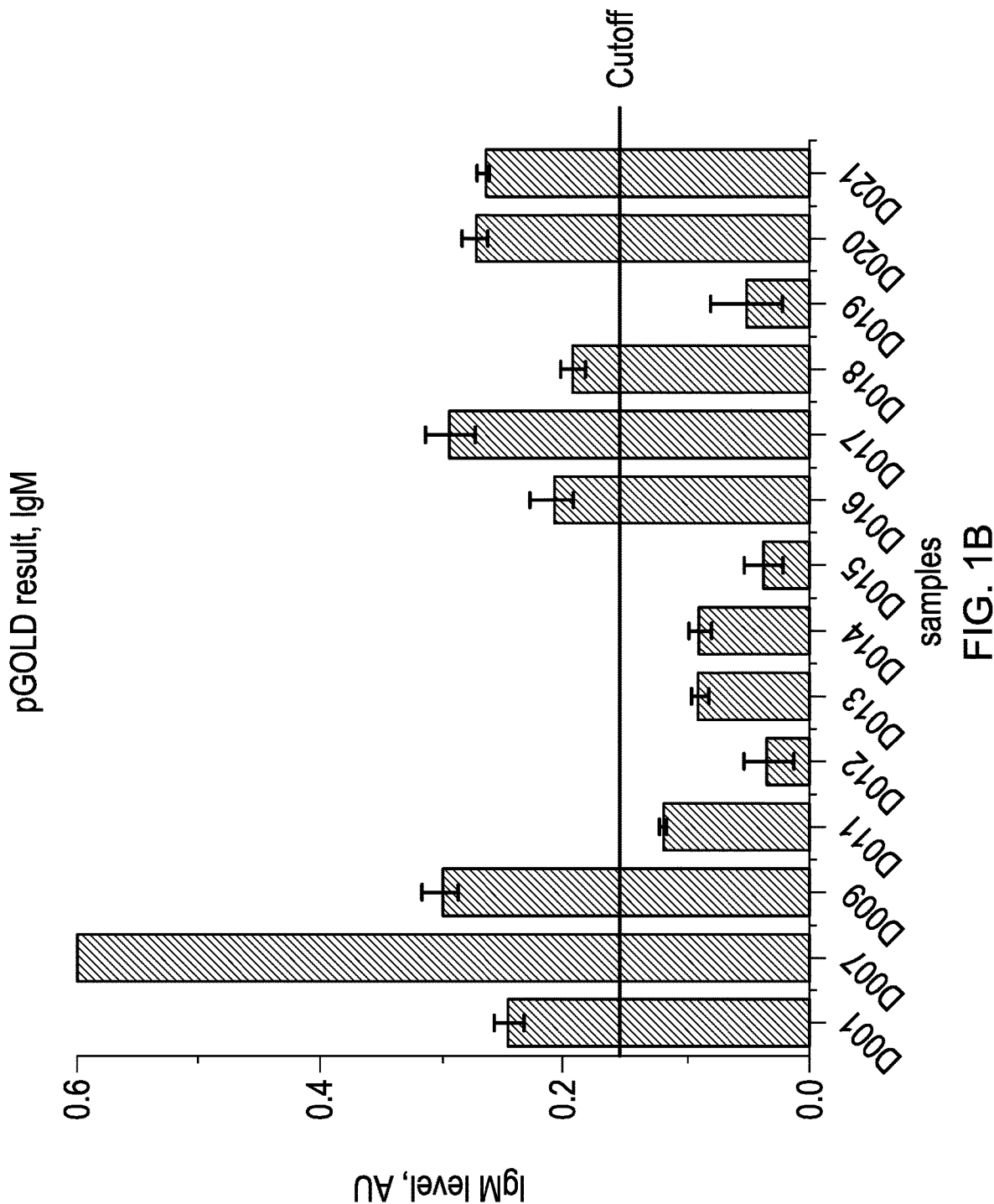
Figure 2A:
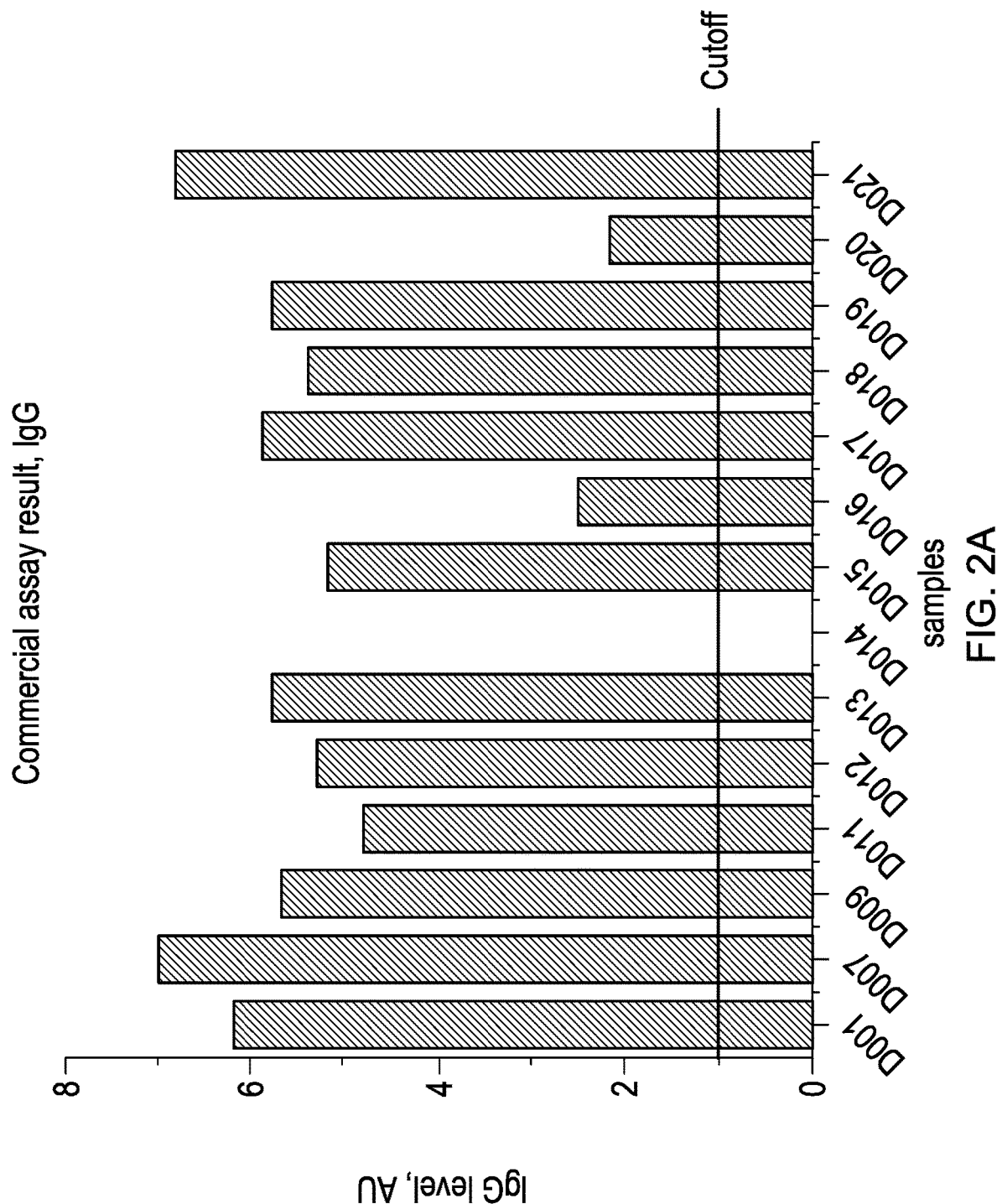
FIGS. 2A-B show example Dengue IgG and IgM antibody levels detected using commercially available assays. Results for Dengue Virus IgG DxSelect test (Focus Diagnostics; Cypress, Calif.) are illustrated in FIG. 2A. Results for Panbio Dengue IgM Capture ELISA (Alere; Waltham, Mass.) are illustrated in FIG. 2B.
Figure 2B:
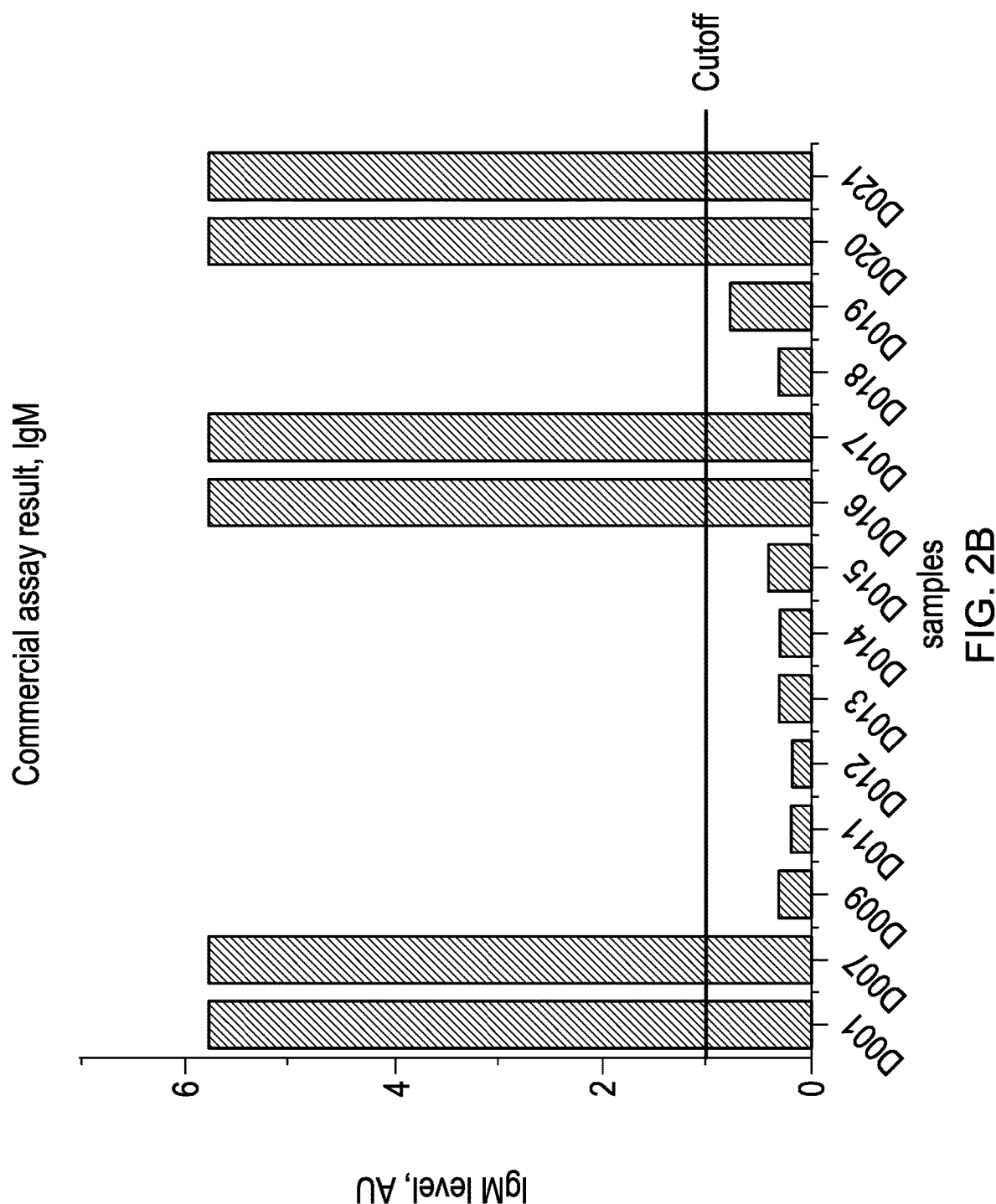

As used herein, the singular form "a", "an" and "the" include plural references unless the context clearly dictates otherwise. For example, the term "a cell" includes a plurality of cells, including mixtures thereof.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A nucleotide analog may be an analog or mimic of a primary nucleotide having modification on the primary nucleobase (A, C, G, T and U), the deoxyribose/ribose structure, the phosphate group of the primary nucleotide, or any combination thereof. For example, a nucleotide analog can have a modified base, either naturally existing or man-made. Examples of modified bases include, without limitation, methylated nucleobases, modified purine bases (e.g. hypoxanthine, xanthine, 7-methylguanine, isodG), modified pyrimidine bases (e.g. 5,6-dihydrouracil and 5-methylcytosine, isodC), universal bases (e.g. 3-nitropyrrole and 5-nitroindole), non-binding base mimics (e.g. 4-methylbezimidazole and 2,4-difluorotoluene or benzene), and no base (abasic nucleotide where the nucleotide analog does not have a base). Examples of nucleotide analogs having modified deoxyribose (e.g. dideoxynucleosides such as dideoxyguanosine, dideoxyadenosine, dideoxythymidine, and dideoxycytidine) and/or phosphate structure (together referred to as the backbone structure) includes, without limitation, glycol nucleotides, morpholinos, and locked nucleotides.

The term "microbe" as used herein refers to a microscopic organism which may be single celled, multicellular, or non-cellular. Examples of microbes include, without limitation, bacteria, fungi, parasites (including, e.g., protozoa, helminths, and ectoparasites), and viruses.

The terms "subject," "individual," and "patient" are used interchangeably herein to refer to a vertebrate, preferably a mammal, more preferably a human. Mammals include, but are not limited to, murines, simians, humans, farm animals, sport animals, and pets.

As used herein, the term "fluorescence" refers to the process wherein a molecule relaxes to its ground state from an excited state by emission of a photon. As used herein, fluorescence can also encompass phosphorescence. For fluorescence, a molecule is promoted to an electronically excited state generally by the absorption of ultraviolet, visible, or near infrared radiation. The excited molecule then decays back to the ground state, or to a lower-lying excited electronic state, by emission of light.

As used herein, the term "plasmonically active" in reference to a material refers to a material which supports plasmons (e.g., surface plasmons), thereby exhibiting plasmonic properties. Surface plasmons may be used to enhance the surface sensitivity of several spectroscopic measurements including fluorescence, Raman scattering, and second harmonic generation.

As used herein, the term "plasmonic properties" refers to properties exhibited by surface plasmons, or the collective oscillations of electrical charge on the surfaces of metals. In this sense, plasmonic properties refers to measurable properties, such as properties described in Nagao et al. "Plasmons in nanoscale and atomic-scale systems," Sci. Technol. Adv. Mater. 11 (2010) 054506 (12 pp), describing plasmonic sensors, such as those used for surface-enhanced IR absorption spectroscopy (SEIRA), surface-enhanced Raman scattering (SERS). Another plasmonic property is plasmon-enhanced fluorescence, described e.g., in Sensors and Actuators B 107 (2005) 148-153.

As used herein, the term "continuous" refers to the inter-connectivity of nanostructures in plasmonic metal film, creating an electrically conductive path, optionally with gaps existing between some of the nanostructures that are not in the conducting path.

As used herein, the term "discontinuous" refers to the presence of one or more isolated nanostructures in plasmonic metal film, where the nanostructures are separated from each other and not interconnected.

As used herein, the term "proximity" refers to a distance between a fluorescent molecule and nanostructures in plasmonic metal film, within which distance the fluorescence intensity of the fluorescent molecule increases, such as by a specified fold-increase. In some cases, proximity may be measured in angstroms (e.g. within 1-1000 angstroms), in nanometers (e.g. within 1-1000 nm), or millimeters (e.g. within 1-10 mm). In some cases, fluorescent intensity is enhanced for fluorophores within about 1000 nm of the surface of the film.

The disclosure provides methods for detecting and diagnosing one or more viral infections such as flaviviral or alphaviral infections in a subject. In certain aspects, the methods of the disclosure may provide advantages over previous diagnostic methods such as rapid turnaround time for diagnosing viral infection, high sensitivity, e.g., for detecting early stage infection, the ability to accurately distinguish one viral infection from another, e.g., Dengue virus infection and Zika virus infection, the ability to test small amounts of biological samples, e.g., microliter volumes, and facile real-time testing of biological samples without the need to transport to a commercial laboratory. In certain embodiments, methods of the disclosure are performed on substrates such as plasmonic substrates described herein.

In one aspect, the methods and systems of the disclosure involve detecting biomarkers, e.g., antibodies selected from IgG, IgM, IgA and combinations thereof, in a biological sample that bind to a binding element, e.g., a flaviviral or alphaviral antigen such as a Zika virus antigen. The amount of detected antibodies in a sample may be compared to values obtained from reference populations with or without viral infection to determine whether the subject is infected with the virus. In certain embodiments, the disclosure provides methods of determining if the subject recently contracted the viral infection. In certain embodiments, the methods of the disclosure for detecting biomarkers, e.g., antibodies selected from selected from IgG, IgM and IgA or combinations thereof, further comprise an avidity wash step such as the one described herein to distinguish between acute and chronic infection.

In general, a biomarker is a detectable analyte that is associated with a particular characteristic, such as presence of a microbe comprising the biomarker (e.g. as in a microbial polynucleotide, or microbial protein), expression of a gene or genes associated with a disease or condition (e.g. oncogenes), or an indirect indicator of the presence of another biomarker (e.g. a host antibody against a microbial protein). The biomarker may be associated with a biological state or condition of an organism, such as a subject. Examples of such biological state or condition include, without limitation, a disease, a disorder, a non-disease condition, a healthy condition, or therapeutic responses to different drug treatments and other therapies.

In certain embodiments, the methods comprise contacting a biological sample with one or multiple flaviviral or alphaviral antigens. The flaviviral or alphaviral antigens may bind to one or more immunoglobulins, for example, antibodies selected from IgA, IgG, and IgM or a combination thereof. The one or more immunoglobulins, if present in the biological sample, may be detected by detecting one or more immunoglobulins bound to each of the flaviviral or alphaviral antigens. In some cases, the detecting comprises detecting a level of one or more immunoglobulins bound to the flaviviral or alphaviral antigen in the biological sample. Based upon the presence, absence or a level of the one or more immunoglobulins bound to each of the flaviviral or alphaviral antigens in the biological sample, the subject may be diagnosed with having one or more viral infections.

In certain aspects, the present disclosure provides a method for detecting antibodies selected from IgA and IgG or a combination thereof in a biological sample of a subject, the method comprising: (a) obtaining a biological sample from the subject; (b) contacting the biological sample with one or multiple flaviviral or alphaviral antigens wherein the flaviviral or alphaviral antigen binds to antibodies selected from IgA and IgG or a combination thereof; (c) detecting antibodies selected from IgA and IgG or a combination thereof in the biological sample by detecting antibodies selected from IgA and IgG bound to each of the flaviviral or alphaviral antigens. In some embodiments, the detecting antibodies selected from IgA and IgG or a combination thereof comprises detecting a level of antibodies selected from IgA and IgG bound to the flaviviral or alphaviral antigens in the biological sample. In some embodiments, the flaviviral or alphaviral antigens are selected from a Zika virus antigen, Dengue virus antigen, yellow fever virus antigen, tick-borne encephalitis virus antigen, West Nile virus antigen, mayaro virus antigen, and Chikungunya virus antigen. In some embodiments, the flaviviral antigens are selected from a Zika virus antigen, Dengue virus antigen. In some embodiments, the flaviviral antigen is a Zika virus antigen.

Any of a variety of substances may be the source of a sample, e.g., a Zika serum sample. The sample may be a fluid, e.g., a biological fluid. A fluidic sample may include, but is not limited to, blood or blood component (e.g., whole blood, plasma), cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof. In cases where threshold values are based on one type of sample (e.g. serum), threshold values for other sample types may be adjusted to account for differences in sample type (e.g. saliva sample threshold values adjusted based on values for serum samples).

The sample volume may vary. In some cases, the sample has a volume that is greater than or equal to about 0.01 microliters (L), 0.05 µL, 0.1 µL, 0.2 µL, 0.3 µL, 0.4 µL, 0.5 µL, 0.6 µL, 0.7 µL, 0.8 µL, 0.9 µL, 1 µL, 2 µL, 3 µL, 4 µL, 5 µL, 6 µL, 7 µL, 8 µL, 9 µL, 10 µL, 15 µL, 20 µL, 30 µL, 40 µL, 50 µL, 60 µL, 70 µL, 80 µL, 90 µL, 100 µL, 200 µL, 300 µL, 400 µL, 500 µL, or higher. In some cases, the sample has a volume that is smaller than or equal to about 1,000 µL, 800 µL, 600 µL, 400 µL, 200 µL, 100 µL, 80 µL, 60 µL, 40 µL, 20 µL, 10 µL, 8 µL, 6 µL, 4 µL, 2 µL, 1 µL, 0.9 µL, 0.7 µL, 0.5 µL, 0.3 µL, 0.1 µL or less. In some cases, the sample has a volume selected from a range of any of the two values described above, for example, from about 0.5 to about 500 µL, from about 0.5 to about 20 µL, from about 0.5 to about 10 µL, or from about 0.5 to about 10 µL. In some cases, the sample is a drop of blood from a prick sample. The sample may or may not be processed prior to the test. In some cases, the sample may be diluted prior to contacting with the viral antigens. Depending on platforms or assays that are employed to perform the methods of the present disclosure, the sample may be diluted by about 1 to $10^{10}$ fold.

In some embodiments, the fluid sample is between 1-100 µL, or 1-10 µL. Fluid sample may be diluted in a diluent solution (e.g. fetal bovine serum, non-cross-reacting animal serum, or a BSA solution in PBST), such as up to a total volume of 500 µL, 250 µL, 100 µL, or less. A sample may be solid, for example, a biological tissue. The sample may comprise normal healthy tissues. The tissues may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof. In certain embodiments, methods of the disclosure are used to analyze an environmental sample (e.g. samples from agricultural fields, lakes, rivers, water reservoirs, air vents, walls, roofs, soil samples, plants, or swimming pools), or an industrial sample (e.g. samples from clean rooms, hospitals, food processing areas, food production areas, food stuffs, medical laboratories, pharmacies, or pharmaceutical compounding centers).

A sample may comprise tumors. Tumors may be benign (non-cancer) or malignant (cancer). Non-limiting examples of tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The tumors may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

In some cases, a sample comprises a variety of cells, including, but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, and circulating cells in the human blood, one or more of which may be the subject of a detection method utilizing a film of the present disclosure. In some cases, the sample comprises contents of a cell, such as, for example, the contents of a single cell or the contents of multiple cells.

In certain embodiments, the methods described herein are used to screen for viral infection and thereby prevent the transmission of disease, e.g., when the biological sample is intended for transplant or transfusion to a subject. The biological sample may be collected from a subject within a certain time period after initial exposure of the subject to a virus or following the onset of symptoms of a viral infection. For example, the biological sample may be collected from the subject within 200 days, within 150 days, within 100 days, within 90 days, within 80 days, within 70 days, within 60 days, within 50 days, within 40 days, within 30 days, within 20 days, within 18 days, within 16 days, within 14 days, within 12 days, within 10 days, within 9 days, within 8 days, within 7 days, within 6 days, within 5 days, within 4 days, within 3 days, within 2 days, or within 1 day of initial exposure of the subject to a virus or following the onset of symptoms of a viral infection. The initial exposure may occur when the subject comes into contact, e.g., sexual contact, with an infected individual, contaminated blood or other bodily fluids of an infected individual, travels to an area with reported cases of viral infections, consumes contaminated food or water which may contain disease-causing virus, gets bitten by an virus-carrying insects such as mosquitoes, or any combinations thereof. For example, in some cases, the biological sample is obtained from a subject who traveled to an area with reported Zika infection within 90 days of the subject's arrival in the area.

As provided herein, symptom onset may refer to the time when one or more symptoms and signs associated with viral infections are first apparent. For example, the biological sample may be collected from the subject and tested for Zika infection within the first 50, within the first 10 days, or within the first 7 days that one or more symptoms, including fever, rash, joint pain, conjunctivitis (red eyes), muscle pain, headache, pain behind the eyes, and vomiting, become apparent. In an exemplary embodiment, the subject exhibits one or more symptoms of viral infection and lives in an area or has recently traveled to an area with reported cases of Zika virus infection.

A biological sample may be obtained from a subject using various approaches. For example, a sample may be obtained from a subject through accessing the circulatory system (e.g., intravenously or intra-arterially via a syringe, fingerstick, fingerprick, or other apparatus), collecting a secreted biological sample (e.g., saliva, sputum, urine, feces, etc.), surgically (e.g., biopsy) acquiring a biological sample (e.g., intra-operative samples, post-surgical samples, etc.), swabbing (e.g., buccal swab, oropharyngeal swab), or pipetting. Such approaches may be used to obtain a biological sample of substantially low volume (e.g., less than or equal to about 5 microliters) from the subject. In some cases, the subject may collect and provide the sample (e.g. a saliva sample) for testing.

The biological sample may be transported to a facility for analysis. The facility may be onsite or a local facility, e.g., a facility within a clinic or hospital where the sample is collected. The facility may also be an offsite or a remote facility which may necessitate shipment of samples. In some cases, the sample may be dried prior to transport, e.g., a dried blood sample. In certain embodiments, the biological sample is tested without transporting to a laboratory facility, e.g., in a remote area without access to a laboratory.

The subject may be, e.g., a mouse, a rat, a hamster, a gerbil, a dog, a cat, a primates such as, e.g., a monkey or human. In some embodiments, the subject is a human. The subject may be an adult, a child, or an infant. The subject can be male or female. The subject may be a female, such as a female who is pregnant, planning to become pregnant or of child-bearing age. The subject can be of any age. The subject may be previously diagnosed with, may be exhibiting a symptom of, or may be suspected of having one or more viral infections.

In certain embodiments, methods of the disclosure comprise contacting a viral antigen, e.g., a Zika virus antigen, with a biological sample for at least about 10 min, at least about 15 min, at least about 20 min, at least about 25 min, at least about 30 min, at least about 35 min, at least about 40 min, at least about 45 min, at least about 50 min, at least about 55 min, or at least about 60 min. In some cases, a viral antigen, e.g., a viral antigen associated with a substrate, may be incubated for a duration between any of the two values described herein, for example, between about 30 min to 40 min, between about 40 min to about 60 min, or between about 30 min to about 60 min.

In certain embodiments, a biological sample of the disclosure, e.g., serum, may be diluted at least about 20×, at least about 30×, at least about 40×, at least about 50×, at least about 60×, at least about 70×, at least about 80×, at least about 90×, at least about 100×, at least about 150×, at least about 200×, at least about 250×, at least about 300×, at least about 350×, at least about 400×, at least about 450×, or at least about 500× prior to analysis in a method described herein. In certain embodiments, the biological sample, e.g., serum, is not modified or is insignificantly modified, e.g., by addition of an anticoagulant or preservative, prior to analysis in a method described herein.

In certain aspects, the present disclosure provides a method of diagnosing Zika virus infection in a subject, the method comprising: (a) obtaining a biological sample from a subject; (b) contacting the biological sample with a Zika virus antigen wherein the Zika virus antigen binds to antibodies selected from IgA and IgG or a combination thereof; (c) detecting antibodies selected from IgA and IgG or a combination thereof in the biological sample by detecting antibodies selected from IgA and IgG or a combination thereof bound to the Zika virus antigen; and (d) diagnosing the subject with Zika virus infection when the presence of antibodies selected from IgA and IgG or a combination thereof in the biological sample is detected.

In certain aspects, the present disclosure provides a method of diagnosing and treating Zika virus infection in a subject in need thereof, the method comprising: (a) obtaining a biological sample from a subject; (b) contacting the biological sample with a Zika virus antigen wherein the Zika virus antigen binds to antibodies selected from IgA and IgG or a combination thereof; (c) detecting antibodies selected from IgA and IgG or a combination thereof in the biological sample by detecting antibodies selected from IgA and IgG bound to the Zika virus antigen; (d) diagnosing the subject with Zika virus infection when the presence of antibodies selected from IgA and IgG or a combination thereof in the biological sample is detected; and (e) optionally administering an effective amount of an antiviral agent to the diagnosed subject.

Antiviral agents are a class of medication used specifically for treating viral infections. Like antibiotics, specific antivirals are used for specific viruses. They are relatively harmless to the host, and therefore can be used to treat infections. Antiviral agents may inhibit various stages of the viral life cycle. For example, an antiviral agent may comprise agents that inhibit attachment of the virus to a cellular receptor. Such antiviral agents may mimic the virus associated protein (VAP and bind to the cellular receptors. Other antiviral agents may inhibit viral entry, viral uncoating (e.g., amantadine, rimantadine, pleconaril), viral synthesis, viral integration, viral transcription, or viral translation (e.g., fomivirsen). In some instances, the antiviral therapy is a morpholino antisense. Antiviral agents may be distinguished from viricides, which actively deactivate virus particles outside the body.

In some instances, the antiviral agents may comprise a reverse transcriptase inhibitor. Reverse transcriptase inhibitors may be nucleoside reverse transcriptase inhibitors or non-nucleoside reverse transcriptase inhibitors. Nucleoside reverse transcriptase inhibitors may include, but are not limited to, combivir, emtriva, epivir, epzicom, hivid, retrovir, trizivir, truvada, videx ec, videx, viread, zerit, and ziagen. Non-nucleoside reverse transcriptase inhibitors may comprise edurant, intelence, rescriptor, sustiva, and viramune (immediate release or extended release).

Protease inhibitors are another example of antiviral agents and may include, but are not limited to, agenerase, aptivus, crixivan, fortovase, invirase, kaletra, lexiva, norvir, prezista, reyataz, and viracept. Alternatively, the antiviral therapy may comprise a fusion inhibitor (e.g., enfuviride) or an entry inhibitor (e.g., maraviroc).

Additional examples of antiviral agents include abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors, ganciclovir, ibacitabine, imunovir, idoxuridine, imiquimod, indinavir, inosine, integrase inhibitor, interferons (e.g., interferon type I, II, III), lamivudine, lopinavir, loviride, maraviroc, moroxydine, methisazone, nelfinavir, nevirapine, nexavir, nucleoside analogues, oseltamivir, peginterferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In certain aspects, the present disclosure provides a method of diagnosing Zika virus infection in a female subject and preventing diseases due to fetal transmission of the infection, the method comprising: (a) obtaining a biological sample from a female subject; (b) contacting the biological sample with a Zika virus antigen wherein the Zika virus antigen binds to antibodies selected from IgA and IgG or a combination thereof; (c) antibodies selected from IgA and IgG or a combination thereof in the biological sample by detecting antibodies selected from IgA and IgG or a combination thereof bound to the Zika virus antigen; (d) diagnosing the subject with Zika virus infection when the presence of antibodies selected from IgA and IgG or a combination thereof in the biological sample is detected; and (e) optionally administering a contraceptive to the diagnosed subject, counseling the female subject to refrain from becoming pregnant while infected with Zika virus, or counseling a pregnant female subject about risks of said Zika virus infection to the fetus.

In certain embodiments, the methods described herein are used to screen subjects for viral infection and thereby prevent the transmission of disease, such as when the subject is pregnant, planning to become pregnant, or of childbearing age. A pregnant subject, such as a pregnant subject living in an area with reported cases of Zika virus infection, may be monitored through the course of the pregnancy. For example, a pregnant subject may be tested one or more times during the course of a pregnancy in order to determine if the subject is infected with Zika virus infection. If a pregnant subject is diagnosed with Zika virus infection, the subject may: receive counseling about risks of said Zika virus infection to the fetus, seek counseling for pregnancy continuation or termination, receive an antiviral agent or other therapy for Zika virus infection, or any combination thereof.

The flaviviral or alphaviral antigens may comprise an antigen with multiple antigenicities wherein the antigen may be strain-specific. The flaviviral or alphaviral antigens may be selected from a Zika virus antigen, Dengue virus antigen, yellow fever virus antigen, tick-borne encephalitis virus antigen, West Nile virus antigen, mayaro virus antigen, Japanese Encephalitis virus (JEV) antigen, and Chikungunya virus antigen. In one example, the antigen comprises a Zika virus antigen, such as an NS1 or NS5 antigen. The NS1 antigen may be a recombinant protein, such as a recombinant NS1 antigen produced in human 293 cells. The recombinant NS1 antigen may comprise an NS1 antigen from the Uganda MR766 strain of Zika virus. In certain embodiments, the flaviviral or alphaviral antigen is a Dengue virus antigen, such as a Dengue Type 2 antigen. As an example, Dengue virus strain 16681 is cultured in Vero cells, and viral particles are concentrated from tissue culture supernatants by precipitation and ultracentrifugation. The antigen may be purified by sucrose density gradient centrifugation. Viral particles are separated from the sucrose containing buffer by ultracentrifugation, and the antigen is resuspended in Medium 199.

A subject may be diagnosed with Zika virus infection if the presence of antibodies selected from IgG and IgA or a combination thereof in a biological sample collected from the subject is detected while the sample is brought into contact with a Zika virus antigen which binds antibodies selected from IgG and IgA or a combination thereof. In certain embodiments, the detecting antibodies selected from IgG and IgA or a combination thereof comprises detecting a level of antibodies selected from IgG and IgA or a combination thereof bound to the Zika virus antigen in the biological sample.

In certain embodiments, the methods further comprise using one or more additional antibodies, with selective affinity for a type of immunoglobulin, e.g., selective affinity for IgG or IgA. The biological sample may be contacted with the one or more additional antibodies wherein the one or more additional antibodies may further include detectable labels. The detecting antibodies selected from IgG and IgA or a combination thereof may comprise detecting a first detectable label, wherein the first detectable label is associated with a first antibody that binds to the IgA bound to the Zika antigen. The first antibody may be an antihuman IgA antibody. In certain embodiments, the first detectable label emits a signal of a primary wavelength. The detecting antibodies selected from IgG and IgA or a combination thereof may comprise detecting a second detectable label, wherein the second detectable label is associated with a second antibody that binds to the IgG bound to the Zika antigen. The second antibody may be an antihuman IgG antibody. In certain embodiments, the second detectable label emits a signal of a secondary wavelength. In certain embodiments, the primary wavelength is different from the secondary wavelength.

In certain embodiments, the first antibody and second antibody each are associated with, e.g., are covalently or non-covalently bound together with, a different delectable label which enables a simultaneous detection of the first and second antibodies in a single assay. Additionally or alternatively, one or more antibodies may be detected separately from others (e.g., in multiple assays), permitting the use of first and second antibodies having the same or similar detectable label, e.g., labels that emit the same or similar wavelength of light, for detection. In some embodiments, a certain percentage of the first or second antibodies comprise the same or a different delectable label such that the presence, absence or a level of the one or more immunoglobulins is detected in more than one assay. For example, in some cases, at least about 5%, 10%, 20%, 30%, 40%, 50%, 60%, 70%, 80%, 90% or 95% of the first or second antibodies comprise the same or a different delectable label. The first detectable label may be associated with a first antibody that binds to the IgA (e.g., an antihuman IgA antibody) bound to the Zika antigen, and the second detectable label may be associated with a second antibody that binds to the IgG (e.g., an antihuman IgG antibody) bound to the Zika antigen. The first and second detectable labels emit a signal of a primary wavelength and a signal of a secondary wavelength, respectively. As described above and elsewhere herein, the primary and the secondary wavelengths may be the same or different. Different detectable labels with non-overlapping emission wavelengths can be used in the same assay to label different classes of proteins or antibodies to achieve multi-color differentiation of antibody isotypes such as IgG, IgM, or IgA in the same assay. As used herein, the detectable labels with overlapping emission wavelengths may be considered different if the peak wavelength of each signal is spaced far enough apart that the beams are distinguishable from each another, e.g., by human observation or by machine.

A wide variety of fluorescent molecules can be used as detectable labels in the present disclosure, for example, fluorophores, small molecules, dyes, fluorescent proteins and quantum dots. Non-limiting examples of fluorescent molecules may include: fluorescent in situ hybridization (FISH) probes, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs-AutoFluorescent Protein-(Quantum Biotechnologies); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexion; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FI; Bodipy FL ATP; Bodipy FI-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-SN; Calcein; Calcein Blue; Calcium Crimson™; Calcium Green; Calcium Green-1 $Ca^{2+}$ Dye; Calcium Green-2 $Ca^{2+}$; Calcium Green-SN $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; CyST™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); Dil (DiIC18(3)); Dinitrophenol; DiO (DiOC18(3)); DiR; DiR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyde Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura RedT/Fluo-3;

Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; *Lucifer* Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PL); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; IR680; IR880; IR-26; IR-1051; IR-1061; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes); Alexa Fluor dye series (such as Alexa Fluor 350, Alexa Fluor 405, 430, 488, 500, 514, 532, 546, 555, 568, 594, 610, 633, 635, 647, 660, 680, 700, and 750); Cy Dye fluorophore series (such as Cy3, Cy3B, Cy3.5, Cy5, Cy5.5, Cy7); Oyster dye fluorophores (such as Oyster-500, -550, -556, 645, 650, 656); DY-Labels series (such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL); ATTO fluorescent labels (such as ATTO 390, 425, 465, 488, 495, 520, 532, 550, 565, 590, 594, 610, 611X, 620, 633, 635, 637, 647, 647N, 655, 680, 700, 725, 740); CAL Fluor and Quasar dyes (such as CAL Fluor Gold 540, CAL Fluor Orange 560, Quasar 570, CAL Fluor Red 590, CAL Fluor Red 610, CAL Fluor Red 635, Quasar 670); EviTags or quantum dots of the Qdot series (such as the Qdot 525, Qdot565, Qdot585, Qdot605, Qdot655, Qdot705, Qdot 800); fluorescein, rhodamine, phycoerythrin, or combinations thereof.

In some examples, the fluorescent molecule is a near-infrared fluorophore, such as IR680 or IR880. In general, the term "near-infrared" (NIR) is used to refer to the near infrared region of the electromagnetic spectrum (e.g. from 0.6 to 2.1 μm). Other examples of NIR fluorophores include Cy5, Cy5.5, and Cy7, each of which are available from GE Healthcare; VivoTag-680, VivoTag-S680, VivoTag-S750, each of which are available from VisEn Medical; AlexaFluor660, AlexaFluor680, AlexaFluor700, AlexaFluor750, and Alexa Fluor790, each of which are available from Invitrogen; Dy677, Dy676, Dy682, Dy752, Dy780, each of which are available from Dyomics; DyLight 677, available from Thermo Scientific; HiLyte Fluor 647, HiLyte Fluor 680, and HiLyte Fluor 750, each of which are available from AnaSpec; IRDye 800, IRDye800CW, IRDye 800RS, IRDye680CW and IRDye 700DX, each of which are available from Li-Cor; and ADS780WS, ADS830WS, and ADS832WS, each of which are available from American Dye Source. Also, quantum dots of CdSe, PbS, CuInS2, rare earth nanoparticles, carbon nanotubes belong to NIR fluorescence agents emitting in the 700-2100 nm range. NIR labels can be enhanced by NIR fluorescence enhancement (NIR-FE), whereby nanostructures of the disclosure favorably modify the spectral properties of fluorophores and alleviate some of their more classical photophysical constraints.

In some examples, the fluorescent molecule is a visible dye such as Alexa 488, Cy3 or Cy5. In general, the terms "visible dye" and "visible label" are used to refer to a label with fluorescence emission wavelength in the visible region of the electromagnetic spectrum (e.g. 300 nm to 650 nm). Other examples of visible dyes include Cy3 available from GE Healthcare; FITC available from Pierce; VivoTag-645, available from VisEn Medical; AlexaFluor350, AlexaFluor405, AlexaFluor430, AlexaFluor488, AlexaFluor514, AlexaFluor532, AlexaFluor546, AlexaFluor555, AlexaFluor594, AlexaFluor610, AlexaFluor633 and Alexa Fluor647, each of which are available from Invitrogen; Dy405, Dy415, Dy430, Dy490, Dy495, Dy505, Dy530, Dy547, Dy560, Dy590, Dy605, Dy610, Dy615, Dy630, and Dy647 each of which are available from Dyomics; DyLight547 and DyLight647, each of which are available from Thermo Scientific; HiLyte Fluor 405, HiLyte Fluor 488, HiLyte Fluor 532, HiLyte Fluor 555, and HiLyte Fluor 594, each of which are available from AnaSpec.

The detecting of one or more immunoglobulins bound to each of the flaviviral or alphaviral antigens in the biological sample can be performed by using various platforms or assays. Non-limiting examples of the platforms or assays include, but are not limited to, microarray platforms based on plasmonic and non-plasmonic substrates including metals, glass, quartz, and nitrocellulose, ELISA, digital ELISA, lateral flow assays, lateral flow immunochromatographic assays, Luminex, chemiluminescence assays, Meso Scale Discovery (MSD) electrochemiluminescence assay, bead-based fluorescence assays, Becton Dickinson Cytometric Bead Array (CBA) flow cytometric assay, and any other antibody-capture assays, chemiluminescence assays, and electro-chemical luminescence assays or a combination thereof. In certain embodiments, the methods of the disclosure for detecting one or more immunoglobulins bound to flaviviral or alphaviral antigens in a biological sample are performed with plasmonic substrates to enhance the fluorescence signals. Exemplary plasmonic substrates may be found in US patent publication nos. 20160146799 and 20130172207, the entire contents of each of which are incorporated by reference herein.

In some situations, the methods of the present disclosure may further comprise comparing the level of one or more immunoglobulins bound to each of the flaviviral or alphaviral antigens in the biological sample to a cutoff value, and making the diagnosis based upon the results. The cutoff value may comprise a control cutoff value of a reference healthy population, a cutoff value of a reference patient population infected with a viral infection other than the viral infections to be diagnosed, a cutoff value of a reference healthy patient population previously infected with the same viral infection to be diagnosed, or any combination thereof. In cases where a level of at least two immunoglobulins bound to each of flaviviral or alphaviral antigens in the biological sample is detected and compared to a cutoff value, the subject may be diagnosed with a viral infection if at least one immunoglobulin has a higher level than the cutoff value. In one example, the diagnosis of Zika infection in the subject comprises comparing the level of IgG bound to the Zika virus antigen to a Dengue-based cutoff value of a reference Dengue infected patient population, and when the level of IgG bound to said Zika virus antigen is greater than the Dengue-based cutoff value, the subject is diagnosed with Zika virus infection. The Dengue-based cutoff value may be at least about 1 standard deviation (SD) (e.g., at least about 2, at least about 3, at least about 4, at least about 5, at least about 6, at least about 7, at least about 8, at least about 9, or at least about 10 SD or range of the preceding values such as from about 2-5 SD) above a mean value of the levels of IgG bound to the Zika virus antigen measured in the biological samples of the reference Dengue infected patient population. Additionally or alternatively, the diagnosing may comprise comparing the level of IgA bound to the Zika virus antigen to a healthy control cutoff value of a reference healthy patient population, and when the level of IgA bound to the Zika virus antigen is greater than the healthy control cutoff value, the subject is diagnosed with acute Zika virus infection. The healthy control cutoff value may be at least about 1 SD (e.g., at least about 2, at least about 3, at least about 4, at least about 5, at least about 6, at least about 7, at least about 8, at least about 9, or at least about 10 SD or any value therebetween such as from about 2-5 SD) above a mean value of the levels of IgA bound to said Zika virus antigen measured from biological samples of the reference healthy population.

A control sample may comprise a positive control sample, a negative control sample, and a calibrator sample. A positive control sample can be a patient serum sample that is confirmed positive for ZIKV IgG antibodies and DENV type 2 IgG antibodies. The positive control sample may elicit fluorescence signal from both ZIKV and DENV antigens. A positive control can be used to confirm the antigen specificity and may be used along with a patient serum sample during the assay procedure. A negative control sample may be a sample that is confirmed negative for ZIKV IgG antibodies and DENV type 2 IgG antibodies. The negative control sample can elicit negligible or no signal from ZIKV and DENV antigens. A negative control may be used to identify and subtract the non-specific binding to ZIKV and DENV antigens and can be used along with a patient serum sample during an assay procedure. A calibrator sample may be a patient serum sample positive for both ZIKV and DENV IgG antibodies with specific concentration of ZIKV IgG and DENV IgG as evidenced by their fluorescence signals. The calibrator can be used to quantify the ZIKV and DENV IgG levels on the patient serum samples and may be used along with serum samples during the assay procedure.

A "reference population," as used herein, refers to a representative sample of individuals used to establish norms for reference ranges or cutoff values. A reference healthy population, for example, is established from a disease-free population, or a group of individuals who do not have the disorders or diseases tested or to be diagnosed. In some cases, the reference healthy population is established from the disease-free population after exclusion of subjects who are at higher risk for the disorders or diseases being tested such as viral infection. Such subjects may include pregnant women, unborn babies or individuals living or traveling in countries where there have been outbreaks of the viral infections. As an example, the reference healthy patient population for diagnosing a flaviviral infection may be a healthy population having no prior or current flaviviral infections such as no prior or current Zika virus infection or Dengue virus infection.

The reference Dengue infected population refers to a reference population or a group of individuals diagnosed with Dengue virus infection. The reference patient population may be diagnosed based upon clinical manifestations, laboratory tests, commercial diagnostic and screening tests, medical records, a subject survey or a combination thereof. The reference Dengue infected population used for diagnosing Zika infection may be a group of individuals that are diagnosed with Dengue virus infection but test negative for Zika virus infection via commercial assays (e.g., Trioplex Real-time RT-PCR Assay, Serologic Test for Zika Virus, The Zika IgM Antibody Capture Enzyme-Linked Immunosorbent Assay (Zika MAC-ELISA), or Plaque Reduction Neutralization Test (PRNT)), show no symptoms of Zika infection or have not preciously exhibited symptoms of Zika infection based upon medical records or a health survey. In some cases, the reference Dengue infected population is further established from the Zika-free population after exclusion of subjects who live or travel in areas with active mosquito-borne transmission of Zika virus or high risks of Zika infection. In some cases, the reference Dengue infected patient population does not have any prior or current Zika virus infection. In certain cases, the reference Dengue infected patient population is characterized by patients with chronic Dengue virus infection.

In some situations, it may be desirable to perform the methods of the present disclosure on two or more biological samples collected from the subject at different times following initial exposure of the subject to the viruses or following onset of symptoms of the viral infections of the subject. For example, the methods may be performed on 2, 3, 4, 5, 6, 7, 8, 9, 10, 11, 12, 13, 14, 15, 16, 17, 19, 20, 25, 30, 35, 40, 45, 50, 55, 60, 65, 70, 75, 80, 85, 90, 95, 100 or more samples collected from the same subject at different times (e.g., at least about 2, 3, 4, 5, 6, 7, 8, 9, 10, 12, 14, 16, 18, 20, 25, 30, 35, 40, 45, 50 times) over a certain time period (e.g., 1, 2, 3, 4, 5, 6, 7, 8, 9, 10, 15, 20, 25, 30, 35, 40, 45, 50, 55, 60, 65, 70, 75, 80, 85, 90, 95, 100, 110, 120 days, 3, 4, 5, 6, 7, 8, 9, 10, 11, 12 months or longer) following initial exposure of the subject to the viruses or following onset of symptoms of the viral infections of the subject. In certain embodiments, when two or more samples are tested, the results from the tests may provide information on disease progression. For example, a sample collected from a subject shortly after exposure to Zika virus infection, e.g., within 10 days of exposure, may show high levels of IgA relative to a sample collected from the same subject 20 days or more after first exposure to Zika virus infection.

In certain embodiments, the methods of the disclosure are performed according to the flow chart in Table 5. In certain embodiments, the method for detecting viral biomarkers, e.g., antibodies, in a biological sample is performed two times, wherein the first time the test is performed, the subject is within 18 days, within 14 days, within 12 days, or even within 10 days of symptom onset or within 18 days, within 14 days, within 12 days, or even within 10 days following initial exposure of the subject to the virus(es). In such embodiments, the second test may be performed 10 days or more days, 12 days or more days, 14 days or more days, 16 days or more days, or 18 days or more days after initial exposure of the subject to the first virus or second virus or 10 days or more days, 12 days or more days, 14 days or more days, 16 days or more days, or 18 days or more days after initial onset of viral infection symptoms. In certain embodiments, said first time the test is performed includes testing for human IgG antibodies, e.g., human IgG antibodies against a Zika virus antigen, human IgG antibodies against Dengue virus antigen, human IgG avidity against Zika virus antigen and human IgG avidity against Dengue virus antigen. In certain embodiments, said second time the test is performed includes testing for human IgG antibodies against a Zika virus antigen, While the flow chart in Table 5 is drawn to detecting and diagnosing Zika virus antigen, the disclosure also includes methods for detecting other viral infections, e.g., flaviviral and alphaviral infections, following an analogous method as for Zika virus described in Table 5.

In certain embodiments, the methods of the disclosure may be used to distinguish between two or more flaviviral or alphaviral infections in a sample from a subject. Non-limiting examples of the viruses include Zika virus (ZIKV), yellow fever virus (YFV), Dengue virus (DENV) serotypes DENV-1, -2, -3, and -4, Japanese encephalitis virus (JEV), West Nile virus (WNV), mayaro virus, Chikungunya virus, Ross River virus, Sindbis virus and Barmah Forest virus. With the methods provided herein, the diagnosing can accurately distinguish between a selected type of viral infection (e.g., Zika virus infection) and other viral infections (e.g., flaviviral or alphaviral infections other than Zika infection) in a high percentage of subjects tested. For example, the diagnosing can accurately distinguish between Zika virus infection and Dengue virus infection in at least about 50%, at least about 60%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or more of subjects tested.

The methods for testing for detecting a first and second viral infection may comprise obtaining a biological sample from a subject who may be previously diagnosed with, at a higher risk for, exhibiting one or more symptoms of, or suspected of having the first or second viral infection. The biological sample may be collected from the subject in any of the methods as described herein. The collected biological sample may then be brought into contact with the first viral antigen and the second viral antigen, which may be independently selected from viral antigens such as flaviviral antigens and alphaviral antigens. The first viral antigen and the second viral antigen may be specifically and with high-affinity bound by one or more immunoglobulins, e.g., IgG, IgA, IgM, IgD and IgE. The one or more immunoglobulins, e.g., IgG, IgA, IgM, IgD and IgE, if present in the biological sample, can be detected by detecting the one or more immunoglobulins bound to the first and second viral antigens. The detection of the one or more immunoglobulins bound to the first and second viral antigens may comprise detecting a presence, an absence, a level or an quantity of the one or more immunoglobulins bound to the first viral antigen in the biological sample and/or the one or more immunoglobulins bound to the second viral antigen in the biological sample. In certain embodiments, the first and second viral antigens are independently selected from Zika virus antigen, Dengue virus antigen, yellow fever virus antigen, tick-borne encephalitis virus antigen, West Nile virus antigen, mayaro virusantigen, and Chikungunya virus antigen.

Based upon detected presence, absence, level or quantity of the one or more immunoglobulins bound to the first and second viral antigens, the methods may further comprise diagnosing the subject with a first viral infection upon detecting one or more immunoglobulins bound to the first viral antigen and diagnosing the subject with a second viral infection upon detecting one or more immunoglobulins bound to the second viral antigen. In some cases, the first viral infection and second viral infection are independently selected from flaviviral infections and alphaviral infections such as Zika virus infections, Dengue virus infections, yellow fever virus infections, tick-borne encephalitis virus infections, West Nile virus infections, mayaro virus infections, and Chikungunya virus infections.

In certain aspects, the disclosure provides a method of diagnosing a first and second viral infection in a subject, the method comprising: (a) obtaining a biological sample from a subject; (b) contacting the biological sample with a first viral antigen and a second viral antigen independently selected from flaviviral antigens and alphaviral antigens; (c) detecting antibodies selected from IgA and IgG or a combination thereof in the biological sample by detecting antibodies selected from IgA and IgG or a combination thereof bound to the first viral antigen and antibodies selected from IgA and IgG or a combination thereof bound to the second viral antigen; and (d) diagnosing the subject with the first viral infection upon detecting antibodies selected from IgA and IgG or a combination thereof bound to the first viral antigen and diagnosing the subject with the second viral infection upon detecting antibodies selected from IgA and IgG or a combination thereof bound to the second viral antigen.

The diagnosing may accurately distinguish between the first and second viral infections in a high percentage (e.g., at least about 50%, 60%, 70%, 75%, 800%, 81%, 82%, 83%, 84%, 85%, 86%, 87%, 88%, 89%, 90%, 91%, 92%, 93%, 94%, 95%, 96%, 97%, 98%, 99% or more) of the subjects that are tested. As an example, multiple biological samples may be collected from a group of individuals that are suspected of having Zika infections and the biological samples are tested against a Zika virus antigen and another flaviviral or alphaviral antigen. With the methods of the present disclosure, the diagnosing may accurately distinguish between Zika virus infection and other flaviviral or alphaviral infections in 90% or more of the tested subjects. In some cases, the first and second viral antigens are Zika virus antigen and Dengue virus antigen respectively and the diagnosing accurately distinguishes between Zika virus infection and Dengue virus infection infections in 90% or more of subjects tested.

The systems and methods for diagnosing viral infections described herein may specifically and sensitively detect a viral infection. Sensitivity of an assay measures the proportion of positives that are correctly identified as such, i.e. the percentage of sick people who are correctly identified as having the condition as determined by another test, e.g., for Zika virus a Zika MAC-ELISA, PNRT, RT-PCR or a combination thereof. The system or method described herein may have few false negatives and therefore high sensitivity, e.g., high sensitivity for detecting Zika virus infection in a sample relative to the number of true positives. The systems and methods of the disclosure may have a sensitivity of at least about 50%, at least about 60%, at least about 70%, at least about 75%, at least about 80%0, at least about 82%, at least about 84%, at least about 86%, at least about 88%, at least about 90%, at least about 92%, at least about 94%, at least about 96%, at least about 98%, or even 99% or more relative to the number of true positives as determined by one or more other tests, e.g., for Zika virus the test may be a Zika MAC-ELISA, PNRT, RT-PCR or a combination thereof.

Specificity measures the proportion of negatives that are correctly identified as such, i.e., the percentage of healthy people who are correctly identified as not having the condition. The system or method described herein may have few false positives and therefore a high specificity, e.g., a high specificity for detecting Zika virus infection in a population relative to the number of well individuals. The systems and methods of the disclosure may have a specificity of at least about 50%, at least about 60%, at least about 700, at least about 75%, at least about 80%, at least about 82%, at least about 84%, at least about 86%, at least about 88%, at least about 90%, at least about 92%, at least about 94%, at least about 96%, at least about 98%, or even 99% or more relative to a to the number of healthy samples in the population as determined by one or more other tests, e.g., for Zika virus the test may be a Zika MAC-ELISA, PNRT, RT-PCR or a combination thereof.

In some situations, the methods may further comprise diagnosing a third, fourth, fifth, sixth or more viral infection by contacting the biological sample collected from the subject with a third, fourth, fifth, sixth or more viral antigens (e.g., flaviviral or alphaviral antigens) and detecting the one or more immunoglobulins bound to the third, fourth, fifth, sixth or more viral antigens. Based upon the presence, absence, or a level of the one or more immunoglobulins bound to the third, fourth, fifth, sixth or more viral antigens detected in the biological sample, the subject may be diagnosed with the third, fourth, fifth, sixth or more viral infection.

The detection of one or more immunoglobulins bound to each of the antigens may comprise detecting a first, second, third, fourth, fifth, sixth, or more wavelength of light. For example, the methods may comprise detecting antibodies selected from IgA and IgG or a combination thereof bound to the first and/or second viral antigens wherein detecting IgG bound to the first and/or second viral antigens comprises detecting a first wavelength of light and detecting IgA bound to the first or second viral antigens comprises detecting a second wavelength of light. The detected wavelengths of light may be the same or differing from one another. Signals with overlapping emission wavelengths are different so long as the peak wavelength of each signal is spaced far enough apart that the wavelengths are distinguishable from one another, visually or with the use of instrumentation.

The detecting may further comprise using one or more additional antibodies, each of which binds to a selected type of immunoglobulins bound to each of flaviviral or alphaviral antigens in the biological sample. The additional antibodies may comprise detectable labels and the immunoglobulins bound to the viral antigens may be detected by detecting the detectable labels attached to the secondary antibodies. The detection of the one or more immunoglobulins bound to each of the viral antigens can be performed simultaneously or separately. The simultaneous detection may be facilitated by using additional antibodies having different detectable labels, e.g., detectable labels that produce distinguishable optical signals. In cases where one or more of the secondary antibodies comprise the same detectable label, more than one assays may be performed and the immunoglobulins bound to each of the viral antigens may be detected separately.

Each of the binding elements, e.g., the first antigen, second antigen, third antigen, etc.) may or may not be isolated from each other. In cases where the antigens are isolated or separated from one another, they may be isolated in separate physical locations such as different assay plates, cartridges, tubes, dishes, reaction vessels, or wells of multiwell plates.

In some cases, the methods may comprise using a plurality of viral antigens for testing, each of which is associated with or coupled to a distinct location, e.g., region, on a substrate. The plurality of binding elements, e.g., viral antigens, may be arranged on the substrate as a microarray, for example, a microarray with rows and columns. Each distinct location may comprise one or more antigen molecules (e.g., at least about 2, 5, 10, 50, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1,000,000, 2,000,000, 3,000,000, 4,000,000, 5,000,000, or more antigen molecules) of a selected type of viral antigens. The substrate, as further described herein, may be plasmonically active and spectroscopically interacts with the antigens associated therewith and/or the detectable label on the antibodies. The substrate may comprise a noble metal film and a solid surface, such as an inert surface that is adapted to support the assay materials and the noble metal film. The noble metal film may comprise ruthenium, rhodium, palladium, silver, osmium, iridium, platinum, gold, or combinations thereof. The noble metal film may be arranged on the substrate in a manner that enhances near infrared fluorescence by 100-fold or more relative to the substrate without said noble metal film. In some cases, the noble metal film is arranged discontinuously on the substrate and comprises a plurality of isolated island areas of between about 100 nm$^2$ and 40,000 nm$^2$ in surface-exposed area which are separated by gaps of about 10 to about 60 nm. The term "isolated island areas," as used herein, refers to nanometer-sized noble metal islands, or discontinuous noble metal nanostructures. The islands may be of various shapes and configurations that provide nanometer sized raised areas of material (e.g. gold) separated by gaps without such material. The isolated island areas may be squares, circles, rectangles, triangles, hexagons, particle or rod like shapes, or any other regular or irregular shapes.

In some cases, the turnaround time from contacting the biological sample with the viral antigens to detecting the one or more immunoglobulins in the biological sample bound to the viral antigens is less than or equal to about 24 hours, 20 hours, 15 hours, 10 hours, 8 hours, 6 hours, 5 hours, 4 hours, 3 hours, 2 hours, 1.5 hours, 1 hour, 0.5 hours or less. In some cases, an entire diagnostic process, i.e., from contacting the biological sample with one or more viral antigens to making a diagnosis of the subject(s) with one or more viral infections, is performed in 24 hours or less, 20 hours or less, 15 hours or less, 10 hours or less, 8 hours or less, 6 hours or less, 5 hours or less, 4 hours or less, 3 hours or less, 2 hours or less, 1.5 hours or less, 1 hour or less, or even 0.5 hours or less. In some cases, each step of the methods, such as obtaining the sample from the subject, contacting the sample with one or more viral antigens, detecting the one or more immunoglobulins in the biological sample bound to the viral antigens, and diagnosing the subject(s) with one or more viral infections, is performed in 10 hours or less, 8 hours or less, 6 hours or less, 5 hours or less, 4 hours or less, 3 hours or less, 2 hours or less, 1.5 hours or less, 1 hour or less, or even 0.5 hours or less.

In certain embodiments, systems and methods of the disclosure may be used to detect and diagnose other infections, e.g., in addition to a flaviviral or alphaviral infection. Infection typically refers to invasion and multiplication of infectious agents in body tissues of a subject, as well as reaction of host tissues to said infectious agents and any toxins produced by said infectious agents. An infectious disease is a disease caused by, for example, an infectious microbe. Infectious diseases include, but are not limited to bacterial diseases, viral diseases, fungal infection, parasitic diseases, and the like. By detecting the presence, probability of presence, or level of one or more microbes in a sample, diseases and conditions associated with such microbes can be diagnosed and appropriate medical action taken. Likewise, by detecting the absence or probability of absence of one or more microbes in a sample, diseases and conditions associated with such microbes may be ruled out. In some embodiments, detecting a microbe comprises detecting one or more biomarkers of the microbe, such as a microbial antigen.

Exemplary diseases or conditions caused by infectious bacteria include, but are not limited to, nosocomial pneumonia, infections associated with continuous ambulatory peritoneal dialysis (CAPD), or catheter-associated bacteruria (*Acinetobacter baumanii*); cutaneous anthrax, pulmonary anthrax, and gastrointestinal anthrax (*Bacillus anthracis*); whooping cough and secondary bacterial pneumonia (*Bordetella pertussis*); Lyme disease (*Borrelia burgdorferi*); brucellosis (*Brucella abortus, Brucella canis, Brucella melitensis, Brucella suis*); acute enteritis (*Campylobacter jejuni*); community-acquired respiratory infection (*Chlamydia pneumoniae*); nongonococcal urethritis (NGU), lymphogranuloma venereum (LGV), trachoma, conjunctivitis of the newborn (*Chlamydia trachomatis*); psittacosis (*Chlamydophila psittaci*); botulism (*Clostridium botulinum*); pseudomembranous colitis (*Clostridium difficile*); gas gangrene, acute food poisoning, anaerobic cellulitis (*Clostridium perfringens*); tetanus (*Clostridium tetani*); diphtheria (*Corynebacterium diphtheriae*); bacteremia, lower respiratory tract infections, skin and soft-tissue infections, urinary tract infections (UTIs), endocarditis, intra-abdominal infections, septic arthritis, osteomyelitis, ophthalmic infections, wound infections, nosocomial infections (*Enterobacter cloacae, Enterobacter aerogenes*); skin, respiratory, and urinary infections (*Enterococcus cloacae*); nosocomial infections (*Enterococcus faecalis, Enterococcus faecium*); urinary tract infections (UTI), diarrhea, meningitis in infants, hemorrhagic colitis, hemolytic-uremic syndrome (*Escherichia coli*); tularemia (*Francisella tularensis*); bacterial meningitis, upper respiratory tract infections, pneumonia, bronchitis (*Haemophilus influenzae*); peptic ulcer (*Helicobacter pylori*); pneumonia, infections of the urinary tract, biliary tract and surgical wounds (*Klebsiella pneumoniae*); Legionnaire's disease, Pontiac fever (*Legionella pneumophila*); leptospirosis (*Leptospira interrogans*); listeriosis (*Listeria monocytogenes*); leprosy (Hansen's disease) (*Mycobacterium leprae*); tuberculosis (*Mycobacterium tuberculosis*); mycoplasma pneumonia (*Mycoplasma pneumoniae*); skin lesions and ulcers (*Mycobacterium ulcerans*); gonorrhea, ophthalmia neonatorum, septic arthritis (*Neisseria gonorrhoeae*); meningococcal disease including meningitis, Waterhouse-Friderichsen syndrome (*Neisseria meningitidis*); pseudomonas infection (localized to eye, ear, skin, urinary, respiratory or gastrointestinal tract or CNS, or systemic with bacteremia, secondary pneumonia bone and joint infections, endocarditis, skin, soft tissue or CNS infections) (*Pseudomonas aeruginosa*); rocky mountain spotted fever (*Rickettsia rickettsii*); typhoid fever type salmonellosis (*Salmonella typhi*); salmonellosis with gastroenteritis and enterocolitis (*Salmonella typhimurium*); bacillary dysentery/shigellosis (*Shigella sonnei*); coagulase-positive staphylococcal infections, including localized skin infections, diffuse skin infection (Impetigo), deep, localized infections, acute infective endocarditis, septicemia, necrotizing pneumonia, toxinoses such as toxic shock syndrome and staphylococcal food poisoning (*Staphylococcus aureus*); infections of implanted prostheses, e.g. heart valves and catheters (*Staphylococcus epidermidis*); Ccystitis in women (*Staphylococcus saprophyticus*); meningitis and septicemia in neonates, endometritis in postpartum women, opportunistic infections with septicemia and pneumonia (*Streptococcus agalactiae*); acute bacterial pneumonia and meningitis in adults, otitis media and sinusitis in children (*Streptococcus pneumoniae*); streptococcal pharyngitis, scarlet fever, rheumatic fever, impetigo and erysipelas puerperal fever, necrotizing fasciitis (*Streptococcus pyogenes*); pulmonary infections, colonization of prosthetic material such as catheters or endotracheal or tracheostomy tubes, pneumonia, urinary tract infection, bacteremia, soft tissue infection, ocular infection, endocarditis, meningitis (*Stenotrophomonas maltophilia*); syphilis (*Treponema pallidum*); cholera (*Vibrio cholerae*); plague, including bubonic plague and pneumonic plague (*Yersinia pestis*), and the like.

Exemplary genera of pathogenic bacteria include, but are not limited to, *Acinetobacter, Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Kleb-*

*siella, Legionella, Leptospira, Listeria, Mycobacterium, Mycoplasma, Neisseria, Pseudomonas, Rickettsia, Salmonella, Shigella, Staphylococcus, Streptococcus, Stenotrophomonas, Treponema, Vibrio, Yersinia,* and the like. Exemplary pathogenic species include, but are not limited to, *Acinetobacter baumanii, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterobacter sazakii, Enterobacter agglomerans, Enterobacter cloacae, Enterobacter aerogenes, Enterococcus faecalis, Enterococcus faecium, Escherichia coli, Francisella tularensis, Haemophilus influenzae, Helicobacter pylori, Klebsiella pneumoniae, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Salmonella enterica, Shigella sonnei, Staphylococcus aureus, Staphylococcus epidermidis, Staphylococcus saprophyticus, Streptococcus agalactiae, Streptococcus pneumoniae, Streptococcus pyogenes, Stenotrophomonas maltophilia, Treponema pallidum, Vibrio cholerae, Yersinia pestis,* and the like.

Fungal infection, or mycoses, of humans and animals may include, for example, superficial fungal infections that affect the outer layers of skin, fungal infections of the mucous membranes including the mouth (thrush), vaginal and anal regions, such as those caused by *Candida albicans,* and fungal infections that affect the deeper layers of skin and internal organs are capable of causing serious, often fatal illness, mucormycosis, entomophthoromycosis, aspergillosis, cryptococcosis, candidiasis, histoplasmosis, coccidiomycosis, paracoccidiomycosis, fusariosis (hyalohyphomycoses), blastomycosis, penicilliosis or sporotrichosis. These and other fungal infections can be found described in, for example, Merck Manual, Sixteenth Edition, 1992, and in Spellberg et al., *Clin. Microbiol. Rev.* 18:556-69 (2005).

Exemplary genera of pathogenic fungi include, but are not limited to, *Cryptococcus, Histoplasma, Pneumocystis,* and *Stachybotrys, Aspergillus, Blastomyces dermatitidis, Candida, Coccidioides immitis, Cryptococcus neoformans, Histoplasma capsulatum, Paracoccidioides brasiliensis, Sporothrix schenckii, Zygomycetes* spp., *Absidia corymbifera, Rhizomucor pusillus,* or *Rhizopus arrhizus.*

Exemplary diseases or conditions caused by viruses (and the associated viruses) include, but are not limited to, Zika virus disease (Zika), Immunodeficiency Syndrome (AIDS), Arbovirus infections, Barmah Forest virus, West Nile virus, mayaro virus, Japanese encephalitis, Kunjin virus, Murray Valley encephalitis virus, Ross River virus, Chickenpox, Chikungunya fever, Dengue fever, Enterovirus 71 infection, Hantavirus infection, Hepatitis A, Hepatitis B, Hepatitis C, Hepatitis D, Hepatitis E, HIV infection, Influenza A (H2), Influenza A (H5), Influenza A (H7), Influenza A (H9), Lyssavirus, Measles, Mumps, Poliomyelitis, Rubella, Smallpox, Yellow fever, Viral hemorrhagic fever including Arenavirus (new world), Crimean-Congo hemorrhagic fever, Dengue hemorrhagic fever, viral encephalitis, such as, e.g., Venezuelan equine encephalitis virus (VEEV), eastern equine encephalitis virus (EEEV), and western equine encephalitis virus (WEEV).

Exemplary virus can be a species of Adenoviridae, Herpesviridae, Papillomaviridae, Polyomaviridae, Poxviridae, Hepadnaviridae, Parvoviridae, Astroviridae, Caliciviridae, Picornaviridae, Coronaviridae, Flaviviridae, Togaviridae, Retroviridae, Orthomyxoviridae, Arenaviridae, Bunyaviridaem, Filoviridae, Paramyxoviridae, Rhabdoviridae, or Reoviridae.

In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfi virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana *myotis* leukoencephalitis virus, Phnom Penh bat virus, Rio Bravo virus, Tamana bat virus, and the Cell fusing agent virus.

In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus.

In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively). In some embodiments, the virus is the Zika virus.

Exemplary diseases or conditions caused by parasites include, but are not limited to, *Acanthamoeba* Infection, *Acanthamoeba Keratitis* Infection, African Sleeping Sickness (African trypanosomiasis), Alveolar Echinococcosis (Echinococcosis, Hydatid Disease), Amebiasis (*Entamoeba histolytica* Infection), American Trypanosomiasis (Chagas Disease), Ancylostomiasis (Hookworm), Angiostrongyliasis (*Angiostrongylus* Infection), Anisakiasis (*Anisakis* Infection, *Pseudoterranova* Infection), Ascariasis (*Ascaris* Infection, Intestinal Roundworms), Babesiosis (*Babesia* Infection), Balantidiasis (*Balantidium* Infection), *Balamuthia*, Baylisascariasis (*Baylisascaris* Infection, Raccoon Roundworm), Bed Bugs, *Bilharzia* (Schistosomiasis), *Blastocystis hominis* Infection, Body Lice Infestation (Pediculosis), Capillariasis (Capillaria Infection), Cercarial Dermatitis (Swimmer's Itch), Chagas Disease (American Trypanosomiasis), *Chilomastix mesnili* Infection (Nonpathogenic [Harmless] Intestinal Protozoa), Clonorchiasis (*Clonorchis* Infection), CLM (Cutaneous Larva Migrans, Ancylostomiasis, Hookworm), "Crabs" (Pubic Lice), Cryptosporidiosis (*Cryptosporidium* Infection), Cutaneous Larva Migrans (CLM, Ancylostomiasis, Hookworm), Cyclosporiasis (*Cyclospora* Infection), Cysticercosis (Neurocysticercosis), Cystoisospora Infection (Cystoisosporiasis) formerly *Isospora* Infection, *Dientamoeba fragilis* Infection, Diphyllobothriasis (*Diphyllobothrium* Infection), *Dipylidium caninum* Infection (dog or cat tapeworm infection), Dirofilariasis (*Dirofilaria* Infection), DPDx, Dracunculiasis (Guinea Worm Disease), Drinking Water, Dog tapeworm (*Dipylidium caninum* Infection), Echinococcosis (Cystic, Alveolar Hydatid Disease), Elephantiasis (Filariasis, Lymphatic Filariasis), *Endolimax nana* Infection (Nonpathogenic [Harmless] Intestinal Protozoa), *Entamoeba coli* Infection (Nonpathogenic [Harmless] Intestinal Protozoa), *Entamoeba dispar* Infection (Nonpathogenic [Harmless] Intestinal Protozoa), *Entamoeba hartmanni* Infection (Nonpathogenic [Harmless] Intestinal Protozoa), *Entamoeba histolytica* Infection (Amebiasis), *Entamoeba polecki*, Enterobiasis (Pinworm Infection), Fascioliasis (*Fasciola* Infection), Fasciolopsiasis (*Fasciolopsis* Infection), Filariasis (Lymphatic Filariasis, Elephantiasis), Foodborne Diseases, Giardiasis (Giardia Infection), Gnathostomiasis (*Gnathostoma* Infection), Guinea Worm Disease (Dracunculiasis), Head Lice Infestation (Pediculosis), Heterophyiasis (Heterophyes Infection), Hookworm Infection, Human, Hookworm Infection, Zoonotic (Ancylostomiasis, Cutaneous Larva Migrans [CLM]), Hydatid Disease (Cystic, Alveolar Echinococcosis), Hymenolepiasis (*Hymenolepis* Infection), Intestinal Roundworms (Ascariasis, *Ascaris* Infection), *Iodamoeba buetschlii* Infection (Nonpathogenic [Harmless] Intestinal Protozoa), *Isospora* Infection (Cystoisospora Infection), Kala-azar (Leishmaniasis, *Leishmania* Infection), Keratitis (*Acanthamoeba* Infection), Leishmaniasis (Kala-azar, *Leishmania* Infection), Lice Infestation (Body, Head, or Pubic Lice, Pediculosis, Pthiriasis), Loiasis (*Loa loa* Infection), Lymphatic filariasis (Filariasis, Elephantiasis), Malaria (*Plasmodium* Infection), Microsporidiosis (Microsporidia Infection), Mite Infestation (Scabies), Myiasis, *Naegleria* Infection, Neurocysticercosis (Cysticercosis), Neglected Parasitic Infections in the U.S., Neglected Tropical Diseases, Nonpathogenic (Harmless) Intestinal Protozoa, Ocular Larva Migrans (Toxocariasis, *Toxocara* Infection, Visceral Larva Migrans), Onchocerciasis (River Blindness), Opisthorchiasis (*Opisthorchis* Infection), Paragonimiasis (*Paragonimus* Infection), Pediculosis (Head or Body Lice Infestation), Pthiriasis (Pubic Lice Infestation), Pinworm Infection (Enterobiasis), *Plasmodium* Infection (Malaria), *Pneumocystis jirovecii* Pneumonia, *Pseudoterranova* Infection (Anisakiasis, *Anisakis* Infection), Pubic Lice Infestation ("Crabs," Pthiriasis), Raccoon Roundworm Infection (Baylisascariasis, *Baylisascaris* Infection), Recreational Water, River Blindness (Onchocerciasis), Sappinia, Scabies, Schistosomiasis (*Bilharzia*), Sleeping Sickness (Trypanosomiasis, African; African Sleeping Sickness), Soil-transmitted Helminths, Strongyloidiasis (*Strongyloides* Infection), Swimmer's Itch (Cercarial Dermatitis), Swimming Pools, Taeniasis (*Taenia* Infection, Tapeworm Infection), Tapeworm Infection (Taeniasis, *Taenia* Infection), Toxocariasis (*Toxocara* Infection, Ocular Larva Migrans, Visceral Larva Migrans), Toxoplasmosis (*Toxoplasma* Infection), Trichinellosis (Trichinosis), Trichinosis (Trichinellosis), Trichomoniasis (*Trichomonas* Infection), Trichuriasis (Whipworm Infection, *Trichuris* Infection), Trypanosomiasis, African (African Sleeping Sickness, Sleeping Sickness), Trypanosomiasis, American (Chagas Disease), Visceral Larva Migrans (Toxocariasis, *Toxocara* Infection, Ocular Larva Migrans), Waterborne Diseases, Whipworm Infection (Trichuriasis, *Trichuris* Infection), Zoonotic Diseases (Diseases spread from animals to people), Zoonotic Hookworm Infection (Ancylostomiasis, Cutaneous Larva Migrans [CLM]).

Non-limiting examples of parasites include *Toxoplasma gondii, Plasmodium falciparum, P. vivax, P. ovale, P. malariae, Trypanosoma* spp., and *Legionella* spp., Sarcodina (e.g., *Entamoeba*), Mastigophora (e.g., Giardia, *Leishmania*), Ciliophora (e.g., *Balantidium*), and Sporozoa (e.g., *Plasmodium, Cryptosporidium*).

Detecting presence or absence of a microbe may comprise detecting presence or absence of antibodies directed to one or more microbial antigens, such as antigens displayed on a substrate in an array.

Avidity Assay

In certain embodiments, the disclosure further provides avidity measurements for flaviviral and alphaviral antigens. Any of the methods described herein for detecting immunoglobulins may further comprise an avidity step, e.g., a wash step with urea or other denaturing agent to remove low avidity antibodies. In an avidity assay, the measurements can provide for qualitative or quantitative detection of an antibody from a biological sample. In certain embodiments, a biological sample may be separated into portions, e.g., a first and second portion, wherein a first portion of the biological sample is evaluated using a method described herein for detecting immunoglobulins and a second portion is tested with the same method and further with an added avidity wash step, e.g., a wash step with a protein denaturing agent such as urea. The protein denaturing agent may be present in a concentration sufficient to destabilize immune complexes containing antibodies of low avidity, but not sufficient to destabilize immune complexes containing antibodies of high avidity. The antigen-antibody binding in the biological sample of the two portions may be compared to evaluate the avidity of antibodies in the biological sample, e.g., a ratio of the antibody-antigen binding results of the second portion to the first portion. The antigen-antibody binding can be determined by any number of methods known in the field for evaluating these interactions.

In certain embodiments, methods described herein for evaluating avidity of an antibody in a biological sample may comprise contacting the biological sample with antigens to form immune complexes. The antigens may be bound, e.g., non-covalently, to a substrate. In certain embodiments, the substrate is selected from any of the substrates described herein, e.g., plasmonic substrates, multi-well substrates, beads, etc.

In certain embodiments, the immune complex may be washed with an avidity wash agent, e.g., a buffer solution containing a protein-denaturing agent. In certain embodiments, the avidity wash may comprise incubating said immune complexes with a protein denaturing agent for at least about 1min, at least about 2 min, at least about 3 min, at least about 4 min, at least about 5 min, at least about 6 min, at least about 7 min, at least about 8 min, at least about 9 min, at least about 10 min, at least about 11 min, at least about 12 min, at least about 13 min, at least about 14 min, at least about 15 min, at least about 16 min, at least about 17 min, at least about 18 min, at least about 19 min, at least about 20 min, at least about 25 min, at least about 30 min, at least about 35 min, or at least about 40 min. In certain embodiments, the protein denaturing agent may be incubated for a duration selected from a range of any of the two values described herein, for example, from about 5 min to about 10 min, from about 10 min to about 20 min, or from about 1 min to about 25 min. The incubation may be followed by a rinse step to remove the protein denaturing agent, and unbound and low avidity antibodies. The protein denaturing agent may be selected from formamide, guanidine, sodium salicylate, dimethyl sulfoxide, propylene glycol, urea and combinations thereof. The protein denaturing agent may be urea. The protein denaturing agent may be a solution comprising from about 1M to about 20 M urea, such as about 5M to about 15M urea, such as about 8M to about 12M urea and buffer, such as a phosphate buffered saline tween solution-20 (PBST).

The immune complex, washed with an avidity wash agent, may be incubated with an anti human antibody coupled to a fluorophore, e.g., IRDye680 or IRDye800. The anti human antibody coupled to a fluorophore may be an antihuman IgG-IRDye680. The washed immune complex may be incubated with an anti human antibody coupled to a fluorophore for at least about 1 min, 2 min, 3 min, 4 min, 5 min, 6 min, 7 min, 8 min, 9 min, 10 min, 15 min, 20 min, 25 min, 30 min, 35 min, or 40 min. In some cases, the washed immune complex may be incubated with an anti human antibody coupled to a fluorophore for aduration between any of the two values described herein, for example, between about 5 min to 10 min, between about 10 min to about 20 min, or between about 1 min to about 25 min. Each well may be washed with washing buffer between each incubation procedure. Additionally, reference samples may be applied to a separate well. The reference sample may be a serum sample that is IgG, IgM, IgA positive to an antigen. The reference sample may also be a serum sample with negative IgG, IgM and IgA binding to antigens. The reference sample may not be treated with a protein denaturing agent.

Methods of detecting antibody-antigen binding that may be used in the methods described herein include, for example, enzyme immunoassay, radioimmunoassay, Western blot or immunofluorescence assay. In certain embodiments, methods described herein, such as methods for evaluating avidity of an antibody in a biological sample, may comprise detecting antibodies that bind to flaviviral or alphaviral antigens.

As discussed, the avidity of an antibody in a biological sample, e.g., IgG avidity to a Zika antigen, may be determined by comparing the binding of the antibody to an antigen, e.g., IgG to a Zika antigen, following a method of the disclosure without a wash step relative to following the same method with an avidity wash step. In certain embodiments, the biological sample is separated into portions such that a first portion is tested for antibody binding to an antigen, e.g., IgG binding to Zika antigen, in a method described herein and a second portion is tested for antibody binding to an antigen, e.g., IgG binding to Zika antigen, following the same method as the first portion and further including a wash step to remove low avidity antibodies. In certain embodiments, the ratio of the binding of antigen to antibody, e.g., IgG to Zika antigen, in the second portion and first portion is about 0.1 or less, about 0.2 or less, about 0.3 or less, about 0.4 or less, or about 0.5 or less. An avidity value of about 0.5 or less may be considered low avidity. In certain embodiments, the ratio of the binding of antigen to antibody, e.g., IgG to Zika antigen, in the second portion and first portion is greater than about 0.5, greater than about 0.6, greater than about 0.7, greater than about 0.8, or greater than about 0.9. An avidity value of greater than about 0.5 may be considered high avidity. The avidity value may range from 0 to 1, or example, an avidity value of 0 can indicate a complete loss of IgG binding after a protein denaturing agent treatment. An avidity value of 1 can indicate no loss of IgG binding after protein denaturing agent treatment.

An avidity measurement can be used to diagnose a subject with either acute infection or a chronic infection. When the avidity is low, the subject may be diagnosed with an acute infection, i.e., a recent infection. When the avidity is high, the subject may be diagnosed with a chronic infection, i.e., an older infection. A subject diagnosed with a recent infection may have been infected for period of at most about 1 day, 2 days, 3 days, 4 days, 5 days, 6 days, 7 days, 8 days, 9 days, 10 days, 15 days, 20 days, or 30 days. The subject may have been infected for a time selected from a range of the two values described herein, for example, from about 1 day to about 7 days, from about 8 days to about 15 days, or from about 1 day to about 15 days. A subject diagnosed with a chronic infection may have been infected of a period of at least about 15 days, 20 days, 25 days, 30 days, 35 days, 40 days, 45 days, 50 days, 55 days, 60 days, 65 days, 70 days, 75 days, 80 days, 85 days, 90 days, 95 days, 100 days, or 150 days. In certain embodiments, the subject may have been infected for a time selected from a range of the two values described herein, for example, between about 16 days to about 50 days, between about 51 days to about 100 days, or between about 16 days to about 100 days.

Substrates

In certain aspects, detecting biomarkers in a biological sample may be performed with binding elements bound to a substrate, e.g., a substrate with a metallic film. Using substrates, such as those described in US patent publication nos. 20160146799 and 20130172207, in the present methods provides high sensitivity and specificity for detecting viral infection and allows for the ability to test small amounts of biological samples, e.g., microliter volumes and facile real-time testing of biological samples without the need to transport to a commercial laboratory.

In certain embodiments, the present disclosure provides substrates with a metallic film. The film may be further characterized in that the nanostructures of the film comprise silver or gold nanoparticles; the nanostructures are separated from one another by gaps; and intensity of a fluorescent signal from a fluorophore in proximity to the film is enhanced relative to the fluorescent signal obtained from the fluorophore in proximity to the substrate in the absence of the film. The film may be applied directly or indirectly to the substrate. For certain applications, the nanostructures comprise a first metal on nanoparticles of a second metal, where the first and second metal may be the same or different (e.g. gold on gold, or silver on gold). The nanostructures may be formed by at least one type of noble metals, for example, ruthenium (Ru), rhodium (Rh), palladium (Pd), silver (Ag), osmium (Os), iridium (Ir), platinum (Pt), and gold (Au). The nanostructures can take various shapes, e.g., sphere, cube, cuboid, cone, cylinder, prism, pyramid, tube, plate, disc, rod, or any regular or irregular shapes. In some cases, the nanostructures comprise nanoparticles. In cases where more than one type of metal are included in the nanostructures, the metals can form a layered or core/shell structure, for example, a silver-on-gold nanoparticle. In some cases, each of the nanostructures has the same shape. In some cases, it may be preferred to have nanostructures of different shapes (or heterogeneous).

Sizes (e.g., length, width, height etc.) of the nanostructures may vary, depending upon, applications that the nanostructures are used for. For example, it may be preferred to have nanostructures that are much smaller than the wavelength of light used for fluorescence excitation and emission. In some cases, the nanostructures may have a width, length, and/or height of less than or equal to about 1 millimeter (mm), such as less than or equal to about 750 micron (μm), 500 μm, 250 μm, 100 μm, 75 μm, 50 μm, 25 μm, 10 μm, 5 μm, 1 μm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 9 nm, 8 nm, 7 nm, 6 nm, 5 nm, 4 nm, 3 nm, 2 nm, 1 nm, 800 picometers (pm), 600 pm, 400 pm, 200 pm, 100 pm, 75 pm, 50 pm, 25 pm or 10 pm. In some cases, the width, length, and/or height of the nanostructures may be greater than or equal to about 1 pm, 5 pm, 10 pm, 25 pm, 50 pm, 75 pm, 100 pm, 250 pm, 500 pm, 750 pm, 1 nm, 2 nm, 3 nm, 4 nm, 5 nm, 6 nm, 7 nm, 8 nm, 9 nm, 10 nm, 15 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 600 nm, 700 nm, 800 nm, 900 nm, 1 μm, 5 μm, 10 μm, 30 μm, 50 μm, 70 μm, 90 μm, 110 μm, 130 μm, 150 μm, 200 μm, 400 μm, 600 μm, 800 μm, or 1 mm. In some cases, the width, length, and/or height of the nanostructures may be selected from a range of any two values described herein, for example, the nanostructures may have an average width and length from about 50 nm to about 500 nm, or from about 100 nm to about 200 nm.

The film may have a height of from about 5 nm to 500 nm, such as from about 30 nm to about 400 nm, from about 5 nm to about 300 nm, from about 5 nm to about 250 nm, from about 5 nm to about 200 nm, from about 5 nm to about 150 nm, from about 5 nm to about 100 nm.

The nanostructures may have a cross-sectional area of at least about $0.001$ $nm^2$, $0.005$ $nm^2$, $0.01$ $nm^2$, $0.05$ $nm^2$, $0.075$ $nm^2$, $0.1$ $nm^2$, $0.5$ $nm^2$, $0.75$ $nm^2$, $1$ $nm^2$, $10$ $nm^2$, $20$ $nm^2$, $40$ $nm^2$, $60$ $nm^2$, $80$ $nm^2$, $100$ $nm^2$, $250$ $nm^2$, $500$ $nm^2$, $750$ $nm^2$, $1,000$ $nm^2$, $2,500$ $nm^2$, $5,000$ $nm^2$, $7,500$ $nm^2$, $10,000$ $nm^2$, $25,000$ $nm^2$, $50,000$ $nm^2$, $75,000$ $nm^2$, $100,000$ $nm^2$, $200,000$ $nm^2$, $300,000$ $nm^2$, $400,000$ $nm^2$, $500,000$ $nm^2$, $600,000$ $nm^2$, $700,000$ $nm^2$, $800,000$ $nm^2$, $900,000$ $nm^2$, $1,000,000$ $nm^2$, $2,500,000$ $nm^2$, $5,000,000$ $nm^2$, $7,500,000$ $nm^2$, or $10,000,000$ $nm^2$. In some cases, the nanostructures may have a cross-sectional area of less than or equal to about $25,000,000$ $nm^2$, $10,000,000$ $nm^2$, $8,000,000$ $nm^2$, $6,000,000$ $nm^2$, $4,000,000$ $nm^2$, $2,000,000$ $nm^2$, $1,000,000$ $nm^2$, $800,000$ $nm^2$, $600,000$ $nm^2$, $500,000$ $nm^2$, $450,000$ $nm^2$, $400,000$ $nm^2$, $350,000$ $nm^2$, $300,000$ $nm^2$, $250,000$ $nm^2$, $200,000$ $nm^2$, $150,000$ $nm^2$, $100,000$ $nm^2$, $80,000$ $nm^2$, $60,000$ $nm^2$, $50,000$ $nm^2$, $40,000$ $nm^2$, $30,000$ $nm^2$, $20,000$ $nm^2$, $10,000$ $nm^2$, $8,000$ $nm^2$, $6,000$ $nm^2$, $4,000$ $nm^2$, $2,000$ $nm^2$, $1,800$ $nm^2$, $1,600$ $nm^2$, $1,400$ $nm^2$, $1,200$ $nm^2$, $1,000$ $nm^2$, $900$ $nm^2$, $800$ $nm^2$, $700$ $nm^2$, $600$ $nm^2$, $500$ $nm^2$, $400$ $nm^2$, $300$ $nm^2$, $200$ $nm^2$, $100$ $nm^2$, $90$ $nm^2$, $80$ $nm^2$, $70$ $nm^2$, $60$ $nm^2$, $50$ $nm^2$, $40$ $nm^2$, $30$ $nm^2$, $20$ $nm^2$, $10$ $nm^2$, $8$ $nm^2$, $6$ $nm^2$, $4$ $nm^2$, $2$ $nm^2$, $1$ $nm^2$, $0.75$ $nm^2$, $0.5$ $nm^2$, $0.25$ $nm^2$, $0.1$ $nm^2$, $0.075$ $nm^2$, $0.05$ $nm^2$, $0.025$ $nm^2$, $0.01$ $nm^2$, $0.0075$ $nm^2$, $0.005$ $nm^2$, $0.0025$ $nm^2$, $0.001$ $nm^2$, $0.0005$ $nm^2$, or $0.0001$ $nm^2$. In some cases, the cross-sectional area of the nanostructures may be selected from a range of any of the two values described herein, for example, from about $100$ $nm^2$ to about $250,000$ $nm^2$, from about $1,000$ $nm^2$ to about $250,000$ $nm^2$, from about $100$ $nm^2$ to about $40,000$ $nm^2$, from about $100$ $nm^2$ to about $35,000$ $nm^2$, from about $100$ $nm^2$ to about $30,000$ $nm^2$, or from about $500$ $nm^2$ to about $40,000$ $nm^2$.

The surface area of the nanostructures may be selected from about $100$ $nm^2$ to about $250,000$ $nm^2$, from about $1,000$ $nm^2$ to about $250,000$ $nm^2$, from about $100$ $nm^2$ to about $40,000$ $nm^2$, from about $100$ $nm^2$ to about $35,000$ $nm^2$, from about $100$ $nm^2$ to about $30,000$ $nm^2$, or from about $500$ $nm^2$ to about $40,000$ $nm^2$.

In some cases, each of the nanostructures comprised in the film may have the same shape, structure, and/or size. In some cases, the nanostructures may be of varied size, shape, and/or structure. Depending on the application, it may be preferred that a certain percentage of the nanostructures have the same or a different size, shape, and/or structure, for example, about 1%, 5%, 10%, 15%, 20%, 30%, 40%, 50%, 60%, 70%, 75%, 80%, 85%, 90%, 91%, 92%, 93%, 94%, 95%, 96%, 97%, 98%, 99%, or 100% of the nanostructures may have the same or a different size, shape, and/or structure.

Nanostructures may or may not be separated from each other. In cases where the nanostructures are separated from one another, they may be separated by gaps. Gap distance, a distance between the nanostructures, may vary. In some cases, a large gap distance may be created. In other cases, a small gap distance may be used. Large and small gaps can be constructed at different locations within the same film. In some cases, the gap distances or an average gap distance may be less than or equal to about 1 mm, such as less than or equal to about 750 μm, 500 μm, 250 μm, 100 μm, 75 μm, 50 µm, 25 µm, 10 µm, 7.5 µm, 5 µm, 2.5 µm, 1 µm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 9 nm, 8 nm, 7 nm, 6 nm, 5 nm, 4 nm, 3 nm, 2 nm, 1 nm, 0.75 nm, 0.5 nm, 0.25 nm, 0.1 nm, 0.075 nm, 0.05 nm, 0.025 nm, 0.01 nm, 0.0075 nm, 0.005 nm, 0.0025 nm, or 0.001 nm. In some cases, the gap distance may be at least about 0.0001 nm, 0.0005 nm, 0.001 nm, 0.005 nm, 0.01 nm, 0.05 nm, 0.1 nm, 0.5 nm, 1 nm, 5 nm, 7.5 nm, 10 nm, 20 nm, 40 nm, 60 nm, 80 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 25 µm, 50 µm, 75 µm, 100 µm, 500 µm and 750 µm. In some cases, the gap distance can be selected from a range of the two values described herein, for example, from about 1 nm and about 1,000 nm, from about 10 nm to about 200 nm, from about 10 nm to about 100 nm, or from about 10 nm to about 80 nm.

Gaps may be of varied widths and/or lengths. For example, the gaps may have widths and/or lengths that are less than or equal to about 5,000 nm, 4,000 nm, 3,000 nm, 2,000 nm, 1,000 nm, 800 nm, 600 nm, 400 nm, 200 nm, 100 nm, 80 nm, 60 nm, 40 nm, 20 nm, 10 nm, 7.5 nm, 5 nm, 1 nm, 0.75 nm, 0.5 nm, 0.25 nm, 0.1 nm, 0.05 nm, 0.01 nm, 0.005 nm, or 0.001 nm. In some cases, the widths and/or lengths of the gaps may be greater than or equal to about 0.005 nm, 0.0075 nm, 0.01 nm, 0.05 nm, 0.075 nm, 0.1 nm, 0.5 nm, 0.75 nm, 1 nm, 2.5 nm, 5 nm, 7.5 nm, 10 nm, 30 nm, 50 nm, 70 nm, 90 nm, 100 nm, 200 nm, 300 nm, 400 nm, 500 nm, 750 nm, 1,000 nm, 2,500 nm, or 5,000 nm. In some cases, the gaps may have widths and/or lengths falling into a range selected from any of the two values described herein, for example, the gaps may have widths from about 5 nm to about 50 nm, and lengths from about 5 nm to about 200 nm.

As provided herein, a film can be continuous, quasi-continuous, or discontinuous, depending upon, the inter-connectivity of nanostructures comprised in the film. For example, the film may be a continuous film, such that it comprises raised nanostructures that are inter-connected, creating an electrically conductive path, with gaps existing between some of the nanostructures that are not in the conducting path. By contrast, the film may be discontinuous, such that at least some portion of the film (e.g. at least 10%, 25%, 50%, 75%, 90%, or more) is comprised of nanostructures that are not connected by an electrically conducting path.

Features (e.g., size, dimension, and/or structure of nanostructures comprised in the film) and characteristics (e.g., roughness, thickness, continuity, electrical conductivity, and/or inter-connection of the nanostructures) of a film as provided in the present disclosure can be determined and characterized by various techniques, such as, for example, electrical conductivity measurement, and/or microscopy techniques including standard light microscopy, transmission electron microscopy (TEM), confocal laser scanning microscopy, scanning electron microscopy (SEM) and atomic force microscopy (AFM). For example, a film that is quasi-continuous through a percolating path and conducting can be determined based on electron microscopy imaging and/or electrical conductivity. In some examples, a discontinuous film nay be characterized based on electron microscopy imaging and electrical conductivity.

Films of the disclosure may have plasmonic resonance peaks selected from about 500 nm to about 2 rpm, from about 600 nm to about 1000 nm, from about 700 nm to about 1000 nm, or from about 700 nm to about 900 nm.

As provided herein, various materials may be used to fabricate a substrate. For example, the materials can be organic or inorganic, synthetic or natural, solid or semi-solid. Non-limiting examples of materials that can be used to form the substrate may comprise glass, silver, quartz, plastic, nitrocellulose, silicon-based material (e.g., silicon, silicon dioxide), polymer (e.g., polystyrene, nylon, polydopamine (PDA), polyvinyl chloride (PVC), poly(dimethylsiloxane) (PDMS), polyvinylidene fluoride etc.), bioassay, or any multiplexed platforms or combinations thereof.

A substrate may be of varied shape, e.g., 3-dimensional or 2-dimensional, regular or irregular, homogeneous or heterogeneous. In some cases, the lateral shape of the substrate can be of round, square, rectangle, polygon, elliptical, elongated bar, polygon, or any other regular or irregular shapes or combinations thereof. For example, in some cases, the substrate is a bead or barcode. The substrate may be a magnetic bead (e.g., a bead comprising a magnetic or paramagnetic core) that may facilitate subsequent separation and detection processes. The substrate may also comprise a flat surface, a curved surface, a spherical surface, or a three-dimensional porous membrane. In some cases, the substrate may be the interior of a well of a multi-well plate, comprised, in some cases, of polystyrene. In some cases, the substrate may be all wells of a multi-well plate.

In some cases, the substrate is a bead. Beads may be made from any of a variety of materials (e.g. a substrate material described herein), and some varieties are commercially available. In some embodiments, the beads have an average diameter of at least about 0.001 microns (e.g. 0.005 microns, 0.01 microns, 0.05 microns, 0.1 microns, 1 micron, 10 microns, 50 microns, 100 microns, 250 microns, 500 microns, or more); less than about 500 microns (e.g. 400 microns, 200 microns, 100 microns, 50 microns, 25 microns, 10 microns, 1 micron, or less); or between any of these (e.g. ranging from about 0.01 microns to about 10 microns, about 0.05 microns to about 500 microns, about 0.1 microns to 200 microns, or about 0.1 microns to about 8 microns). Beads may be provided in a container, such as in a tube or a well of a multi-well plate. As with any of the other substrates described herein, the bead and/or the film on the bead may be conjugated to one or more binding elements, such as multiple copies of a single binding element, or a plurality of different binding elements. In some cases, the beads are further disposed in or on a support, such as a porous substrate material. A variety of porous substrates are available, selection of which may depend on the particular application, the size of the beads, and the like. Non-limiting examples of porous membranes for use as bead supports include nitrocellulose, hydrogels, 3D polymers, glass fiber, nylon, or cellulose acetate.

With the film of the present disclosure, intensity of a fluorescent signal from a fluorescent molecule (e.g., a fluorophore) in proximity to the film may be enhanced relative to the fluorescent signal obtained in the absence of the film. Such enhancement of the fluorescent signal may be characterized or quantified by an enhancement factor, which is defined as the ratio of a fluorescent signal obtained with the presence of the film to the same signal obtained without the film. For example, if a fluorescent signal is 410 and 15, with and without the presence of the film, respectively, then the enhancement factor is about 27. With the aid of a film provided herein, fluorescent signal in the range of 400 nm to 2100 nm can be enhanced with varied enhancement factors, dependent upon, e.g., wavelength of the fluorescent signals, features and characteristics of the film etc. For example, the intensity of a near-infra-red fluorescent signal having an emission of about 700 nm to about 800 nm may be enhanced by about 30-fold or more (e.g. at least 50-fold, 100-fold, 250-fold, 500-fold, or more) by using a film of the present disclosure. In some examples, the intensity of the fluorescent signal of a visible dye having an emission of about 400 nm to about 700 nm may be enhanced by about 3-fold or more (e.g. at least 5-fold, 10-fold, 25-fold, 50-fold, 100-fold, or more). In some cases, the film has fluorescence enhancement of fluorescent signals up to about 1,000-fold, 800-fold, 700-fold, 600-fold, 500-fold, 400-fold, 300-fold, 200-fold, 100-fold, 90-fold, 80-fold, 70-fold, 60-fold, 50-fold, 40-fold, 30-fold, 20-fold, 10-fold, 9-fold, 8-fold, 7-fold, 6-fold, 5-fold, 4-fold, 3-fold, or 2-fold. In some cases, by utilizing the film of the present disclosure, the intensity of the fluorescent signals can be enhanced by at least about 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 150-fold, 200-fold, 250-fold, 300-fold, 350-fold, 400-fold, 450-fold, 500-fold, 600-fold, 700-fold, 800-fold, 900-fold, or 1,000-fold. In some cases, the enhancement factor may be selected from a range of two values described herein, for example, about 10- to 30-fold, or about 100- to 200-fold. In some cases, enhancement is obtained for a fluorescent signal having a wavelength of at least 300 nm, 400 nm, 500 nm, 600 nm, 700 nm, 800 nm, 900 nm, 1000 nm, 1200 nm, 1400 nm, 1600 nm, 1800 nm, 2000 nm, or more; less than 2200 nm, 2000 nm, 1800 nm, 1600 nm, 1400 nm, 1200 nm, 1000 nm, 900 nm, 800 nm, 700 nm, 600 nm, 500 nm, or less; or for a range of wavelengths between any of these, such as between 300 nm to 2200 nm, 400 nm to 800 nm, 500 nm to 900 nm, or 800 nm to 1400 nm.

In some cases, a fluorescent molecule may be a member of a fluorescence resonance energy transfer (FRET) pair and FRET is used to produce a signal that can be correlated with the binding of binding elements and analytes. FRET arises from the properties of certain fluorophores. Such produced signals for one or both members of the pair may be enhanced with the presence of a film as provided herein. Molecules that can be used in FRET may include the fluorophores described above, and include fluorescein, 5-carboxyfluorescein (FAM), 2'7'-dimethoxy-4'5'-dichloro-6-carboxyfluorescein (JOE), rhodamine, 6-carboxyrhodamine (R6G), N,N, N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl) aminonaphthalene-1-sulfonic acid (EDANS).

In some cases, the acceptor of the FRET pair is used to quench the fluorescence of the donor. In some cases, the acceptor has little to no fluorescence. The FRET acceptors that are useful for quenching are referred to as quenchers. Quenchers useful in the methods of the present invention include, without limitation, Black Hole Quencher Dyes (Biosearch Technologies such as BHQ-0, BHQ-1, BHQ-2, BHQ-3, BHQ-10; QSY Dye fluorescent quenchers (from Molecular Probes/Invitrogen) such as QSY7, QSY9, QSY21, QSY35, and other quenchers such as Dabcyl and Dabsyl; Cy5Q and Cy7Q and Dark Cyanine dyes (GE Healthcare), which can be used, for example, in conjunction with donor fluorophors such as Cy3B, Cy3, or Cy5; DY-Quenchers (Dyomics), such as DYQ-660 and DYQ-661; and ATTO fluorescent quenchers (ATTO-TEC GmbH), such as ATTO 540Q, 580Q, 612Q.

In certain aspects, the disclosure provides binding elements, e.g., a Zika antigen, bound to a substrate for use in detecting antibodies in biological samples. In certain embodiments, in addition to an antigen binding element, a substrate of the disclosure may comprise additional binding elements. The plurality of binding elements may be an array of binding elements. The array of binding elements may be a microarray. In some embodiments, the plurality of binding elements are in direct or indirect contact with the film, such as by way of direct attachment or indirectly attached to an intermediate that is attached to the film. The binding elements may be on top of the film. The binding elements may be underneath the film. In some cases, the binding elements may be attached to a substrate and indirectly contact the film. For example, the substrate may comprise an avidin or streptavidin layer which is between the film and the binding elements. The binding elements may be attached to the substrate via a linking molecule (or a linker). The linker may be any type of molecule (e.g. chemical or biological) that is capable of linking the binding elements with the substrate. In some cases, the linker is a chemical bond. For example, the binding elements can be attached covalently to the surface of the substrate.

A number of different chemical surface modifiers can be added to substrates to attach the binding elements, e.g., Zika antigen, to the substrates. Examples of chemical surface modifiers may include, but not limited to, N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, phosphines, and combinations thereof. In one cases, substrate surfaces reactive towards amines may be utilized. Examples of such surfaces may include NHS-esters, aldehyde, epoxide, acyl halide, and thio-ester. Molecules (e.g., proteins, peptides, glycopeptides) with free amine groups may react with such surfaces to form covalent bond with the surfaces. Nucleic acid probes with internal or terminal amine groups can also be synthesized, (e.g., from IDT or Operon) and bound (e.g., covalently or non-covalently) to surfaces using similar chemistries.

In some cases, an array of capture agents or binding elements may be attached to a film via an extra layer, for example, a self-assembled monolayer on the film. In some examples, a hydrophilic polymer (e.g., Polyethylene glycol (PEG)) or dextran is linked to a self-assembled monolayer on the film, wherein the binding elements (e.g., biological molecules) are linked to the hydrophilic polymer or dextran.

Depending upon the specific applications, a binding element, e.g. a Zika antigen, as provided herein may be designed or selected to bind to one or more specific analytes, e.g. Zika antibodies, with greater affinity than it binds to other substances contained in a sample. The binding between the binding elements and the analytes can be through various types of molecular recognition mechanisms, for example, hybridization. The strength of binding can be referred to as "affinity". Affinities between biological molecules can be influenced by non-covalent intermolecular interactions including, for example, hydrogen bonding, hydrophobic interactions, electrostatic interactions and Van der Waals forces. In some cases, for example, for multiplexed analysis, a plurality of analytes and binding elements are involved. For example, an experiment may involve testing the binding between a plurality of different nucleic acid molecules or between different proteins. In such experiments, analytes may be preferred to bind to binding elements for which they have greater affinity. In some cases, the plurality of binding elements may be configured to conjugate to the film at different known locations and each of the binding element binds to a different analyte. For example, an array may comprise at least 2 (e.g. at least 10, 25, 50, 100, 1000, 5000, 10000, or more) different binding elements, each having binding specificity for a different analyte (e.g. a different polynucleotide sequence, a different protein, and/or a different antibody). Based on the location of a detected fluorescent signal, the analyte can be identified.

The binding can be, for example, a receptor-ligand, enzyme-substrate, antibody-antigen, or a nucleic acid hybridization interaction. The binding element/analyte binding pair can be nucleic acid to nucleic acid, e.g. DNA/DNA, DNA/RNA, RNA/DNA, RNA/RNA, RNA. The binding element/analyte binding pair can be a polypeptide and a nucleic acid, e.g. polypeptide/DNA and polypeptide/RNA, such as a sequence specific DNA binding protein. The binding element/analyte binding pair can be any nucleic acid, including synthetic DNA/RNA binding ligands (such as polyamides) capable of sequence-specific DNA or RNA recognition. The binding element/analyte binding pair can comprise natural binding compounds such as natural enzymes and antibodies, and synthetic binding compounds. The binding element/analyte binding can comprise aptamers, which are nucleic acid or polypeptide species that have been engineered to have specific binding properties, usually through repeated rounds of in vitro selection or equivalently, SELEX (systematic evolution of ligands by exponential enrichment).

Substrates of the disclosure may include additional binding elements for detecting additional biomarkers in a sample. Binding elements as provided herein can be any type of organic or inorganic molecules or compounds, for example, biomolecules. In some cases, the binding elements and/or analytes comprise proteins, peptides, antibodies, antigen-binding antibody fragments, polysaccharides, enzymes, aptamers, nucleic acids, antigens, cells, tissues, or disease-causing agents such as viruses, bacteria, fungi, protozoa, and worms. In some cases, the protein may be derived from cell or tissue lysate, body fluid, or other sample source, such as in the case of reverse phase protein array analysis. For example, the binding elements and/or analytes can be antigens for detecting antibodies in a sample. Non-limiting examples of antibodies include, total human IgG, IgM, IgA and IgE; anti-HLA (human leukocyte antigen) antibodies; anti-dsDNA antibodies; anti-Smith antibodies; antibodies diagnostic of Systemic Lupus Erythematosus (SLE), Toxoplasmosis, Rubella, Rabies, Malaria, lyme disease, African Trypanosomiasis, cholera, cryptosporidiosis, dengue, influenza, Japanese Encephalitis, Leishmaniasis, measles, meningitis, onchocerciasis, pneumonia, tuberculosis, typhoid, or yellow fever; antibodies specific for cytomegalovirus (CMV), *Toxoplasma gondii*, Rubella virus, Herpes simplex virus 1 and 2 (HSV-1/2), anti-Hemoglobin Alpha (HBA), Hepatitis B virus (HBV), Hepatitis C virus (HCV), Hepatitis D Virus (HDV), human immunodeficiency virus (HIV); Human papillomavirus (HPV), Ebola virus, rotavirus, human leukocyte antigens, Thyroid Stimulating Hormone Receptor (TSHR), thyroperoxidate, Thyroglobulin, tissue transglutaminase (tTG), endomysium, deamidated gliadin peptide; antibodies specific for tumor-associated antigens selected from p53, NY-ESO-1, MAGE A4, HuD, CAGE, GBU4-5, and SOX2, or combinations thereof. Multiple diagnostic antibodies may be assessed in a single assay, such as antibodies for *Toxoplasma gondii*, Rubella, cytomegalovirus (CMV), and herpes simplex virus (HSV), as in the case of a TORCH assay. TORCH infections are a group of congenitally acquired infections that cause significant morbidity and mortality in neonates. These infections are acquired by the mother and passed either transplacentally or during the birth process. While each infection is distinct, there are many similarities in how these infections present. It is important to consider TORCH infections whenever a neonate presents with intrauterine growth restriction (IUGR), microcephaly, intracranial calcifications, conjunctivitis, hearing loss, rash, hepatosplenomegaly, or thrombocytopenia. Although the five classic infections are mentioned above, other categories of infections may also assessed (e.g. in the same binding reaction), such as human immunodeficiency virus (HIV), varicella zoster virus (VZV), Herpes, Syphilis, parvovirus B19, enteroviruses, and others. Examples of antibodies of a TORCH assay may include, but is not limited to *Toxoplasma gondii* Antibody, Immunoglobulin G (IgG); Rubella Antibody, IgG; Herpes Simplex Virus Type 1 and/or 2 antibodies, IgG; Cytomegalovirus Antibody, IgG; *Toxoplasma gondii* IgM Antibody, Immunoglobulin M (IgM); Rubella Antibody, IgM; Herpes Simplex Virus Type 1 and/or 2 Antibodies, IgM; and Cytomegalovirus Antibody, IgM. In a typical TORCH assay, the binding element is an antigen (e.g. one or more Toxoplasmosis *gondii* antigens, one or more Rubella antigens, one or more CMV antigens, and one or more HSV antigens) and the analyte is an antibody directed against one or more of the antigens.

In general, an antibody diagnostic of a given condition is one that binds a molecule associated with that condition. In the case of infection, the antibody may be one that binds a protein of the infectious agent, such as a viral capsid protein or a bacterial cell surface protein. In some cases, the antigen is an infectious agent or component thereof. Where the disease is an autoimmune disorder, the antibody may be an autoantibody, and the antigen is a human protein or portion thereof.

As provided in the present disclosure, any of the binding elements and/or analytes may be tagged with one or more reporting molecules (or labels). The labels may comprise fluorescent molecules. Binding of the binding elements and the analytes that comprise the fluorescent molecules may produce a fluorescent signal that may be enhanced by a film of the present disclosure. In some cases, the binding elements and/or analytes may be tagged with a primary antibody, which may be bound by a secondary antibody comprising at least one fluorescent molecule. Occurrence of binding events between the binding elements and the analytes may then produce a fluorescent signal that can be enhanced with the presence of the film.

In some cases, the binding element is an antibody, e.g. antihuman IgA or an antihuman IgG antibody, which may be used for capturing, labeling, or otherwise detecting an analyte. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively.

The antibody may be a monoclonal antibody. As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies can be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

Substrates of the present disclosure can be applied for a wide context of applications. Any methods or techniques that utilize fluorescence detection may fall into the scope of the applications as provided herein. Examples of applications include, but are not limited to, microarrays of proteins, nucleic acids, and antibodies for detection via direct and indirect fluorescence antibody techniques with or without multiplexing, gene sequencing, in vitro diagnostics including fluorescence in situ hybridization (FISH), immunohistochemical staining (IHC), exosome capture for IHC staining and FISH, cell-free DNA capture and quantitation assay, chemical imaging (e.g., Mid-infrared chemical imaging, Near-infrared chemical imaging, Raman chemical imaging, Fluorescence Imaging (Ultraviolet, visible and near infrared regions)), Fluorescence Intensity Decay Shape Microscopy (FIDSAM), Fluorescence anisotropy, Fluorescence correlation spectroscopy (FCS), Fluorescence image-guided surgery (FIGS), Fluorescence Loss in Photobleaching (FLIP), Lattice light-sheet microscopy, immunofluorescence assay (IFA), single molecule wide field imaging, super-resolution imaging techniques such as Stimulated emission depletion (STED) and single molecular localization (PALM/STORM), cellular and tissue imaging by wide field, confocal scanners and laser scanning cytometry instruments, Enzyme-Linked Immunospot (ELISPOT), Fluorescence (Forster) Resonance Energy Transfer (FRET) based imaging, Fluorescence Recovery after Photobleaching (FRAP) based imaging, imaging substrates for circulating tumor cells (CTC), imaging substrates for single molecule and single nanoparticle imaging, and for fluorescence-based microarrays of antigens, antibodies, peptides, DNA, RNA, aptamers, tissues, cells and reverse phase microarrays, or combinations thereof.

Some aspects of the present disclosure provide methods of detecting one or more analytes. The methods may comprise: (a) providing a film as described herein; (b) applying to the film an analyte and a label for the analyte, wherein the label may comprise a fluorescent molecule (e.g., a fluorophore) and the analyte may or may not be bound to the label; and (c) detecting the analyte by detecting a fluorescent signal of the fluorescent molecule, wherein the intensity of the fluorescent signal can be enhanced relative to the fluorescent signal in the absence of the film. Various methods and techniques may be used to detect the fluorescent signals, e.g., Fluorescence spectroscopy (or fluorometry, spectrofluorometry), Fluorescence microscopes, Fluorescence scanners and Flow cytometers. In some examples, the detection of fluorescent signals may comprise imaging by microscopy. In general, methods of detecting one or more analytes may further comprise diagnosing a subject as having a condition associated with the presence, absence, or level of the one or more analytes. For example, detection of a biomarker for the presence of an infectious agent in a sample from a subject may be followed by diagnosing the subject as being infected with or a carrier of the infectious agent. Likewise, detection of one or more cancer-related biomarkers may be followed by a diagnosis of cancer, and so forth, depending on the one or more biomarkers assayed. Multiple examples of such biomarkers are provided herein. In some cases, a method may further comprise taking medical action on the basis of detecting one or more analytes and/or a resulting diagnosis. Medical action can include therapeutic intervention, and further testing. Detection can comprise detecting a fluorescent signal from a complex comprising a binding element, an analyte bound to the binding element, and a fluorescent label, all of which may be complexed to the film. The film, binding element, analyte, and fluorescent label can be any of those described herein.

Methods may utilize any of the films described herein. As an example, a film that can be utilized in the methods may have one or more of characteristics including, e.g., (a) the gaps having widths between about 5 nm to about 50 nm, and lengths between about 5 nm and about 200 nm; (b) the nanostructures having an average width and length between about 50 nm to about 500 nm; (c) the film having a nanoplate size of between about 1000 $nm^2$ to about 250,000 $nm^2$; (d) the height of the film being between about 5 nm and about 500 nm; (e) the film comprising irregular features and a heterogenous structure; (f) the film imparting a plasmon from about 400 nm to about 2100 nm; (g) the substrate comprising a flat surface, a curved surface, a spherical surface, or a three-dimensional porous membrane; and (h) the substrate being a bead. The film may comprise silver on gold nanoparticles.

In some cases, the methods can further comprise determining the presence, absence, concentration, identity (e.g., a phenotype of a cell, or sample source), and/or location of one or more analytes, or other characteristic of the sample or sample source based upon the detected fluorescent signal. Examples of characteristics include identity of a sample source (e.g. an individual subject or location), presence or absence of contamination, presence or absence of disease or condition, type of protein, nucleotide sequence, or other identifying characteristic. In some cases, the methods comprise identifying a disease or condition of a sample, or identifying a sample source (e.g. a subject). Examples of these are provided above, and include diseases or conditions such as a cardiovascular disease or condition, a kidney-associated disease or condition, a prenatal or pregnancy-related disease or condition, a neurological or neuropsychiatric disease or condition, an autoimmune or immune-related disease or condition, a cancer, an infectious disease or condition (e.g., a microbial infection), a pediatric disease, disorder, or condition, a mitochondrial disorder, a respiratory-gastrointestinal tract disease or condition, a reproductive disease or condition, an ophthalmic disease or condition, a musculo-skeletal disease or condition, or a dermal disease or condition. Other diseases may be identified, such as by identifying the presence of one or more biomarkers or a degree of match with a biosignature associated with the condition. Examples of biomarkers are provided herein.

Various arrangements for the detection of an analyte via fluorescence are available. For example, a sample comprising an analyte may be applied directly to the surface of the film, such as by adding a sample liquid to a well having an inner surface coated with the film. A sample may be directly contacted to the film after first contacting the sample to a sample surface, such as a slide, which can result in sandwiching the analyte between the sample surface and the film. In yet a further example, a sample containing an analyte is contacted with a sample substrate having a first surface in contact with the sample (such as the inner surface of a well, the top surface of a slide, or a channel within a microfluidic device) and a second surface that is not in contact with the sample (such as the bottom surface of a well or slide), and detection of a fluorescent signal associated with the analyte comprises bringing the second surface in proximity with the film (e.g. contact with, or bringing within 1000 nm). The analyte may be labeled with a fluorescent label at any point preceding detection of the analyte in proximity with the film. When the film is on the surface of a bead, the film is brought in proximity to the analyte to be detected by contacting the sample with the beads. Fluorescence may then be detected, such as in the sample container (e.g. as in a well of a multi-well plate). In some cases, film-coated beads that have been contacted with a sample are analyzed by flow cytometry, fluorescence imaging microscopes, or scanners.

In some cases, an analyte may be on a surface. The analyte may be directly or indirectly attached to the surface. The analyte may be bound to the surface via a binding element. The binding elements may be the same or different, and may be any of a variety of binding elements, examples of which are provided herein. The microarray can comprise a DNA microarray, a RNA microarray, a miRNA microarray, a peptide microarray, a protein microarray, an antibody microarray, or any types of microarray of biological or chemical molecules. In cases where the analyte is bound to the surface, a film of the present disclosure may be applied to the analyte on the surface. As discussed above and elsewhere herein, the film may comprise a plurality of binding elements or capture agents (e.g., an array of binding elements). Each of the binding elements may be configured to bind to the same or a different type of analyte. In cases where a non-uniform film which comprise a plurality heterogeneous and irregular nanostructures is utilized, the film may comprise a plurality of discrete and isolated locations. The plurality of locations may be independently addressable and each of the locations may include a specific type of binding element that is able to bind to a certain analyte. Binding of each pair of binding element and analyte may produce a fluorescent signal that can be enhanced by the film and captured by a detector. Based on the location of the detected signal, the analyte can be determined or identified. In some examples, the binding element is an oligonucleotide (e.g., a primer) conjugated to the film which is applied to a substrate (e.g., a bead), and the analyte is a target polynucleotide that can hybridize to the oligonucleotide via sequence complementary or an amplification product thereof. Once the target polynucleotide successfully hybridizes to the oligonucleotide, an amplification reaction may be initiated to produce a detectable amplified product (or amplicon). Since the film may be fabricated to include a plurality of isolated and independently addressable locations, and each of the locations may contain only a single analyte, the detection may further comprise single molecule analysis, e.g., single molecule imaging and tracking, or single nanoparticle tracking and imaging.

In some cases, the array of binding elements is a protein array. Protein microarrays can be prepared in a number of ways, such as by spotting the desired proteins onto the film or onto a sample substrate. Exemplary methods for preparing protein arrays are described e.g. in US 2003/0013130, US 2003/0108726, US 2009/0088329, and US 2013/0172207. In some cases, the array of binding elements is a polynucleotide array, such as in an array of oligonucleotide probes on the film or a sample substrate. Exemplary methods for fabricating polynucleotide arrays include the use of fine-pointed pins onto glass slides, photolithography using pre-made masks, photolithography using dynamic micromirror devices, ink-jet printing, or electrochemistry. Exemplary methods are described e.g. in Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270.

Any of a variety of binding assays that utilize fluorescence as a means for detecting an analyte may be enhanced through use of a film according to the presence disclosure. In some embodiments, the assay is a receptor based assay. In general, receptor based assays comprise detecting an interaction between two binding partners, an analyte receptor (also referred to as a binding element) and an analyte. In general, an analyte receptor and an analyte in a given pair of binding partners are distinguished on the basis of which one is known (the analyte receptor), and which is being detected (the analyte). As such, exemplary analyte receptors described herein may be detected as analytes in other embodiments, and exemplary analytes as described herein may be used as analyte receptors for detection of respective binding partners in other embodiments. In some embodiments, the analyte receptor, the analyte, or both comprise a protein. Analyte receptors include, but are not limited to: natural or synthetic proteins, cellular receptor proteins, antibodies, enzymes, polypeptides, polynucleotides (e.g. nucleic acid probes, primers, and aptamers), lipids, small organic or inorganic molecules, antigens (e.g. for antibody detection), metal binding ligands, and any other natural or synthetic molecule having a binding affinity for a target analyte. In some embodiments, the binding affinity of an analyte receptor for an analyte is a $K_D$ of less than about $5\times10^{-6}$M, $1\times10^{-6}$M, $5\times10^{-7}$M, $1\times10^{-7}$M, $5\times10^{-8}$M, $1\times10^{-8}$M, $5\times10^{-9}$M, $1\times10^{-9}$M, $5\times10^{-10}$M, $1\times10^{-10}$M, $5\times10^{-11}$, $1\times10^{-11}$, or less. A variety of analytes and analyte receptors are available, as well as assays employing the same. See e.g. U.S. Pat. No. 8,435,738. In some cases, where an array comprises a plurality of different binding elements, a corresponding plurality of different analytes may be detected in a single reaction. In general, by increasing the fluorescent signal from a label associated with the presence or absence of an analyte, the sensitivity of detecting for that analyte is increased, such that smaller amounts of analyte may be detected above a background level than is possible in the absence of a film of the present disclosure.

In vitro diagnostic imaging may consist of adhering cells and cellular vesicles to a substrate, typically surface-modified glass, and detecting certain cellular membrane molecules using a complementary antibody or antigen conjugated to a fluorescent dye. In this method, autofluorescence from the cell and photobleaching of the dye are both concerns. Endogenous autofluorescence of cells is highest in the visible region from 350-500 nm, decreasing out towards the near-infrared. By performing cellular imaging in conjunction with a film of the disclosure, fluorescence signal of selected labels can be amplified (e.g. for fluorophores with peak excitation wavelengths at 680 nm and 800 nm regions) with minimal autofluorescence. By amplifying fluorescence 10-200 fold in this region, lower intensity excitation can be used, reducing photobleaching.

In some embodiments, the detection assay comprises detecting amplification of one or more target polynucleotides. Methods of amplification may include, for example, polymerase chain reaction (PCR), strand displacement amplification (SDA), and nucleic acid sequence based amplification (NASBA), and Rolling Circle Amplification (RCA). The amplification method can be temperature cycling or be isothermal. The amplification method can be exponential or linear. For amplifications with temperature cycling, a temperature cycle may generally correspond to an amplification cycle. Isothermal amplifications can in some cases have amplification cycles, such as denaturing cycles, and in other cases, the isothermal amplification reaction will occur monotonically without any specific amplification cycle. The amplification method may be used to amplify specific regions (i.e., target regions), or nucleotide sequences of a nucleic acid molecule (e.g., DNA, RNA). This region can be, for example, a single gene, a part of a gene, or a non-coding sequence.

As described herein, the film may be coated on a substrate, wherein the substrate is a bead. In one particular implementation of this embodiment, the beads are further coated with polynucleotide probes as binding elements. A plurality of beads may be provided, and each bead may be coated with multiple copies of the same polynucleotide, or with a plurality of different polynucleotides. The probes may comprise sequences that are complementary to specific target sequences, or may comprise random or partially random sequences for detecting a plurality of different target sequences. Detection may be by way of hybridization alone, such as where a target polynucleotide bearing a fluorescent label hybridizes to the bead and fluorescence is detected. Alternatively, detection may comprise additional manipulation steps, such as in an amplification reaction in which the probes bound to the beads are extended along target polynucleotides that are used as templates in an amplification reaction. Amplified products may be detected during amplification and/or after amplification is completed. A variety of labels for the detection of amplification products are available, such as ethidium bromide, SYBR green, SYBR blue, DAPI, acriflavine, fluorcoumanin, ellipticine, daunomycin, chloroquine, distamycin D, chromomycin, propidium iodine, Hoeste, SYBR gold, acridines, proflavine, acridine orange, homidium, mithramycin, ruthenium polypyridyls, anthramycin, and other suitable agents.

Immunoassay detection via ELISA is utilized in both clinical diagnostics and as a life science research tool as a method to quantify nucleic acid, antibody, or protein concentration in a solution. In practice, a capture antibody or antigen is coated on the surface of a glass slide or 96-well plate at a given concentration, in order to bind to the target molecule in solution. After binding, a detection antibody or antigen is incubated and luminescence, either via absorption or fluorescence spectroscopy, is used to quantify the concentration of the target analyte in solution, typically using a calibration curve as reference. ELISA performed in the absence of films of the disclosure is typically limited to <3 logs of dynamic range, as well as a lower limit of detection and quantification at ~1 nanogram analyte/milliliter solution. Many biological molecules have clinically relevant concentrations below 1 ng/ml and dynamic ranges that span 6 or more log, such as cytokines and proteins indicative of a disease-state at an early stage. By performing the detection step with labels in proximity to a film of the disclosure, the dynamic range and limit of detection can be expanded to detect analytes at and even below such ranges. For example, the dynamic range may span at least 3, 4, 5, 6, 7, or more logs. Over this range, biomarkers may be detected down to a level of 100 fM, 50 fM, 25 fM, 10 fM, 1 fM, or lower.

In some embodiments, a film as described herein may be used in conjunction with any of a variety of microscopy techniques, examples of which are described herein. The label selected will depend on the target analyte and detection technique. In some case, the detection method is fluorescence in situ hybridization (FISH). In a typical implementation of this technique, a labeled polynucleotide (a FISH probe) complementary to a sequence of interest is annealed to fixed chromosomes preparations, and the presence of the sequence of interest as well as the chromosomal localization is detected by microscopy. FISH can be performed by immobilizing the nucleic acids of interest on a substrate including without limitation glass, silicon, or fiber. FISH may also be used quantitatively (Q-FISH) to detect the presence and length of repetitive sequences such as telomeres. This may be done by quantitating the intensity of emitted fluorescence as measured by microscopy. FISH assays utilizing the subject fluorescent compounds can be performed for detecting a specific segment of a DNA molecule or a chromosome. These features can be used in genetic counseling (e.g., prenatal-screens), medicine, and species identification. The assay may be performed directly on the film, or on a substrate (e.g. a slide) under which the film is placed to enhance fluorescence for detection.

Also provided herein are methods for sequencing a nucleic acid molecule by using the systems and compositions of the present disclosure. In one embodiments, the methods may comprise: (a) providing a film as provided herein (e.g. silver on gold nanoparticles or gold on gold nanoparticles); (b) hybridizing an oligonucleotide to a target polynucleotide; (c) extending the oligonucleotide with one or more bases complementary to corresponding positions on the target sequence in the direction of extension; and (d) identifying the one or more bases added in step (c) by detecting a fluorescent signal of one or more fluorescent molecules (e.g., fluorophores), wherein intensity of the fluorescent signal is enhanced relative to the fluorescent signal of the fluorescent molecules in the absence of the film. The oligonucleotide can be extended by a polymerase or a ligase. The four bases used for extension may comprise the same or a different type of fluorescent molecules. In some cases, each of the four bases may be associated with a different fluorescent molecule such that incorporation of each type of the bases produces a distinguishable detectable signal. By detecting the fluorescent signal, sequence of the nucleic acid molecule can be determined. In some cases, the film is on a plurality of beads, which may be flowing through or conjugated to a flow cell. Sequencing can be performed by any of a variety of sequencing methods, including next-generation sequencing (NGS) platforms. NGS technology can involve sequencing of clonally amplified DNA templates or single DNA molecules in a massively parallel fashion (e.g. as described in Volkerding et al. Clin Chem 55:641-658 [2009]; Metzker M Nature Rev 11:31-46 [2010]). The next-generation sequencing platform can be a commercially available platform. Commercially available platforms include, e.g., platforms for sequencing-by-synthesis, ion semiconductor sequencing, pyrosequencing, reversible dye terminator sequencing, sequencing by ligation, single-molecule sequencing, sequencing by hybridization, and nanopore sequencing. Platforms for sequencing by synthesis are available from, e.g., Illumina, 454 Life Sciences, Helicos Biosciences, and Qiagen. Illumina platforms can include, e.g., Illumina's Solexa platform, Illumina's Genome Analyzer, and are described in Gudmundsson et al (Nat. Genet. 2009 41:1122-6), Out et al (Hum. Mutat. 2009 30:1703-12) and Turner (Nat. Methods 2009 6:315-6), U.S. Patent Application Pub nos. US20080160580 and US20080286795, U.S. Pat. Nos. 6,306,597, 7,115,400, and 7,232,656. 454 Life Science platforms include, e.g., the GS Flex and GS Junior, and are described in U.S. Pat. No. 7,323,305. Platforms from Helicos Biosciences include the True Single Molecule Sequencing platform. Platforms for ion seminconductor sequencing include, e.g., the Ion Torrent Personal Genome Machine (PGM) and are described in U.S. Pat. No. 7,948,015. Platforms for pryosequencing include the GS Flex 454 system and are described in U.S. Pat. Nos. 7,211,390; 7,244,559; 7,264,929. Platforms and methods for sequencing by ligation include, e.g., the SOLiD sequencing platform and are described in U.S. Pat. No. 5,750,341. Platforms for single-molecule sequencing include the SMRT system from Pacific Bioscience and the Helicos True Single Molecule Sequencing platform.

Exosomes in a sample (e.g. a body fluid, a cell, tissue culture media, or samples derived therefrom) can be captured on a surface (e.g. slides or beads) coated with the fluorescence enhancing films through immobilized exosome specific binding elements, such as antibodies (e.g. anti-CD63, -CD81 and -CD9), and further subjected to a fluorescence based tagging assay. In some embodiments, the tagging assay is for identification and quantitation of protein biomarkers or nucleic acids including DNA and RNA, or assessing signaling pathways or disease states of a subject from which the sample is derived.

Exosomes may be isolated from biological samples, which may include, for example, cell culture media, tissue, fluid, or any samples that may contain exosomes. Non-limiting examples of biological samples include peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. Biological samples may also include samples from the blastocyl cavity, umbilical cord blood, or maternal circulation which may be of fetal or maternal origin. In some cases, the biological sample is a tissue sample or biopsy, from which exosomes may be obtained. For example, if the sample is a solid sample, cells from the sample can be cultured to induce exosome product. In some cases, the sample is ascites fluid from a subject, e.g., ascites fluid from a human subject with ovarian cancer; cell culture media supernatant from a human primary melanoma cell line; cell culture media supernatant from a human primary colon cancer cell line; or murine macrophage, e.g., murine macrophage infected with tuberculosis.

In some cases, exosomes are cancer exosomes. Cancer exosomes may include exosomes obtained or derived from cancer cells and/or tumor cells (primary or cell culture) such as breast cancer, ovarian cancer, lung cancer, colon cancer, hyperplastic polyp, adenoma, colorectal cancer (such as CRC Dukes B or Dukes C-D), high grade dysplasia, low grade dysplasia, prostatic hyperplasia, prostate cancer, melanoma, pancreatic cancer, brain cancer (such as a glioblastoma), hematological malignancy (such as B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma), hepatocellular carcinoma, cervical cancer, endometrial cancer, head and neck cancer, esophageal cancer, gastrointestinal stromal tumor (GIST), renal cell carcinoma (RCC) or gastric cancer. Cancer exosomes may also be derives from a premalignant condition, for example, but not limited to, Barrett's Esophagus.

Cell free polynucleotides (e.g., cell free DNA or cfDNA) from a sample (e.g. a body fluid) can be captured on a surface (e.g. slides or beads) coated with the fluorescence enhancing films through immobilized DNA-specific antibodies (e.g. anti-dsDNA, -ssDNA, and -DNA/RNA complexes) or complementary polynucleotides, and further subjected to a fluorescence based tagging assay for identification and quantitation of cfDNA for assessing the biology or disease states of a subject from which the sample was derived. In general, cell-free polynucleotides are extracellular polynucleotides present in a sample (e.g. a sample from which cells have been removed, a sample that is not subjected to a lysis step, or a sample that is treated to separate cellular polynucleotides from extracellular polynucleotides). For example, cell-free polynucleotides include polynucleotides released into circulation upon death of a cell, and are isolated as cell-free polynucleotides from the plasma fraction of a blood sample.

Cell free polynucleotides may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself. Isolation and extraction of cell free polynucleotides may be performed through collection of bodily fluids using a variety of techniques. In some cases, collection may comprise aspiration of a bodily fluid from a subject using a syringe. In some cases collection may comprise pipetting or direct collection of fluid into a collecting vessel.

After collection of bodily fluid, cell free polynucleotides may be isolated and extracted using a variety of techniques. In some cases, cell free polynucleotides may be isolated, extracted and prepared using commercially available kits such as the Qiagen Qiamp® Circulating Nucleic Acid Kit protocol. In some examples, Qiagen Qubit™ dsDNA HS Assay kit protocol, Agilent™ DNA 1000 kit, or TruSeq™ Sequencing Library Preparation; Low-Throughput (LT) protocol may be used.

Generally, cell free polynucleotides are extracted and isolated by from bodily fluids through a partitioning step in which cell free DNAs, as found in solution, are separated from cells and other non-soluble components of the bodily fluid. Partitioning may include, but is not limited to, techniques such as centrifugation or filtration. In some cases, cells are not partitioned from cell free DNA first, but rather lysed. In this example, the genomic DNA of intact cells is partitioned through selective precipitation. Cell free polynucleotides, including DNA, may remain soluble and may be separated from insoluble genomic DNA and extracted. Generally, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments, one or more, or all, of the steps in a method of detecting a fluorescent signal are automated, such as by use of one or more automated devices. In general, automated devices are devices that are able to operate without human direction—an automated system can perform a function during a period of time after a human has finished taking any action to promote the function, e.g. by entering instructions into a computer, after which the automated device performs one or more steps without further human operation. Software and programs, including code that implements any of the methods disclosed herein, may be stored on some type of data storage media, such as a CD-ROM, DVD-ROM, tape, flash drive, or diskette, or other appropriate computer readable medium, which may be executed by one or more processors, such as may be part of a computer system. Various embodiments of the present invention can also be implemented exclusively in hardware, or in a combination of software and hardware. For example, in one embodiment, rather than a conventional personal computer, a Programmable Logic Controller (PLC) is used. PLCs are frequently used in a variety of process control applications where the expense of a general purpose computer is unnecessary. PLCs may be configured to execute one or a variety of control programs, and are capable of receiving inputs from a user or another device and/or providing outputs to a user or another device, in a manner similar to that of a personal computer. An automated system can include a liquid handler. Examples of liquid handlers include liquid handlers from Perkin-Elmer, Beckman Coulter, Caliper Life Sciences, Tecan, Eppendorf.

A variety of assays and techniques that utilize fluorescence detection will benefit from the methods and compositions of the present disclosure. Examples of such assays include, but are not limited to, microarray detection methods (e.g. of proteins, nucleic acids, and antibodies), gene sequencing, fluorescence in situ hybridization (FISH) assays, immunohistochemical staining (IHC), Fluorescence (Forster) Resonance Energy Transfer (FRET) based imaging, and enzyme-linked immunosorbent assays (ELISA). Due to enhanced signal intensity, detection sensitivity is increased, providing a host of benefits. A typical assay comprises contacting an analyte with a binding element that binds to the analyte. A fluorescent tag is used to detect formation of the complex. This can be done in a number of ways. For example, the binding element may comprise a fluorescent label. A second binding element that binds to the initial binding element and comprising a fluorescent label may alternatively (or additionally) be used. As a further example, a fluorescent label that recognizes the complex may be used, such as a fluorescent DNA intercalator for recognizing binding between a probe polynucleotide and a complementary sample polynucleotide. Regardless of the particular tagging approach, detection of the analyte can be enhanced by detecting the fluorescent signal from the label in proximity to a film of the present disclosure. The film can take a variety of forms, as described herein. In some cases, the film comprises a binding element on a surface of the film, which binding element binds a target analyte, and which binding is subsequently detected by application of a fluorescent tag that binds the complex formed by the binding element and the analyte.

As an illustrative example, a film of the disclosure is disposed on the surface of a substrate. Complexed at discrete locations on a surface of the film are a plurality of different binding elements, such as viral antigens. A sample potentially comprising target analytes that will bind to the binding elements, such as antibodies in the case of binding elements that are antigens, is then applied to the film. If the target analytes are present, these are bound to the binding elements, while the remaining components of the sample are washed away. A label is then applied to the bound analytes. In the case of analytes that are antibodies, the label can be an antibody against a class of antibodies in the sample (e.g. antibodies of a particular isotype) conjugated to a fluorescent tag. A plurality of different labels may also be used (e.g. a different detection antibody for each of a plurality of different antibody isotypes). The resulting complex comprises the target analyte sandwiched between the binding element and the label, all in close proximity to the film. The fluorescent tag is then excited by light at an excitation wavelength, and resulting fluorescent signals are enhanced by proximity to the film. The enhanced fluorescent signal is detected by a photodetector, which is indicative of presence of one or more of the target analytes of the one or more binding elements (and existence of any associated condition(s)). Because the sensitivity of detection is increased (e.g. with ~10-fold higher signal/background ratio), this also increases the confidence that the absence of a signal is indicative of the absence of the analyte, and thus absence of any associated condition. The presence or absence of any of a variety of analytes may be assessed in this manner. Examples of compositions for enhancing fluorescent signals are provided herein, as well as a variety of assays in which these compositions may be advantageously employed.

In one aspect, the disclosure provides a method of detecting and/or distinguishing between different viruses in a sample. In some embodiments, the method comprises measuring a level of one or more antibodies in a sample of a subject (e.g. a blood sample, or blood fraction such as plasma), wherein the one or more antibodies are antibodies against one or more antigens (e.g. 1, 2, 3, 4, 5, or more antigens) of one or more viruses (e.g. 1, 2, 3, 4, 5, 10, or more viruses), and the antibodies are selected from one or more different antibody isotypes (e.g. IgG, IgM, and IgA). Example Zika virus antigens include, but are not limited to, NS1 antigens, viral particles, and recombinant proteins comprising Zika virus antigens. Example Dengue virus antigens include, but are not limited to, Dengue virus 1-4 antigens, viral particles, and recombinant proteins comprising Zika virus antigens. Detecting different antibodies can be performed separately, such as on different samples or different aliquots of a sample. In some embodiments, multiple antibodies (e.g. antibodies to antigens of different viruses, and/or different isotypes) are detected simultaneously (e.g. as in a single reaction). In some embodiments, the method comprises distinguishing between different flaviviruses in a sample. For example, acute infection by Zika virus can be distinguished from infection with Dengue virus. In some embodiments, the method comprises detecting presence or absence of IgG antibodies (and optionally IgM antibodies) against one or more flaviviral antigens in a sample, such as one or more antigens from Zika virus, Dengue virus, West Nile virus, tick-borne encephalitis virus, and yellow fever virus. In some embodiments, the one or more antigens comprise one or more Zika virus antigens, which may optionally be distinguished from one or more other viral infections, such as other flaviviral infections. In some cases, the sample is a sample from a subject obtained within 24 weeks (e.g. within 20 weeks, 15 weeks, 10 weeks, 5 weeks, 4 weeks, 3 weeks, 2 weeks, 1 week, 5 days, 4 days, 3 days, 2 days, or 1 day) of the onset of symptoms of infection in the subject, and/or a sample from a subject that was not previously diagnosed with Zika infection. In some embodiments, the sample is a sample obtained within 4 weeks, or within 1 week of the onset of symptoms. Typical symptoms include one or more of: fever, headache, retro-orbital pain, conjunctivitis, a maculopapular rash, myalgias, and arthralgias. In some embodiments, the method comprises identifying whether or not the subject has a Zika virus infection based on the detecting. In some embodiments, the subject is identified as having a Zika virus infection (and optionally, not having a Dengue virus infection) if the level of IgG binding a Zika virus antigen is above a threshold level. In some embodiments, the subject is diagnosed as having a Zika virus infection (and optionally, not having a Dengue virus infection) if the level of IgG binding a Zika virus antigen is above a threshold level and the level of IgM binding a Zika virus antigen is above a threshold level. The threshold levels for antibodies binding a Zika virus antigen may be set at a level that is statistically significantly higher than that observed for samples having a Dengue virus infection without a Zika virus infection. In some embodiments, the subject is diagnosed as having a Zika virus infection (and optionally, not a Dengue virus infection) if the level of IgG binding a Zika virus antigen is above a threshold level and the level of IgG binding a Dengue virus antigen is above a threshold level. In some embodiments, the method comprises (a) measuring, in a sample of a subject, levels of IgG against a Zika virus antigen, IgM against a Zika virus antigen, IgG against a Dengue virus antigen, and IgM against Dengue virus antigen, and (b) identifying whether the subject has an infection based on the levels measured in (a), wherein the infection is selected from: (i) Zika virus and not Dengue virus, (ii) Dengue virus and not Zika virus, or (iii) Zika virus and Dengue Virus. Identifying whether there is an infection may take place within 24 weeks (e.g. within 20 weeks, 15 weeks, 10 weeks, 5 weeks, 4 weeks, 3 weeks, 2 weeks, 1 week, 5 days, 4 days, 3 days, 2 days, or 1 day) of the onset of symptoms of infection in the subject. In some cases, the subject has no history of diagnosis with Zika virus infection and/or Dengue virus infection. In some embodiments, presence or absence of the IgG and IgM antibodies against Zika virus and Dengue virus are all detected simultaneously as part of a multiplex assay. Alternatively, the target antibodies may be detected separately or in various other combinations. Various methods and compositions for the detection of binding elements, such as antibodies, are provided herein. In some embodiments, detection comprises use of a film comprising raised nanostructures on a substrate to enhance a detection signal, in accordance with any of the various aspects of the disclosure. In some embodiments, assays do not use a film comprising raised nanostructures on a substrate. Examples of assays for the detection of antibodies include ELISA and other antibody-capture assays (e.g. sandwich assays on beads, as in assays provided by Luminex), chemiluminescence assays, bead-based fluorescence assays, and electro-chemical luminescence assays. In an example assay, one or more antigens are provided on a solid substrate, the solid substrate is reacted with a test sample potentially comprising antibodies to the antigen (sample antibodies), and then a secondary antibody comprising a detectable label is added, wherein the secondary antibody specifically binds a selected type of sample antibody (e.g. a human antibody of a particular isotype). The resulting signal can then be compared to an internal standard, and/or a reference level (e.g. a threshold level, above which is diagnostic of an infection). In some embodiments, medical action is selected, and optionally taken, based on the results of a method described herein. For example, if Zika infection is detected, contraceptive measures may be prescribed to avoid negative impacts of Zika infection on a potential fetus. For assays involving a threshold for positive diagnosis, a subject may be diagnosed as not suffering from the indicated infection if a signal (or combination of signals) is below the indicated threshold(s).

Film Fabrication

In one aspect, the disclosure provides methods for preparing a film on the substrates described herein. In certain embodiments, the method comprises the steps of: (a) adsorbing nanoparticle seeds, such as gold nanoparticle seeds, on a substrate, or growing nanoparticle seeds in a solution or vapor phase on a substrate; and (b) growing nanostructures, such as silver nanostructures, around the nanoparticle seeds. The nanoparticles seeds and the nanostructures grown around the nanoparticle seeds can be made of various types of materials, for example, small molecules, chemical compounds, polymers or metals. The substrate may or may not be treated or modified prior to the seeding process. An example method for preparing the film of the present disclosure may comprise: (a) applying to a substrate a first solution containing metal ions; (b) precipitating the metal ions from the solution onto the substrate using a basic solution; (c) reducing the metal ions precipitated onto the substrate in step (b) to produce seed particles on the substrate; and (d) adding a second solution comprising metal ions to the seed particles from step (c) to grow isolated areas in a film. As discussed elsewhere herein, the film can be continuous, quasi-continuous or discontinuous. Once the film is prepared, in some cases, an array of biological or chemical molecules used as capture agents or binding elements that can specifically bind to one or more analytes may be applied to the film. The array of molecules may be disposed as different molecular species at discrete locations on the film and coupled to the film, whereby fluorescent signals produced by the capturing events between the binding elements and the analytes can be enhanced by the film. As will be appreciated, the first and the second solutions of metal ions may comprise the same type of metal, or different types of metals to form a metallic composite. For example, in some cases, the first solution comprises a plurality of Au ions and therefore Au(0) seed particles are produced on a substrate. The second solution provided may comprise Au or Ag ions, which may grow Au or Ag nanostructures around Au(0) seeds. Depending on the inter-connectivity of produced nanostructures, a continuous, discontinuous, or quasi-continuous Ag/Au or Au/Au film may be fabricated.

Height or thickness of a film may vary. In some cases, the height of the film is less than or equal to about 5,000 nm, 4,000 nm, 3,000 nm, 2,000 nm, 1,000 nm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 9 nm, 8 nm, 7 nm, 6 nm, 5 nm, 4 nm, 3 nm, 2 nm, 1 nm, 0.5 nm, 0.1 nm, 0.05 nm, 0.01 nm, 0.005 nm, or 0.001 nm. In some cases, the height of the film may be greater than or equal to about 0.0001 nm, 0.00025 nm, 0.0005 nm, 0.00075 nm, 0.001 nm, 0.0025 nm, 0.005 nm, 0.0075 nm, 0.01 nm, 0.025 nm, 0.05 nm, 0.075 nm, 0.1 nm, 0.25 nm, 0.5 nm, 0.75 nm, 1 nm, 2 nm, 3 nm, 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 200 nm, 300 nm, 400 nm, 500 nm, 600 nm, 700 nm, 800 nm, 900 nm, 1,000 nm, 1,500 nm, 2,000 nm, 2,500 nm, or 3,000 nm. In some cases, the height of the film may be selected from a range of two values described herein, for example, from about 5 nm to about 500 nm, from about 5 nm to about 300 nm, from about 5 nm to about 200 nm, or from about 5 nm to about 100 nm.

With a film of the present disclosure, fluorescent signals produced within a certain distance of the surface of the film may be enhanced, with enhancement factor varying as a function of a number of factors including such distance. The fluorescent signals may be in the range of about 400 nm to about 2100 nm. Other non-limiting examples of factors that may influence the enhancement factor of a fluorescent signal may include film characteristics and/or features (film thickness, gap size, size of raised nanostructures, type of substrate, shape of substrate, roughness of film surface, roughness of substrate surface), type of fluorescent molecules, light source, or combinations thereof. For example, given a certain film, the fluorescent signal may be enhanced for fluorophores within 1,000 nm of the surface of the film. In some examples, the fluorophore is a near-infra-red fluorophore having an emission of about 700 nm to about 800 nm, and the intensity of the fluorescent signal is enhanced by at least 30-fold. In some examples, the fluorophore is a visible dye having an emission of about 400 nm to about 700 nm, and the intensity of the fluorescent signal is enhanced by at least about 3-fold.

In cases where seed particles are prepared by precipitation out of solution of metal ions, the seeding density may be varied by tuning the initial concentration and/or pH values of the solution. The seeding density may in turn determine the film density and morphology (e.g., gap size, interparticle spacing, nanoparticle sizes etc.). In some cases, a high seeding density may be required. In some cases, a low seeding density may be preferred. In some cases, the seeding density may be less than or equal to about $1\times10^9$ seeds/mm$^2$, $5\times10^8$ seeds/mm$^2$, $1\times10^8$ seeds/mm$^2$, $5\times10^7$ seeds/mm$^2$, $2.5\times10^7$ seeds/mm$^2$, $1\times10^7$ seeds/mm$^2$, $5\times10^6$ seeds/mm$^2$, $1\times10^6$ seeds/mm$^2$, $5\times10^5$ seeds/mm$^2$, $1\times10^5$ seeds/mm$^2$, $5\times10^4$ seeds/mm$^2$ or $1\times10^4$ seeds/mm$^2$. In some cases, the seeding density may be greater than or equal to about $1\times10^4$ seeds/mm$^2$, $5\times10^4$ seeds/mm$^2$, $1\times10^5$ seeds/mm$^2$, $5\times10^5$ seeds/mm$^2$, $1\times10^6$ seeds/mm$^2$, $5\times10^6$ seeds/mm$^2$, $1\times10^7$ seeds/mm$^2$, $5\times10^7$ seeds/mm$^2$, $1\times10^8$ seeds/mm$^2$, $5\times10^8$ seeds/mm$^2$, $1\times10^9$ seeds/mm$^2$ or $5\times10^9$ seeds/mm$^2$. In some cases, the seeding density may be between any of the two values described herein, for example, about $4.3\times10^7$ seeds/mm$^2$.

In some embodiments, the methods and materials employ solution phase growth of plasmonic discontinuous silver on gold (dAg/Au) and continuous silver on gold (cAg/Au) films in a method that begins with rapid, in situ "seeding" of gold nanoparticles by deposition/precipitation of Au$^{3+}$ ions onto unmodified surfaces, followed by solution-phase reduction of the ions to Au$^0$. For Ag/Au structures, subsequent to the reduction step, the gold seeds are grown into a film by the glucose reduction of Ag$^{1+}$ and the resulting films with different degrees of growth are referred to as continuous silver-on-gold (cAg/Au) or discontinuous silver-on-gold (dAg/Au) films. In some embodiments, this involves a three step process in the preparation of the present nanoscopic cAg/Au and dAg/Au films:

(1) seeding of gold onto a substrate by precipitation out of solution of Au$^{3+}$ ions. The ions are precipitated from HAuCl$_4$ by raising its pH with a nitrogenous base, such as with NH$_4$OH, urea, etc;

(2) reducing the ions precipitated in step (1) to Au$^0$ clusters on the substrate by a reducing agent such as Hydrazine, NaBH$_4$, heat, H2, or photo-reduction; and (3) growing seeds from step (2) by selectively adding silver to the initial seeds by reduction of an Ag$^{1+}$ halide in a second solution to form nanoplates and raised structures. This can be done by a reducing agent such as photo-reduction, D-glucose, or ultrasound treatment in a hydrogen enriched atmosphere. Typically, the silver in step (3) only attaches to the previously deposited seeds, leading to the so-called "cAg/Au" and "dAg/Au" construction.

The initial seeding (precipitation) step can be carried out on a variety of substrates by immersing the substrate in the ionic gold solution. The substrate does not need to be but can be pretreated in any way to increase gold adhesion. The ionic concentration of the gold salt is selected to control the size and spacing of the "seeds." Without wishing to be bound by theory, it is believed that the final size of and distance between nanoplates affects the fluorescent enhancement properties of the substrate and can be optimized to maximize fluorescence enhancement in the visible and near-infrared region. As described below, near infrared fluorescence from an infrared fluorophore (IRDye800) was increased 10-200 fold by controlling the cAg/Au nano-nanoplates size to be on the order of hundreds of nanometers spaced at several to tens of nanometer gaps. As described below, visible fluorescence from a visible fluorophore (Cy5) and a near-infrared fluorophore (IRDye800) were increased between 2-100-fold as compared with bare glass substrates by controlling the cAg/Au raised nanostructure size to have average feature width between 5 nm to 100 nm and gap width of 1 to 20 nm.

As the uniformity and morphology of the film as described herein can be easily tuned, assays or methods utilizing the film to capture or detect fluorescent signals can be highly multiplexed. Different types of capture agents (or binding elements) can be deposited on different locations of the film, wherein each location may have different morphology or properties (e.g., size, shape and density of nanostructures, gap size, roughness of the surface of the film etc.). It can enable multiplexed detection of up to hundreds or thousands of analytes (e.g., cytokines or other proteins) in an array with substantially lower limit of detection (e.g., down to about 0.01 pg/mL (~1-10 fM) minimum detectable concentration), with high sensitivity, specificity and signal-to-noise ratio. Different fluorescent molecules with non-overlapping emission wavelengths can be used in the same assay to label different classes of analytes (e.g., proteins or antibodies) to achieve multi-color differentiation of subtypes of analytes such as IgG, IgM, IgA in the same assay. For example, the film can be utilized to build multi-color microarrays capable of measuring different sub-types of antibodies with low and high abundances in human serum, with the maximally enhanced fluorophore for reporting the least abundant molecule.

As provided herein, the ratio of the signal to the noise (e.g., ratio of their amplitudes) can be any suitably high value (i.e., suitably high to achieve a certain accuracy). For example, the signal to noise ratio may be at least about 2 to 1, about 3 to 1, about 4 to 1, about 5 to 1, about 6 to 1, about 7 to 1, about 8 to 1, about 9 to 1, about 10 to 1, about 100 to 1, about 1,000 to 1, about 10,000 to one, or more.

Reduction of ions contained in the first and/or the second solutions may be achieved by various methods, for example, via thermal- or photo-induced reduction, or with the aid of chemical reagents such as reducing agents. Non-limiting examples of reducing agents may include Ascorbic acid, Hydrazine, Hydroxylamine, Ammonium or sodium borohydrate, Formic acid, D-glucose, a hydrogen gas atmosphere, Lithium aluminum hydride (LiAlH$_4$), Nascent (atomic) hydrogen, Sodium amalgam, Diborane, Sodium borohydride (NaBH$_4$), Compounds containing the Sn$^{2+}$ ion, such as tin(II) chloride, Sulfite compounds, Hydrazine (Wolff-Kishner reduction), Zinc-mercury amalgam (Zn(Hg)) (Clemmensen reduction), Diisobutylaluminum hydride (DIBAL-H), Lindlar catalyst, Oxalic acid (C$_2$H$_2$O$_4$), Phosphites, hypophosphites, and phosphorous acid, Dithiothreitol (DTT)—used in biochemistry labs to avoid S—S bonds, Compounds containing the Fe2+ ion, such as iron(II) sulfate, Carbon monoxide (CO), Carbon (C), Tris(2-carboxyethyl) phosphine HCl (TCEP), or combinations thereof.

Kits

In certain aspects, the disclosure provides a kit for detecting viral infections in a subject. In some embodiments, the kit comprises a substrate with a binding element, e.g. an antibody or antigen. In certain embodiments, the substrate may be selected from a plasmonic substrate for signal amplification. The kit may additionally comprise instructions for using the kit to assay for the presence of an infection in the subject. The substrate may comprise one or more slides comprising one or more wells. The one or more wells may comprise identical ZIKV and DENV antigen arrays.

In certain embodiments, the kit comprises one or more viral antigens, wherein the viral antigens may be immobilized on a substrate. The one or more viral antigens may be selected from flaviviral antigens or alphaviral antigens. The one or more viral antigens can be selected from a Zika virus antigen, Dengue virus antigen, yellow fever virus antigen, tick-borne encephalitis virus antigen, Japanese Encephalitis virus (JEV), West Nile virus antigen, mayaro virus antigen, and Chikungunya virus antigen. The one or more viral antigens can be selected from a Zika virus antigen and a Dengue virus antigen. The Zika virus antigen may be a recombinant Zika viral antigen. The recombinant Zika viral antigen can be a Zika virus NS1 protein or Zika virus NS5 protein. The recombinant Zika viral antigen may be Uganda MR 766 and Suriname Z1106033. In certain embodiments, the kit further comprises a protein denaturing agent. The protein denaturing agent can be selected from urea, formamide, guanidine, sodium salicylate, dimethyl sulfoxide, propylene glycol, and combinations thereof. The protein denaturing agent may comprise urea.

In other embodiments, the kit comprises one or more detectable labels associated with an antihuman IgA or an antihuman IgG antibody. The kit may further comprise additional components such as diluent buffers, washing buffers, a calibrator, a positive control, a negative control, an IR fluorescence scanner, a slide holder, incubation chambers, deionized water, a vortex, pipettes, centrifuge tubes, well plates, a reagent reservoir, and vials. Incubation chambers may have at least about 6 wells, at least about 8 wells, at least about 10 wells, at least about 12 wells, at least about 14 wells, at least about 16 wells, at least about 18 wells, at least about 20 wells, at least about 40 wells, at least about 60 wells, or at least about 80 wells. The pipettes may be a single channel or multichannel pipette. The multichannel pipette can hold at least about 1 µL, at least about 2 µL, at least about 3 µL, at least about 4 µL, at least about 5 µL, at least about 6 µL, at least about 7 µL, at least about 8 µL, at least about 9 µL, at least about 10 µL, at least about 20 µL, at least about 30 µL, at least about 40 µL, at least about 50 µL, at least about 60 µL, at least about 70 µL, at least about 80 µL, at least about 90 µL, at least about 100 µL, at least about 150 µL, at least about 200 µL, at least about 250 µL, or at least about 300 µL of sample. The glass vial may hold at least about at least about 1 mL, at least about 5 mL, at least about 10 mL, at least about 20 mL, at least about 30 mL, or at least about 40 mL of a sample mixture. The well plates may be 96 well plates, 384 well plates, or 1536 well plates.

The plasmonic substrate of a kit described herein may be any plasmonic substrate described herein or incorporated herein by reference. The kit may be stable when stored at most at about 8° C., 4° C., 0° C., −2° C., −4° C., −6° C., −8° C., −10° C., −20° C., or −40° C. For example, the kit may be stored at 4° C. (or −20° C.) for at least about 1 day, 1 week, 2 weeks, 1 month, 2 months, 4 months, 6 months. Accelerated stability test may also be performed, which may factor in exaggerated environmental conditions e.g. light, temperature, humidity.

EXAMPLES

The following examples are given for the purpose of illustrating various embodiments in accordance with the disclosure and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Multiplexed Assay of Zika and Dengue IgG and IgM Isotypes for Diagnosis of Zika Infection Zika virus (ZIKV) and Dengue virus (DENV) are mosquito-borne flaviviruses that co-circulate throughout much of the tropical and subtropical Western Hemisphere. ZIKV was once an obscure mosquito-borne flavivirus that caused only sporadic human infections in Africa and Southeast Asia. Following an outbreak on the Yap Islands, Micronesia in 2007, ZIKV spread across the islands of the Pacific and into the Western Hemisphere, emerging in Brazil in 2015. ZIKV now co-circulates with DENV and chikungunya virus throughout the tropical and subtropical Americas. Perhaps most significantly, ZIKV infection during pregnancy has been linked to microcephaly and severe birth defects, drawing much attention to ZIKV diagnostics and the importance of distinguishing ZIKV from DENV infection.

The clinical presentation of symptomatic patients with acute ZIKV infection typically includes a combination of fever, headache, retro-orbital pain, conjunctivitis, a maculopapular rash, myalgias and arthralgias. However, based on clinical criteria alone, ZIKV is difficult to be reliably distinguished from infection with other pathogens that cause an undifferentiated systemic febrile illness. Patients with Zika fever may be suspected of having dengue or a mild presentation of chikungunya. This overlap in clinical presentations and the potential for severe fetal outcomes, including congenital neurologic malformations and fetal demise, and non-fetal manifestations, such as Guillain-Barré syndrome, underscore the importance of accurate ZIKV diagnostics.

The pGOLD Zika and Dengue IgG Assay for clinical use can provide a rapid diagnostic method for patients, which enables faster intervention. True positive test results may provide support for the diagnosis of a Zika virus infection. The results can be used in conjunction with clinical and epidemiological information to guide patient management. In pregnant women, a positive Zika result for the test benefits the patient and fetus may indicate the need for further ultrasound monitoring for birth defects such as microcephaly. In men, identification of a potential recent Zika infection can allow intervention to prevent sexual transmission to pregnant partners.

Multiplexed flavivirus antibody test over an array of viral antigens on a chip was developed for simultaneous detection and quantification of IgG and IgM isotypes of Zika and Dengue viruses. It was first confirmed that the multiplexed assay on pGOLD chip gives consistent results of Dengue IgG and IgM assay data from FDA approved commercial kits (compare FIGS. 1A-1B and FIGS. 2A-2B). The pattern of antibody binding signals (e.g., fluorescence on the IgG and IgM specific secondary antibodies in the current case) over the antigen array can be used for differentiating each specific flavivirus infection and diagnosing acute/chronic infection.

Build of Biochip:

A protein microarray chip was built on plasmonic gold substrate through microarray printing. There were 14-16 identical microarrays on each plasmonic gold substrate (25 mm×75 mm surface dimension, with 1 mm thickness). Each microarray comprised 3 spots of Zika NS1 antigen (the Native Antigen Company, UK), 9 spots of Dengue antigen (3 types, 3 spots for each type, from Microbix Biosystems Inc. Canada), and 12 control spots composed of human IgG/M mixture. The microarray spots had a diameter of 300-700 microns.

Capture of Human IgG/IgM Antibodies:

The biochip was integrated in a module where each of the microarrays was separated from the others, and could be used to capture human IgG/IgM antibody for one specimen. Human specimens were diluted in biological medium and applied to a microarray, where IgG/IgM antibodies against Zika or Dengue antigen (if present) would be captured on corresponding Zika/Dengue antigens, through specific antigen-antibody interaction. Non-specific proteins in the human specimen were washed away through a washing step.

Labeling of Human IgG/IgM Antibodies with Near-Infrared Fluorophores:

Following the washing step, a mixture of anti-human IgG and anti-human IgM (Vector Laboratories, US) secondary antibodies, each labeled with a specific near-infrared fluorophore, with non-overlapping emission spectra, was applied to each microarray to label the captured human IgG/IgM antibodies (if present) specific to each antigen. Specifically, anti-human IgG was labeled with IRdye680 (LI-COR, US) and anti-human IgM was labeled with IRdye800 (LI-COR, US). Unbound fluorophore conjugated secondary antibodies were washed away through a washing step.

Data Readout and Analysis:

The fluorophore labeled biochips was scanned with a near-infrared fluorescence scanner specific for the two fluorophores. Average fluorescence intensity of the 3 spots of each antigen for each microarray was measured and calculated to reflect the abundance of IgG/IgM of each specimen against the antigen. The intensity was normalized to standards to give normalized abundance of IgG/IgM antibodies against each antigen for each specimen.

Figure 3B:
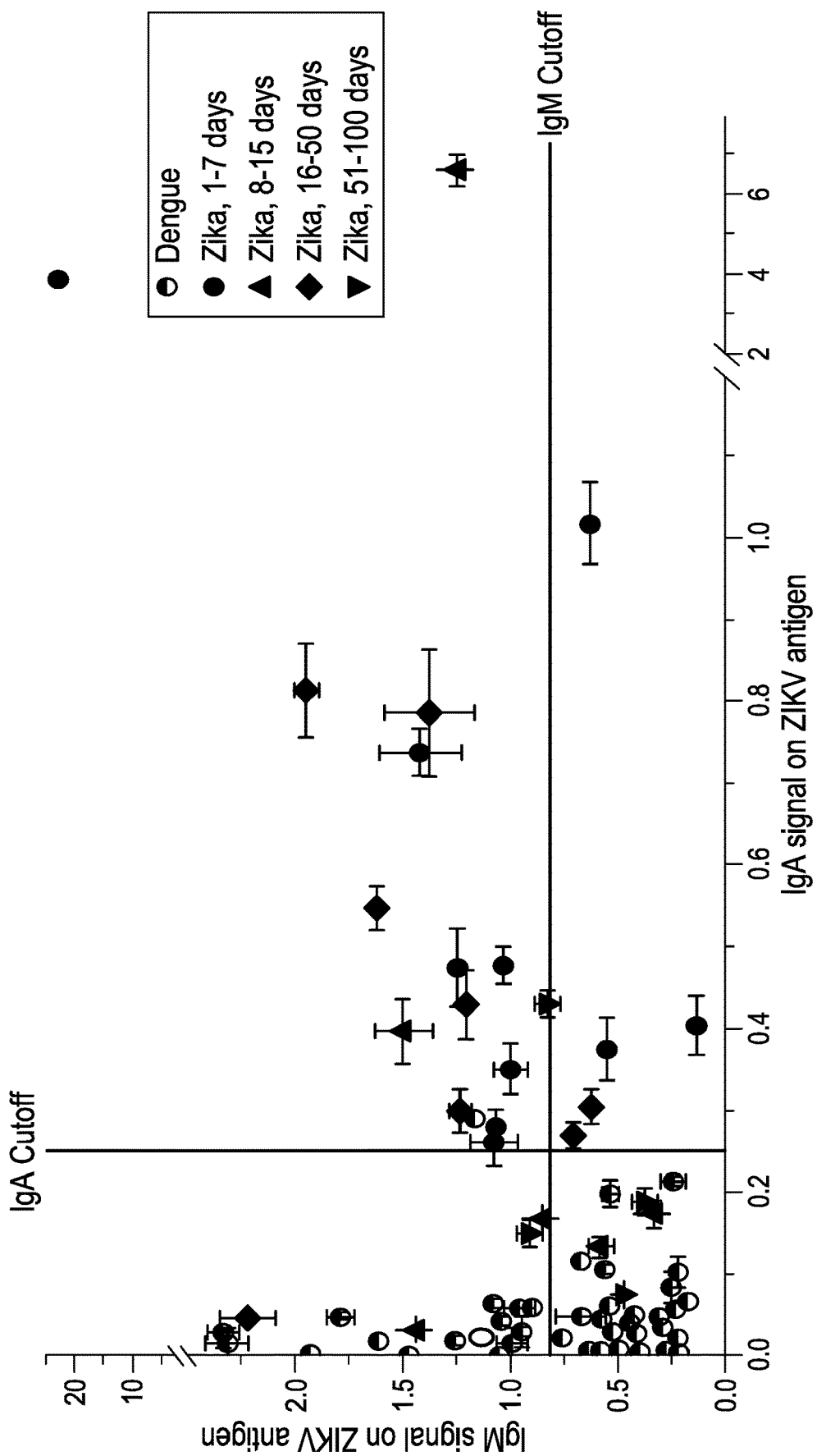
FIG. 3B shows an example 2D plot (panel A) for IgG/IgA antibody level against ZIKV antigen, for serum samples with ZIKV infection and DENV infection, and an example 2D plot (panel B) for IgA/IgM antibody level against ZIKV antigen, for serum samples with ZIKV infection and DENV infection. In panel (A), one sample with ZIKV infection positive for ZIKV IgA and negative for ZIKV IgG is shown as an empty circle. In both plots, ZIKV infected samples were differentiated into 4 subgroups based on the number of days between the onset of illness and sample collection (filled circle-1-7 days; point-up triangle-8-15 days; diamond-16-50 days; point-down triangle-51-100 days). All signal levels are normalized by reference samples.
Figure 4A:
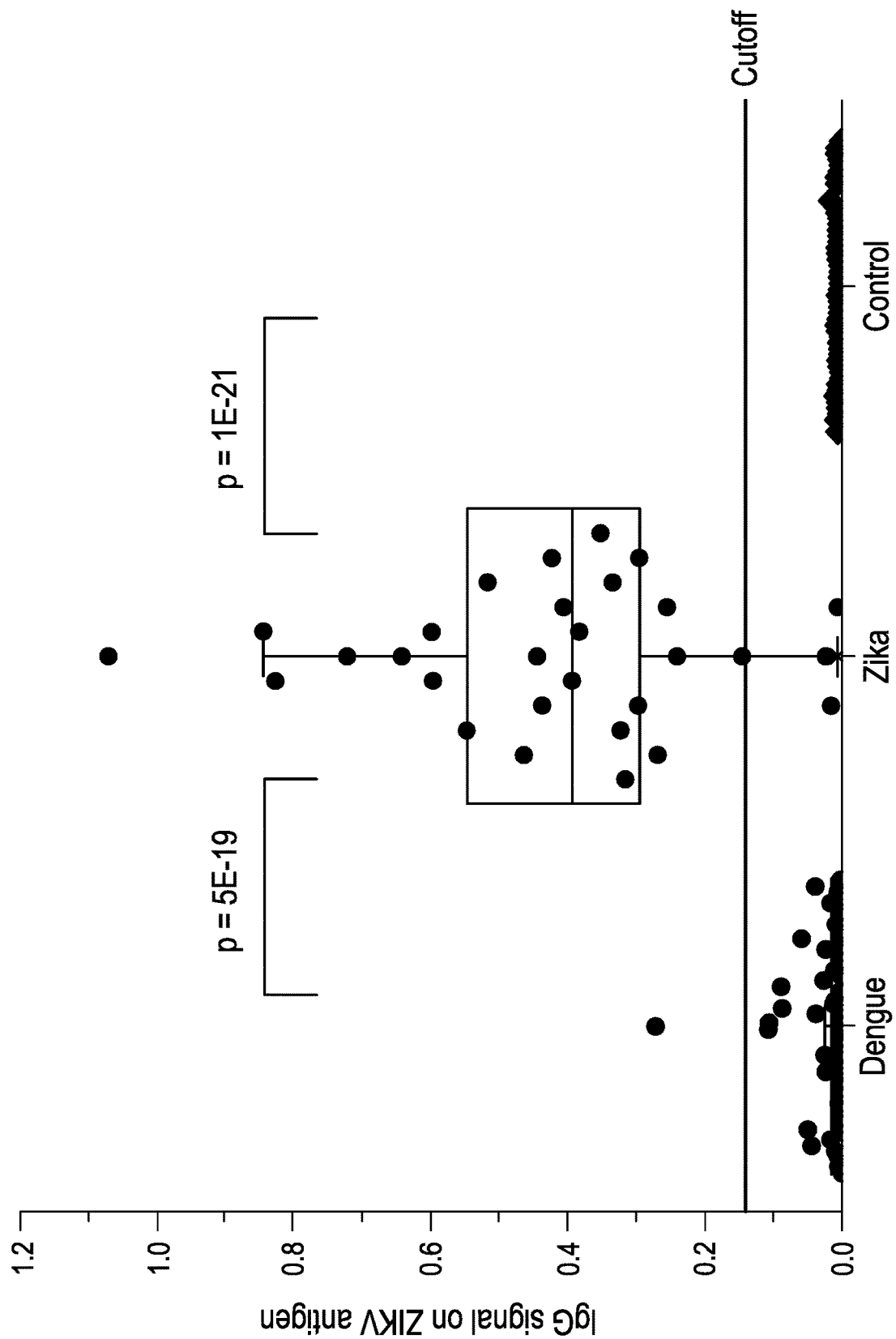
FIG. 4 shows example box plots (A-C) for ZIKV IgG, IgM and IgA antibody levels for samples with Dengue infection, Zika infection, or no known flavivirus infection (control), (filled circle-1-7 days; point-up triangle-8-15 days; diamond-16-50 days; point-down triangle-51-100 days). In panel (A), the illustrated cutoff for IgG signal on ZIKV antigen represents 3 standard deviations (SD) above the mean ZIKV IgG level detected for DENV infected samples. In panel (B), the illustrated "Cutoff" for IgM signal on ZIKV antigen represents 3 standard deviations (SD) above the mean ZIKV IgM level detected for the control samples. In panel (C), the illustrated "Cutoff" for IgA signal on ZIKV antigen represents 3 standard deviations (SD) above the mean ZIKV IgA level detected for the control samples. All signal levels are normalized by reference samples
Figure 4B:
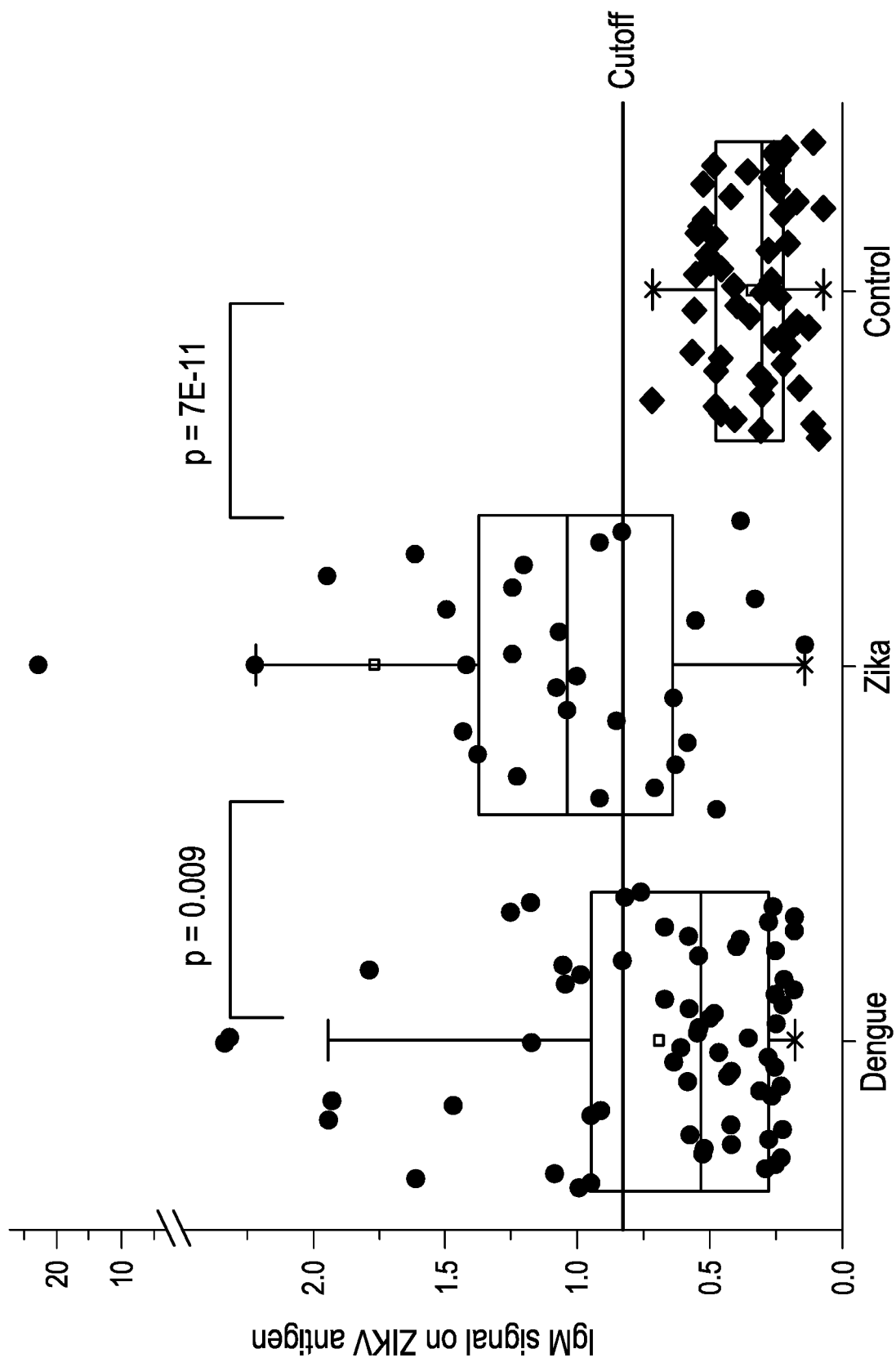
Figure 4C:
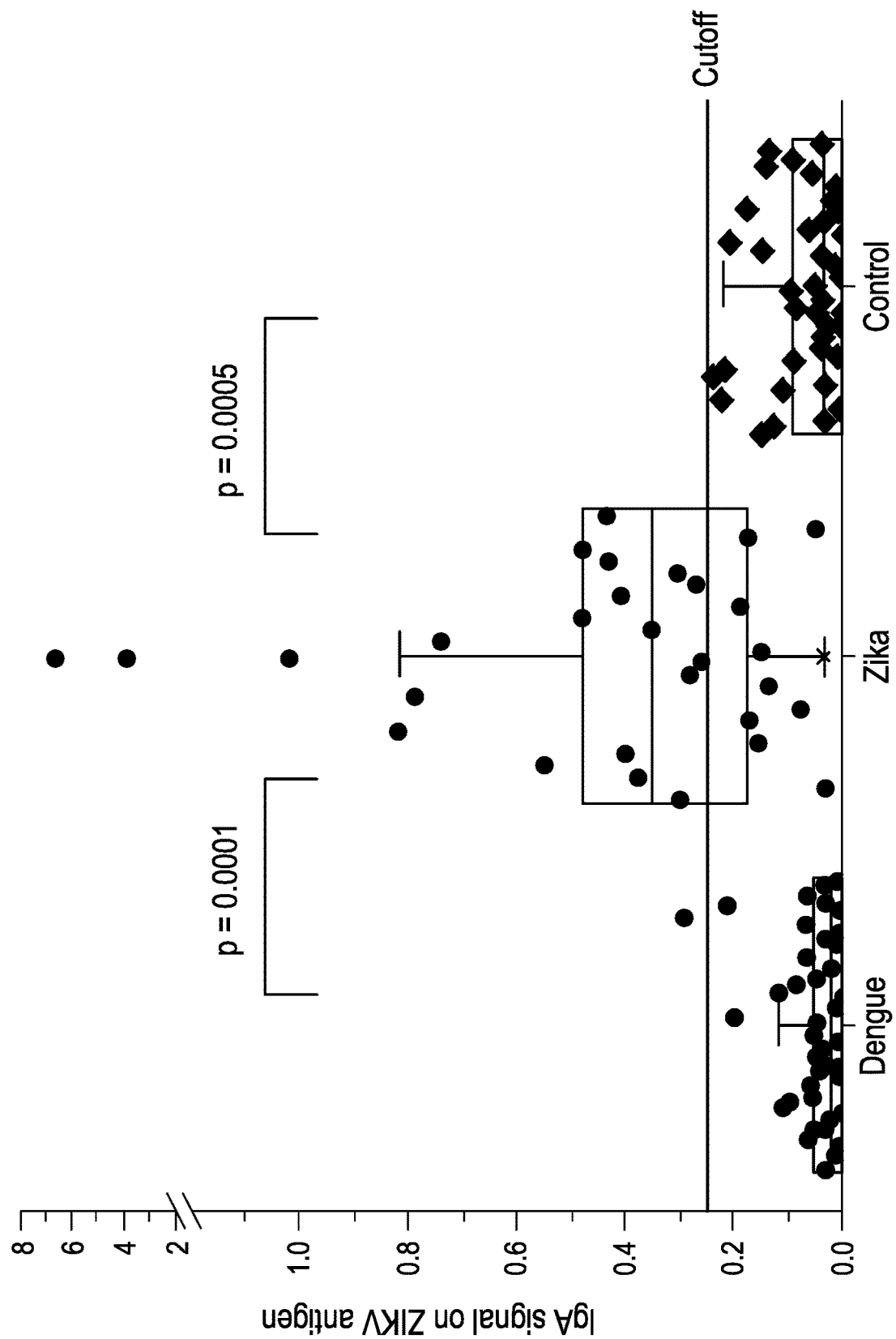
Figure 5:
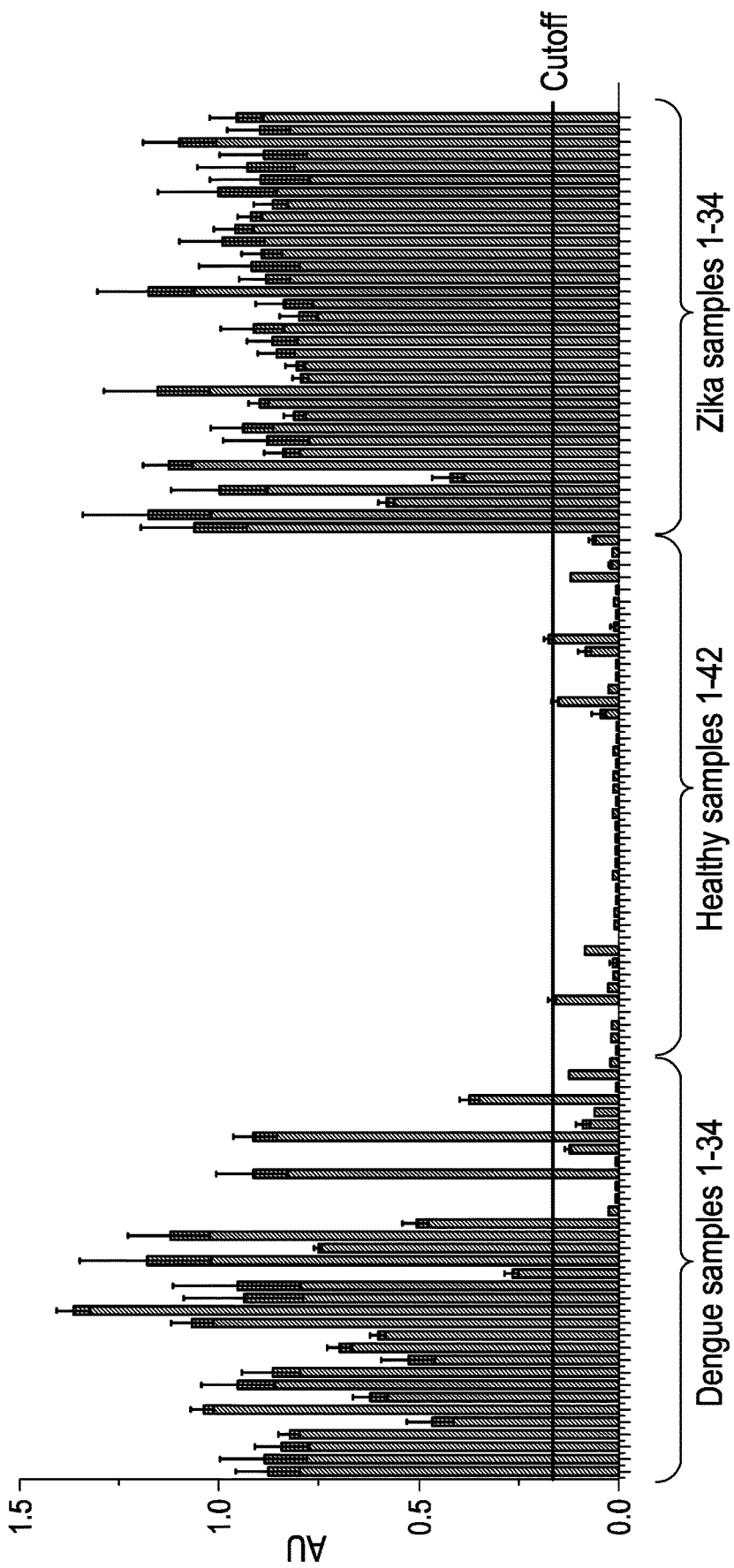
FIG. 5 shows an example bar chart for Dengue IgG antibody levels detected on a plasmonic gold substrate (pGOLD) in accordance with an embodiment, for specimens with Dengue infection, Zika infection, or no known flavivirus infection (healthy control). Antibody signals were detected using Dengue 2 antigen.
Figure 6:
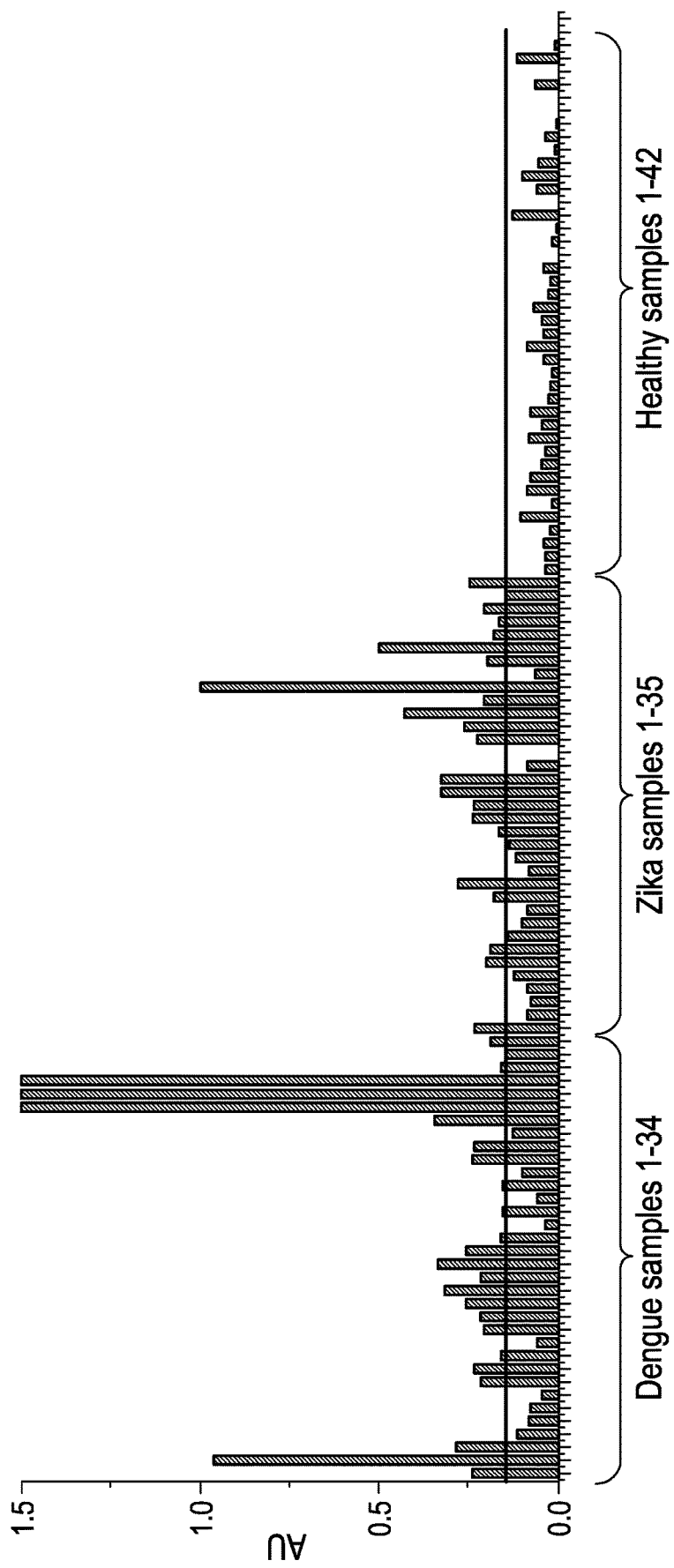
FIG. 6 shows an example bar chart for Dengue IgM antibody levels detected on plasmonic gold substrate (pGOLD) in accordance with an embodiment, for specimens with Dengue infection, Zika infection, or no known flavivirus infection (healthy control).
Figure 7A:
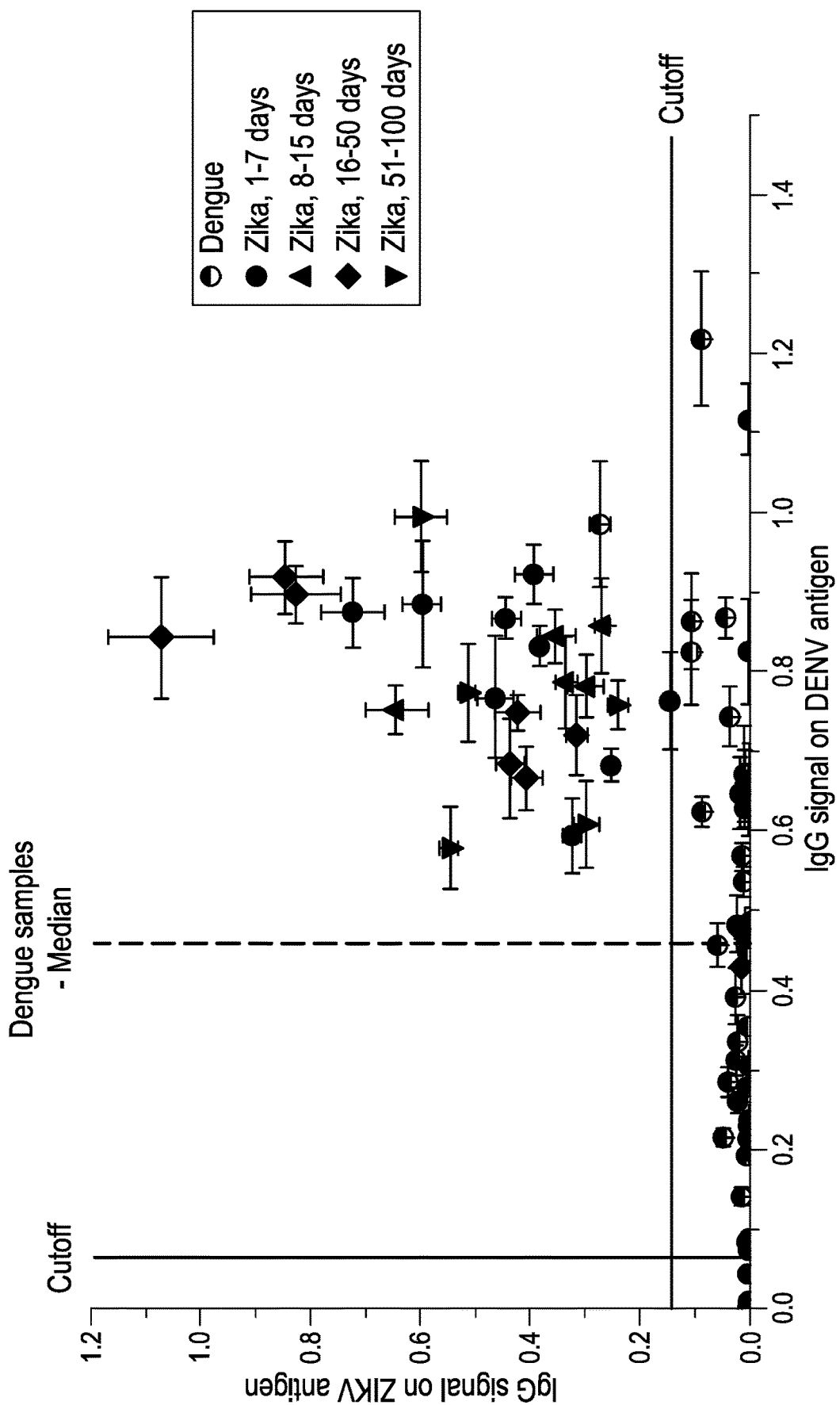
FIG. 7A-C shows example 2D plots of assay results. Panel A shows IgG antibody levels against ZIKV antigen and DENV2 antigen for samples with ZIKV infection or DENV infection. Panel B shows IgA antibody levels against ZIKV antigen and DENV2 antigen for samples with ZIKV infection or DENV infection. Panel C shows IgA/IgM antibody levels against DENV2 antigen for serum samples with ZIKV infection or DENV infection. In all plots, ZIKV infected samples were differentiated into 4 subgroups based on the number of days between the onset of illness and sample collection (filled circle—1-7 days; point-up triangle—8-15 days; diamond—16-50 days; point-down triangle—51-100 days). All signal levels are normalized by reference samples.
Figure 7B:
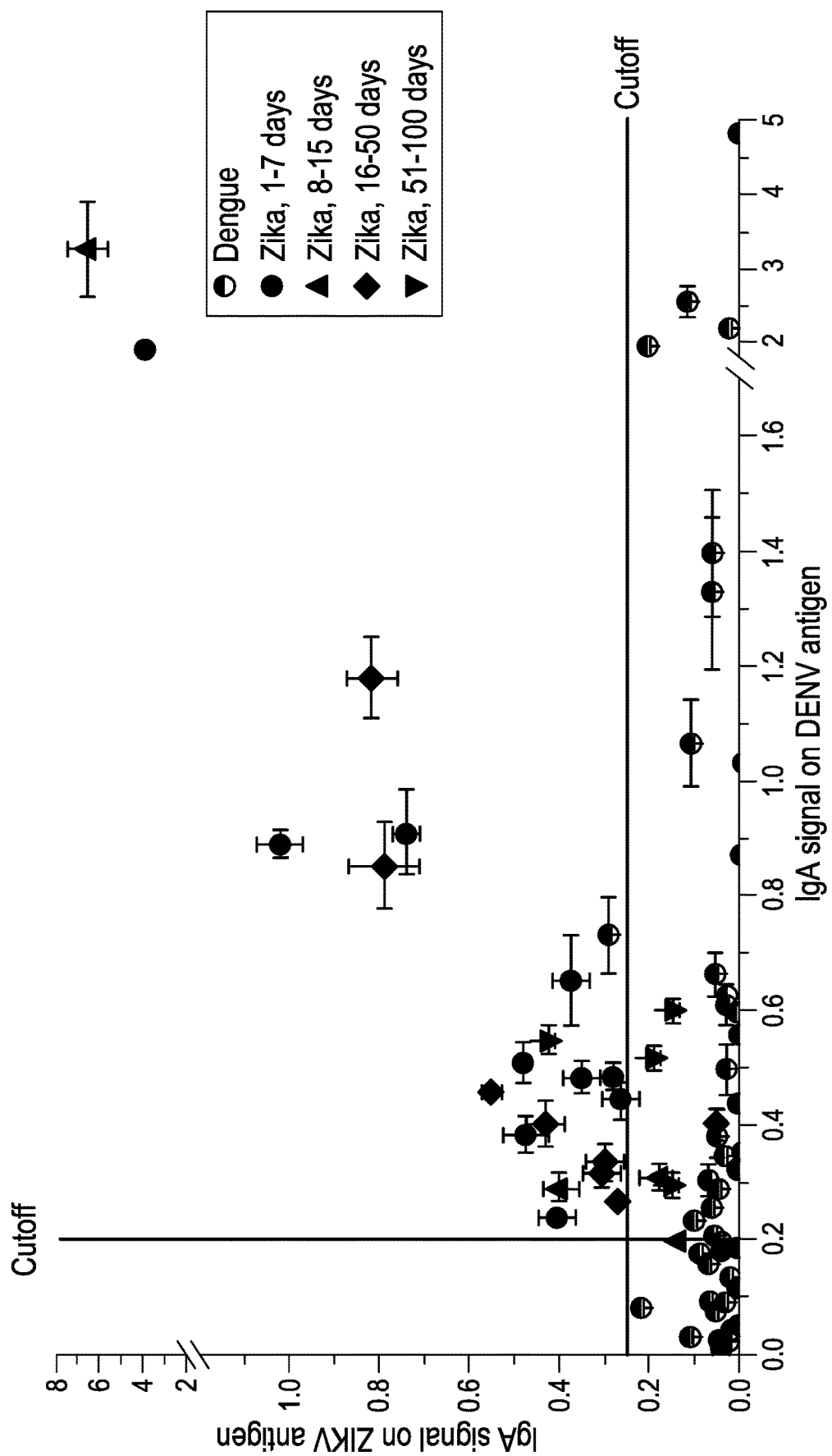
Figure 7C:
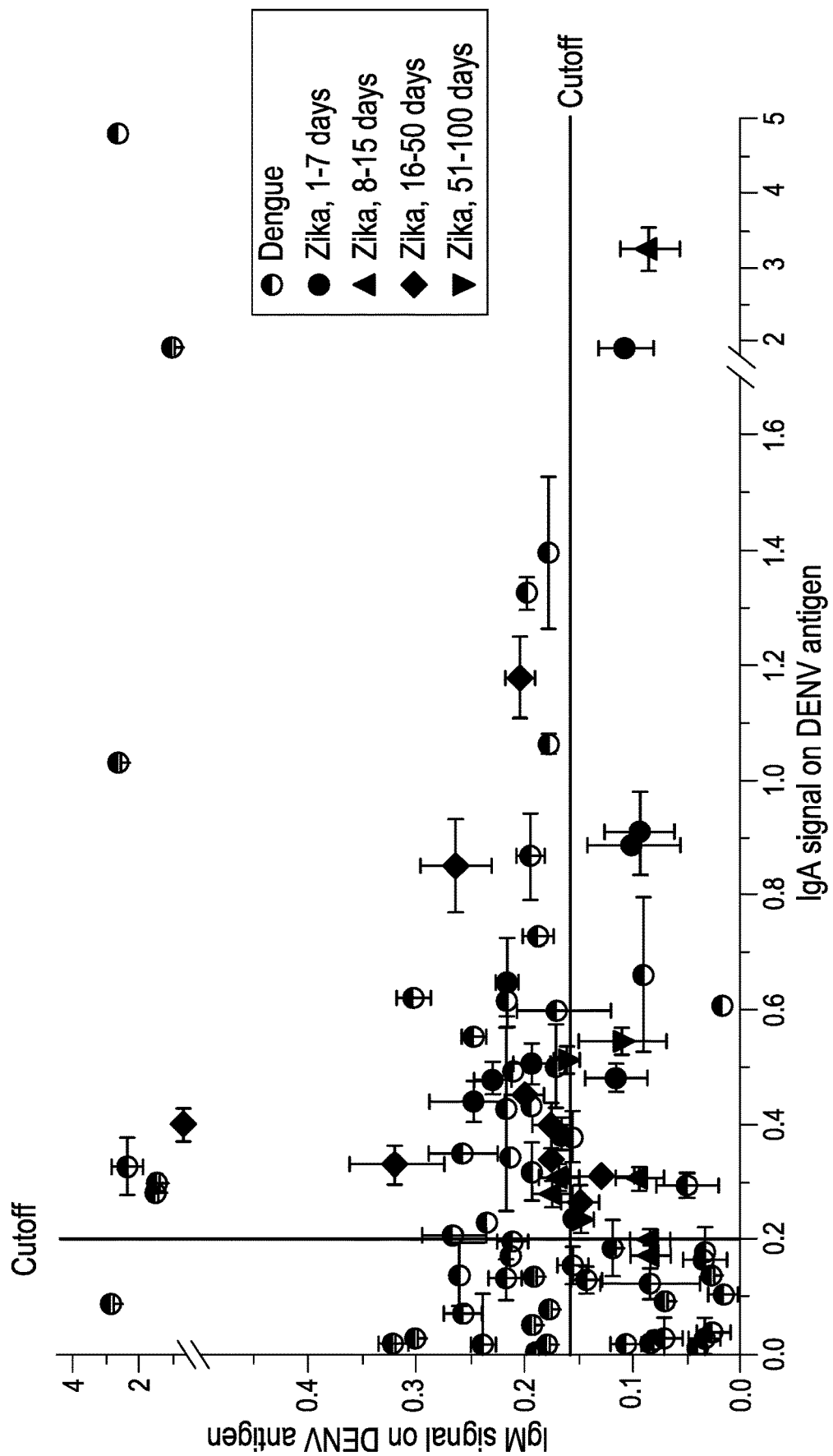
Figure 8A:
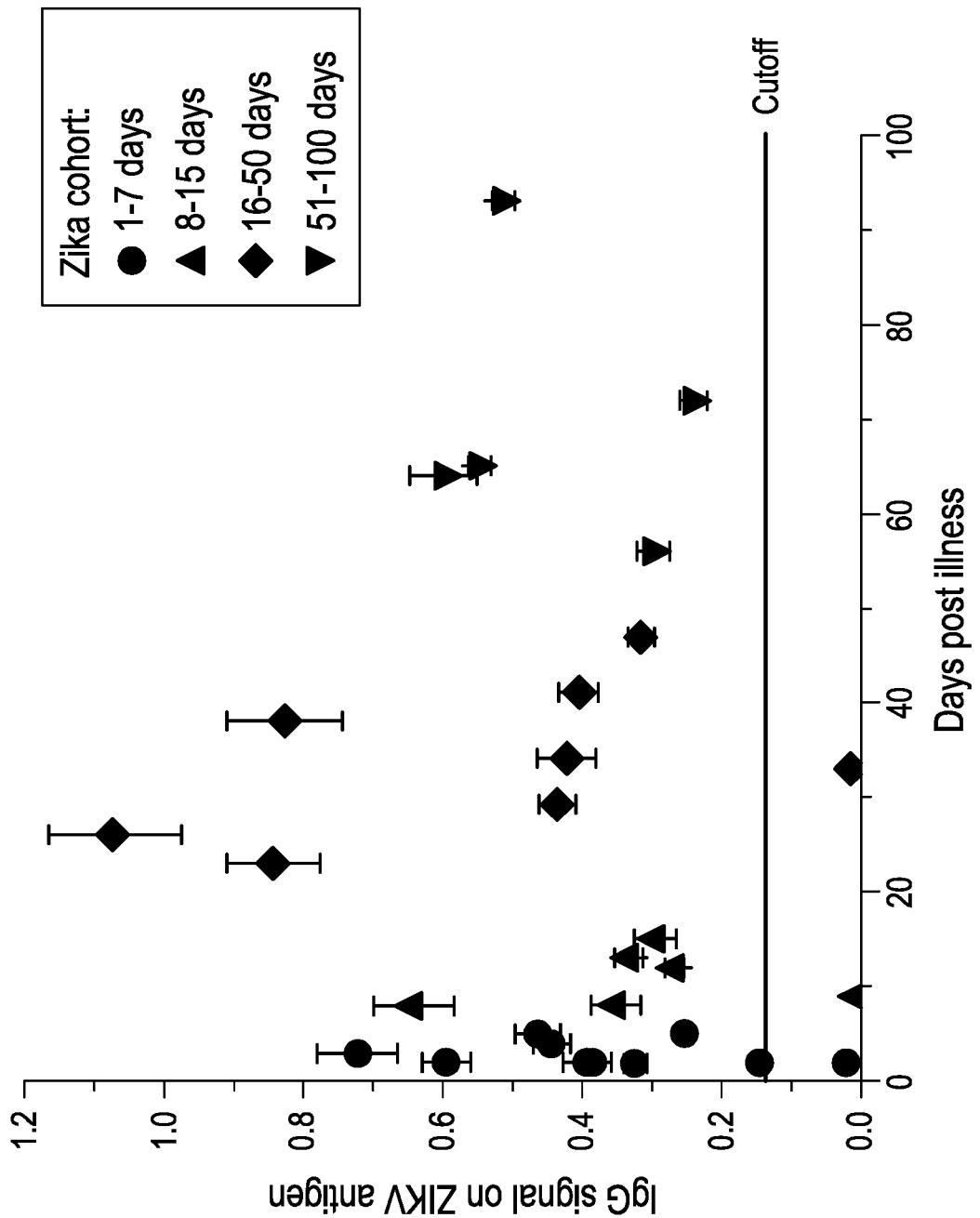
FIG. 8 shows example box plots (A-C) for ZIKV IgG, IgM, and IgA levels for samples having a ZIKV infection at the specified range of days after the onset of illness (filled circle—1-7 days; point-up triangle—8-15 days; diamond—16-50 days; point-down triangle—51-100 days). In panel (A), the illustrated cutoff for IgG signal on ZIKV antigen represents 3 standard deviations (SD) above the mean ZIKV IgG level detected for DENV infected samples. In panel (B), the illustrated "Cutoff" for IgM signal on ZIKV antigen represents 3 standard deviations (SD) above the mean ZIKV IgM level detected for the control samples. In panel (C), the illustrated "Cutoff" for IgA signal on ZIKV antigen represents 3 standard deviations (SD) above the mean ZIKV IgA level detected for the control samples. In panel (B), the illustrated "Cutoff" for IgM signal on ZIKV antigen represents 3 standard deviations (SD) above the mean ZIKV IgM level detected for the control samples. In panel (C), the illustrated "Cutoff" for IgA signal on ZIKV antigen represents 3 standard deviations (SD) above the mean ZIKV IgA level detected for the control samples. All signal levels are normalized by reference samples.

Samples:

Serum samples from three groups of patients were obtained: 1) 29 patients from Columbia (20 female, 9 male, with ages between 18-82 years, purchased from Medical Research Networx, LLC) with a clinical diagnosis of Zika virus (ZIKV) infection and no history of Dengue virus (DENV) infection; 2) 34 patients from Colombia, Ecuador, Honduras and Sri Lanka with a clinical diagnosis of DENV infection; and 3) 42 individuals with no history of ZIKV or DENV infection. Each serum sample was applied to a multiplexed ZIKV/DENV antigen array on a plasmonic gold substrate, for multiplexed detection of IgG and IgM antibodies against ZIKV and DENV antigens. IgG and IgM levels against DENV antigens were also measured with commercial kits, Focus Dengue Virus IgG DxSelect and Panbio Dengue IgM Capture ELISA, respectively, for a subset of DENV infected patients. DENV antibody detection on plasmonic gold substrate demonstrated good correlation with the commercial assays Results of these experiments are illustrated in FIGS. 1-7, and are described in the following. Where indicated, measurements are reported in arbitrary units (AU). IgG antibodies in the serum samples of Zika infected subjects showed high positive binding signals to Dengue antigens (FIG. 5), which can be used to differentiate Zika virus infection from Dengue virus infection, despite a degree of IgG antibody cross-reactivity. IgM antibodies in serum samples of Zika infected subjects and Dengue infected subjects showed high positive binding signals to Zika antigens, but the difference is not sufficient to adequately differentiate Zika virus infection from Dengue virus infection due to the degree of cross-reactivity (FIG. 4). Some Zika infected samples also showed high levels of IgM antibodies binding to Dengue antigens (FIG. 6), possibly due to cross-reactivity. IgG antibodies in the serum samples of Zika infected subjects showed high positive binding signals to Zika antigens (FIG. 3 and FIG. 4), even for acute infection for which the serum samples were collected within 1-2 days after the first sign of symptoms (FIG. 8A). Levels of IgG antibodies binding Zika virus antigens peaked in the subgroup of patients with samples collected between 16-50 days of illness, and remained positive but decreased gradually thereafter (FIG. 8A). Levels of IgM antibodies binding Zika virus antigens were also positive after 1-7 days and peaked at 16-50 days, but quickly decreased, becoming negative after about 70 days from illness onset. Importantly, in most of the samples tested, the Zika specific IgG signals were much higher than non-specific IgG signals on Dengue antigens (FIG. 4), which allowed the differentiation of Zika from Dengue infection. This was a surprising result as it suggested that despite the lack of specificity in IgM signals, the high Zika IgG signal was specific to most Zika infected samples over Dengue. It also suggested that IgG levels in blood against Zika rose very rapidly upon Zika infection and could be used as an important marker for acute Zika infection, and as a marker to differentiate Zika from Dengue infection. Zika samples exhibited not only high Zika IgG signals, but also Dengue IgG signals above a high threshold, in some cases even higher than those of Dengue infected samples (FIG. 7). Some Zika infected samples were negative for Zika IgM (below the IgM cutoff), which may indicate that the respective subjects were past the acute phase of Zika infection. Some Zika samples were low in Zika IgG, but high in Zika IgM, which may indicate acute phase Zika infection. Many samples were high in both Zika IgG and Zika IgM. The course of a Zika infection can also be monitored over time, as the level of IgG antibodies against Zika antigen increases with time after onset of symptoms. Moreover, Zika IgG levels may be used to stage Zika infections. Taken together, results indicate that measuring only IgM antibodies against Zika antigens may be insufficient to distinguish Zika infections from Dengue infections, whereas measuring IgG antibodies against Zika antigens (alone or in combination with IgM antibodies to Zika antigens, and/or IgG/IgM antibodies against Dengue antigens) greatly increase the ability to distinguish these two infections.

The results indicate that simultaneously detecting different antibody isotypes (e.g. IgG, IgM, and IgA) may be used to distinguish different types of flaviviral infections. The results also validate the use of plasmonic films as an example of sensitive detection platforms that can be used in conducting such assays. Results also indicate that small volumes of fluid are sufficient for sensitive detection of infections, such as less than 1 μL of serum or whole blood (as from a finger prick), or saliva samples. Processing time was also relatively rapid, with results obtained within about 2 hours.

Example 2: Assay Cut-Off Criteria

ZIKV IgG cutoff (ZIKV IgG=0.02) is based on the mean ZIKV IgG levels of a cohort of healthy samples with no prior flaviviral infection and is determined by ROC analysis on ZIKV IgG levels of confirmed Zika positive samples (with clinical reference results) and healthy control samples.

ZIKV IgG cutoff (ZIKV IgG=0.14) is based on the mean ZIKV IgG levels of a cohort of samples from DENV endemic regions with past DENV infection and is determined by ROC analysis on ZIKV IgG levels of confirmed Zika positive samples (with clinical reference results) from patients with chronical DENV infection.

DENV IgG cutoff (DENV IgG=0.08) is based on the mean DENV IgG levels of healthy control samples and was determined by ROC analysis on confirmed DENV infected samples (with clinical reference results) and healthy control samples with no prior flaviviral infection.

ZIKV IgG or DENV IgG avidity cutoff (IgG Avidity<0.5 for recent infection and IgG Avidity>0.6 for prior infection) is defined by ZIKV or DENV IgG levels remaining on serum samples post treatment with 10 M Urea solution and determined by Dengue infected samples with no ZIKV infection and Zika infected samples with prior DENV infection.

Example 3: Multiplexed Testing of Zika Virus Infection on a Nanotechnology Platform A multiplexed assay on a nanostructured plasmonic gold (pGOLD) platform for ZIKV and DENV IgG/IgM/IgA detection in sera was developed. The plasmonic gold platform was capable of amplifying near infrared (NIR) fluorescence by up to ~100 times, allowing analysis and/or quantification of multiple proteins or antibodies over 6-7 logs of dynamic range (FIG. 14) with a high signal/noise ratio. pGOLD was able to simultaneously detect up to three antibody subtypes in a single assay using ~1 μL serum sample volume. A single diluted sample undergone a single assay protocol can accurately detect IgG/IgM/IgA against multiple antigens with >6 logs of dynamic range to match reference data 16, owing to fluorescence enhancement in the visible to NIR range enabled by nanoscience.

Multiplexed Antigen Microarray Fabrication on Plasmonic Gold (pGOLD) Slides:

0.2 mg/ml ZIKV NS1 antigen (the Native Antigen Company, UK), 0.33 mg/ml Dengue2 antigen (purified Dengue 2 virus particles, Microbix Biosystems Inc. Canada) were prepared and delivered to pGOLD slides using GeSiM Nano-Plotter 2.1. Each microarray consisted of 3 microarray spots of ZIKV NS1 antigen and 3 microarray spots of Dengue2 antigen. About 3.2 nL antigen solution was delivered to each spot. Microarray followed a 2×3 layout with a spot diameter of about 400 μm, and a distance between spots of 1,000 μm. 16 identical microarrays were formed on each pGOLD slide. The fabricated biochips were vacuum sealed and stored at −20° C. before use.

Multiplexed Assay Process:

The fabricated biochip was integrated in a module where 16 identical microarrays on each biochip was separated into 16 wells for processing a total of 16 samples. Each biochip was blocked with a blocking buffer for 10 min, followed by incubation of human sera (300-400 times dilution) for 40 minutes-one hour, and incubation of a mixture of anti-human IgG-IRDye680 conjugate and anti-human IgA-IRDye800 conjugate for 15 min (in a separate assay, anti-human IgG-IRDye680 and anti-human IgM-IRDye800 were applied to label captured IgG and IgM antibody). Each well was washed with a washing buffer before each incubation procedure. 14 samples, together with two reference samples (one serum sample that was IgG, IgM, and IgA positive to ZIKV NS1 antigen and DENV antigen, and one serum sample was negative for IgG, IgM and IgA binding to ZIKV NS1 antigen and DENV antigen) were applied to each biochip. The amount of IgG and IgA bound to each antigen was analyzed through the fluorescence intensities of the IRDye680 and IRDye800, respectively. In a separate assay, IgG and IgM antibodies were detected simultaneously by detecting IgG in the same way while tagging the captured human IgM with an anti-human IgM-IRDye800.

Multiplexed Assay Process:

The fabricated biochip was integrated in a module where 16 identical microarrays on each biochip were separated into 16 wells to process 16 samples. Each well was incubated with human sera (400 times dilution) for 40 min, followed by incubation of 10M Urea/PBST solution for 10 min. Then, the anti human IgG-IRDye680 conjugates were applied to each well and incubated for 15 min. Each well was washed with a washing buffer between each incubation procedure. Two reference samples (one serum sample that is IgG, IgM, IgA positive to ZIKV NS1 antigen and DENV antigen, and one serum sample that is IgG, IgM and IgA negative to ZIKV NS1 antigen and DENV antigen) were applied to each biochip, but was not treated with 10M urea/PBST solution.

Qualitative RT-PCR Testing:

ZIKV RT-PCR results were obtained from Boca Biolistics. According to the vendor, ZIKV RT-PCR results were obtained with the LightMix Modular Zika Virus Real Time PCR Assay running on the COBAS Z480 or Light Cycler 2.0 system and by a clinical reference laboratory. DENV RT-PCR results were obtained with the CDC DENV-1-4 real-time RT-PCR kit. The assay was performed in multiplex on the Rotor-Gene Q instrument as described in the package insert.

Data Analysis:

After the assay process, each biochip was scanned with MidaScan-IR™ near-infrared scanner. IRDye680 and IRDye800 fluorescence images were generated and the median fluorescence signal for each channel on each microarray spot was quantified by MidaScan software. For each sample, antigen and channel, an average of 3 median fluorescence signals for 3 spots was calculated and normalized by reference samples through a two point calibration. ZIKV IgG cutoff is defined by mean ZIKV IgG levels of DENV infected samples+3 standard deviations (3SD). ZIKV IgM cutoff is defined by mean ZIKV IgM levels of control samples+3SD. ZIKV IgA cutoff is defined by mean ZIKV IgA levels of control samples+3SD. DENV IgG cutoff is defined by mean DENV IgG levels of control samples+3SD. DENV IgM cutoff is defined by mean DENV IgM levels of control samples+3SD. DENV IgA cutoff is defined by mean DENV IgA levels of control samples+3SD. The cutoff determined by mean+3SD method resulted in the optimal combination of sensitivity and specificity of the ZIKV/DENV IgG/IgA assay on pGOLD.

Figure 12:
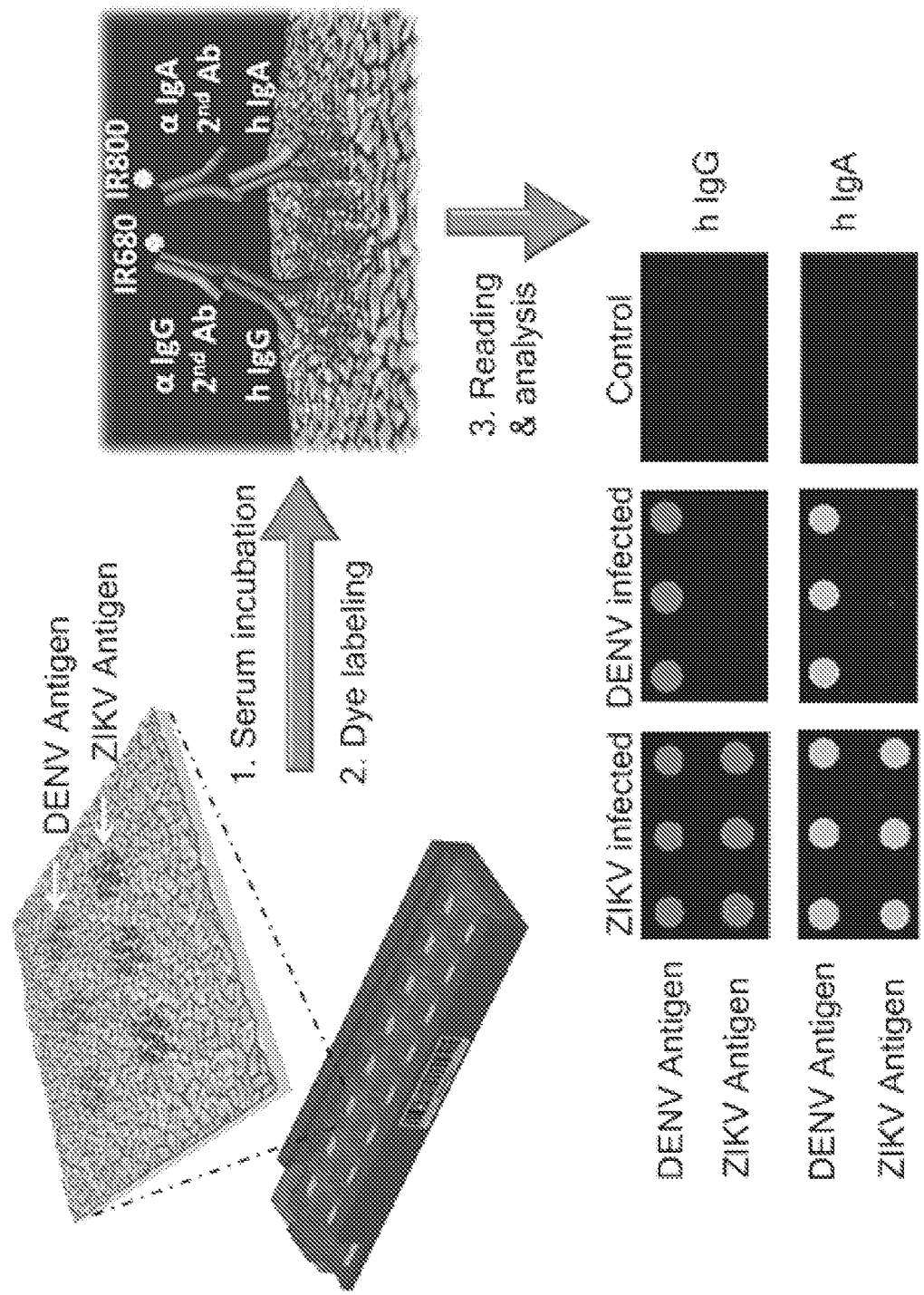
FIG. 12 is an illustration of an array of binding elements on a plasmonic gold film, in accordance with an embodiment. A pGOLD biochip comprises a pGOLD slide separated into 16 wells, with each well having identical ZIKV/DENV antigen microarray. For each microarray, ZIKV antigen and DENV antigen spots are immobilized on pGOLD in triplicates. During assay test, human serum is applied to the microarray, where different isotypes of human antibodies against ZIKV and DENV antigens, if present, will be captured on corresponding ZIKV and DENV antigens. After a washing step, a mixture of antihuman IgG-IRDye680 conjugate and antihuman IgA-IRDye800 conjugate is applied to the microarray to label captured human IgG antibody with IRDye680 and human IgA antibody with IRDye800. Then the pGOLD biochip is scanned and analyzed with a fluorescence reader. Fluorescence channel and intensity at specific antigen spots is correlated to the amount of specific antibody isotypes against certain antigen.
Figure 13:
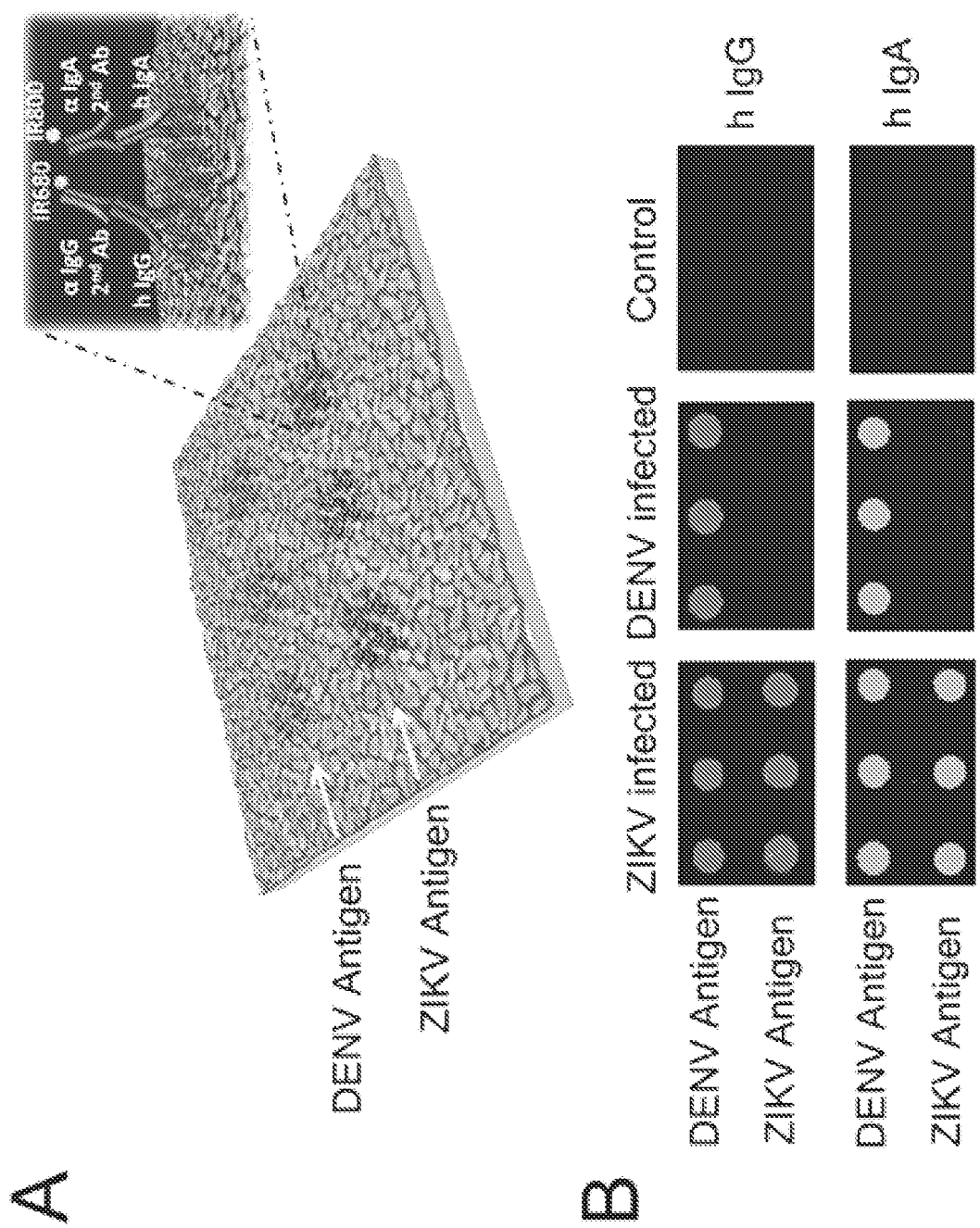
FIG. 13 in panels (A)-(B) shows an example multiplexed Zika virus/Dengue virus (ZIKV/DENV) antigen microarray on a plasmonic gold film (pGOLD) in accordance with an embodiment. Panel (A) schematically illustrates an example multiplexed assay structure on pGOLD. ZIKV antigen, DENV antigen and Control spots are immobilized on pGOLD in triplicate. Human serum is applied to the microarray, where different isotypes of human antibodies against ZIKV and DENV antigens, if present, can be captured on corresponding ZIKV and DENV antigens. After a washing step, a mixture of IRDye680 labeled anti human IgG secondary antibody and IRDye800 labeled anti human IgA secondary antibody is applied to the microarray to label captured human IgG antibody with IRDye680 and human IgA antibody with IRDye800. Panel (B) shows example IRDye680 fluorescence images (upper panel) and IRDye800 fluorescence images (bottom panel) of the assay performed for three individuals with ZIKV infection, DENV infection, or no known flavivirus infection (healthy control), respectively.

A microarray comprised of ZIKV NS1 recombinant antigen (Sequence strain: Uganda MR 766, produced in 293 human cells, the Native Antigen Company, UK) and Dengue 2 antigen (purified Dengue 2 virus particles, strain: 16681, cultured in vero cells, Microbix Biosystems Inc., Canada) was constructed on pGOLD™ slides (Nirmidas Biotech, Inc., USA) (FIG. 12). Antigens of Dengue serotypes 1, 3 and 4 were also investigated. A microarray biochip was fabricated using pGOLD slide, where pGOLD was integrated into a frame with 16 wells, with each containing a 2×3 microarray composed of ZIKV antigen and DENV antigen (FIG. 12). Each diluted human serum sample was applied to one well of the biochip, where human antibodies with affinity to ZIKV and DENV antigens were captured on the corresponding antigen spots. Subsequently, a mixture of antihuman IgG-IRDye680 conjugate and antihuman IgA-IRDye800 conjugate was applied to each well to label captured human IgG and IgA antibodies (FIG. 12). After washing, the pGOLD chip was read by a fluorescence reader and the amount of IgG and IgA bound to each antigen were analyzed through the fluorescence intensities of the IRDye680 and IRDye800, respectively. The turnaround time of the whole process is about 2 hours. In a separate assay, IgG and IgM antibodies were detected simultaneously by detecting IgG in the same way while tagging the captured human IgM with an antihuman IgM-IRDye800.

Serum samples from six groups of patients were obtained and studied using pGold ZIKV and DENV IgG and IgG avidity assay:

Group1_Z: 29 patients from DENV endemic Colombia (purchased from Medical Research Networx, LLC) clinically diagnosed (people showing ZIKV symptoms who lived or had traveled to regions with ZIKV transmission confirmed by RT-PCR) with ZIKV infection 2-93 days post symptom onset during the recent outbreak in Colombia (samples collected in the end of 2015 to early 2016 period; Table 1A and Table 1B];

Group2_D: 64 patients with a clinical diagnosis of DENV infection from Colombia, Ecuador, and Honduras, collected before the introduction of ZIKV to the Americas, as well as Sri Lanka, which has no known ZIKV cases (Table 2);

Group3_H: 50 control individuals with no history of ZIKV or DENV infection.

Group4_Z: 49 patients from DENV endemic Dominican Republic (purchased from Boca Biolistics) confirmed to be acute ZIKV infection (2-6 days post symptom onset) by laboratory ZIKV RT-PCR tests;

Group5_DD: 8 patients from Sri Lanka with secondary DENV infection (confirmed to be acute DENV infection by laboratory DENV RT-PCR test and previous DENV infection with high DENV IgG avidity).

Group6_ZS: 2 sets of serially collected serum samples from 2 ZIKV infected individuals with prior DENV infection (purchased from Boca Biolistics) (Table 3A-C).

As used herein, "positive", "pos", "+" and "+ive" refer to a positive test. "Negative", "neg", "−" and "−ive" refer to a negative test.

TABLE 1A

Patients from DENV endemic Colombia clinically diagnosed with ZIKV infection 2-93 days post symptom onset

| | PATIENT INFORMATION | | | | | PREVIOUS |
|---|---|---|---|---|---|---|
| SAMPLE NO. | AGE | SEX | COUNTRY OF ORIGIN | GESTATIONAL WEEK. | COLLECTION DATE | HISTORY DENGUE |
| 1. | 49 | M | Colombia | NO | Dec. 17, 2015 | NO |
| 2. | 44 | F | Colombia | NO | Dec. 10, 2015 | NO |
| 3. | 20 | F | Colombia | NO | Dec. 17, 2015 | NO |
| 4. | 59 | F | Colombia | NO | Dec. 26, 2015 | NO |
| 5. | 25 | F | Colombia | NO | Dec. 17, 2015 | NO |
| 6. | 75 | F | Colombia | NO | Jan. 5, 2016 | NO |
| 7. | 38 | F | Colombia | 5 WEEKS | Jan. 9, 2016 | NO |
| 8. | 40 | M | Colombia | NO | Jan. 15, 2016 | NO |
| 9. | 38 | F | Colombia | NO | Jan. 18, 2016 | NO |
| 10. | 34 | F | Colombia | 8 WEEKS | Jan. 23, 2016 | NO |
| 11. | 31 | F | Colombia | 17 WEEKS | Jan. 28, 2016 | NO |
| 12. | 23 | F | Colombia | 24 WEEKS | Jan. 28, 2016 | NO |
| 13. | 33 | F | Colombia | NO | Jan. 28, 2016 | NO |
| 14. | 50 | M | Colombia | NO | Jan. 28, 2016 | NO |
| 15. | 79 | M | Colombia | NO | Jan. 28, 2016 | NO |
| 16. | 25 | F | Colombia | 5 WEEKS | Jan. 28, 2016 | NO |
| 17. | 24 | F | Colombia | 27.5 WEEKS | Jan. 29, 2016 | NO |
| 18. | 26 | F | Colombia | 19 WEEKS | 1/22016 | NO |
| 19. | 23 | F | Colombia | 30 WEEKS | Jan. 29, 2016 | NO |
| 20. | 22 | F | Colombia | 1 WEEKS | Jan. 29, 2016 | NO |
| 21. | 21 | F | Colombia | NO | Jan. 29, 2016 | NO |
| 22. | 59 | M | Colombia | NO | Jan. 29, 2016 | NO |
| 23. | 25 | M | Colombia | 2 WEEKS | Jan. 29, 2016 | NO |
| 24. | 65 | M | Colombia | NO | Feb. 4, 2016 | NO |
| 25. | 22 | F | Colombia | 36 WEEKS | Feb. 3, 2016 | NO |
| 26. | 18 | F | Colombia | 20 WEEKS | Feb. 3, 2016 | NO |
| 27. | 35 | M | Colombia | NO | Feb. 12, 2016 | NO |
| 28. | 82 | M | Colombia | NO | Feb. 12, 2016 | NO |
| 29. | 22 | F | Colombia | NO | Feb. 12, 2016 | NO |

TABLE 1B

Patients from DENV endemic Colombia clinically diagnosed with ZIKV infection 2-93 days post symptom onset

| PATIENT SAMPLE NO. | DIAGNOSIS INFORMATION | | Zika Symptoms | | | | | | | | Rapid Test result (Zika IgG) | Rapid Test result (Zika IgM) | pGOLD Zika/Dengue IgG Assay | |
|---|---|---|---|---|---|---|---|---|---|---|---|---|---|---|
| | DIAGNOSIS | DATE OF 1ST ZIKA SYMPTOM | FEVER | SKIN RASH | JOINT PAIN | MYALGIA | EYE PAIN | CEPHALAGIA | CONJUNCTIVITIS | DIARRHEA | | | Interpretation (Zika IgG >0.02) Reference: Health Patients with N prior Flaviviral Infection | Interpretation (Zika IgG >0.14) Reference: Health Patients with prior DENV Infection |
| 1. | ACUTE ZIKA INFECTION | Dec. 15, 2015 | Y | Y | Y | Y | Y | Y | Y | N | | | + | + |
| 2. | ACUTE ZIKA INFECTION | Dec. 8, 2015 | Y | Y | Y | Y | Y | Y | N | N | | | + | − |
| 3. | ACUTE ZIKA INFECTION | Dec. 15, 2015 | Y | Y | Y | Y | Y | Y | Y | N | + | | + | + |
| 4. | ACUTE ZIKA INFECTION | Dec. 24, 2015 | Y | Y | Y | Y | Y | Y | N | Y | + | + | + | + |
| 5. | ACUTE ZIKA INFECTION | Dec. 15, 2015 | Y | Y | Y | Y | Y | Y | Y | N | + | + | + | + |
| 6. | ACUTE ZIKA INFECTION | Jan. 3, 2016 | Y | Y | Y | Y | N | N | Y | N | + | + | + | + |
| 7. | ACUTE ZIKA INFECTION | Jan. 4, 2016 | Y | Y | Y | Y | N | Y | Y | N | | | + | + |
| 8. | ACUTE ZIKA INFECTION | Dec. 31, 2015 | Y | Y | Y | Y | N | N | Y | N | | | + | + |
| 9. | ACUTE ZIKA INFECTION | Jan. 14, 2016 | Y | Y | Y | Y | Y | Y | Y | N | | | + | + |
| 10. | ACUTE ZIKA INFECTION | Jan. 20, 2016 | Y | Y | Y | Y | Y | Y | Y | N | | | + | + |
| 11. | ACUTE ZIKA INFECTION | Nov. 25, 2015 | Y | Y | Y | Y | N | N | Y | N | | | + | + |
| 12. | ACUTE ZIKA INFECTION | Jan. 20, 2016 | Y | Y | Y | N | N | N | Y | N | | | + | + |
| 13. | ACUTE ZIKA INFECTION | Jan. 20, 2016 | Y | Y | Y | Y | Y | Y | Y | N | | | + | − |
| 14. | ACUTE ZIKA INFECTION | Jan. 5, 2016 | Y | Y | Y | Y | N | Y | Y | N | | | + | + |
| 15. | ACUTE ZIKA INFECTION | Jan. 16, 2016 | Y | Y | N | Y | N | Y | Y | N | | | + | + |
| 16. | ACUTE ZIKA INFECTION | Jan. 15, 2016 | Y | Y | Y | Y | Y | Y | N | Y | | | + | + |
| 17. | ACUTE ZIKA INFECTION | Dec. 31, 2015 | Y | Y | Y | N | Y | Y | Y | Y | | | + | + |
| 18. | ACUTE ZIKA INFECTION | Jan. 3, 2016 | Y | Y | Y | Y | Y | N | Y | N | | | + | + |

TABLE 1B-continued

Patients from DENV endemic Colombia clinically diagnosed with ZIKV infection 2-93 days post symptom onset

| PATIENT SAMPLE NO. | DIAGNOSIS INFORMATION DIAGNOSIS | DATE OF 1ST ZIKA SYMPTOM | Zika Symptoms FEVER | SKIN RASH | JOINT PAIN | MYALGIA | EYE PAIN | CEPHALAGIA | CONJUNCTIVITIS | DIARRHEA | Rapid Test result (Zika IgG) | Rapid Test result (Zika IgM) | pGOLD Zika/Dengue IgG Assay Interpretation (Zika IgG >0.02) Reference: Health Patients with N prior Flaviviral Infection | Interpretation (Zika IgG >0.14) Reference: Health Patients with prior DENV Infection |
|---|---|---|---|---|---|---|---|---|---|---|---|---|---|---|
| 19. | ACUTE ZIKA INFECTION | Dec. 22, 2015 | Y | Y | Y | Y | Y | Y | N | N | | | + | + |
| 20. | ACUTE ZIKA INFECTION | Dec. 19, 2015 | Y | Y | Y | Y | Y | N | N | Y | | | + | − |
| 21. | ACUTE ZIKA INFECTION | Dec. 27, 2015 | Y | Y | Y | Y | Y | N | Y | N | | | + | + |
| 22. | ACUTE ZIKA INFECTION | Jan. 20, 2016 | Y | Y | Y | Y | Y | N | N | Y | | | + | + |
| 23. | ACUTE ZIKA INFECTION | Dec. 13, 2015 | Y | Y | Y | Y | N | N | Y | Y | | | + | + |
| 24. | ACUTE ZIKA INFECTION | Dec. 1, 2015 | Y | Y | Y | Y | N | Y | Y | N | | | + | + |
| 25. | ACUTE ZIKA INFECTION | Dec. 31, 2015 | Y | Y | Y | Y | N | Y | Y | N | | | + | + |
| 26. | ACUTE ZIKA INFECTION | Dec. 9, 2015 | Y | Y | Y | Y | Y | Y | Y | N | | | + | + |
| 27. | ACUTE ZIKA INFECTION | Nov. 11, 2015 | Y | Y | Y | Y | Y | Y | N | N | | | + | + |
| 28. | ACUTE ZIKA INFECTION | Dec. 2, 2015 | Y | Y | Y | Y | Y | Y | N | Y | | | + | + |
| 29. | ACUTE ZIKA INFECTION | Feb. 7, 2016 | Y | Y | Y | Y | Y | Y | Y | N | | | + | + |

*** Note:
Y = YES; N = No

TABLE 2

Clinical and test info on 64 DENV infected patients, including patient demographic information, cinical history, and DENV IgG/IgM/PCR reference test result (DENV ELISA IgG kit and Panbio DENV IgM capture ELISA)

| Sample ID | Origin | Clinical History | IgG Reference Result | IgM Reference Result | PCR Result |
|---|---|---|---|---|---|
| Dengue-1 | Colombia | | POS | POS | |
| Dengue-2 | Colombia | | POS | POS | |
| Dengue-3 | Honduras | | POS | NEG | |
| Dengue-4 | Honduras | | POS | NEG | |
| Dengue-5 | Honduras | | POS | NEG | |
| Dengue-6 | Honduras | | POS | NEG | |
| Dengue-7 | Honduras | | NEG | NEG | |
| Dengue-8 | Honduras | | POS | NEG | |
| Dengue-9 | Ecuador | | POS | POS | |
| Dengue-10 | Colombia | | POS | POS | |
| Dengue-11 | Honduras | | POS | NEG | |
| Dengue-12 | Honduras | | POS | NEG | |
| Dengue-13 | Ecuador | | POS | POS | |
| Dengue-14 | Ecuador | | POS | POS | |
| Dengue-15 | Sri Lanka | Fever | | POS | Neg |
| Dengue-16 | Sri Lanka | Fever | | POS | Neg |
| Dengue-17 | Sri Lanka | Fever | | POS | Neg |
| Dengue-18 | Sri Lanka | Fever | | POS | |
| Dengue-19 | Sri Lanka | Fever | | POS | |
| Dengue-20 | Sri Lanka | Fever | | POS | Neg |
| Dengue-21 | Sri Lanka | Fever | | POS | Neg |
| Dengue-22 | Sri Lanka | Fever; low platelets | | POS | Neg |
| Dengue-23 | Sri Lanka | Fever, H'ache | | POS | Neg |
| Dengue-24 | Sri Lanka | Fever; low platelets | | NEG | Neg |
| Dengue-25 | Sri Lanka | Fever | | NEG | Neg |
| Dengue-26 | Sri Lanka | Fever; low platelets | | NEG | |
| Dengue-27 | Sri Lanka | Fever; low platelets | | NEG | Neg |
| Dengue-28 | Sri Lanka | Fever; low platelets | | NEG | Neg |
| Dengue-29 | Sri Lanka | Fever | | NEG | Neg |
| Dengue-30 | Sri Lanka | Fever, H'ache | | NEG | DENV |
| Dengue-31 | Sri Lanka | Fever, H'ache | | NEG | DENV |
| Dengue-32 | Sri Lanka | Fever | | NEG | |
| Dengue-33 | Sri Lanka | Fever | | NEG | Neg |
| Dengue-34 | Sri Lanka | Fever; low platelets | | NEG | Neg |
| Dengue-35 | Sri Lanka | Fever; low platelets | | NEG | Neg |
| Dengue-36 | Sri Lanka | Fever; low platelets | | NEG | |
| Dengue-37 | Sri Lanka | Fever | | NEG | Neg |
| Dengue-38 | Sri Lanka | Fever | | NEG | Neg |
| Dengue-39 | Sri Lanka | Fever | | NEG | Neg |
| Dengue-40 | Sri Lanka | Fever, H'ache | | NEG | Neg |
| Dengue-41 | Sri Lanka | Fever | | NEG | |
| Dengue-42 | Sri Lanka | Fever; low platelets | | NEG | |
| Dengue-43 | Sri Lanka | Fever | | NEG | Neg |
| Dengue-44 | Sri Lanka | Fever, H'ache | | NEG | DENV |
| Dengue-45 | Sri Lanka | Fever, H'ache | | NEG | Neg |
| Dengue-46 | Sri Lanka | Fever | | NEG | Neg |
| Dengue-47 | Sri Lanka | Fever, H'ache | | NEG | Neg |
| Dengue-48 | Sri Lanka | Fever | | POS | Neg |
| Dengue-49 | Sri Lanka | Fever | | NEG | Neg |
| Dengue-50 | Sri Lanka | Fever, H'ache | | POS | Neg |
| Dengue-51 | Sri Lanka | Fever | | POS | Neg |
| Dengue-52 | Sri Lanka | Fever, Mayalgia | | POS | Neg |
| Dengue-53 | Sri Lanka | Fever; low platelets | | POS | Neg |
| Dengue-54 | Sri Lanka | Fever, Abdominal pain | | POS | Neg |
| Dengue-55 | Sri Lanka | Fever, Mayalgia | | POS | DENV |
| Dengue-56 | Sri Lanka | Fever, Mayalgia | | POS | |
| Dengue-57 | Sri Lanka | Fever; low platelets | | POS | Neg |
| Dengue-58 | Sri Lanka | Fever, cough, Chest pain | | POS | DENV |
| Dengue-59 | Sri Lanka | Fever, Mayalgia | | POS | |
| Dengue-60 | Sri Lanka | Fever; low platelets | | POS | Neg |
| Dengue-61 | Sri Lanka | Fever; low platelets | | POS | DENV |
| Dengue-62 | Sri Lanka | Fever, Mayalgia | | POS | Neg |
| Dengue-63 | Sri Lanka | Fever, Abdominal pain | | POS | Neg |
| Dengue-64 | Sri Lanka | Fever; low platelets | | POS | Neg |

TABLE 3A

Clinical information and Reference test results on serum samples collected at different timepoints during the course of infection from two ZIKV infected patients

| BBID | Indication | Geographic Region | Suspected Tropical Disease | Days Between Symptom Onset and Collection |
|---|---|---|---|---|
| 1043-TDS-0123 | Tropical Disease Symptomatic | Dominican Republic | Zika | 2 |
| 1043-TDS-0123V2 | Tropical Disease Symptomatic | Dominican Republic | Zika | 5 |
| 1043-TDS-0123V3 | Tropical Disease Symptomatic | Dominican Republic | Zika | 13 |
| 1043-TDS-0123V4 | Tropical Disease Symptomatic | Dominican Republic | Zika | 20 |
| 1043-TDS-0123V5 | Tropical Disease Symptomatic | Dominican Republic | Zika | 31 |
| 1043-TDS-0123V6 | Tropical Disease Symptomatic | Dominican Republic | Zika | 40 |
| 1043-TDS-0123V7 | Tropical Disease Symptomatic | Dominican Republic | Zika | 46 |
| 1043-TDS-0123V8 | Tropical Disease Symptomatic | Dominican Republic | Zika | 54 |
| 1043-TDS-0150 | Tropical Disease Symptomatic | Dominican Republic | Zika | 5 |
| 1043-TDS-0150V2 | Tropical Disease Symptomatic | Dominican Republic | Zika | 7 |
| 1043-TDS-0150V3 | Tropical Disease Symptomatic | Dominican Republic | Zika | 11 |
| 1043-TDS-0150V4 | Tropical Disease Symptomatic | Dominican Republic | Zika | 14 |
| 1043-TDS-0150V5 | Tropical Disease Symptomatic | Dominican Republic | Zika | 21 |
| 1043-TDS-0150V6 | Tropical Disease Symptomatic | Dominican Republic | Zika | 28 |
| 1043-TDS-0150V7 | Tropical Disease Symptomatic | Dominican Republic | Zika | 34 |
| 1043-TDS-0150V8 | Tropical Disease Symptomatic | Dominican Republic | Zika | 42 |

TABLE 3B

Clinical information and Reference test results on serum samples collected at different timepoints during the course of infection from two ZIKV infected patients

| BBID | Fever | Joint and Muscle Pain | Head Pain | Conjunctivitis (red eyes) | Rash | Severe Eye Pain | Malaise | General Light Bleeding | Low White Blood Cells | No Symptoms | Other |
|---|---|---|---|---|---|---|---|---|---|---|---|
| 1043-TDS-0123 | Yes | Yes | Yes | No | Yes | Yes | Yes | No | No | No | N/A |
| 1043-TDS-0123V2 | Yes | Yes | Yes | No | Yes | Yes | Yes | No | No | No | N/A |
| 1043-TDS-0123V3 | Yes | Yes | Yes | No | Yes | Yes | Yes | No | No | No | N/A |
| 1043-TDS-0123V4 | Yes | Yes | Yes | No | Yes | Yes | Yes | No | No | No | N/A |
| 1043-TDS-0123V5 | Yes | Yes | No | No | Yes | Yes | Yes | No | No | No | N/A |
| 1043-TDS-0123V6 | Yes | Yes | Yes | No | Yes | Yes | Yes | No | No | No | N/A |
| 1043-TDS-0123V7 | Yes | Yes | Yes | No | Yes | Yes | Yes | No | No | No | N/A |
| 1043-TDS-0123V8 | Yes | Yes | Yes | Yes | Yes | Yes | Yes | No | No | No | N/A |
| 1043-TDS-0150 | Yes | No | Yes | Yes | Yes | Yes | Yes | No | No | No | N/A |
| 1043-TDS-0150V2 | Yes | No | No | Yes | Yes | No | Yes | No | No | No | N/A |
| 1043-TDS-0150V3 | Yes | No | Yes | Yes | Yes | No | No | No | No | No | N/A |
| 1043-TDS-0150V4 | Yes | No | Yes | Yes | Yes | No | No | No | No | No | N/A |
| 1043-TDS-0150V5 | Yes | No | Yes | Yes | Yes | Yes | Yes | No | No | No | N/A |
| 1043-TDS-0150V6 | Yes | No | Yes | Yes | Yes | Yes | Yes | No | No | No | N/A |
| 1043-TDS-0150V7 | Yes | No | Yes | Yes | Yes | No | Yes | No | No | No | N/A |
| 1043-TDS-0150V8 | Yes | No | Yes | Yes | Yes | Yes | Yes | No | No | No | N/A |

TABLE 3C

Clinical information and Reference test results on serum samples collected at different timepoints during the course of infection from two ZIKV infected patients

| Sample No. | 1 | 2 | 3 | 4 | 5 | 6 | 7 | 8 |
|---|---|---|---|---|---|---|---|---|
| 1_Assay Name | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Vims ELISA (IgM) | Eurroimmun Anti-Zika Virus ELISA (IgM) |
| 1_Test Result | − | − | + | = | − | − | − | − |
| 3_Assay Name | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA |
| 3_Test Result | − | − | Zika IgM+ | Zika IgM+ | Zika IgM+ | Zika IgM+ | Zika IgM+ | Zika IgM+ |
| 3_Assay Name | InBios Dengue Detect IgM Capture ELISA | InBios Dengue Detect IgM Capture ELISA | InBios Dengue Detect IgM Capture ELISA | InBios Dengue Detect IgM Capture ELISA | InBios Dengue Detect IgM Capture ELISA | InBios Dengue Detect IgM Capture ELISA | InBios Dengue Detect IgM Capture ELISA | InBios Dengue Detect IgM Caphire ELISA |
| 3_Test Result | + | − | − | − | − | − | − | − |
| 3_Assay Name | LightMix Modular | LightMix Modular | LightMix Modular | LightMix Modular | | | | |

TABLE 3C-continued

Clinical information and Reference test results on serum samples collected at different timepoints during the course of infection from two ZIKV infected patients

| 3_Test Result | Zika Virus Real Time PCR Assay Detected | Zika Virus Real Time PCR Assay Detected | Zika Virus Real Time PCR Assay Detected | Zika Virus Real Time PCR Assay Not Detected | | | |
|---|---|---|---|---|---|---|---|
| 11_Assay Name | EuroImmun Anti-Dengue Virus ELISA (IgG) | | | EuroImmun Anti-Dengue Virus ELISA (IgG) | EuroImmun Anti-Dengue Virus ELISA (IgG) | EuroImmun Anti-Dengue Virus ELISA (IgG) | |
| 11_Test Result | + | | | + | + | + | |
| Assay Name | CDC MAC ELISA | CDC MAC ELISA | CDC MAC ELISA | CDC MAC ELISA | CDC MAC ELISA | CDC MAC ELISA | CDC MAC ELISA | CDC MAC ELISA |
| Test Result | − | − | + | + | + | + | + | + |

| | Sample No. | 1 | 2 | 3 | 4 | 5 | 6 | 7 | 8 |
|---|---|---|---|---|---|---|---|---|---|
| pGOLD Zika/Dengue IgG Assay | Zika IgG Interpretation (Zika IgG >0.02) Referenced to healthy population | + | + | + | + | + | + | + | + |
| | DENV IgG Interpretation (DENV IgG ≥0.08) | + | + | + | + | + | + | + | + |
| | Zika IgG Interpretation (Zika IgG >0.14) Referenced to population with prior DENV Infection | + | + | + | + | + | + | + | + |

| Sample No. | 9 | 10 | 11 | 12 | 13 | 14 | 15 | 16 |
|---|---|---|---|---|---|---|---|---|
| 1_Assay Name | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) | Eurroimmun Anti-Zika Virus ELISA (IgM) |
| 1_Test Result | − | − | + | + | − | − | − | − |
| 3_Assay Name | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA | InBios ZikV Detect IgM Capture ELISA |
| 3_Test Result | − | +sible Zika+ | Zika IgM+ | Zika IgM+ | +sible Zika+ | +sible Zika+ | +sible Zika+ | +sible Zika+ |
| 3_Assay Name | InBios Dengue Detect IgM Capture ELISA | InBios Dengue Detect IgM Capture ELISA | InBios Dengue Detect IgM Capture ELISA | InBios Dengue Detect IgM Capture ELISA | InBios Dengue Detect IgM Capture ELISA | InBios Dengue DetectIgM Capture ELISA | InBios Dengue DetectIgM Capture ELISA | InBios Dengue DetectIgM Capture ELISA |
| 3_Test Result | − | − | − | − | − | − | − | − |
| 3_Assay Name | LightMix Modular Zika Virus Real Time PCR Assay | LightMix Modular Zika Virus Real Time PCR Assay | LightMix Modular Zika Virus Real Time PCR Assay | LightMix Modular Zika Virus Real Time PCR Assay | LightMix Modular Zika Virus Real Time PCR Assay | | | |
| 3_Test Result | Detected | Not Detected | Not Detected | N/A | N/A | | | |
| 11_Assay Name | | | | EuroImmun Anti-Dengue Virus ELISA (IgG) | EuroImmun Anti-Dengue Virus ELISA (IgG) | EuroImmun Anti-Dengue Virus ELISA (IgG) | EuroImmun Anti-Dengue Virus ELISA (IgG) | |
| 11_Test Result | | | | + | + | + | + | |
| Assay Name | | CDC MAC ELISA | CDC MAC ELISA | | CDC MAC ELISA | CDC MAC ELISA | | CDC MAC ELISA |
| Test Result | | + | + | | + | + | | + |

| | Sample No. | 9 | 10 | 11 | 12 | 13 | 14 | 15 | 16 |
|---|---|---|---|---|---|---|---|---|---|
| pGOLD Zika/Dengue IgG Assay | Zika IgG Interpretation (Zika IgG >0.02) Referenced to healthy population | − | + | + | + | + | + | + | + |
| | DENV IgG Interpretation (DENV IgG ≥0.08) | + | + | + | + | + | + | + | + |

TABLE 3C-continued

Clinical information and Reference test results on serum samples collected at different timepoints during the course of infection from two ZIKV infected patients

| Zika IgG Interpretation (Zika IgG >0.14) Referenced to population with prior DENV Infection | − | − | + | + | + | + | + | + |
|---|---|---|---|---|---|---|---|---|

TABLE 4A

Serum samples from three groups of patients

PATIENT INFORMATION

| Sample No. | AGE | SEX | COUNTRY OF ORIGIN | GESTATIONAL WEEK | DAYs between 1ST ZIKA SYMPTOM to SAMPLE COLLECTION | PREVIOUS HISTORY DENGUE | DIAGNOSIS INFORMATION DIAGNOSIS |
|---|---|---|---|---|---|---|---|
| 1. | 49 | M | Colombia | NO | 2 | NO | ACUTE ZIKA INFECTION |
| 2. | 44 | F | Colombia | NO | 2 | NO | ACUTE ZIKA INFECTION |
| 3. | 20 | F | Colombia | NO | 2 | NO | ACUTE ZIKA INFECTION |
| 4. | 59 | F | Colombia | NO | 2 | NO | ACUTE ZIKA INFECTION |
| 5. | 25 | F | Colombia | NO | 9 | NO | ACUTE ZIKA INFECTION |
| 6. | 75 | F | Colombia | NO | 2 | NO | ACUTE ZIKA INFECTION |
| 7. | 34 | F | Colombia | 8 WEEKS | 3 | NO | ACUTE ZIKA INFECTION |
| 8. | 38 | F | Colombia | NO | 4 | NO | ACUTE ZIKA INFECTION |
| 9. | 38 | F | Colombia | 5 WEEKS | 5 | NO | ACUTE ZIKA INFECTION |
| 10. | 22 | F | Colombia | NO | 5 | NO | ACUTE ZIKA INFECTION |
| 11. | 23 | F | Colombia | 24 WEEKS | 8 | NO | ACUTE ZIKA INFECTION |
| 12. | 33 | F | Colombia | NO | 8 | NO | ACUTE ZIKA INFECTION |
| 13. | 59 | M | Colombia | NO | 9 | NO | ACUTE ZIKA INFECTION |
| 14. | 79 | M | Colombia | NO | 12 | NO | ACUTE ZIKA INFECTION |
| 15. | 25 | F | Colombia | 5 WEEKS | 13 | NO | ACUTE ZIKA INFECTION |
| 16. | 40 | M | Colombia | NO | 15 | NO | ACUTE ZIKA INFECTION |
| 17. | 50 | M | Colombia | NO | 23 | NO | ACUTE ZIKA INFECTION |
| 18. | 26 | F | Colombia | 19 WEEKS | 26 | NO | ACUTE ZIKA INFECTION |
| 19. | 24 | F | Colombia | 27.5 WEEKS | 29 | NO | ACUTE ZIKA INFECTION |
| 20. | 21 | F | Colombia | NO | 33 | NO | ACUTE ZIKA INFECTION |
| 21. | 22 | F | Colombia | 36 WEEKS | 34 | NO | ACUTE ZIKA INFECTION |
| 22. | 23 | F | Colombia | 30 WEEKS | 38 | NO | ACUTE ZIKA INFECTION |
| 23. | 22 | F | Colombia | 1 WEEKS | 41 | NO | ACUTE ZIKA INFECTION |
| 24. | 25 | F | Colombia | 2 WEEKS | 47 | NO | ACUTE ZIKA INFECTION |
| 25. | 18 | F | Colombia | 20 WEEKS | 56 | NO | ACUTE ZIKA INFECTION |
| 26. | 31 | F | Colombia | 17 WEEKS | 64 | NO | ACUTE ZIKA INFECTION |
| 27. | 65 | M | Colombia | NO | 65 | NO | ACUTE ZIKA INFECTION |
| 28. | 82 | M | Colombia | NO | 72 | NO | ACUTE ZIKA INFECTION |
| 29. | 35 | M | Colombia | NO | 93 | NO | ACUTE ZIKA INFECTION |

TABLE 4B

Serum samples from three groups of patients

| SAMPLE NO. | ZIKA SYMPTOMS ||||||||| OTHER INFORMATION || pGOLD TEST RESULT ||||
|---|---|---|---|---|---|---|---|---|---|---|---|---|---|---|
| | FEVER | SKIN RASH | JOINT PAIN | MYALGIA | EYE PAIN | CEPHALAGIA | CONJUNCTIVITIS | DIARRHEA | Rapid Test result (Zika IgG) | Rapid Test result (Zika IgM) | ZIKV IgG (using cut off based on control samples) | ZIKV IgG (using cut off based on Dengue samples) | ZIKV IgM | ZIKV IgA |
| 1. | Y | Y | Y | Y | Y | Y | Y | N | | | + | + | + | + |
| 2. | Y | Y | Y | Y | Y | Y | N | N | + | + | + | − | + | + |
| 3. | Y | Y | Y | Y | Y | Y | Y | N | + | + | + | + | + | + |
| 4. | Y | Y | Y | Y | Y | Y | N | Y | + | + | + | + | + | − |
| 5. | Y | Y | Y | Y | N | N | Y | N | | | + | + | + | − |
| 6. | Y | Y | Y | Y | Y | Y | Y | N | | | + | + | + | − |
| 7. | Y | Y | Y | Y | Y | Y | Y | N | | | + | + | − | − |
| 8. | Y | Y | Y | Y | N | N | Y | N | | | + | + | + | + |
| 9. | Y | Y | Y | Y | N | Y | Y | N | | | + | + | − | − |
| 10. | Y | Y | Y | N | N | Y | Y | N | | | + | + | + | + |
| 11. | Y | Y | Y | Y | Y | Y | Y | N | | | + | − | − | − |
| 12. | Y | Y | Y | Y | Y | Y | N | N | | | + | + | + | + |
| 13. | Y | Y | Y | Y | Y | Y | Y | N | | | + | + | − | − |
| 14. | Y | Y | Y | Y | N | Y | Y | N | | | + | + | + | + |
| 15. | Y | Y | N | Y | Y | Y | Y | N | | | + | + | + | + |
| 16. | Y | Y | Y | Y | Y | Y | N | N | | | + | + | + | + |
| 17. | Y | Y | Y | Y | N | Y | Y | N | | | + | + | + | − |
| 18. | Y | Y | Y | Y | Y | Y | Y | N | | | + | + | + | + |
| 19. | Y | Y | Y | N | N | Y | N | Y | | | + | − | − | − |
| 20. | Y | Y | Y | Y | Y | Y | Y | Y | | | + | + | + | + |
| 21. | Y | Y | Y | Y | Y | Y | Y | N | | | + | + | + | − |
| 22. | Y | Y | Y | Y | N | Y | N | N | | | + | + | + | + |
| 23. | Y | Y | Y | Y | Y | Y | Y | Y | | | + | + | + | − |
| 24. | Y | Y | Y | Y | N | Y | Y | Y | | | + | + | + | − |
| 25. | Y | Y | Y | Y | Y | Y | Y | N | | | + | + | + | − |
| 26. | Y | Y | Y | Y | N | Y | Y | Y | | | + | + | + | − |
| 27. | Y | Y | Y | Y | Y | Y | Y | Y | | | + | + | + | − |
| 28. | Y | Y | Y | Y | N | Y | N | N | | | + | + | − | − |
| 29. | Y | Y | Y | Y | Y | Y | N | N | | | + | + | − | − |

***Note:
Y = Yes; N = No

Figure 14A:
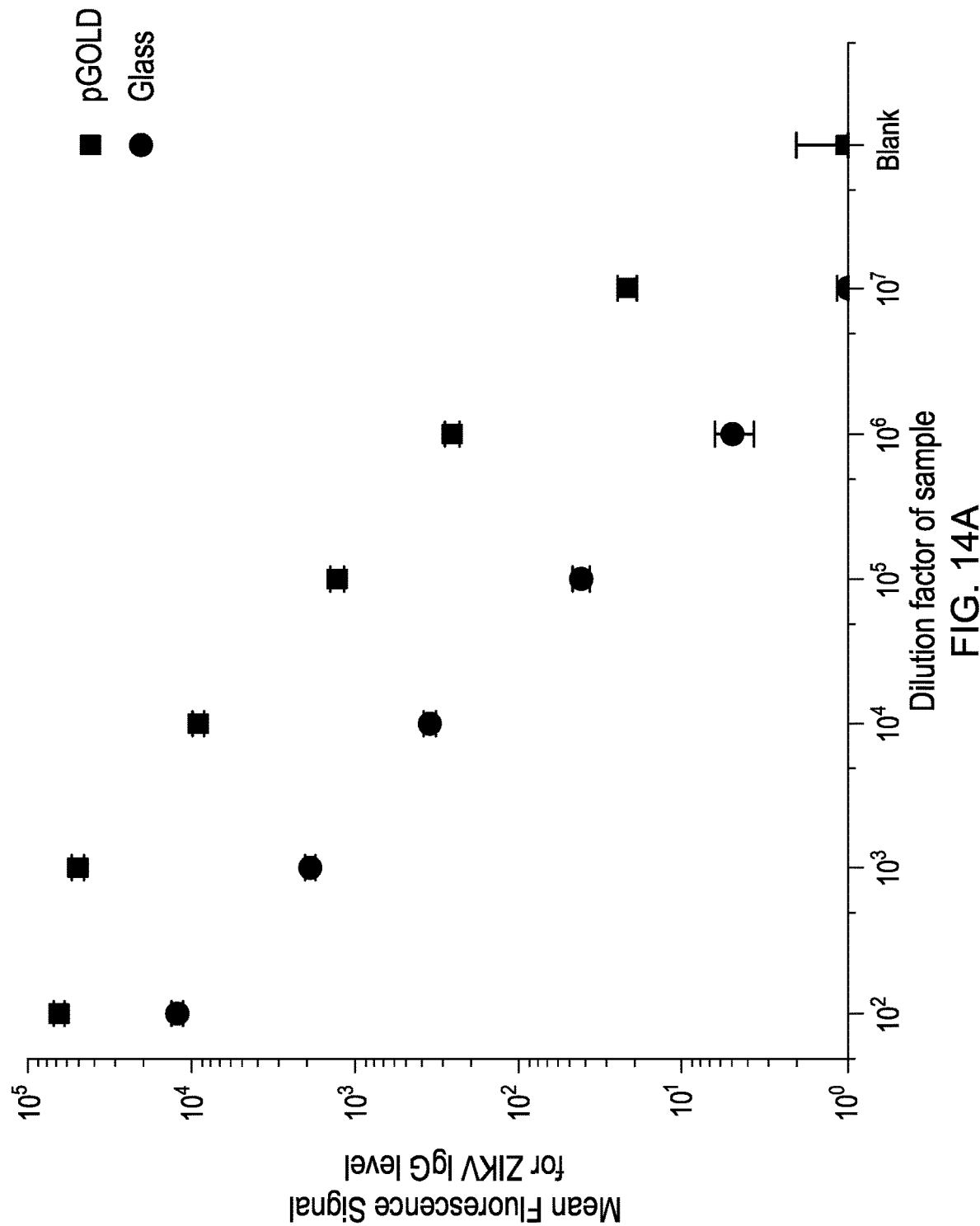
FIG. 14 in panels (A)-(B) shows an example titration curve for ZIKV IgG and IgA antibodies on a plasmonic gold film (pGOLD) in accordance with an embodiment. Panel a shows example titration curves for ZIKV IgG generated by averaging the median fluorescence intensity of IRDye680 emission over the triplicate microarray spots at various dilution of a ZIKV IgG positive serum sample on plasmonic gold slide and glass microscope slide (Fisher Healthcare, US), from 100 times dilution to 10 million times dilution. Panel b shows example titration curves for ZIKV IgA generated by averaging the median fluorescence intensity of IRDye800 emission over the triplicate microarray spots at various dilution of a ZIKV IgA positive serum sample on plasmonic gold slide and glass slide, from 100 times dilution to 10 million times dilution. Error bars represent the standard deviation of the assay over 4 replicate assays on 2 slides.
Figure 14B:
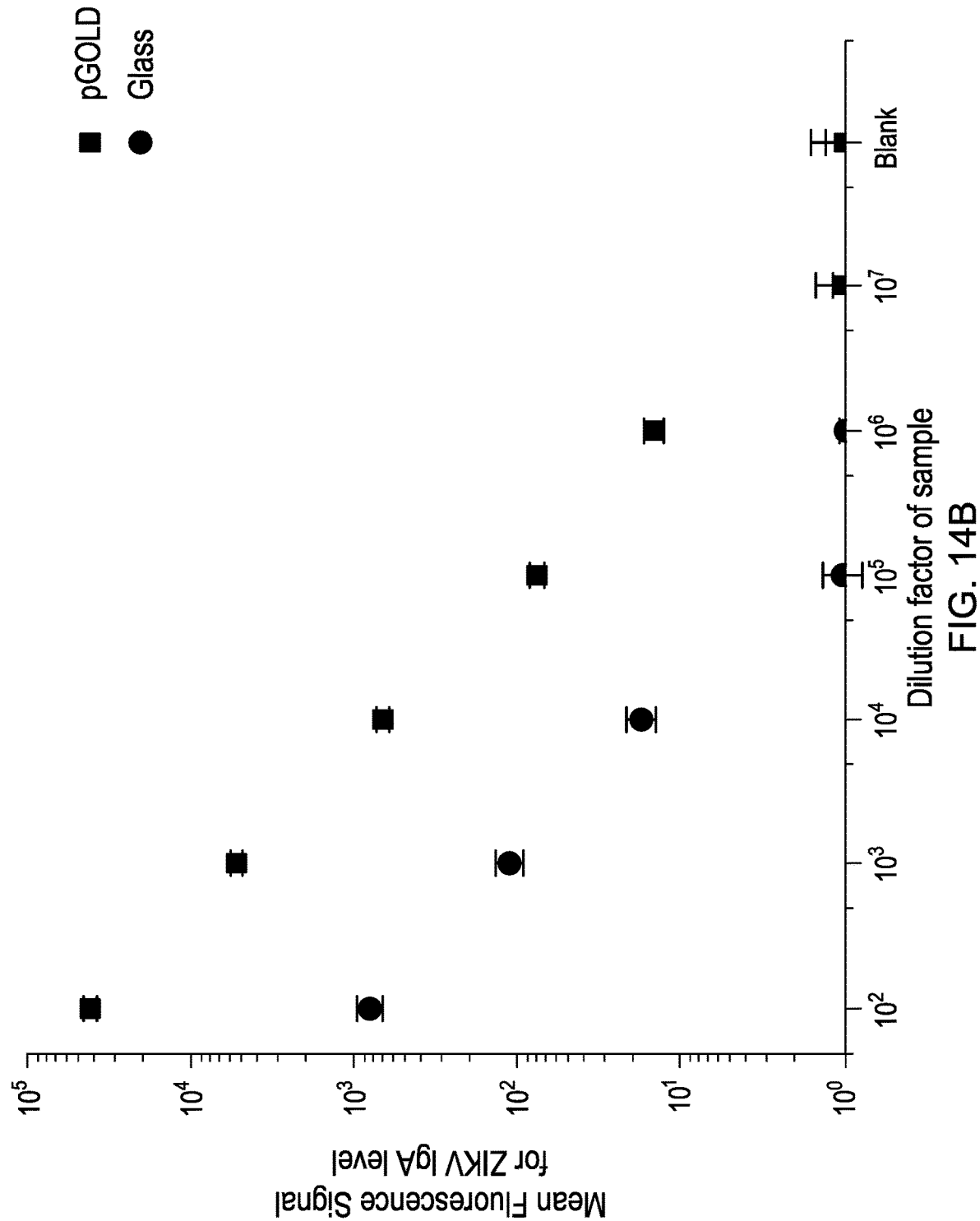

Serum samples from three groups of patients were obtained (Table 4A and 4B): (1) 29 patients from Colombia (purchased from Medical Research Networx, LLC) who were clinically diagnosed with ZIKV infection during the recent outbreak in Colombia (samples collected in the end of 2015 to early 2016 period and with no history of DENV infection; (2) 34 patients with a clinical diagnosis of DENV infection from Colombia, Ecuador, and Honduras, collected before the introduction of ZIKV to the Americas, as well as Sri Lanka which has had no known ZIKV cases; and (3) 42 control individuals with no history of ZIKV or DENV infection. Each serum sample was applied to the ZIKV/DENV antigen array, for multiplexed detection of antibody subtypes against ZIKV and DENV antigens. A sample from a ZIKV infected patient was diluted by $10^2$ to $10^7$ fold over 6-logs and greater than 45 logs of NIR fluorescence signal change was observed, which was superior to conventional platforms such as planar glass (FIG. 14). To validate the assay quality of the present disclosure, IgG and IgM tests against DENV antigens with pGOLD substrates were performed and compared with commercial kits (Focus Dengue Virus IgG DxSelect and Panbio Dengue IgM Capture ELISA, respectively). As described above, and shown in FIGS. 1A-B and 2A-B, the multiplexed assay on pGOLD chip yielded test results that were comparable to the commercially available assays.

Figure 8B:
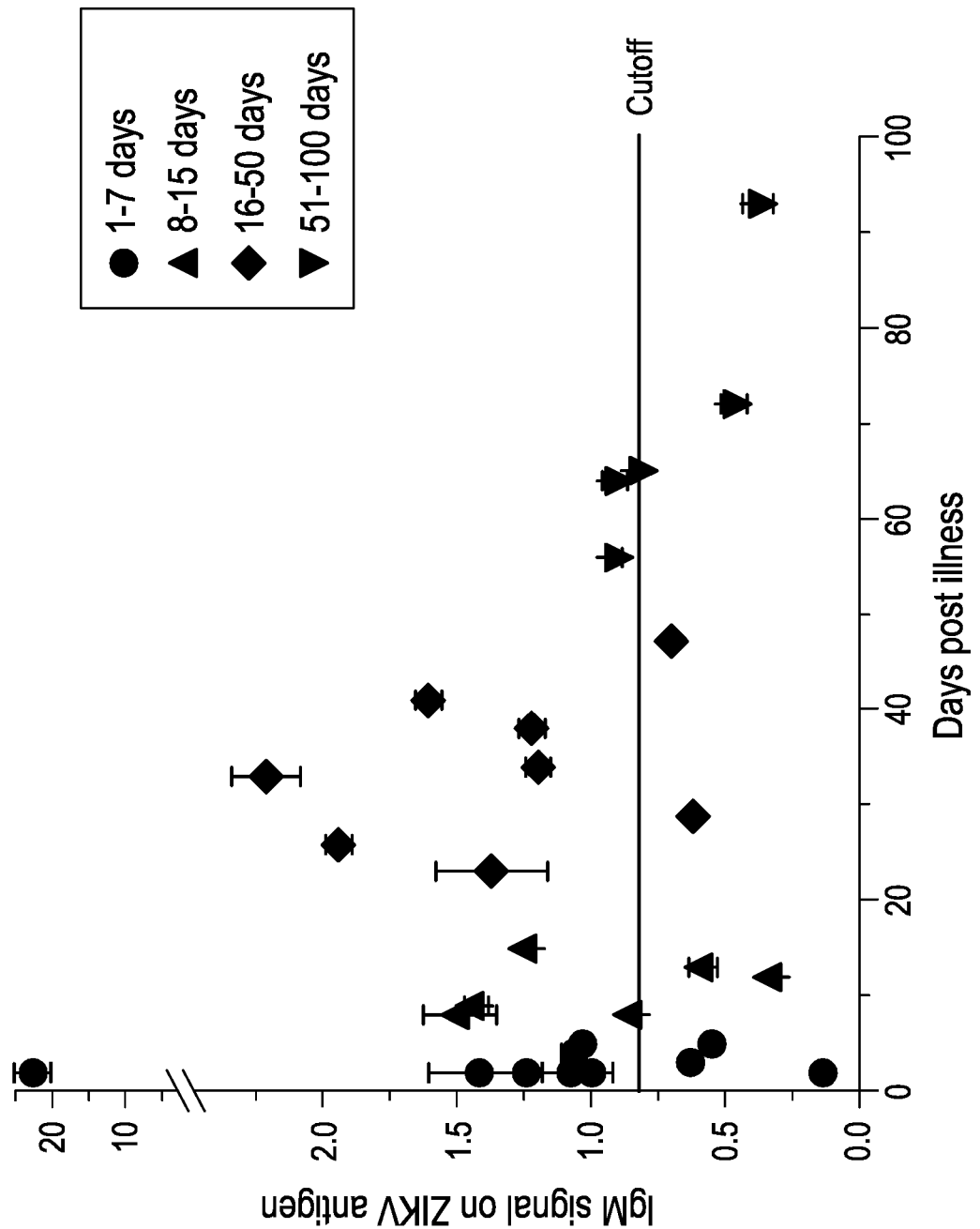
Figure 8C:
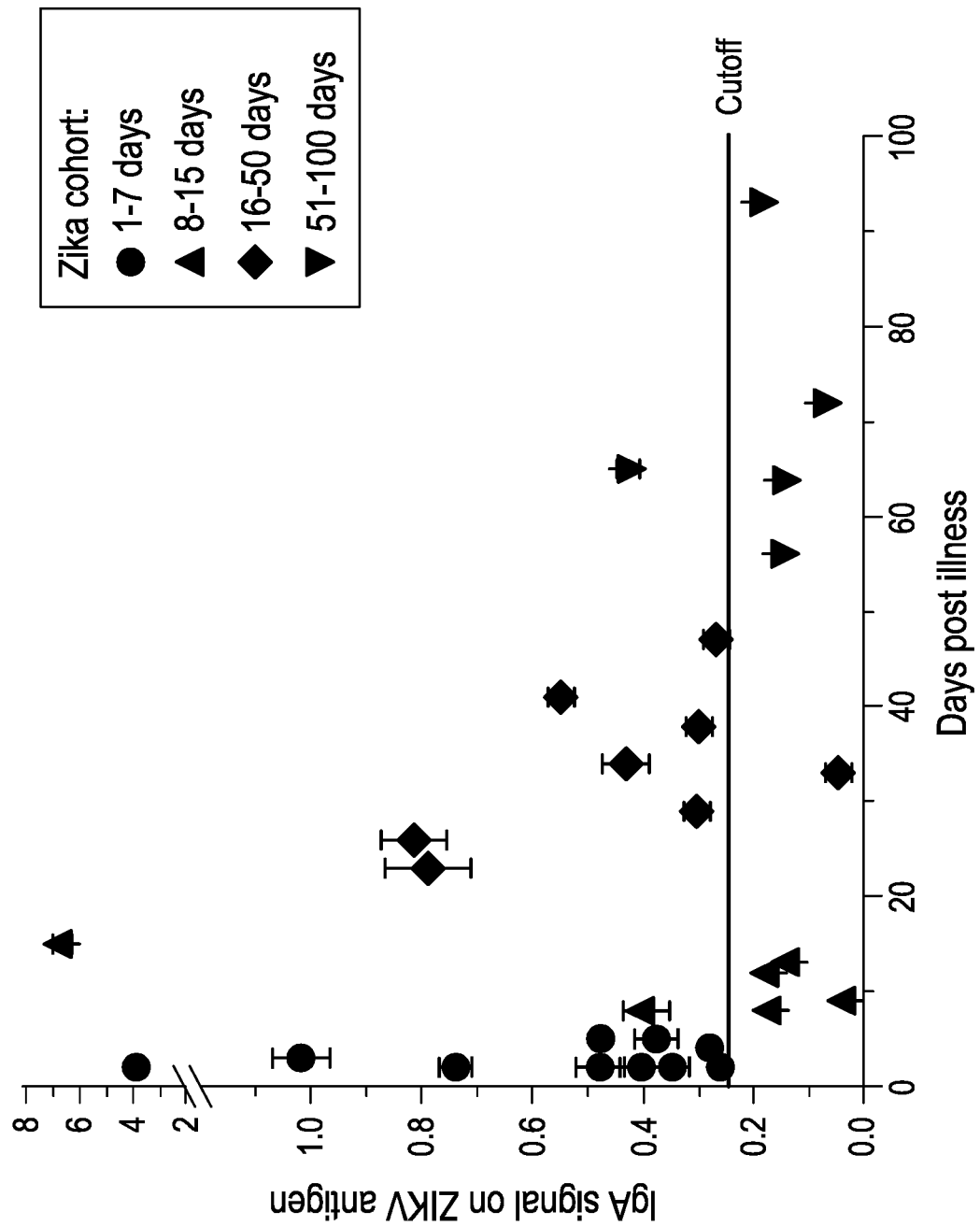
Figure 9:
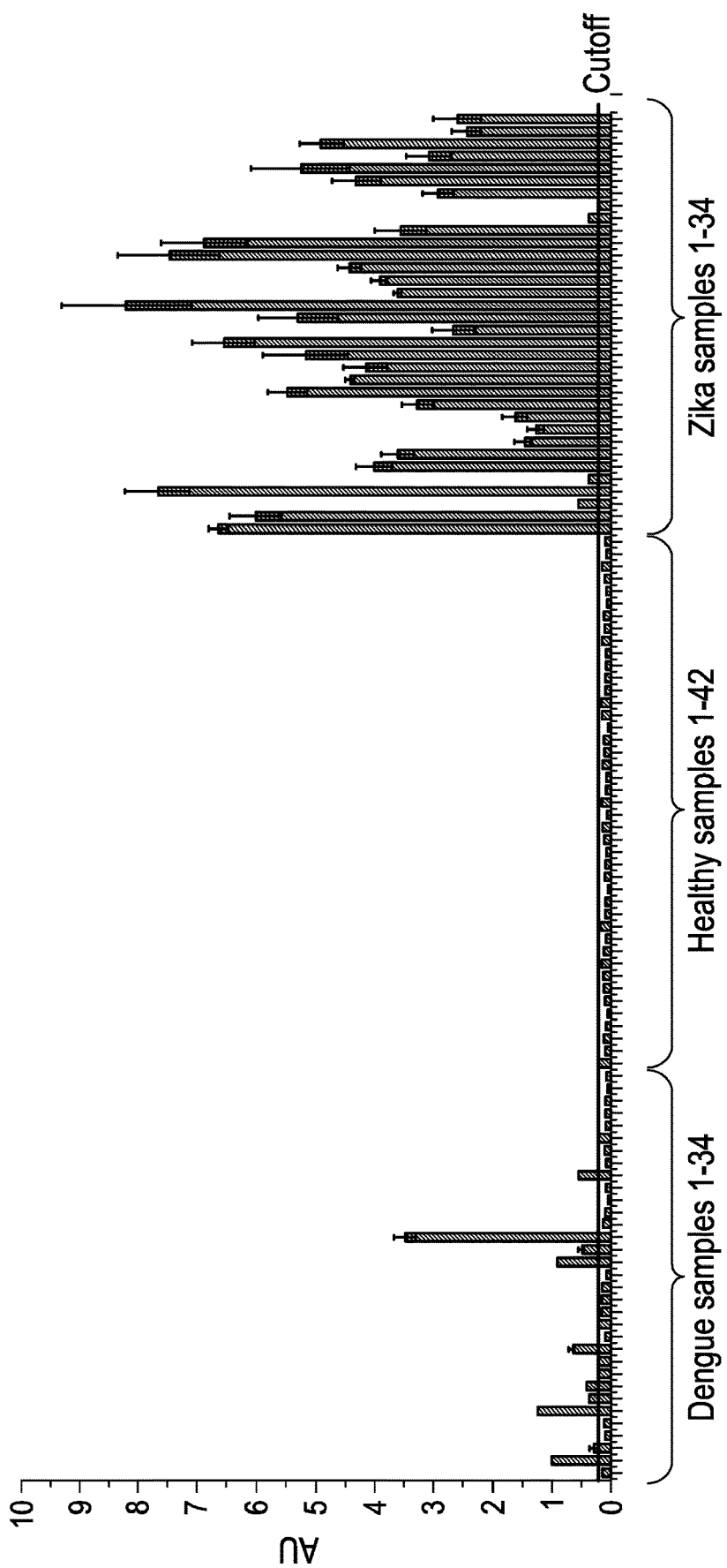
FIG. 9 shows an example bar chart for Zika IgG antibody levels detected on a plasmonic gold substrate (pGOLD) in accordance with an embodiment, for specimens with Dengue infection, Zika infection, or no known flavivirus infection (healthy control).

There was an overlap of ZIKV NS1 IgM antibody levels in the sera from patients with ZIKV infection and DENV infection (FIG. 4, panel b, consistent with the high IgM cross-reactivity observed by the CDC). However, the levels of IgG (FIG. 4, panel a) and IgA (FIG. 4, panel c) antibodies against ZIKV NS1 antigen in the sera of ZIKV infected patients were markedly higher than those in the sera of DENV infected and control patients. Although some DENV-infected individuals showed higher serum ZIKV IgG signal than controls (FIG. 4, panel a, suggesting finite but small IgG cross-reactivity), a ZIKV IgG cutoff of 0.14 was able to differentiate ~90% (26 out of 29) of ZIKV infected individuals from DENV infected individuals (FIG. 4, panel a). The ZIKV IgG level was high even in sera from ZIKV infected patients collected during the first seven days of illness (i.e., 1-7 days between first reported symptoms and sample collection, FIG. 4, panel d & Table 4A and 4B), peaked in samples collected between 16-50 days of illness, and decreased gradually, but remained positive ~100 days after onset of illness (FIG. 8, panel a).

It was noted that the ZIKV IgA levels detected in the samples from ZIKV infected patients were substantially higher than those detected in samples from DENV infected and control groups (FIG. 4, panel c). A cutoff of 0.25 for the IgA antibody level against ZIKV NS1 antigen provided a high negative percent agreement (NPA~98%, 63 out of 64) and good positive percent agreement (PPA~69%, 20 out of 29) compared to clinical diagnosis of ZIKV infection (FIG. 4, panel c). Positive ZIKV IgA levels were detected in sera collected from ZIKV infected patients 1 to 65 days after illness onset (FIG. 8, panel c). Positive ZIKV IgA was detectable over a shorter time period than ZIKV IgG as IgA turned negative >65 days (FIG. 8, panel a vs. panel c). Positive ZIKV IgM antibodies were also detected in sera collected 1 to 65 days after illness onset (FIG. 8, panel b).

Figure 11:
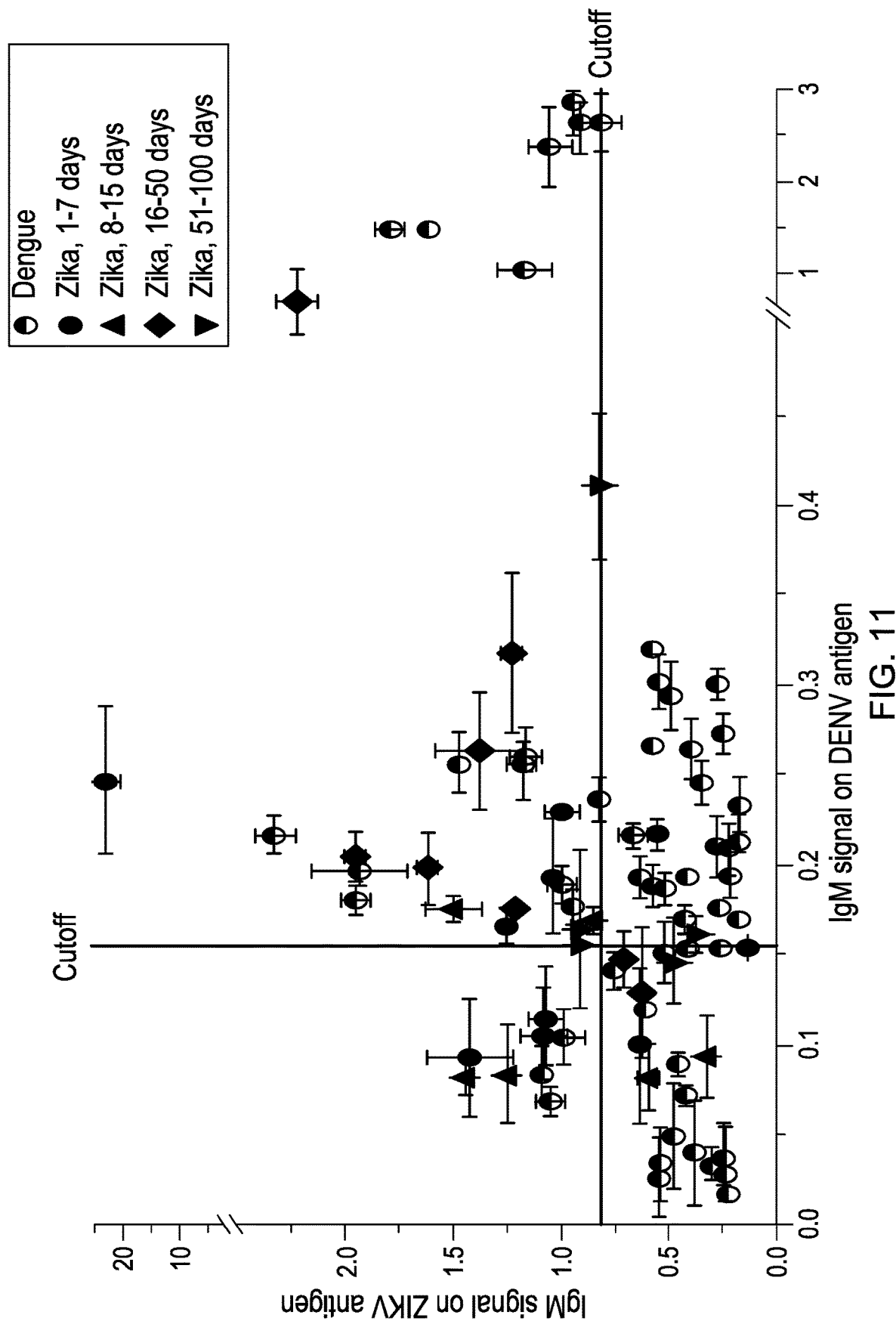
FIG. 11 shows an example 2D plot of signals for IgM antibodies against Zika NS1 antigen and IgM antibodies signals against Dengue antigen for samples having a Dengue infection (half-filled circle), or Zika infection at the specified range of days after the onset of symptoms (filled circle—1-7 days; point-up triangle—8-15 days; diamond—16-50 days; point-down triangle—51-100 days). Both Illustrated cutoffs represent 3 standard deviations above the mean signal detected for control samples. Samples from Zika virus-infected patients showed higher average IgM signals on Zika virus antigen than on Dengue virus antigen, and samples from Dengue virus infected patients showed higher average IgM signals on Dengue virus antigen than on Zika virus antigen.

In one of the three samples from ZIKV infected patients that were negative for ZIKV IgG antibodies (open circle in FIG. 3, panel a, well below IgG Cutoff), a ZIKV IgA level well above the cutoff was detected (FIG. 3, panel a, empty circle), suggesting recent ZIKV infection. Thus, the combined ZIKV IgA and IgG test could lead to improved diagnostic sensitivity of acute ZIKV infection. In cases where cross-reactivity between ZIKV and DENV IgM antibodies might preclude the use of IgM to differentiate these infections (FIG. 4, panel b and FIG. 11), both ZIKV IgG and IgA antibodies were specific to ZIKV-infected individuals.

Close examination revealed that 50% (10 out of 20) of the ZIKV IgA positive samples were collected 1-7 days post symptom onset and 75% (15 out of 20) of the ZIKV IgA positive samples were also ZIKV IgM positive (FIG. 3, panel b & Table 4A and 4B), suggesting that ZIKV IgA may be a specific biomarker for recent ZIKV infection. In most of the cases, the ZIKV IgA positive samples were also ZIKV IgG positive (Table 4A and 4B), suggesting the specificity of both antibody sub-types and the value of serial measurement of ZIKV IgG beyond the initial IgG-negative period for identifying ZIKV infection (FIG. 8, panel a and FIG. 3, panel a).

Figure 10A:
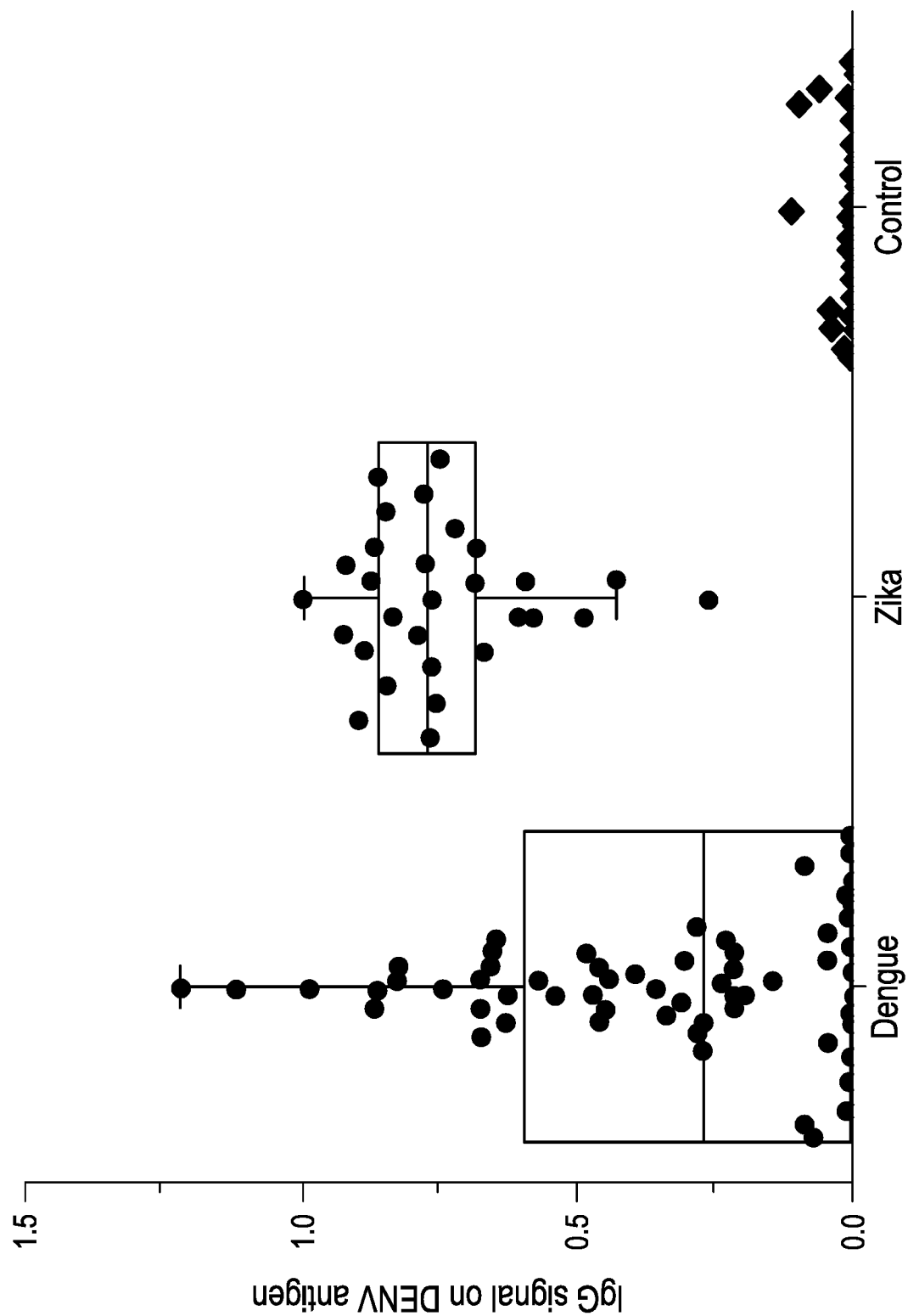
FIG. 10 in panels (A)-(C) shows example box plots for DENV IgG, IgM and IgA antibody levels for serum samples with DENV infection, ZIKV infection, or no known history of ZIKV or DENV infection (controls). All signal levels are normalized by a reference sample.
Figure 10B:
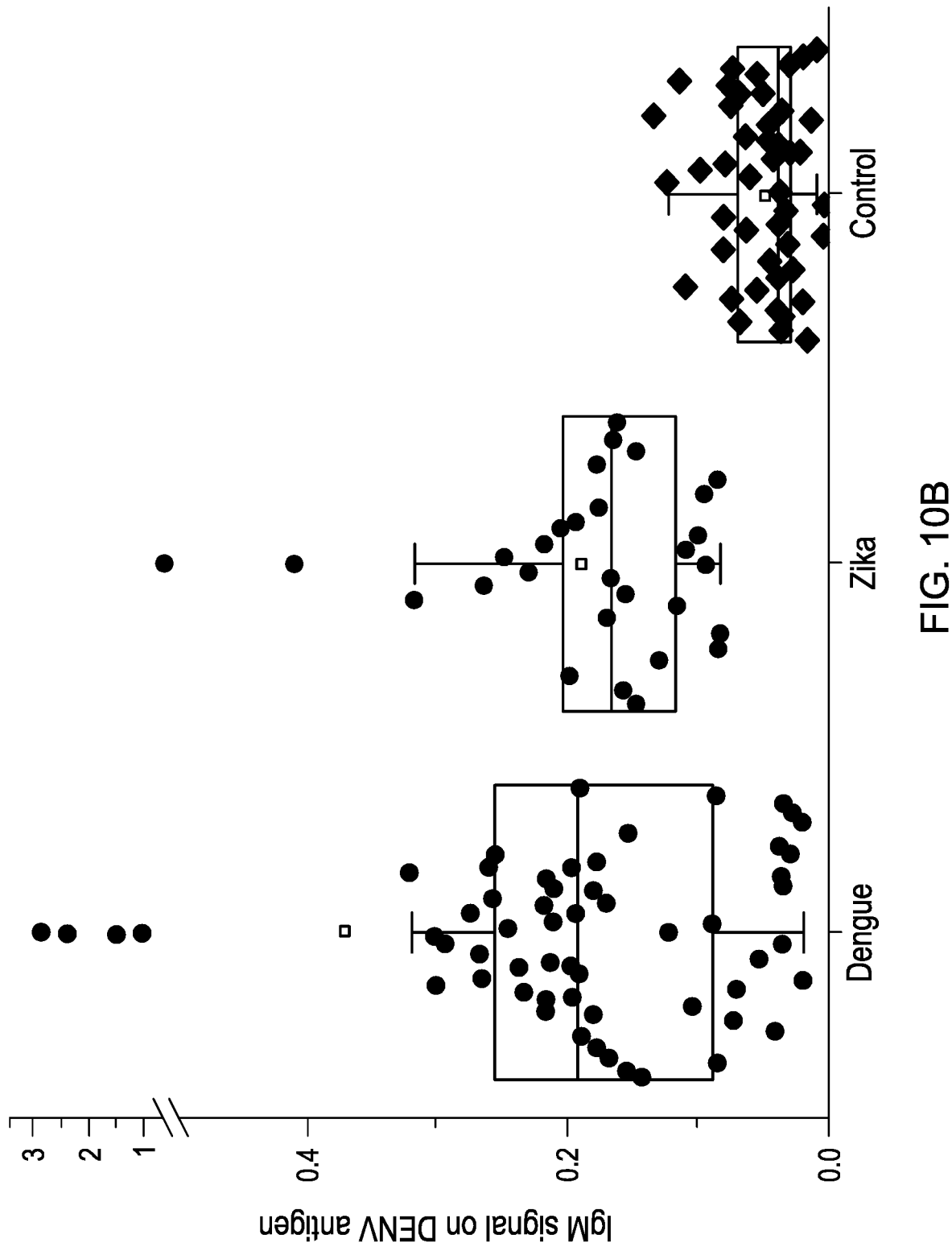
Figure 10C:
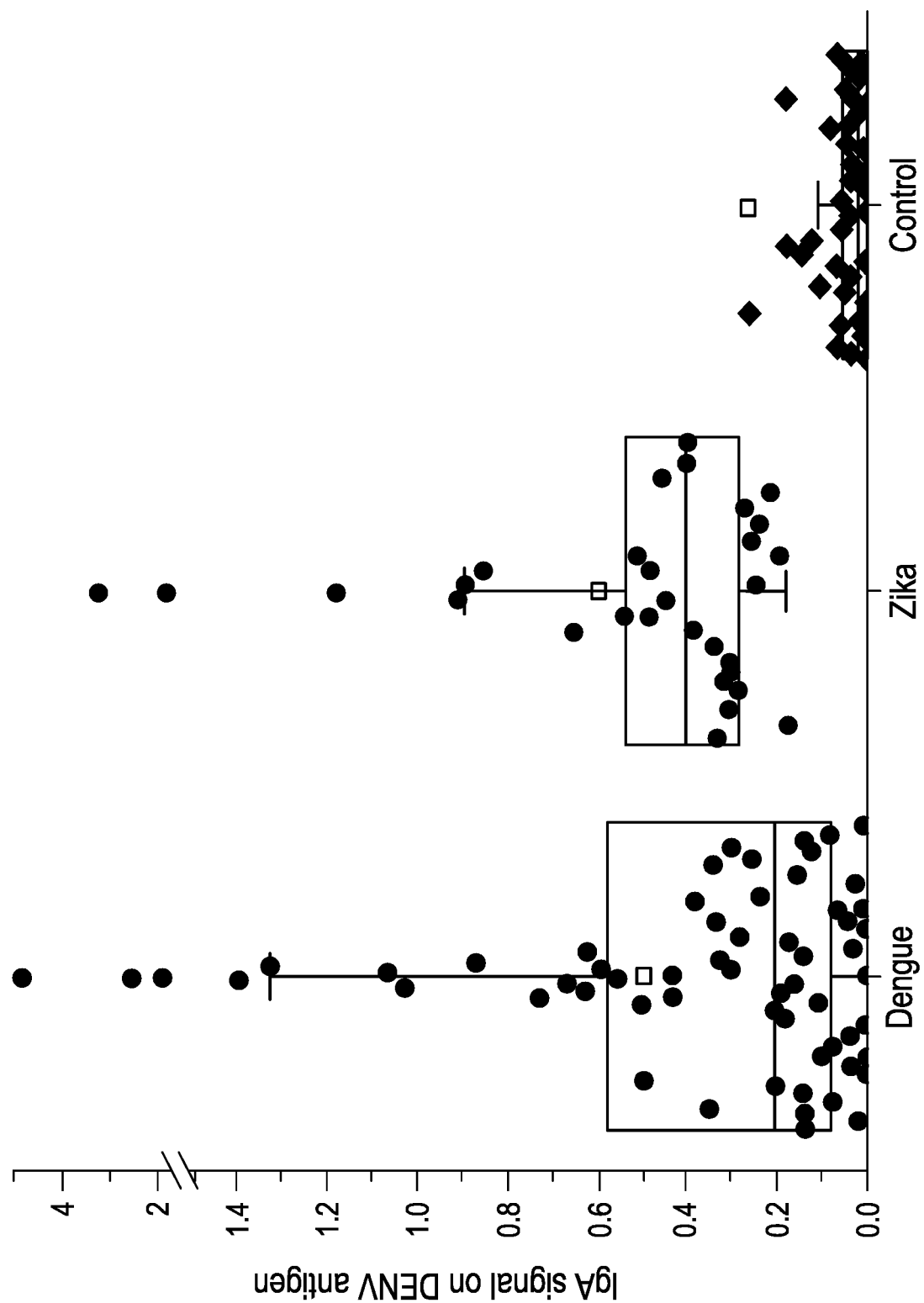

Next analyzed in sera from ZIKV infected patients were the IgG signals detected on DENV2 antigens and high antibody levels were observed (FIG. 7, panel a and FIG. 10). Given that DENV is endemic in Colombia and that all of these patients were over 18 years of age, it is likely that they had been previously exposed to DENV. A large fraction (27 out of 29) of the samples from ZIKV infected patients showed higher levels of IgG binding to DENV2 antigens than the median of the samples collected from the patients recently infected with DENV (FIG. 7, panel a). This may reflect the secondary response to flavivirus infection of the Colombia cohort. IgG/IgM/IgA assay using Dengue 1, 3 and 4 antigens (purified Dengue 1, 3 and 4 virus particles, West Pacific 74, CH53489 and TVP-360 strains respectively was also constructed, all cultured in vero cells from Microbix Biosystems Inc. Canada) and similar results of high IgG signals in ZIKV infected samples against these antigens were observed (FIG. 10).

The IgA antibodies against DENV2 antigen in the sera of samples collected from DENV infected patients demonstrated varying signal intensities associated with phase of the DENV infection (FIG. 7, panel b). However, IgA levels in the samples from DENV infected patients were low against ZIKV antigen (FIG. 7, panel b), suggesting high ZIKV IgA specificity to ZIKV infection. Also, for the DENV infected cohort, 88%0 of the DENV2 IgA positive serum samples exhibited high DENV2 IgM levels (FIG. 7, panel c), corresponding to DENV infection in the acute phase.

Figure 15A:
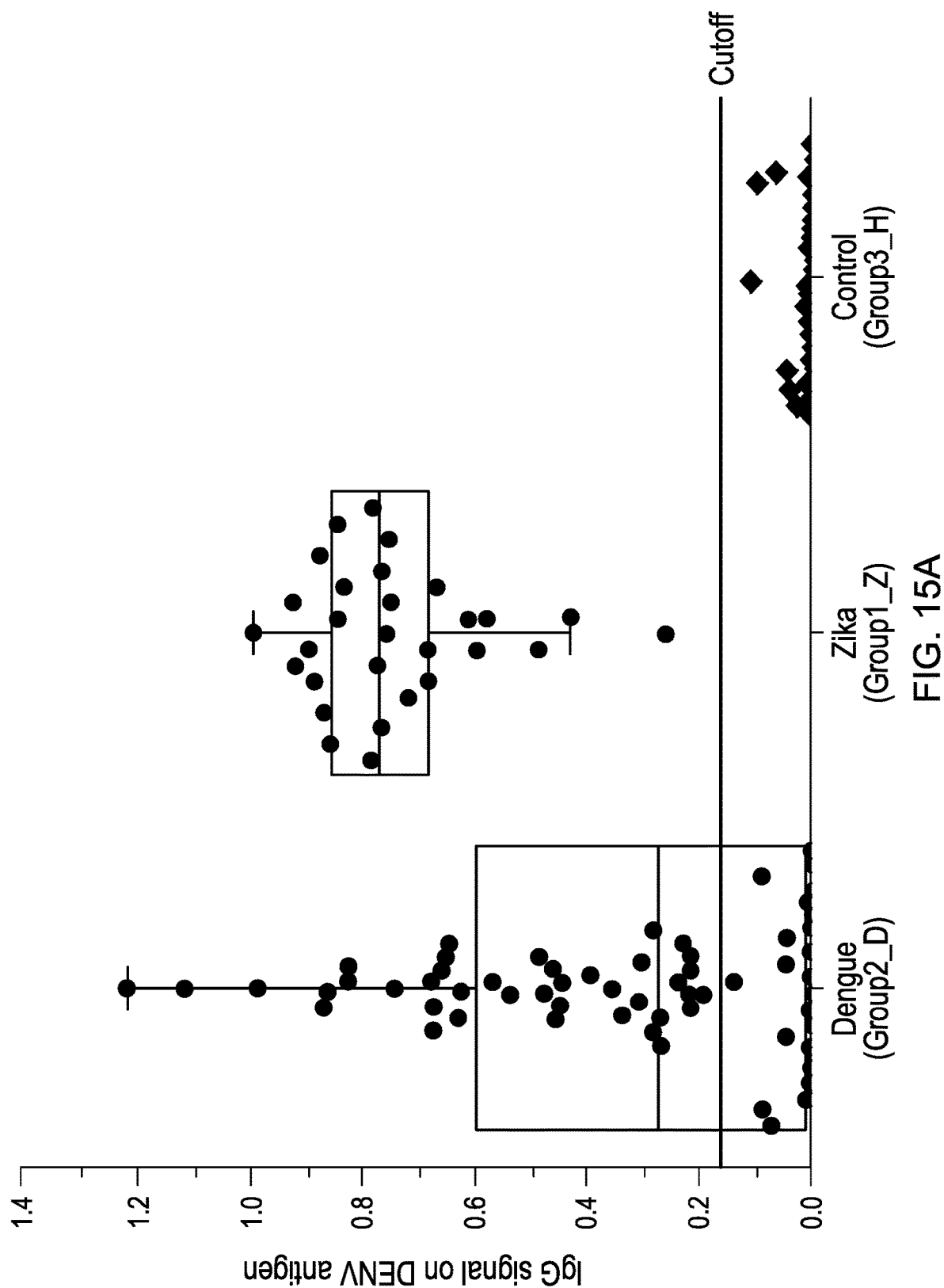
FIG. 15 shows an example box plots (A-B) for DENV IgG antibody levels for samples with Dengue infection (64 patients), Zika infection (29 patients), or no known flavivirus infection (control, 50 patients) and DENV IgG avidity levels for samples with Dengue infection and Zika infection. Also shown is an example plot (C) for ZIKV IgG avidity levels during four groups of days between onset of illness and sample collection (1-7 days, 8-15 days, 16-50 days, and 51-100 days post illness). DENV and ZIKV IgG avidity is calculated by dividing IgG levels measured with urea treatment by the IgG levels measured without urea treatment.
Figure 15B:
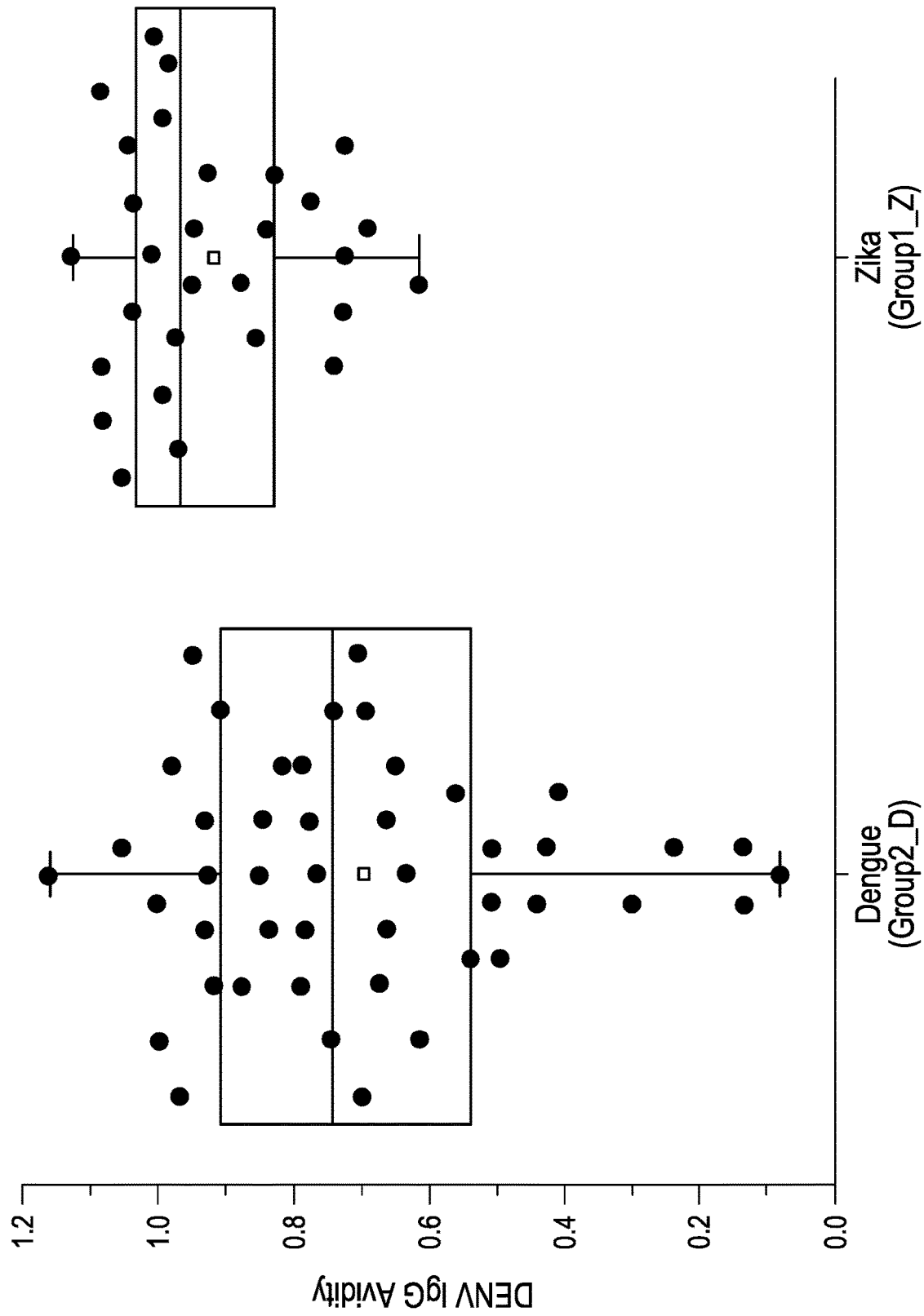
Figure 15C:
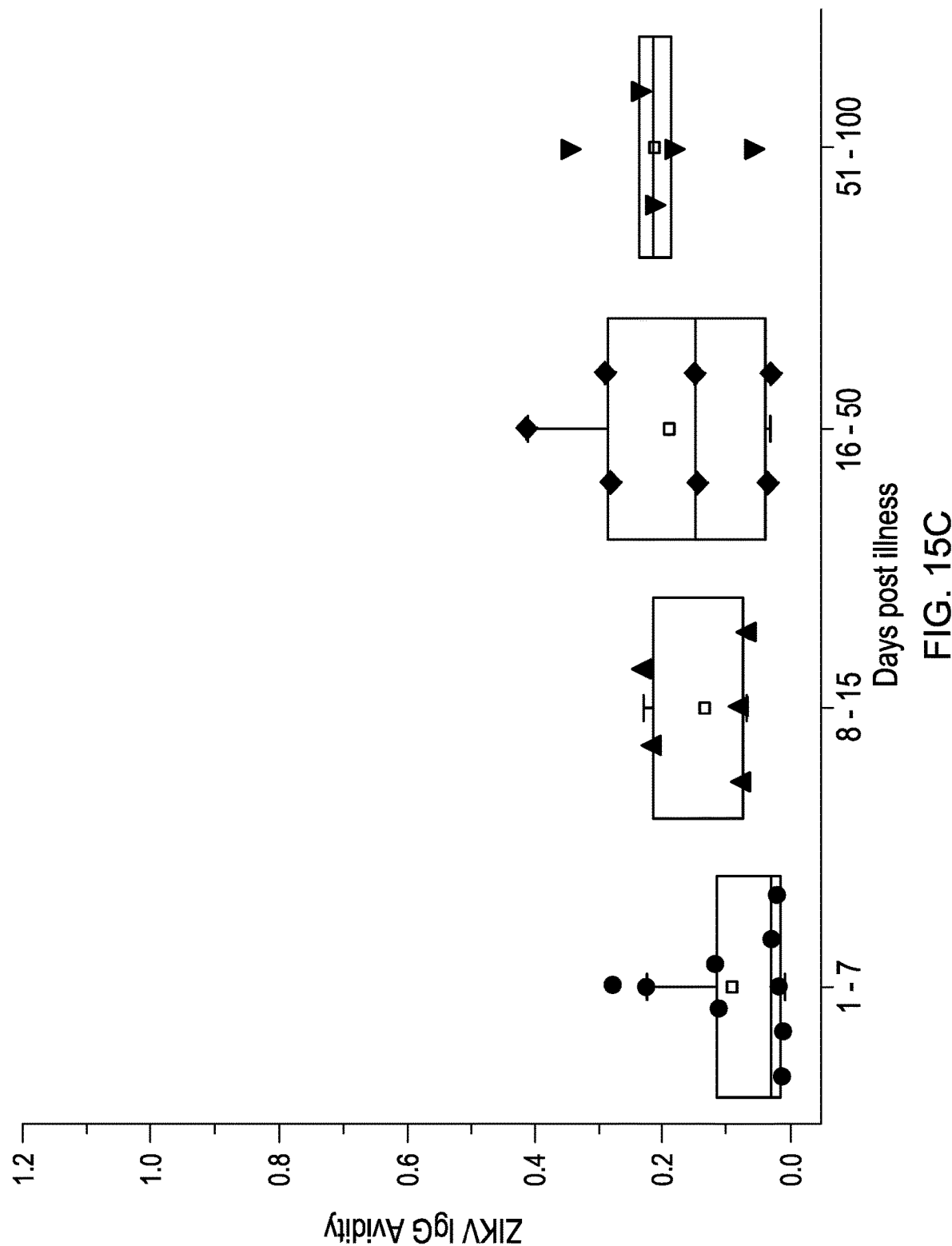
Figure 16A:
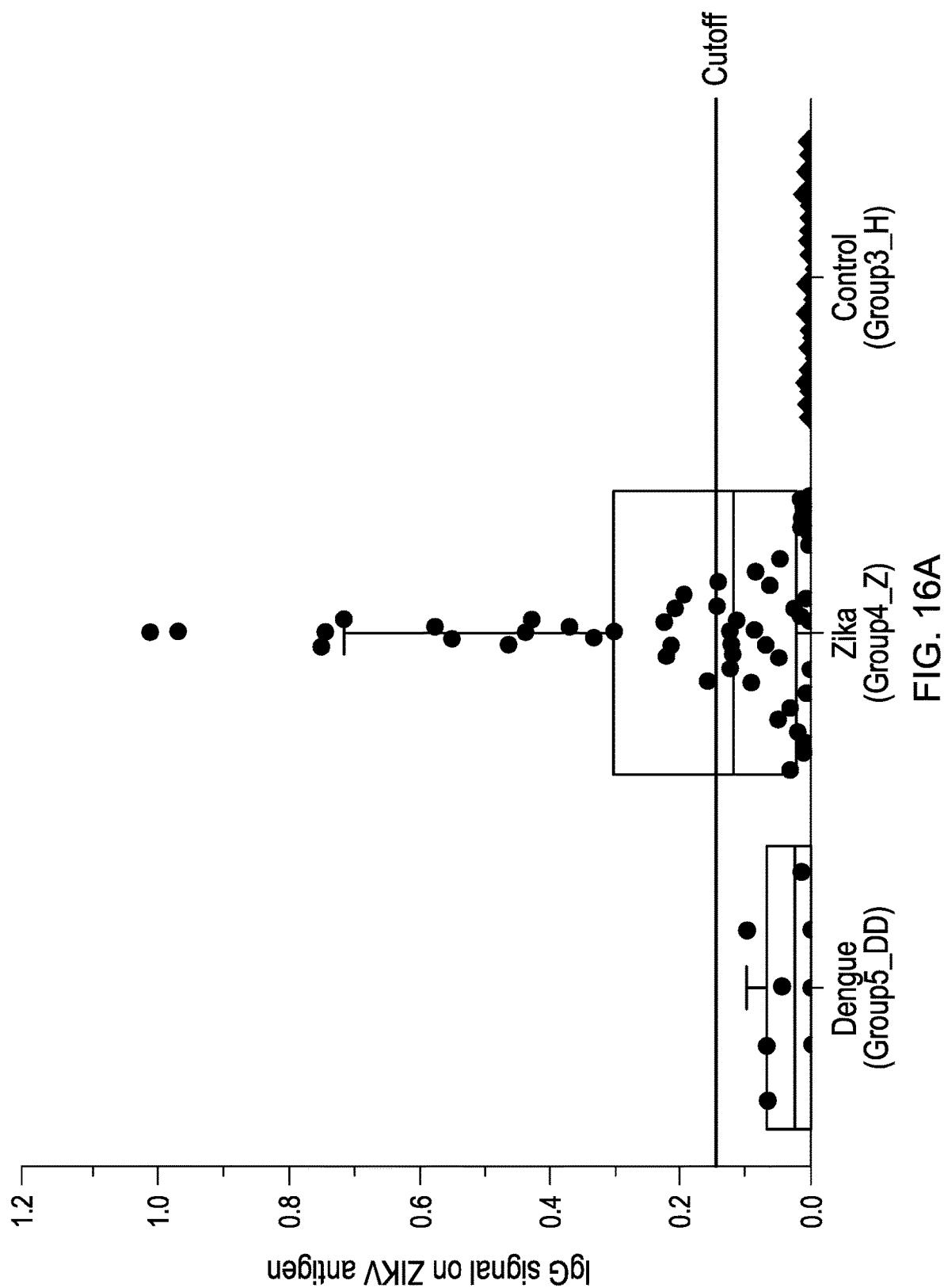
FIG. 16 shows example box plots (A and E) for ZIKV IgG and IgA antibody levels and (C and F) for DENV IgG and IgA antibody levels for samples with Dengue infection (8 patients with secondary DENV infection and detectable DENV RNA), Zika infection (49 patients with secondary ZIKV infection), or no known flavivirus infection (control, 50 patients). Also shown are example plots (B) for ZIKV IgG avidity levels for two different samples for Zika infection (49 patients with detectable ZIKV RNA and 29 patients clinically diagnosed with ZIKV infection) and (D) for DENV IgG avidity levels for samples with Dengue infection (8 patients with secondary DENV infection and detectable DENV RNA) and Zika infection (49 patients with secondary ZIKV infection and detectable ZIKV RNA).
Figure 16B:
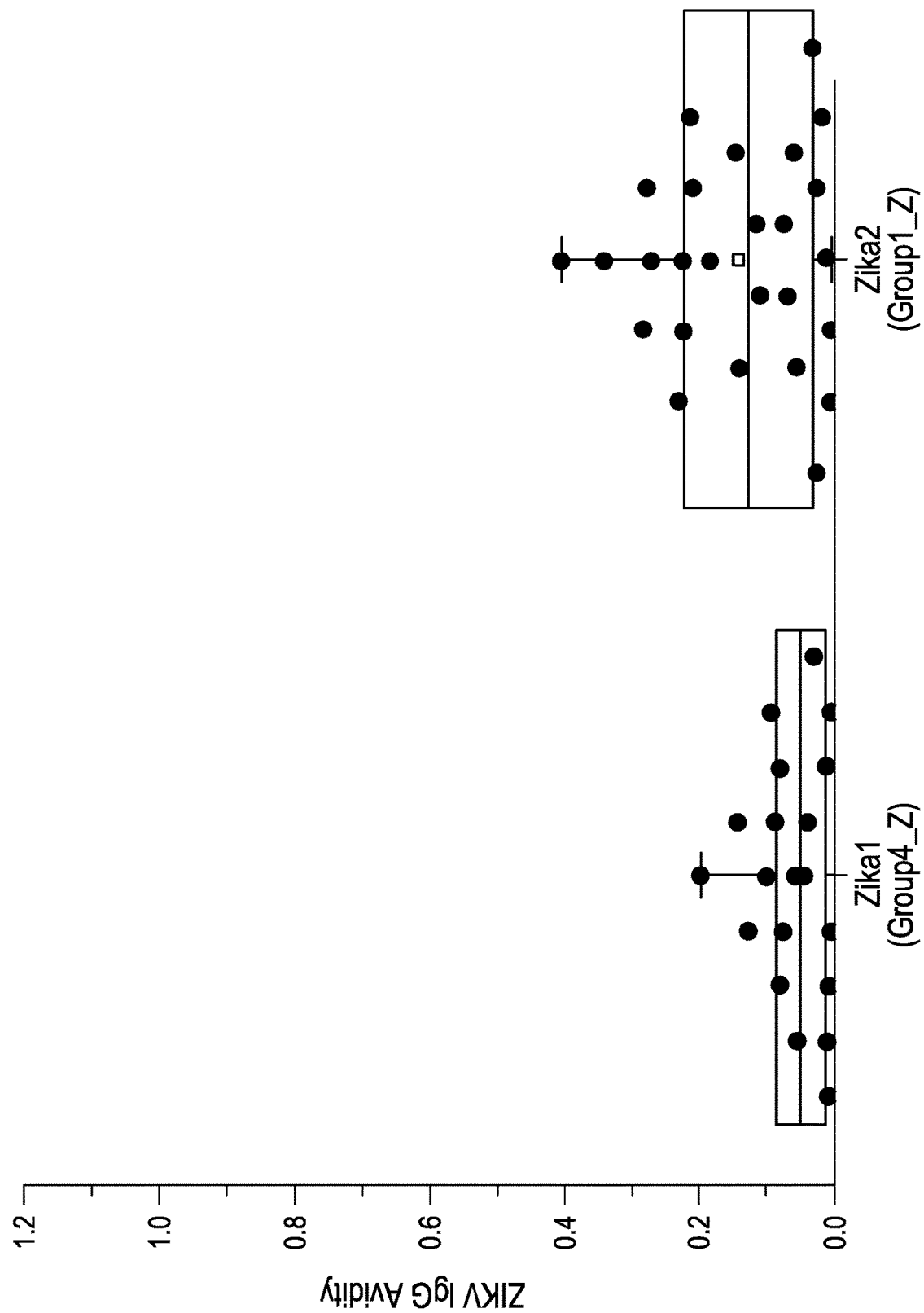
Figure 16C:
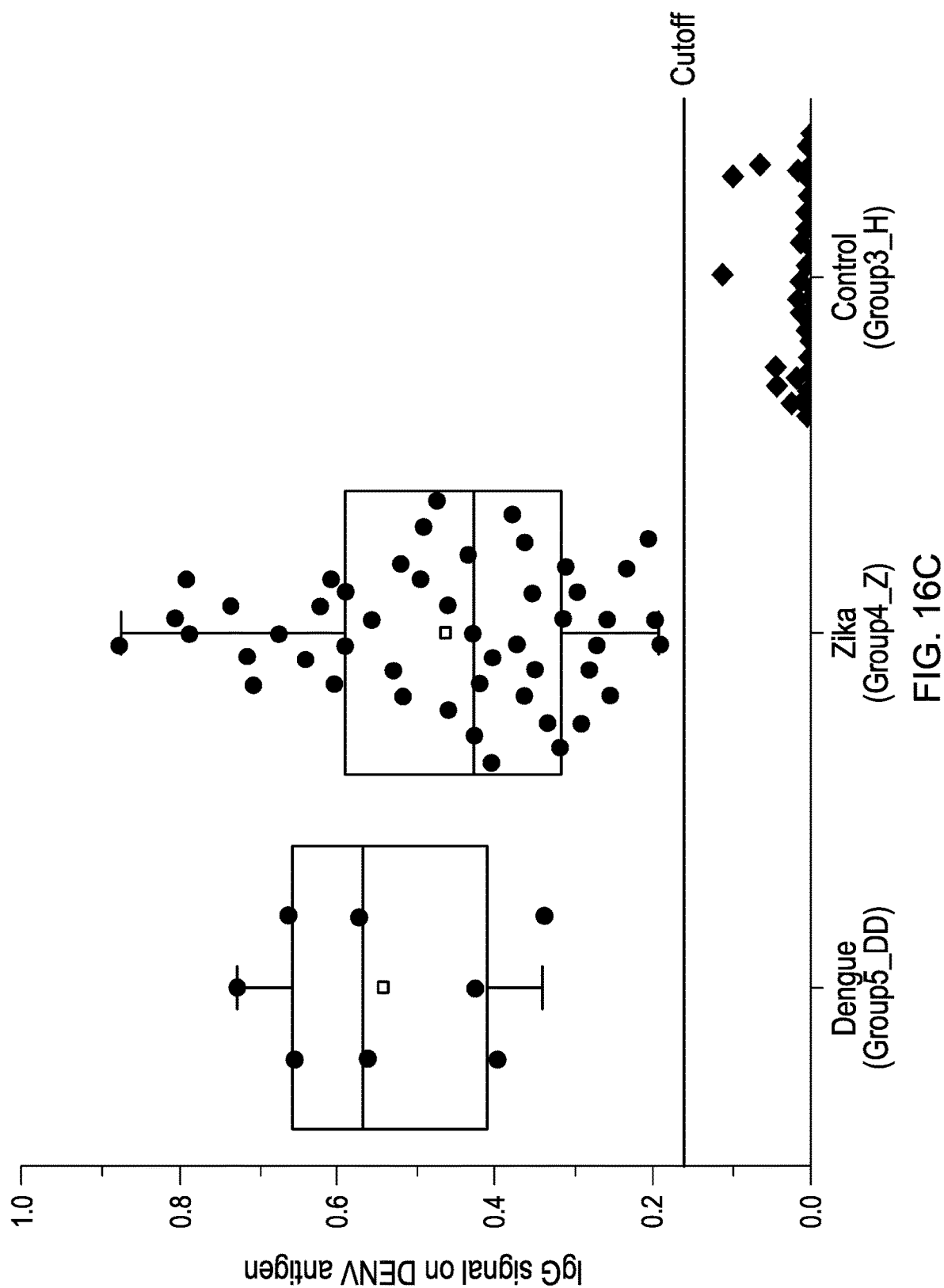
Figure 16D:
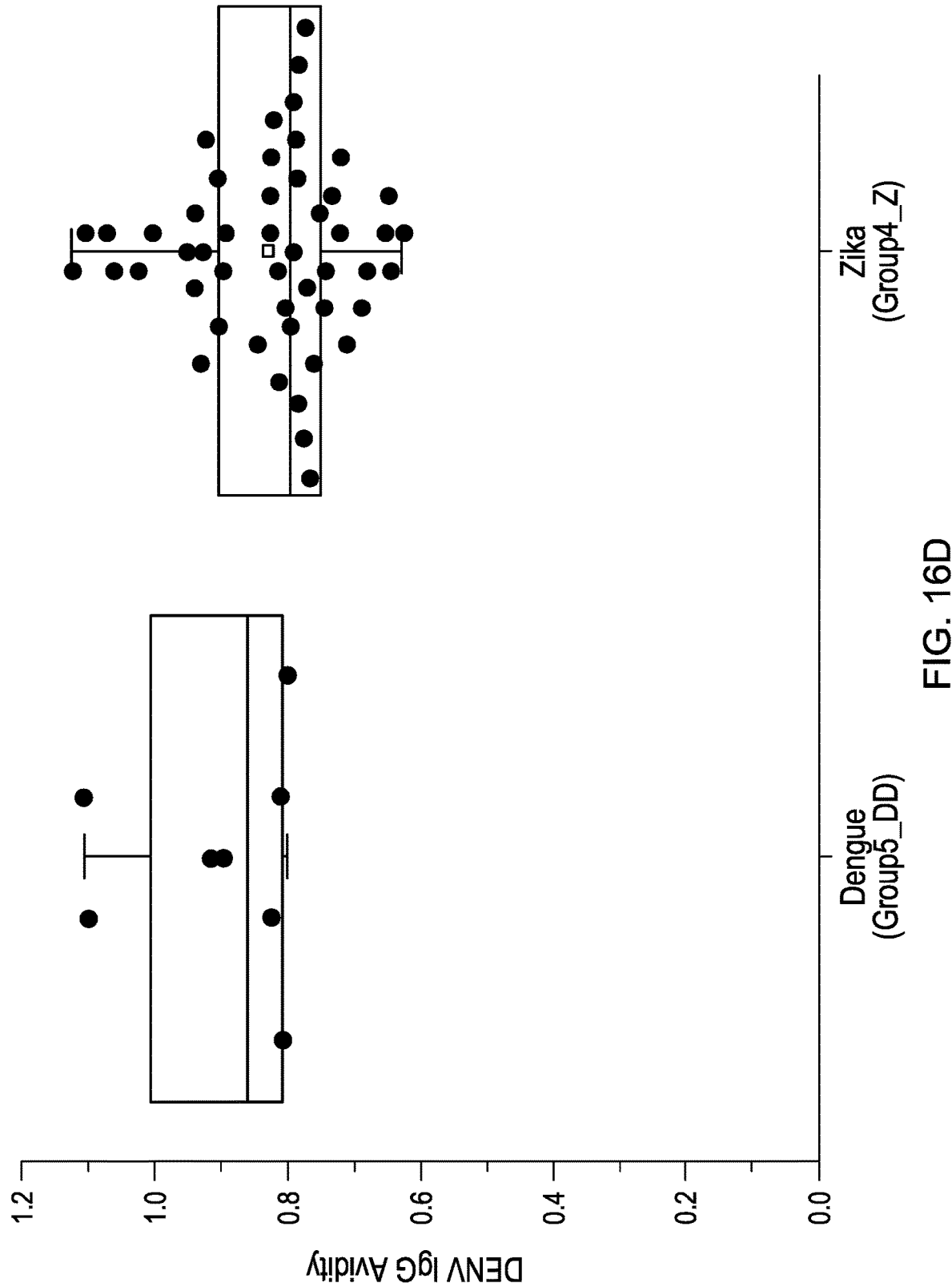
Figure 16E:
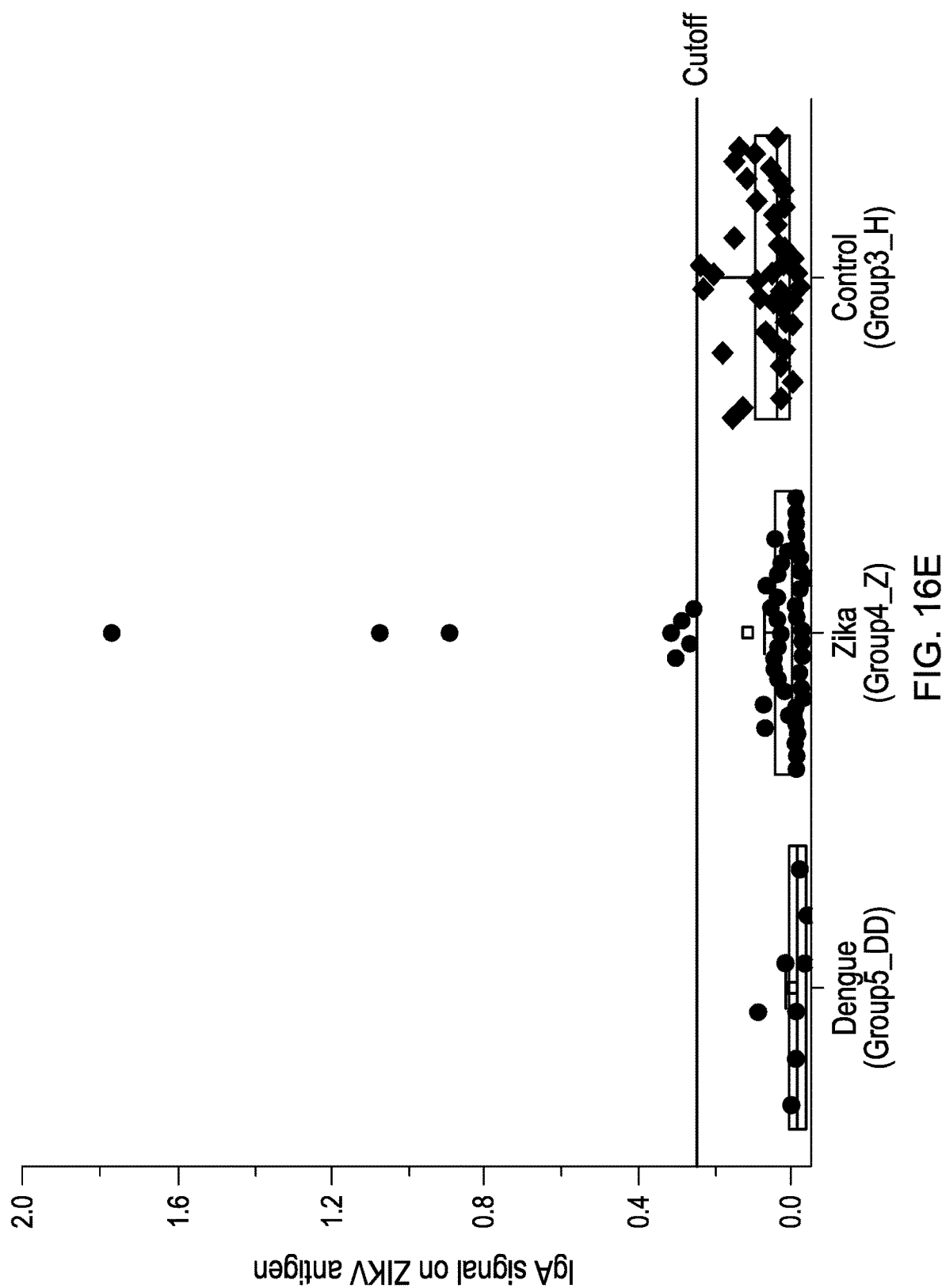
Figure 16F:
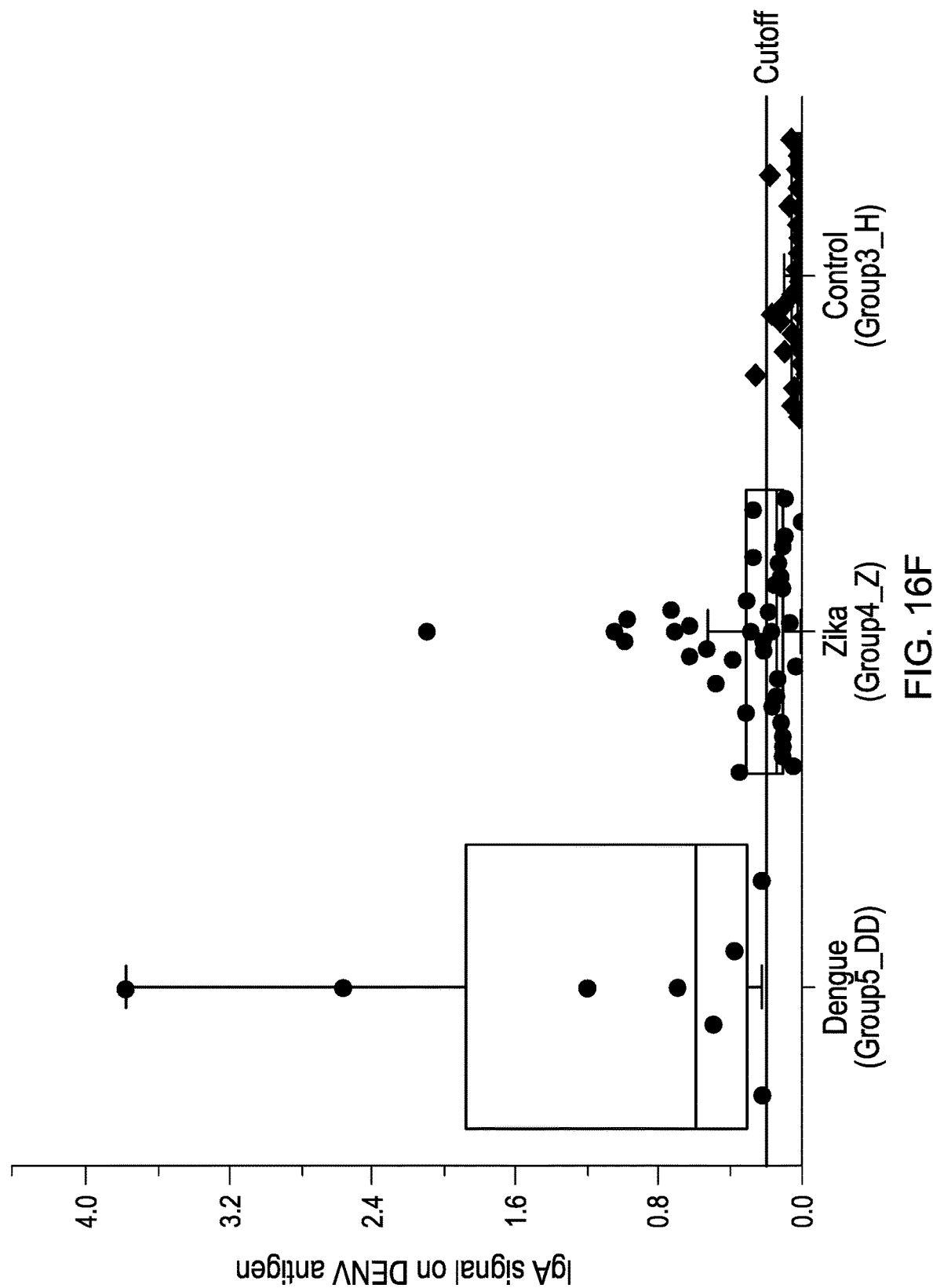

In the sera of ZIKV infected patients from Colombia, high IgG antibody levels to DENV2 antigens (FIG. 15, panel a) was observed, as well as on DENV serotype 1, 3 and 4 antigens (purified DENV 1, 3 and 4 virus particles, West Pacific 74, CH53489 and TVP-360 strains respectively). Given that DENV was endemic in Colombia and that all of those patients were over 18 years of age, it is likely that they had been previously exposed to DENV. High (greater than 0.6) DENV IgG avidity levels was detected for all of the ZIKV infected patients from Columbia (FIG. 15 panel b), confirming that those patients had past DENV infections. All ZIKV infected patients in Columbia demonstrated low (<0.5) ZIKV IgG avidity levels (FIG. 15 panel c), confirming the fact that the Colombia patients were recently infected with ZIKV for the first time. The trend of increasing ZIKV IgG avidity with the increase in the number of days post illness onset (FIG. 15 panel c) revealed the potential of using the ZIKV IgG avidity test to differentiate recent and past ZIKV infection. The results further suggested that in a dengue endemic region, due to a finite but small IgG antibody cross-reactivity for ZIKV and DENV, a ZIKV IgG cutoff that is referenced to a population that has been previously infected with DENV should be used. This approach allows the highly specific serologic diagnosis of ZIKV infection several days post symptom onset as observed with the Colombia cohort.

The high ZIKV IgG level in some of the Colombia samples collected within days of symptom onset prompted further investigation of ZIKV IgG for infections in the very early acute phase, using a cohort of 49 samples from the Dominican Republic that were ZIKV RNA positive by RT-PCR. For comparison, 8 DENV serum samples with acute secondary DENV infection that were DENV RNA positive by RT-PCR and that showed high DENV IgG avidity were tested. Positive DENV IgG levels (FIG. 16 panel c) and high (greater than 0.6) DENV IgG avidity (FIG. 16 panel d) suggest that all of these patients from dengue endemic regions had past DENV infections.

Consistent with findings from the Colombia cohort, highly positive ZIKV IgG and/or IgA levels in about 47% of the samples were detected from ZIKV infected patients, all of which were positive for ZIKV RNA by RT-PCR (FIG. 16 panel a and FIG. 16 panel e). Since all 49 patients in this group had acute ZIKV infection with specimens collected 2-6 days post symptom onset, the sensitivity of ZIKV IgG and IgA test for this cohort was lower than that from the ZIKV infected patients from the Columbia cohort. All of the ZIKV IgG positive samples from the Dominican Republic showed low (<0.2) ZIKV IgG avidity (FIG. 16 panel b). Interestingly, these values are lower than the values from the specimens of the Colombia ZIKV infected cohort, many of which were collected in the convalescent phase. This further confirms that primary acute ZIKV infection in the early phase is detectable by RT-PCR.

Samples from patients with secondary DENV infection in the acute phase with detectable DENV RNA in blood and high DENV IgG avidity due to past DENV infection showed positive DENV IgG and IgA levels (FIG. 16 panel c and FIG. 16 panel f), but negative ZIKV IgG and ZIKV IgA levels (FIG. 16 panel a and FIG. 16 panel e), suggesting that the positive ZIKV IgG and IgA levels observed with the two ZIKV cohorts from DENV endemic regions were not due to pre-existing cross-reactive anti-DENV antibodies, but were nascent, specific anti-ZIKV antibodies.

Figure 17A:
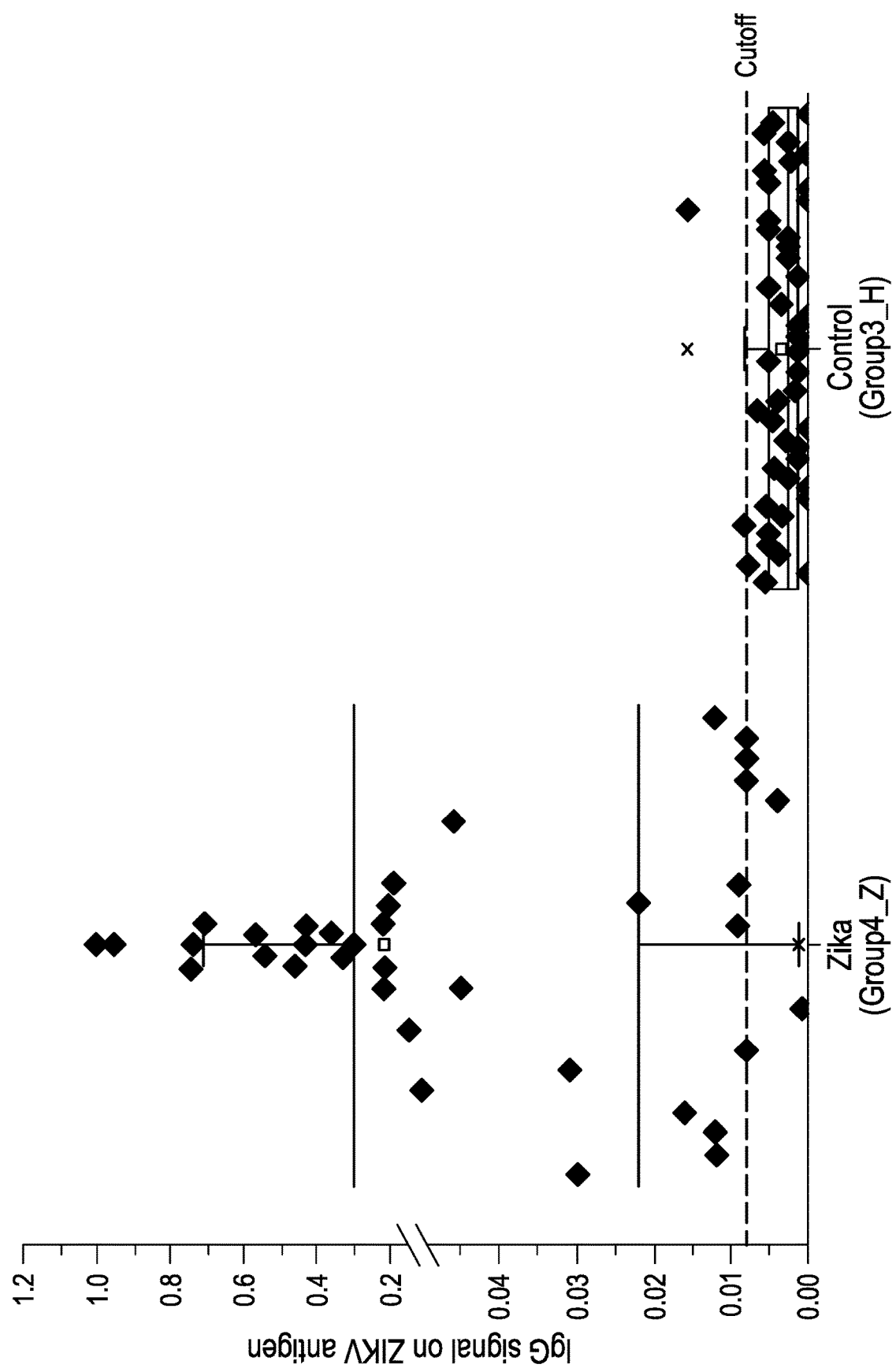
FIG. 17 shows example box plots (A) for ZIKV IgG antibody levels for serum specimens from two groups of patients: 49 patients with secondary ZIKV infection and detectable ZIKV RNA (Zika) and 50 patients with no known history of ZIKV or DENV infection (control). Also shown (B) are ZIKV IgG avidity levels for the 49 patients with detectable ZIKV RNA (Zika 1), and 29 patients clinically diagnosed with ZIKV infection (Zika 2).
Figure 17B:
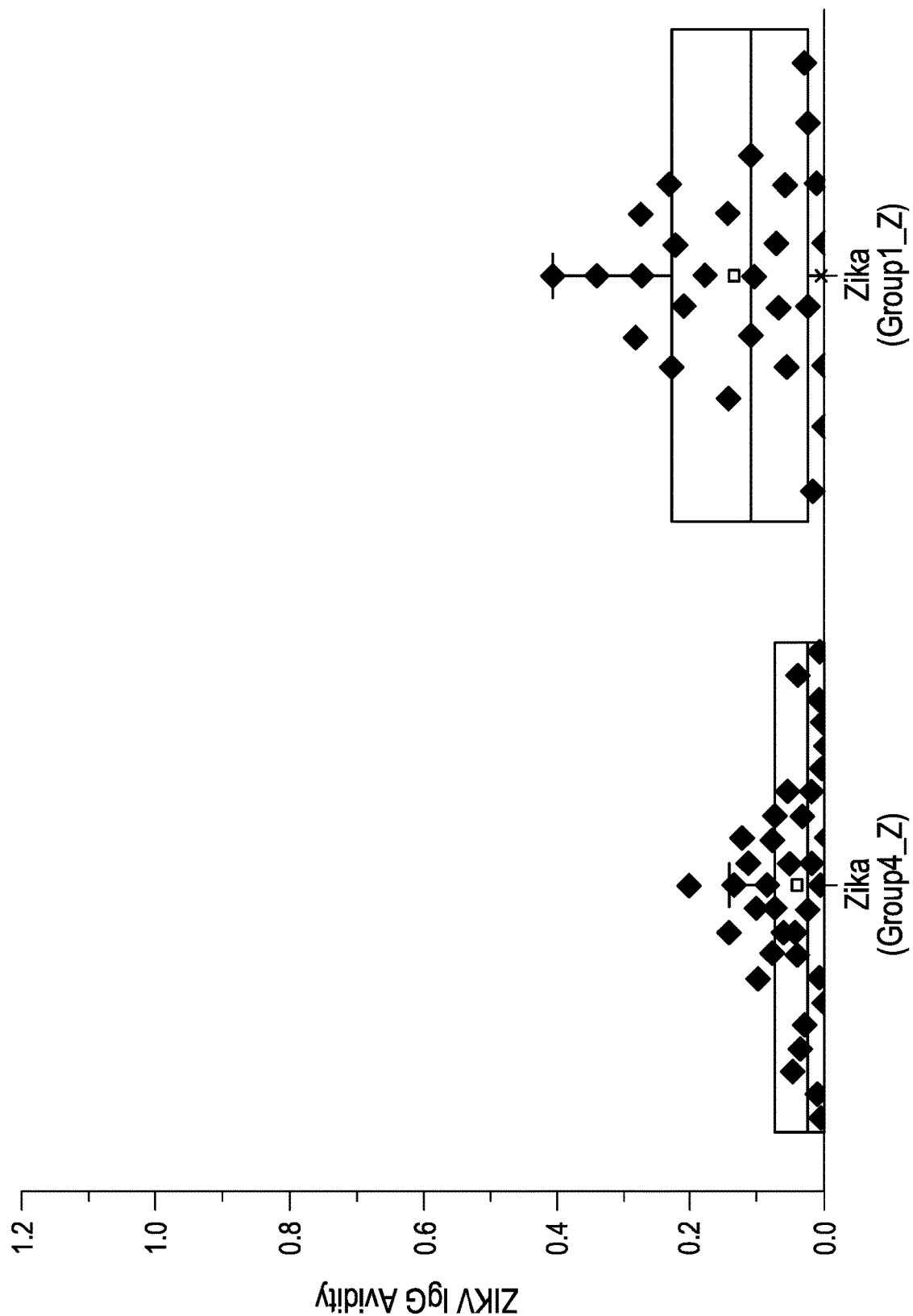

In the case of high ZIKV IgG level in some samples obtained from Colombia and collected within 1-7 days of symptom onset prompted further investigation of ZIKV IgG for infections in the very early acute phase. A cohort of 49 serum samples of acute ZIKV infection patients from the Dominican Republic RT-PCR positive for ZIKV RNA were tested. For comparison, 8 DENV serum samples from patients in an acute secondary DENV infection phase that were identified as DENV RNA positive by RT-PCR (due to acute DENV infection) were also tested. Concurrently the results showed high DENV IgG avidity (due to past DENV infection). Consistent with findings from the Colombia cohort, highly positive ZIKV IgG levels were detected in many samples from the Dominican Republic that were positive for ZIKV RNA by RT-PCR (FIG. 17 panel a). All of the ZIKV IgG positive samples from the Dominican Republic showed low (less than about 0.2) ZIKV IgG avidity (FIG. 17 panel b), and the average avidity value was lower than that for the specimens from Colombia in convalescent ZIKV infection phase (Zika 1, FIG. 17 panel b). These results confirmed the presence of detectable ZIKV IgG levels and low IgG avidity in the primary, acute ZIKV infected samples during a very early PCR+ phase.

Additionally, when referenced to a healthy group without prior flavivirial infection, 96% positivity in ZIKV IgG levels was detected in the cohort of 49 serum samples of acute ZIKV infection patients that were ZIKV RNA positive by RT-PCR (ZIKA, FIG. 17 panel a). The specificity reached about 96%, confirming that ZIKV IgG rose rapidly in people with acute ZIKV infection in dengue endemic regions.

The earlier than usual appearance of ZIKV IgG within days of the onset of the illness could be due to the secondary infection nature of the ZIKV infected cohorts from the dengue endemic regions. These regions are where almost all of the adults were previously exposed to DENV. Previous work suggested that robust IgG and IgA responses may occur early during a secondary infection event.

A multi-color, multiplexed nano-platform was developed to simultaneously detect IgG and IgA antibodies against ZIKV NS1 and DENV-2 whole virus antigens for differentiating ZIKV infection from DENV infection, using ~1 μL of human serum samples. It was found that for PCR negative samples collected 4 or more days after the onset of illness, ZIKV IgG testing in a naïve population may allow the accurate diagnosis of ZIKV infected patients. The addition of ZIKV IgA may further increase test sensitivity and confirm recent ZIKV infection. Serial detection of ZIKV IgG level could further improve the accuracy of ZIKV diagnosis.

Detection of high levels of ZIKV NS1 IgG and IgA antibodies within days of the onset of illness is specific for ZIKV infection, a finding differs from commonly pursued IgM testing plagued by cross-reactivity problems in the ZIKV case. Compared to conventional single-plex methods (i.e. ELISA, PRNT), multiplexed and multi-antibody-isotype detection on pGOLD as provided herein greatly facilitated the detection and could drastically reduce the number of tests required for future diagnostic use, thus enhancing the capability of screening large number of samples during pandemic disease outbreak. In addition, combined IgG/IgA ZIKV/DENV assay uses only ~1 μL of human serum and obtains quantitative results in about 2 hours, which is a challenging task on other immunoassay platforms. Thus, the detection of anti-ZIKV NS1 IgG and IgA antibodies on the pGOLD platform could facilitate screening for recent Zika fever during the pandemic spread of ZIKV infection through the naïve population of the Americas. ZIKV IgG/IgA testing could also be utilized as a first trimester serological screen to identify at-risk seronegative women and to monitor for infection during pregnancy.

Figure 18A:
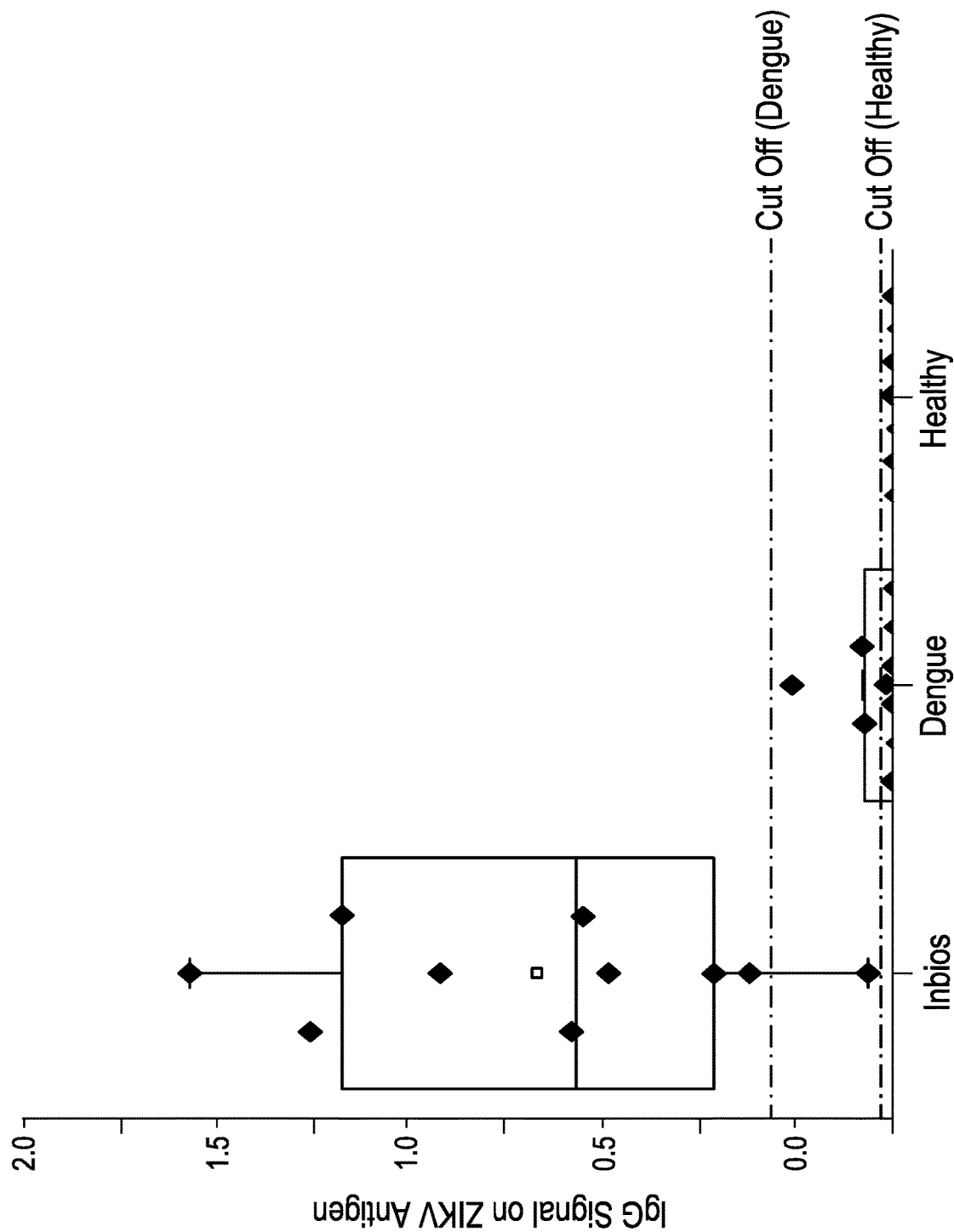
FIG. 18 shows example box plots (A) for ZIKV IgG antibody levels for three groups of individuals: a cohort of 10 ZIKV infected patients, confirmed by ZIKV Detect™ IgM Capture ELISA (Inbios), a cohort of 10 patients who were chronic DENV infected (Dengue) and a control cohort without any prior ZIKV or DENV infection (Healthy). Also shown are (B) ZIKV IgM levels for the same three groups of individuals.
Figure 18B:
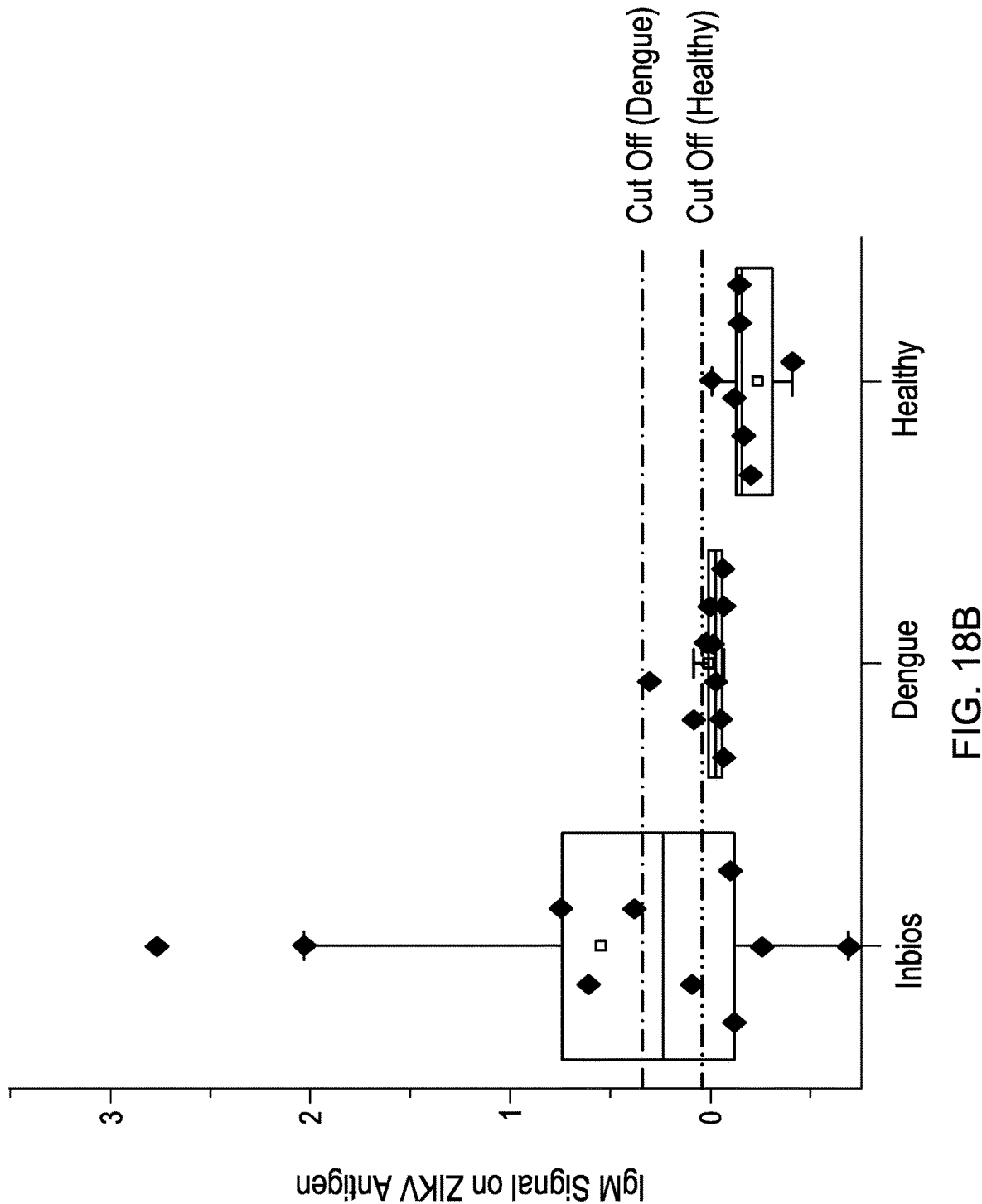

The robustness of the pGOLD ZIKV IgG assay was tested by measuring ZIKV IgG antibody levels in 10 samples that were diagnosed as Zika positive by ZIKV Detect™ IgM Capture ELISA (InBios International, Inc.). The ZIKV Detect™ IgM Capture ELISA is an IgM based assay authorized by the U.S. Food and Drug Administration (FDA). For the other group of ZIKV infected patients, increased ZIKV IgG levels on all of the ZIKV infected patients were observed (FIG. 18). With a high IgG cutoff referenced to patients with chronic DENV infection, the pGOLD IgG assay detected positive ZIKV infections with 90% sensitivity on a small sample size of 10 and 100% specificity (FIG. 18 panel a). Furthermore, with IgG cutoff referenced to healthy population with no prior flaviviral infection, ZIKV infection with 100% sensitivity and 100% specificity with the Inbios IgM+ samples were detected (FIG. 18 panel a).

All of the ZIKV infected samples (Inbios IgM+) tested were additionally confirmed as IgM positive by IgM-based ELISA assay. However, when ZIKV IgM levels on the same group of samples were tested, a significantly reduced sensitivity (50%) with an IgM cutoff referenced to chronic DENV infected patients was observed (FIG. 18 panel b). Based on these IgG/IgM results and the well documented cross reactivity issues with IgM-based testing, it can be concluded that the IgG antibody based detection using the pGOLD ZIKV assay provides for highly sensitive testing of the ZIKV infection with a higher specificity than ZIKV IgM. It is highly recommended to include the ZIKV IgG testing in dengue endemic regions, to achieve higher specificity of ZIKV diagnosis than IgM testing.

A highly sensitive and specific serologic diagnosis of ZIKV infection can be achieved by the pGOLD ZIKV IgG and IgG avidity test in dengue endemic regions where most adults have had previous DENV infections. At the symptom onset point, ZIKV IgG test can give 100% sensitivity for acute ZIKV infection, and greater than 90% specificity, when using a cutoff referenced to healthy people without prior flaviviral infection. Avidity testing can detect recent ZIKV infection. As a follow up test in about one month (or 2-3 weeks similar to the convalescent Colombia samples), it is recommended to re-test with pGOLD ZIKV IgG assay using a cutoff referenced to prior DENV infected population. The positivity result can confirm the ZIKV infection with both sensitivity and specificity greater than 95%. The ZIKV IgG avidity can also be retested to assess the degree of convalescence of ZIKV infection.

Using the pGOLD Zika and Dengue IgG assay, levels of ZIKV specific IgG antibodies in Zika infected patients (Group1_Z; mostly in convalescent phase) were markedly higher than those in the serum of flaviviral free control cohort and in the patients with chronic Dengue infection (Group2_D). The pGOLD Zika IgG assay identified ZIKV infected patients in convalescent phase of infection with 100% sensitivity and 100% specificity from flaviviral free control cohort (cutoff 0.02), and detected ZIKV infection with >93% sensitivity and ~98% specificity for the cohort with chronical DENV infection (ZIKV IgG level cutoff 0.14). Since some cross-reactivity of prior DENV IgG to the ZIKV NS1 antigen exists, a slightly higher cutoff in ZIKV IgG can be used for patients with past DENV infection than for flaviviral-free cohort. Using the pGOLD Zika and Dengue IgG assay for avidity testing on ZIKV infected patients from Columbia; low ZIKV IgG avidity (≤0.4) suggests a recent infection of ZIKV. High DENV IgG levels and DENV IgG avidity >0.5 were observed with this patient cohort suggesting there was previous exposure to Dengue in the DENV endemic Colombia.

Samples from patients with secondary DENV infection in the acute phase (Group5_DD) revealed positive DENV IgG levels, but low ZIKV IgG levels. This suggests that the positive ZIKV IgG level observed with the ZIKV infected cohort from dengue-endemic regions were not due to pre-existing cross-reactive anti-DENV antibodies, but were due to nascent, specific anti-ZIKV antibodies.

When testing a cohort of 49 patients with acute ZIKV infection (Group4_Z; ZIKV RNA positive by RT-PCR, sample collected 2-7 days post symptom onset) the pGOLD Zika and Dengue IgG assay detected most of the samples with ZIKV IgG level higher than the cutoff of 0.02 relative to flaviviral-free control cohort. The appearance of ZIKV IgG within 7 days of symptotic onset of illness can be a result of the secondary infection nature of the ZIKV infected cohorts from dengue endemic regions. In these regions most of the adults had previous exposure to DENV. Other results suggest that robust IgG response may occur early during a secondary infection event.

Two sets of serially collected serum samples at various time points after symptom onset (i.e. serial draw samples; Group6_ZS) were tested using the pGOLD Zika and Dengue IgG and IgG avidity assay. In patient 1, positive ZIKV IgG levels>0.14 as early as 2 and 5 days post symptom onset were detected, and the ZIKV IgG level increased to a much higher level 13 days post symptom onset. In patient 2, ZIKV IgG level was >0.02 but below 0.14 at day 7 post symptom onset were detected, but increased well above the higher cutoff 0.14 at day 11 post symptom onset. These results indicate that ZIKV IgG is a highly sensitive and specific diagnostic marker using the pGOLD ZIKV IgG testing at disease onset with a follow up measurement 2 weeks post symptom onset using the algorithm. Additionally, the two patients in Group6_ZS with ZIKV IgG avidity levels below <0.5 (low avidity) on serum samples collected at all time points, suggesting a recent infection. However, the two patients tested for DENV IgG avidity levels>0.6 (high avidity) at all time points, confirming their history of past infection with DENV. The pGOLD Zika and Dengue IgG and IgG Avidity assay can afford highly sensitive and specific ZIKV diagnosis using 1 μL serum sample in about 2 hours of assay time.

Example 4: Control Sample Testing

Positive and negative controls for ZIKV IgG may be tested together with human serum samples on each biochip. If assay results show negative results for positive control samples or show positive results for negative control samples, the assay result cannot be reported. All control samples may be examined prior to interpretation of patient results. If the controls are not valid, the patient results may not be interpreted. Assessment of clinical specimen test results may be performed after the positive and negative controls have been examined and determined to be valid and acceptable.

Two tests have been proposed. Test 1 can be performed at disease onset stage to measure: (a) Human IgG antibodies against Zika virus NS1 antigen; (b) Human IgG antibodies against Dengue virus Type 2 antigens; (c) Human IgG avidity against Zika virus NS1 antigen; and (d) Human IgG avidity against Dengue virus Type 2 antigens. Test 2 may be performed at 14 days post disease onset to measure Human IgG antibodies specific against Zika virus NS1 antigen.

Table 5 illustrates that during test 1, IgG against ZIKV NS1, IgG against DENV2, Zika IgG avidity, and Dengue IgG avidity were tested for all the serum samples. Additionally, if samples are collected before 14 days post symptom onset in test1, a follow-up testing (test 2) may be performed on serum samples collected at day 14 post symptom onset. During test 2, IgG against ZIKA NS1 was detected.

TABLE 5

Analysis of two tests conducted on patients for detection and diagnosis of Zika.

| Test 1 Prior | | Days Post | | | Follow-up Test 14 days post onset | | Zika IgG (Test 1) |
|---|---|---|---|---|---|---|---|
| DENV Infection? | Test 1 Zika IgG | Symptom Onset | Initial Interpretation | Follow-up Testing | Test 2 Zika IgG | Final Interpretation | Avidity Result/ Interpretation |
| Yes DENV IgG ≥0.08 & DENV IgG Avidity >0.6 | >0.14 | <14 days | Possible Zika +ive | This result should be confirmed by follow-up test | >0.14 | Presumptive Zika +ive | <0.5 Recent ZIKV Infection |
| | | | | | | | >0.6 Prior ZIKV Infection |
| | | >14 days | Presumptive Zika +ive | None | N/A | N/A | <0.5 Recent Infection |
| | | | | | | | >0.6 Prior Infection |

TABLE 5-continued

Analysis of two tests conducted on patients for detection and diagnosis of Zika.

| Test 1 Prior DENV Infection? | Test 1 Zika IgG | Days Post Symptom Onset | Initial Interpretation | Follow-up Testing | Follow-up Test 14 days post onset | | Zika IgG (Test 1) Avidity Result/ Interpretation |
|---|---|---|---|---|---|---|---|
| | | | | | Test 2 Zika IgG | Final Interpretation | |
| | <0.14 | <14 days | Possible Zika +ive | The result should be confirmed by follow-up test | >0.14 | Presumptive Zika +ive | <0.5 Recent Infection >0.6 Prior Infection |
| | | | | | <0.14 | Presumptive Zika –ive | N/A |
| | | >14 days | Presumptive Zika –ive | None | N/A | N/A | N/A |
| No DENV IgG <0.08 & DENV IgG Avidity <0.5 | >0.02 | <14 days | Possible Zika +ive | The result should be confirmed by follow-up test | >0.02 | Presumptive Zika –ive | <0.5 Recent Infection >0.6 Prior Infection |
| | | ≥14 days | Presumptive Zika –ive | None | N/A | N/A | <0.5 Recent Infection >0.6 Prior Infection |
| | <0.02 | <14 days | Possible Zika –ive | The result should be continued by follow-up test | <0.02 | Presumptive Zika –ive | N/A |
| | | | | | >0.02 | Presumptive Zika –ive | <0.5 Recent Infection |
| | | >14 days | Presumptive Zika –ive | None | N/A | N/A | N/A |

Table 5: (1) During Test 1, we detect IgG against ZIKV NS1, IgG against DENV2 and Zika IgG avidity and Dengue IgG avidity for all the serum samples (2) If samples are collected before 14 days post symptom onset in Test1, follow-up testing (Test 2) will be performed on serum samples collected at day 14 post symptom onset. In Test 2, we detect IgG against ZIKA NS1

There are four experimental cases of test 1 for serum samples collected at 14 days or later post symptom onset. In case 1, if DENV IgG is negative (DENV IgG<0.08), then the patient has no prior DENV infection. If ZIKV IgG>0.02, then the patient is ZIKV infected. And there is no need for follow-up testing (i.e Test 2). ZIKV IgG avidity can determine recent (avidity<0.5) from past infection (avidity>0.6). In case 2, if DENV IgG is negative (DENV IgG<0.08), then the patient has no prior DENV infection. If ZIKV IgG<0.02, then the patient is not ZIKV infected. And, there is no need for follow-up testing (i.e. Test 2). In case 3, if DENV IgG is positive (DENV IgG>0.08) and DENV avidity>0.6, then the patient has prior chronic DENV infection. If ZIKV IgG>0.14, then the patient is ZIKV infected. There is no need for follow-up testing (i.e. Test 2). ZIKV IgG avidity can determine recent (avidity<0.5) from past infection (avidity>0.6). In case 4, if DENV IgG is positive (DENV IgG>0.08) and DENV avidity>0.6, then the patient has prior chronic DENV infection. If ZIKV IgG<0.14, then the patient is not ZIKV infected. There is no need for follow-up testing (i.e. Test 2).

Additionally, there are four experimental cases of test 1 for serum samples collected before 14 days post symptom onset. In case 1, if DENV IgG is negative (DENV IgG<0.08), then the patient has no prior DENV infection. If ZIKV IgG>0.02, then the patient is possibly ZIKV infected. Test 2 may be required at 14 days post symptom onset if ZIKV IgG remains positive (ZIKV IgG>0.02) or increases in positive value, resulting in confirmation of ZIKV infection. ZIKV IgG avidity tested in test 1 can determine recent (avidity<0.5) from past infection (avidity>0.6). In case 2, if DENV IgG is negative (DENV IgG<0.08), then the patient has no prior DENV infection. If ZIKV IgG<0.02, test 2 may be required at 14 days post symptom onset. If ZIKV IgG becomes positive (ZIKV IgG>0.02) then a recent ZIKV infection is confirmed. If ZIKV IgG remains negative (ZIKV IgG<0.02) then the patient does not have a ZIKV infection. In case 3, if DENV IgG is positive (DENV IgG>0.08) and DENV IgG avidity>0.6, then the patient has prior chronic DENV infection. If ZIKV IgG>0.14, then the patient is ZIKV infected. Test 2 may be required. At 14 days post symptom onset, if ZIKV IgG remains positive (ZIKV IgG>0.14) or increases in positive value, then ZIKV infection is confirmed in the patient. ZIKV IgG avidity tested in test 1 can determine recent (avidity<0.5) from past infection (avidity>0.6). In case 4, if DENV IgG is positive (DENV IgG>0.08) and DENV IgG avidity>0.6, then the patient has prior chronic DENV infection. If ZIKV IgG<0.14, then test 2 maybe required. At 14 days post symptom onset, if ZIKV IgG became positive (ZIKV IgG>0.14) then the patient is confirmed of ZIKV infection. If ZIKV IgG is <0.14 then the sample is negative for ZIKV infection.

Example 5: Cross Reactivity and Interfering Substances Testing

Cross-reactivity may be evaluated by testing specimens from patients with antibodies to other microorganisms and autoantibodies which could potentially cause false positive results. A minimum of 3-5 samples can be tested for each infectious agent listed in Table 6, except for other flaviviruses known to cross-react with Zika IgM serology assays. In this case, a larger number of specimens should be tested (≥10).

The potential cross-reactivity with IgG that would be present for other diseases may be evaluated by testing specimens from patients with confirmed IgG antibodies to other microorganisms that could potentially cause false positive results. This cross-reactivity evaluation comprised IgG positive sera against organisms whose infection produces symptoms similar to those observed at the onset of Zika virus infection and also viral strains which have a significant likelihood of cross-reactivity due to genetic similarity with Zika virus. Also included were IgG positive sera against organisms and strains that are likely to be observed in the currently affected and endemic area (i.e., Brazil and South America) because these organisms and strains may be an important part of the differential diagnosis of Zika virus infection and sera from other disease states.

TABLE 6

| Reference test results on infectious agents used for cross-reactivity studies | | | |
|---|---|---|---|
| Disease/Infectious agent Positive Sera* | Number of samples N = 3-5 each condition^$ | [pGOLD Zika/Dengue IgG Assay] Equivocal or positive results | % Cross-reactivity |
| Anti-Chikungunya virus | 5 | 0 | 0 |
| Anti-Cytomegalovirus (CMV) | 5 | 0 | 0 |
| Anti-Dengue virus$ | 69 | 1 | 1.5 |
| Anti-Epstein Barr Virus (EBV) | 6 | 0 | 0 |
| Anti-Parvovirus B19 | 5 | 0 | 0 |
| Anti-Varicella zoster virus | 6 | 0 | 0 |
| Yellow fever virus post-immunization$ | | | |
| Anti-West Nile Virus$ | 6 | 0 | 0 |
| Anti-nuclear Antibodies (ANA) | 6 | 0 | 0 |
| Anti- Malaria/anti-*plasmodiurn falciparum* | 2 | 0 | 0 |
| Adenovirus (optional) | | | |
| Enterovirus (optional) | | | |
| Anti-Leptospira (optional) | | | |
| Anti-Eastern Equine Encephalitis (optional) | | | |
| Anti-Japanese Encephalitis (optional) | | | |
| Anti-Hepatitis (C) virus (optional) | | | |
| Anti-Ross River virus (optional) | | | |

TABLE 6-continued

| Reference test results on infectious agents used for cross-reactivity studies | | | |
|---|---|---|---|
| Disease/Infectious agent Positive Sera* | Number of samples N = 3-5 each condition^$ | [pGOLD Zika/Dengue IgG Assay] Equivocal or positive results | % Cross-reactivity |
| Anti-Saint Louis encephalitis (SLE) (optional) | | | |
| Antinuclear antibodies (ANA)# | | | |
| Rheumatoid Factor# | | | |

*The positive sera used in this study should be from infected individuals in the early stages of infection where IgM levels will be predominating.

^If possible please include concentration/titer of IgM antibody in the specimen.

$Due to the known cross-reactivity of these agents with Zika IgM serology assays a larger number of specimens should be tested (≥10).

To evaluate the potential of autoimmune conditions to interfere with Zika IgM serology, a larger number of specimens should be tested (≥10)

Positive serum samples were obtained for (with clinical reference data; Table 7 Chikungunya IgG, Epstein Barr Virus IgG, Parvovirus IgG, Varicella Zoster Virus IgG, West Nile Virus IgG, Cytomegalo Virus IgG, and antinuclear antibodies from Laboratory of Pathology and Mycology in Universitie de Nice-Sophia Antipolis (France; Supplementary Table 4). All samples were tested on the pGOLD Zika and Dengue IgG assay platform and evaluated for their reactivity with ZIKV and DENV antigens printed on pGOLD biochip. All non-DENV samples (DENV IgG<0.08, i.e. patients with no prior DENV infection) showed ZIKV IgG<0.02, suggesting no IgG cross reactivity with ZIKV for antibodies in the sera samples of Chikungunya, Epstein Barr Virus, Parvovirus, Varicella Zoster Virus, West Nile Virus, Cytomegalo infections, or other antinuclear antibodies in autoimmune patients.

Additionally, some of the samples that were positive for other infectious diseases also tested positive for DENV IgG on pGOLD Zika and Dengue assay. For these samples (DENV IgG level≥0.08, i.e. identified as patients with prior DENV infection), ZIKV IgG were <0.14, suggesting these patients did not have ZIKV infection with prior DENV infection. The slightly higher cutoff in the algorithm eliminates the issues from cross reactivity.

TABLE 7

| Reference test results on serum samples used for cross-reactivity studies | | | | | | | | | | | |
|---|---|---|---|---|---|---|---|---|---|---|---|
| | NoGLIMS | CMV IgG | CMV IgG titer | CMV IgM | Anti nuclear antibody | Anti nuclear antibody titer | PARVO IgG | PARVO IgM | VZV | VZV Titer | EBV VCA IgG |
| 1 | 1602242117 | POS | 6 | Pos(but in 2014 so it could be now negative) | POS | 1/1280 | Neg | Neg | | | |
| 2 | 1605182467 | POS | 100 | NEG | POS | 1/640 | UK | UK | | | |
| 3 | 1601050980 | POS | 140 | NEG | POS | 1/80 | | | POS | 969.6 | POS |
| 4 | 1509072803 | NEG (2015) | | NEG | POS | 1/320 | | | POS | 1754 | POS |
| 5 | 1601042795 | POS | 179 | NEG | POS | 1/2560 | | | | | |
| 6 | 1509022043 | POS (2015) | 84.5 | NEG | POS | 1/320 | NEG | NEG | | | POS |
| 7 | 1508251528 | NEG (2015) | | NEG | POS | 1/80 | POS | NEG | | | POS (2015) |
| 8 | 1601113436 | POS (2015) | 133 | POS | POS | 1/80 | | | | | POS (2015) |
| 9 | 1601121045 | POS | 68.3 | NEG | POS | 1/160 | NEG | NEG | | | |
| 10 | 1601121649 | POS | 119 | POS | POS | 1/2560 | | | | | POS |

TABLE 7-continued Reference test results on serum samples used for cross-reactivity studies

|  | NoGLIMS |  |  |  |  |  |  |  |  |  |  |
|---|---|---|---|---|---|---|---|---|---|---|---|
| 11 | 1601122366 |  |  | POS | 1/80 |  |  |  |  |  |  |
| 12 | 1605170658 | NEG |  | NEG | POS | 1/2560 |  |  | POS | 2474 | POS |
| 20 | 1407071390 |  |  |  |  |  |  |  |  |  |  |
| 19 | 1410162401 | POS | 98 | NEG |  |  |  |  |  |  |  |
| 21 | 1405192771 |  |  |  | NEG |  |  |  |  |  |  |
| 16 | 1512240975 | NEG |  | NEG |  |  |  |  |  |  | POS |
| 15 | 1509112721 | NEG |  | NEG |  |  |  |  |  |  | POS |
| 18 | 1602291212 | NEG |  | NEG |  |  |  |  |  |  | POS |
| 17 | 1608021228 |  |  |  |  |  |  |  |  |  |  |
| 28 | 1507152558 | POS | 128 | NEG |  |  |  |  |  |  | POS |
| 29 | 1512240969 |  |  |  |  |  |  |  |  |  |  |
| 30 | 1603222931 |  |  |  |  |  |  |  |  |  |  |
| 31 | 1607271022 |  |  |  |  |  |  |  |  |  |  |
| 32 | 1610102296 |  |  |  |  |  |  |  |  |  |  |
| 13 | 1607063163 | POS | 85.1 | NEG |  |  | POS | NEG |  |  | POS |
| 14 | 1603042566 |  |  |  |  |  |  |  |  |  |  |
| 22 | 1506032170 | NEG | <5.00 | POS 47.3 |  |  | NEG | NEG | POS | 1325 | NEG |
| 27 | 1506160918 | NEG | 11.5 | NEG <5.00 |  |  | POS 2.8 | NEG | POS | 1319 | POS |
| 23 | 1506172272 | NEG | <5.00 | NEG 7.43 |  |  |  |  | NEG (<114 UI) | 79.57 | NEG |
| 25 | 1507072315 | POS | 49.5 | NEG <5.00 |  |  | NEG | NEG | NEG (<114 UI) | <10.00 | POS |
| 24 | 1507222450 | POS | 80.5 | NEG <5.00 |  |  | POS 1.8 | NEG | NEG (<114 UI) | 56.47 | POS |
| 26 | 1507272859 | POS | 98.1 | NEG 7.51 |  |  | POS 16 | NEG | POS | 332.3 | POS |

|  | NoGLIMS | EBV VCA IgG titer | EBV EBNA IgG | EBV VCA IgM | CHIK IgG | CHIK IgM | WN IgG | WN IgM | DENGUE IgG | DENGUE IgM |
|---|---|---|---|---|---|---|---|---|---|---|
| 1 | 1602242117 |  |  |  |  |  |  |  |  |  |
| 2 | 1605182467 |  |  |  |  |  |  |  |  |  |
| 3 | 1601050980 | >750 | NEG | NEG |  |  |  |  |  |  |
| 4 | 1509072803 | >750 | GRAY ZONE | NEG |  |  |  |  |  |  |
| 5 | 1601042795 |  |  |  |  |  |  |  |  |  |
| 6 | 1509022043 | >750 | POS 106 |  |  |  |  |  |  |  |
| 7 | 1508251528 | 66.4 | NEG | NEG |  |  |  |  |  |  |
| 8 | 1601113436 | 323 | POS 175 |  |  |  |  |  |  |  |
| 9 | 1601121045 |  |  |  |  |  |  |  |  |  |
| 10 | 1601121649 | 204 | POS 309 |  |  |  |  |  |  |  |
| 11 | 1601122366 |  |  |  |  |  |  |  |  |  |
| 12 | 1605170658 | 345 | POS 363 |  |  |  |  |  |  |  |
| 20 | 1407071390 |  |  |  | POS | POS |  |  |  |  |
| 19 | 1410162401 |  |  |  | POS | POS WEAK |  |  |  |  |
| 21 | 1405192771 |  |  |  | POS | POS |  |  |  |  |
| 16 | 1512240975 | >750 | POS 370 |  | POS | NEG |  |  |  |  |
| 15 | 1509112721 |  | POS |  |  |  | POS | POS | POS | POS |
| 18 | 1602291212 | 556 | POS >600 |  |  |  |  |  |  |  |
| 17 | 1608021228 |  |  |  |  |  |  |  |  |  |
| 28 | 1507152558 | 500 | POS 65 |  |  |  | POS |  | POS |  |
| 29 | 1512240969 |  |  |  |  |  | POS | NEG | POS | POS |
| 30 | 1603222931 |  |  |  |  |  | POS | NEG | POS | POS |
| 31 | 1607271022 |  |  |  |  |  | POS | NEG | POS | POS |
| 32 | 1610102296 |  |  |  | POS | NEG | NEG | NEG | NEG | NEG |
| 13 | 1607063163 | >750 | POS 513 |  |  |  | POS | POS | POS | POS |
| 14 | 1603042566 |  |  |  |  |  |  |  |  |  |
| 22 | 1506032170 | 10.8 | NEG | NEG |  |  |  |  |  |  |
| 27 | 1506160918 | 180 | GRAY ZONE (5-19 UI) 10 UI |  |  |  |  |  |  |  |
| 23 | 1506172272 | 13.1 | NEG | NEG |  |  |  |  |  |  |
| 25 | 1507072315 | 123 | POS 220 |  |  |  |  |  |  |  |
| 24 | 1507222450 | 35.8 | GRAY ZONE (5-19 UI) 15 UI | NEG |  |  |  |  |  |  |
| 26 | 1507272859 | 315 | POS 415 |  |  |  |  |  |  |  |

In another set of experiments, the impact of potentially interfering substances on the pGOLD Zika/Dengue IgG Assay was evaluated. The evaluation demonstrated that the potential interferents do not generate false positive results in known negative specimens, and do not lead to false negative results in known positive specimens.

Potentially interfering substances commonly occurring in serum were evaluated with the pGOLD Zika IgG Assay. Interfering substances include bilirubin (0.2 mg/mL), hemoglobin (160 mg/mL), and albumin (150 mg/mL). These interfering substances were spiked into low reactive (n=3) and normal human serum samples (n=3) to evaluate their impact on assay performance. None of the interfering substances caused a statistically significant change in the ZIKV IgG levels for either the low reactive samples or normal human serum samples evaluated and did not alter the interpretation results.

The impact of interfering substances may be evaluated over the expected clinical range of the potential interfering substance. Potential sources of endogenous interference include, but are not limited to the ones listed in Tables 8A and 8B. The evaluation of interference and the generation of false negative results may be done using samples at or near the assay cut-off(s), and it is acceptable to prepare contrived samples (i.e., dilution of a high titer positive clinical specimen in negative clinical matrix) to reach assay cut-off values. If interference is observed during these studies, the interferent should be tested by serial dilutions to determine the lowest concentration that provides interference. Assay limitations may be added to the Instructions for Use to address any observed interferences.

TABLE 8A

Interfering Substances: pGOLD Zika and Dengue IgG Assay. Evaluation of interfering substances for the ability to generate false positive results:

| Potential Interfering Substance | Concentration | Results (Detected X/3 replicates) |
|---|---|---|
| Hemoglobin | 160 mg/mL | 0/3 |
| Bilimbin | 0.20 mg/mL | 0/3 |
| Serum proteins | 150 mg/mL | 0/3 |

TABLE 8B

Interfering Substances: pGOLD Zika and Dengue IgG Assay. Example table below for evaluation of interfering substances for the ability to generate false negative results:

| Potential Interfering Substance | Concentration | Volume of Positive Clinical Specimen Diluted | Results (Detected X/3 replicates) |
|---|---|---|---|
| Hemoglobin | 160 mg/mL | 1 µL | 0/3 |
| Bilirubin | 0.20 mg/mL | 1 µL | 0/3 |
| Serum proteins | 150 mg/mL | 1 µL | 0/3 |

If interference is observed during these studies, the interferent should be tested by serial dilutions to determine the lowest concentration that provides interference. Assay limitations may be added to the Instructions for use to address any observed interferences.

Example 6: Clinical Sensitivity and Specificity

The pGOLD Zika and Dengue IgG assay (test 1 and 2 combined, test 2 completed at 14 days post symptom onset) detected ZIKV infected patients≥14 days post symptom onset with 100% sensitivity referenced to flaviviral free control cohort (cutoff~0.02). Samples from group1_Z (14 samples) and group3_H (50 samples) were used for this study. Additionally, the pGOLD Zika and Dengue IgG assay detected ZIKV infected patients≥14 days post symptom onset with 93% sensitivity for cohort with chronical DENV infection (ZIKV IgG level cutoff 0.14). Samples from group1_Z (14 samples), group6_ZS (2 samples), group2_D (64 samples) and group 3_H (50 samples) were used for this study. Lastly, the pGOLD Zika and Dengue IgG assay detected ZIKV infected patients≥14 days post symptom onset with 95% sensitivity for cohort with chronical DENV infection (ZIKV IgG level cutoff 0.14). Samples from group 1_Z (14 samples), group6_ZS (10 samples), group2_D (64 samples) and group 3_H (50 samples) were used for this study. The serial draw serum samples (group6_ZS) collected from ZIKV infected patients at ≥14 days post symptom onset were considered as individual samples. A slightly higher cutoff in ZIKV IgG is needed in the algorithm for patients with past DENV infection than flaviviral-free cohort because there was is slight DENV IgG cross-reactivity to ZIKV NS1 antigen.

The pGOLD Zika and Dengue IgG assay (test 1 and 2 combined, test 2 done at 14 days post disease onset) detected ZIKV infected patients in convalescent phase (≥14 days) of infection with 100% specificity from flaviviral free control cohort (cutoff~0.02). Samples from group1_Z (14 samples) and group3_H (50 samples) were used for this study. Additionally, the pGOLD Zika and Dengue IgG assay detected ZIKV infected patients in convalescent phase (≥14 days) of infection with 98% specificity from chronically DENV infected cohort (ZIKV IgG level cutoff 0.14). Samples from group1_Z (14 samples), group 6_ZS (2 samples), group2_D (64 samples) and group 3_H (50 samples) were used for this study. A slightly higher cutoff in ZIKV IgG is required in the algorithm for patients with past DENV infection than flaviviral-free cohort because there is a slight DENV IgG cross-reactivity to ZIKV NS1 antigen.

Example 7: Clinical Truth Evaluation

In the case of positive specimens used to establish clinical sensitivity for the Zika virus IgM assay, specimens obtained from serial bleeds of individuals that initially tested positive by an EUA rRT-PCR Zika virus assay represent the most convincing clinical truth. Based on the information provided by CDC, it is expected that the initial positive result for Zika virus by rRT-PCR would be followed by a positive result for Zika virus IgM in the concurrent or the subsequent serial specimens over a short period of time. The presence of IgM in these specimens may be characterized by an EUA serological IgM assay. Ideally, the patients may also be negative, by molecular methods, for acute infections with other flaviviruses—dengue, West Nile and Yellow Fever (infection or vaccination) and the alphavirus chikungunya virus. Additionally, clinical specimens that were tested using a validated testing algorithm that includes testing against an EUA serological IgM assay used for both positive and negative samples maybe used in the Clinical Truth Evaluation.

Example 8: Clinical Sample Testing

Initially, the feasibility of the method by testing serially collected serum samples from 10 patients confirmed positive for Zika virus from a dengue endemic region was demonstrated. Serially collected samples at disease symptom onset point and one month later may also be obtained.

Specimens obtained from serial bleeds of individuals (in DENV endemic region) that initially tested positive by an EUA or FDA cleared rRT-PCR Zika virus assay can be acquired. It is likely to observe positive ZIKV IgG results with these samples relative to a cutoff referenced to healthy people without any prior flaviviral infection and positive ZIKV IgG levels one month later using a higher cutoff relative to a population with prior chronic DENV infection. ZIKV IgG avidity may also be measured sequentially, and initially low avidity with an increasing trend for the serial bleed may be observed. A high ZIKV avidity greater than 0.5 may suggest chronic ZIKV infection. This may be true in some of the current ZIKV endemic regions.

Specimens from 10 patients confirmed negative by CDC MAC-ELISA (EUA) or InBios ZIKV Detect IgM Capture ELISA (EUA) for Zika virus infection may be collected. Of the 10 clinical negative patients, about 50% may be from individuals in a flavivirus non-endemic region and about 50% may be from individuals in regions where other flavivirus infections have significant prevalence. A negative ZIKV IgG test result for these samples at disease symptom onset point and at one month follow up test point can be expected.

After the feasibility test, a final clinical validation may be conducted using serum samples from 50 ZIKV infected patient at acute disease onset stage confirmed by rRT-PCR and 1 month post onset point, and 100 negative samples, all for people in a DENV endemic region. Negative samples will be confirmed clinically (no Zika symptom), or by CDC MAC-ELISA (EUA) or InBios ZIKV Detect IgM Capture ELISA (EUA).

Fifty ZIKV infected patient samples at the acute PCR+ stage combined with the pGOLD ZIKV IgG assay can fully establish the sensitivity and specificity to be about 100% of the ZIKV IgG test referenced to a healthy uninfected population. The 50 ZIKV infected patient samples sequentially tested at the convalescent stage of one month post infection can result in establishing greater than about 95% sensitivity and specificity for ZIKV infection diagnosis in dengue endemic regions for adult populations with chronic dengue infections. As a result, the ZIKV IgG avidity assay of these samples sequentially can either reveal an increase in IgG avidity over time, adding a confirmation to recent ZIKV infection, or detect high ZIKV IgG avidity, which indicates prior ZIKV infection.

ZIKV infected samples may also be obtained from people without prior flaviviral infection in non-dengue endemic regions, for example in the US or Europe. ZIKV IgG cutoff relative to healthy uninfected population may be used to check for ZIKV IgG levels in the acute phase as well as well as for ZIKV IgG levels one month later. Whether ZIKV IgG rises as rapidly as the population in dengue endemic regions can be determined. The two stage IgG and avidity test can diagnose ZIKV infection with near 100% sensitivity and specificity. IgM tests may be further performed to determine whether ZIKV IgM assay may be more specific to ZIKV for individuals without any prior dengue infection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detecting antibodies selected from IgA and IgG in a biological sample of a subject, said method comprising:

(a) contacting a first portion of said biological sample with one or multiple flaviviral or alphaviral antigens wherein said flaviviral or alphaviral antigens bind to antibodies selected from IgA and IgG thereby forming immune complexes;

(b) contacting the immune complexes of step (a) with a mild protein denaturing agent, wherein said mild protein denaturing agent is present in a concentration sufficient to destabilize immune complexes containing antibodies of low avidity, but not sufficient to destabilize immune complexes containing antibodies of high avidity;

(c) detecting antibodies selected from IgA and IgG in the biological sample by detecting antibodies selected from IgA and IgG bound to each of said flaviviral or alphaviral antigen; and (d) evaluating an avidity of IgG by taking a ratio of a level of said IgG in step (c) to a control value of IgG in a second portion of said biological sample not exposed to said protein denaturing agent, wherein when the ratio is about 0.5 or less, then the avidity is low and when the ratio is about 0.6 or greater, then the avidity is high.

2. The method of claim 1, wherein said detecting comprises detecting a level of antibodies selected from IgA and IgG bound to said flaviviral or alphaviral antigen in said biological sample.

3. The method of claim 1, wherein said flaviviral or alphaviral antigens are selected from a Zika virus antigen, Dengue virus antigen, yellow fever virus antigen, tick-borne encephalitis virus antigen, Japanese Encephalitis virus (JEV), West Nile virus antigen, mayaro virus antigen, and Chikungunya virus antigen.

4. The method of claim 3, wherein said flaviviral antigens are selected from a Zika virus antigen, and Dengue virus antigen.

5. The method of claim 4, wherein said flaviviral antigen is Zika virus antigen.

6. The method of claim 1, wherein said protein denaturing agent comprises urea, formamide, guanidine, sodium salicylate, dimethyl sulfoxide, or propylene glycol, or a combination thereof.

7. The method of claim 6, wherein said protein denaturing agent comprises urea.

8. A method of diagnosing Zika virus infection in a subject, the method comprising:

(a) contacting a first portion of a biological sample obtained from the subject with a Zika virus antigen wherein said Zika virus antigen binds to antibodies selected from IgA and IgG thereby forming immune complexes;

(b) contacting the immune complexes of step (a) with a mild protein denaturing agent, wherein said mild protein denaturing agent is present in a concentration sufficient to destabilize immune complexes containing antibodies of low avidity, but not sufficient to destabilize immune complexes containing antibodies of high avidity;

(c) detecting antibodies selected from IgA and IgG in the biological sample by detecting antibodies selected from IgA and IgG bound to said Zika virus antigen;

(d) diagnosing the subject with Zika virus infection when the presence of antibodies selected from IgA and IgG in the biological sample is detected; and (e) evaluating an avidity of IgG by taking a ratio of a level of IgG in step (c) to a control value of IgG in a second portion of said biological sample not exposed to said protein denaturing agent, wherein when the ratio is about 0.5 or less, then the avidity is low and when the ratio is about 0.6 or greater, then the avidity is high.

9. The method of claim 8, further comprising (f) administering an effective amount of an anti-viral agent to the diagnosed subject.

10. The method of claim 8, wherein the subject is a female subject and the method further comprises:

(f) administering a contraceptive to the diagnosed subject.

11. The method of claim 8, wherein said detecting comprises detecting a first detectable label, wherein said first detectable label is associated with a first antibody that binds to said IgA bound to said Zika antigen.

12. The method of claim 11, wherein said first antibody is an antihuman IgA antibody.

13. The method of claim 8, wherein said detecting comprises detecting a second detectable label, wherein said second detectable label is associated with a second antibody that binds to said IgG bound to said Zika antigen.

14. The method of claim 13, wherein said second antibody is an antihuman IgG antibody.

15. The method of claim 8, wherein said detecting comprises detecting both of IgA and IgG bound to said Zika virus antigen in said biological sample.

16. The method of claim 8, wherein said Zika virus antigen comprises a recombinant Zika viral antigen.

17. The method of claim 16, wherein said recombinant Zika viral antigen is Zika virus NS I protein or Zika virus NS5 protein.

18. A method of diagnosing a first viral infection and a second viral infection in a subject, the method comprising:
   (a) contacting a first portion of a biological sample obtained from the subject with a first viral antigen and a second viral antigen independently selected from flaviviral antigens and alphaviral antigens thereby forming immune complexes;
   (b) contacting the immune complexes of step (a) with a mild protein denaturing agent, wherein said mild protein denaturing agent is present in a concentration sufficient to destabilize immune complexes containing antibodies of low avidity, but not sufficient to destabilize immune complexes containing antibodies of high avidity;
   (c) detecting antibodies selected from IgA, IgM, and IgG in said biological sample by detecting antibodies selected from IgA, IgM and IgG bound to said first viral antigen and antibodies selected from IgA, IgM and IgG bound to said second viral antigen; and
   (d) diagnosing said subject with said first viral infection upon detecting antibodies selected from IgA, IgM and IgG bound to said first viral antigen and diagnosing the subject with said second viral infection upon detecting antibodies selected from IgA, IgM and IgG bound to said second viral antigen; and
   (e) evaluating an avidity of IgG by taking a ratio of a level of said IgG in step (c) to a control value of IgG in a second portion of said biological sample not exposed to said protein denaturing agent, wherein when the ratio is about 0.5 or less, then the avidity is low and when the ratio is about 0.6 or greater, then the avidity is high.

19. The method of claim 18, wherein said method further comprises diagnosing a third, fourth, fifth, sixth or seventh viral infection, the method further comprising:
   in step (a), contacting said biological sample with a third, fourth, fifth or sixth viral antigen independently selected from flaviviral antigens and alphaviral antigens;
   in step (c), detecting antibodies selected from IgA, IgM, and IgG in said biological sample by detecting antibodies selected from IgA, IgM, and IgG bound to said third, fourth, fifth or sixth viral antigen; and
   in step (d), diagnosing said subject with said third viral infection upon detecting antibodies selected from IgA, IgM, and IgG bound to said third viral antigen, diagnosing said subject with said fourth viral infection upon detecting antibodies selected from IgA, IgM, and IgG bound to said fourth viral antigen, diagnosing said subject with said fifth viral infection upon detecting antibodies selected from IgA, IgM, and IgG bound to said fifth viral antigen, and diagnosing the subject with said sixth viral infection upon detecting antibodies selected from IgA, IgM, and IgG bound to said sixth viral antigen.

20. A method for determining the extent of binding of IgG in a biological sample to flaviviral or alphaviral antigens, comprising the steps of:
   (a) contacting a first portion of said biological sample with said flaviviral or alphaviral antigens, under conditions which permit immune complexes to form;
   (b) contacting said immune complexes with a protein denaturing agent, wherein said protein denaturing agent is present in a concentration sufficient to destabilize immune complexes containing antibodies of low avidity, but not sufficient to destabilize immune complexes containing antibodies of high avidity; and
   (c) determining an avidity of IgG in said biological sample by determining a ratio of a level of said IgG in step (b) to a control value of IgG in a second portion of said biological sample not exposed to said protein denaturing agent, wherein when the ratio is about 0.5 or less, then the avidity is low and when the ratio is about 0.6 or greater, then the avidity is high.

21. The method of claim 20, wherein said antigens are immobilized on a substrate.

22. The method of claim 21, wherein said detecting comprises contacting said substrate with one or more detectable labels associated with anti-IgG.

23. A kit for diagnosing a viral infection in a subject, the kit comprising:
   (a) a substrate with a plasmonic film;
   (b) one or more viral antigens wherein said one or more viral antigens are immobilized on said substrate, the viral antigens including flaviviral or alphaviral antigens that bind to antibodies selected from IgA and IgG to form immune complexes; and
   (c) instructions for using said substrate to assay for the presence of an infection in a sample, the instructions including:
      contacting a first portion of the sample with the viral antigens to form the immune complexes;
      contacting the immune complexes with a mild protein denaturing agent, wherein said mild proten denaturing agent is present in a concentration sufficient to destabilize immune complexes containing antibodies of low avidity, but not sufficient to destabilize immune complexes containing antibodies of high avidity;
      detecting antibodies selected from IgA and IgG in the sample by detecting antibodies selected from IgA and IgG bound to each of said flaviviral or alphaviral antigens; and
      evaluating an avidity of IgG by taking a ratio of a level of the detected antibodies to a control value of IgG in a second portion of the sample not exposed to said protein denaturing agent, wherein when the ratio is about 0.5 or less, then the avidity is low and when the ratio is about 0.6 or greater, then the avidity is high.

* * * * *